(12) United States Patent
Wolkenberg et al.

(10) Patent No.: US 9,024,032 B2
(45) Date of Patent: May 5, 2015

(54) INHIBITORS OF CATECHOL O-METHYL TRANSFERASE AND THEIR USE IN THE TREATMENT OF PSYCHOTIC DISORDERS

(75) Inventors: Scott Wolkenberg, Wyndmoor, PA (US); James C. Barrow, Arnold, MD (US); Michael S. Poslusney, Nashville, TN (US); Scott T. Harrison, Glenside, PA (US); B. Wesley Trotter, Medfield, MA (US); James Mulhearn, Elkins Park, PA (US); Kausik K. Nanda, Norristown, PA (US); Peter J. Manley, Harleysville, PA (US); Zhijian Zhao, Wilmington, DE (US); Jeffrey W. Schubert, Ambler, PA (US); Nathan Kett, Columbia, TN (US); Amy Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/582,601

(22) PCT Filed: Feb. 28, 2011

(86) PCT No.: PCT/US2011/026399
§ 371 (c)(1),
(2), (4) Date: Dec. 13, 2012

(87) PCT Pub. No.: WO2011/109254
PCT Pub. Date: Sep. 9, 2011

(65) Prior Publication Data
US 2013/0084346 A1   Apr. 4, 2013

Related U.S. Application Data

(60) Provisional application No. 61/310,410, filed on Mar. 4, 2010.

(51) Int. Cl.
| | | |
|---|---|---|
| A61K 31/44 | (2006.01) |
| C07D 211/90 | (2006.01) |
| C07D 213/69 | (2006.01) |
| A61K 31/4412 | (2006.01) |
| A61K 31/4418 | (2006.01) |
| A61K 31/4439 | (2006.01) |
| A61K 31/444 | (2006.01) |
| A61K 31/4545 | (2006.01) |
| A61K 31/4709 | (2006.01) |
| A61K 31/4725 | (2006.01) |
| A61K 31/5377 | (2006.01) |
| A61K 31/541 | (2006.01) |
| A61K 31/69 | (2006.01) |
| A61K 45/06 | (2006.01) |
| C07D 213/73 | (2006.01) |
| C07D 213/74 | (2006.01) |
| C07D 401/10 | (2006.01) |
| C07D 401/14 | (2006.01) |
| C07D 413/10 | (2006.01) |
| C07D 413/12 | (2006.01) |
| C07D 417/10 | (2006.01) |
| C07D 471/04 | (2006.01) |
| C07F 5/02 | (2006.01) |
| C07D 401/04 | (2006.01) |
| C07D 401/06 | (2006.01) |

(52) U.S. Cl.
CPC .......... *C07D 213/69* (2013.01); *A61K 31/4412* (2013.01); *A61K 31/4418* (2013.01); *A61K 31/4439* (2013.01); *A61K 31/444* (2013.01); *A61K 31/4545* (2013.01); *A61K 31/4709* (2013.01); *A61K 31/4725* (2013.01); *A61K 31/5377* (2013.01); *A61K 31/541* (2013.01); *A61K 31/69* (2013.01); *A61K 45/06* (2013.01); *C07D 213/73* (2013.01); *C07D 213/74* (2013.01); *C07D 401/10* (2013.01); *C07D 401/14* (2013.01); *C07D 413/10* (2013.01); *C07D 413/12* (2013.01); *C07D 417/10* (2013.01); *C07D 471/04* (2013.01); *C07F 5/025* (2013.01); *C07D 401/04* (2013.01); *C07D 401/06* (2013.01)

(58) Field of Classification Search
None
See application file for complete search history.

(56) References Cited

U.S. PATENT DOCUMENTS

| | | |
|---|---|---|
| 7,435,734 B2 | 10/2008 | Crescenzi et al. |
| 2004/0058945 A1 | 3/2004 | Chaudhari et al. |
| 2005/0025774 A1 | 2/2005 | Crescenzi et al. |
| 2007/0232663 A1 | 10/2007 | Pirrung et al. |
| 2007/0293464 A1 | 12/2007 | Martin et al. |
| 2008/0275004 A1 | 11/2008 | Crescenzi et al. |

OTHER PUBLICATIONS

CAPLUS 1962:45619.*
CAPLUS 1983:594781.*
CAPLUS 1994:163917.*
CAPLUS 1966:473325.*
Agrawal, A. et al., ChemMedChem 2010, vol. 5, pp. 195-199.*
(Continued)

*Primary Examiner* — Heidi Reese
(74) *Attorney, Agent, or Firm* — Fox Rothschild LLP; Gerard P. Norton; Jin Zhu

(57) ABSTRACT

The present invention relates to 4-pyridinone compounds which are inhibitors of catechol O-methyltransferase (COMT), and are useful in the treatment and prevention of neurological and psychiatric disorders and diseases in which COMT enzyme is involved. The present invention also relates to pharmaceutical compositions comprising these compounds and the use of these compounds and compositions in the prevention or treatment of such diseases in which COMT is involved.

86 Claims, No Drawings

(56) References Cited

OTHER PUBLICATIONS

Tasman et al., Psychiatry, West Sussex, John Wiley & Sons, Ltd. Second Edition, vol. 1 (2003) pp. 254-272.
Sadock and Sadock et al., Kaplan & Sadock's Comprehensive Textbook of Psychiatry, 7th Edition, vol. 1 (2005) Philadelphia PA; Lippincott Williams & Wilkins pp. 236-272 and 1330-1395.
Okubo et al., Letters to Nature, vol. 385 (1997), pp. 634-636.
Carter, at al., The American Journal of Psychiatry (1998), vol. 115, pp. 1281-1284.
Williams, et al., Human Molecular Genetics (2003), vol. 12, Review Issue 2, pp. R125-R133.
Takahashi at al., The Journal of Bone & Joint Surgery, vol. 85-A, No. 1, pp. 122-125 (2003).
Tunbridge at al., Biol. Psychiatry, vol. 60 pp. 141-151 (2006).
Chen at al., Biological Psychiatry, vol. 49, pp. 13-16 (2004).
Smiley at al., Proc. Natl. Acad. Sci. USA, vol. 91, pp. 5720-5724 (1994).
Sesack et al., Cerebral Cortex, pp. 614-622 (1998).
Lewis at al., Am. J. Psychiatry, vol. 158, pp. 1411-1422 (2001).
Moron et al., The Journal of Neuroscience, vol. 22(2), pp. 389-395 (2002).
Mazei et al., Brain Research, vol. 936, pp. 58-67.
Boulton et al., Advances in Pharmacology vol. 42, pp. 273-292 (1998).
Barch at al., Arch. Gen. Psychiatry vol. 58, pp. 280-288 (2001).
Callicott et al., Cerebral Cortex, vol. 10, pp. 1078-1092 (2000).
Abi-Dargham et al., The Journal of Neuroscience, vol. 22(9) pp. 3708-3719 (2002).
Weinberger D., Arch. Gen. Psychiatry vol. 43, pp. 114-124 (1988).
Weinberger J., J. Neural Transm. vol. 69, pp. 265-275 (1987).
Weinberger, D., Mesocortical Dopaminergic Function, pp. 330-338 (1988).
Daniel et al., The Journal of Neuroscience, vol. 11(7) pp. 1907-1917 (1991).
Lieberman et al., The New England Journal of Medicine, vol. 353, No. 12, pp. 1209-1223 (2005).
Lachman et al., Pharmacogenetics, vol. 6, pp. 243-250 (1996).
Green, M. F., Am. J. Psychiatry, vol. 153 (1996) pp. 321-330.
Akil et al., Am. J. Psychiatry, vol. 156 (1999) pp. 1580-1589.
Addington et al., British Journal of Psychiatry, vol. 163 (1993) p. 6.
Looker et al., "Convenient preparative methods for n-aryl-gamma-pyridones from gamma-pyrones," Journal of Heterocyclic Chemistry (1986); 23(5):5-8.
Herak et al., "Extraction and separation of thorium (IV) and protactinium(V) by 2-carbethoxy-5-hydroxy-1-(4-tolyl)-4-pyridone," Journal of Inorganic and Nuclear Chemistry (Aug. 1972); 34(8):2627-2632.
Imafuku et al., "Substituent effects on the dissociation constants of 1-aryl-5-hydroxy-2-hydroxymethy1-4-pyridones," Bulletin of the Chemical Society of Japan (1983); 564(5):1879.
Hahn et al., "Studies on 4-pyrones and 4-pyridones. I. The Preparation of 1-aryl-3-hydroxy-4-pyridones and Related Compounds," Croatica CHemica ACTA (1961); 33:137-144.

\* cited by examiner

INHIBITORS OF CATECHOL O-METHYL TRANSFERASE AND THEIR USE IN THE TREATMENT OF PSYCHOTIC DISORDERS

CROSS REFERENCE TO RELATED APPLICATIONS

This application is the National Stage of International Application No. PCT/US2011/026399 filed on Feb. 28, 2001, which claims the benefit under 35 U.S.C. 119(e) of U.S. Provisional Application No. 61/310,410, filed Mar. 4, 2010.

BACKGROUND OF THE INVENTION

The symptoms of schizophrenia are generally divided into three categories; positive, negative and cognitive. Positive symptoms include hallucinations, delusions and disorganized behavior while negative symptoms are characterized by a lack of pleasure and/or interest in life. Cognitive deficit includes difficulties in the organization of thoughts and prioritization of tasks. Patients with bipolar disorder generally display circular mood changes ranging from severe depression to severe mania with or without psychotic features. Schizophrenia and bipolar disorder are among the most severe forms of psychiatric disorders that elicit overlapping cognitive deficits (Tasman et al., Psychiatry, West Sussex, John Wiley & Sons, Ltd., Second Edition, Volume 1, 2003, pp 254-272; and Sadock and Sadock, Kaplan and Sadock's Comprehensive Textbook of Psychiatry, 7 ed., Vol. 1, 2005, Philadelphia, Pa.; Lippincott Williams & Wilkins, pp 236-272 and 1330-1395) and they tend to be chronic/progressive. In contrast to positive symptoms, the negative and cognitive symptoms of schizophrenia are thought to have a greater impact on long-term disability, treatment outcome and functional recovery (Addington and Addington, 1993; Green, 1996), Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved in the pathogenesis of schizophrenia leading to negative and cognitive symptoms, much attention has focused on reduced dopamine neurotransmission in the prefrontal cortex (Weinberger, 1987; Weinberger et al., 1988; Akil et al., 1999). Evidence for reduced dopamine neurotransmission in the prefrontal cortex is supported by reduced regional cerebral blood flow or hypoactivation of the dorsolateral prefrontal cortex in schizophrenia patients (Weinberger et al., 1988; Daniel et al., 1991; Okubo et al., 1997; Abi-Dargham et al., 2002). Schizophrenia related prefrontal deficits, independent from treatment or psychotic state, have been correlated with poor performance in tasks of executive function (e.g. n-back or Wisconsin Card Sorting Test) that evaluate prefrontal engagement (Weinberger et al., 1986, 1988; Carter et al., 1998; Callicott et al., 2000; Barch et al., 2001). In addition to deficits in executive function, reduced dopamine neurotransmission in the prefrontal cortex is involved in several brain activities including; attention, hedonic activities, natural rewards, and biologic activities such as cell signaling. Therefore, a compound which selectively enhances dopamine neurotransmission within the prefrontal cortex may have therapeutic potential for the treatment of cognitive and negative symptoms.

Dopamine levels in the brain are determined by biosynthesis and release, as well as its rate of diffusion, reuptake, and degradation. Catechol-O-methyltransferase (COMT), is an important enzyme involved in the breakdown of dopamine in the cortex. COMT converts dopamine to 3-methoxytyramine and the dopamine metabolite dihydroxyphenylacetic acid (DOPAC) to homovanillic acid (HVA) (Boulton and Eisenhofer, 1998). In fact, COMT acts on a variety of biogenic catecholamines as well as catecholestrogens, dietary phytochemicals and ascorbic acid. In subcortical structures (e.g. striatum), dopaminergic signalling is primarily regulated by removal of dopamine from the synaptic cleft via rapid uptake by the dopamine transporter (DAT) and/or norepinephrine transporter (NET). Regulation of dopamine transmission in the prefrontal cortex is markedly different. DAT is less densely expressed in synapses within the prefrontal cortex where dopamine is eliminated by uptake through the NET, diffusion, or metabolism by COMT and monoamine oxidase (Mazei et al., 2002; Moron et al., 2002; Lewis et al., 2001; Sesack et al., 1998; Smiley et al., 1994). COMT inhibitors would therefore be predicted to selectively increase cortical dopaminergic signaling and thereby improve cognitive function.

The COMT gene is located in the chromosome 22q11.21 region which has been linked to schizophrenia, bipolar disorder, ADHD and substance dependency (Williams, et 2003 and Takahashi et al., 2003). There are two major isoforms of COMT, membrane-bound COMT (MB-COMT) is the predominant form involved in the degradation of synaptic frontal lobe dopamine in human brain (Lachman et al., Pharmacogenetics (1996). 6(3):243-250). The other form is soluble COMT (S-COMT) which is transcribed from a different promoter than MB-COMT and is otherwise identical to human MB-COMT minus 50 amino acids at the N-terminus of the protein. In humans, COMT activity is modulated by a single nucleotide polymorphism at Val158Met (MB-COMT). Due to differences in enzyme thermostability, homozygous Met carriers have lower COMT activity, heterozygotes exhibit intermediate activity and homozygous Val carriers have greater enzyme activity (Chen et al., 2004). Despite the differences observed in activity based on genotype, only a modest relationship between Val158Met genotype and cognitive performance has been demonstrated by meta-analysis in normal individuals, while no effect was observed in schizophrenia. Based on an inverted-U relationship thought to exist between dopamine receptor activation and prefrontal cortical functioning, these findings might be reconciled with the fact that disease state, along with multiple environmental and genetic factors, contribute to prefrontal efficiency and dopamine levels (reviewed in Tunbridge et al., Biol Psych, 2006).

Although clozapine, Zyprexa, Risperdal and other antipsychotic drugs have been useful for the treatment of positive and arguably the negative symptoms of schizophrenia and bipolar disorder, they have not been free from side effects such as agranulocytosis, sedation, weight gain, hyper-lipidemia and hyperglycemia, all of which limit their applications (Tasman et al., 2003; Sadock and Sadock 2005). Thus, there remains a need for medications that effectively treat negative symptoms and cognitive deficit, have no major side effects, and are effective in the treatment of schizophrenia, bipolar disorder, depression, substance dependency, and ADD/ADHD, etc. Such medications might also be used to reduce such symptoms when they occur as part of another psychiatric syndrome or when they are incidental to a neurological disorder.

SUMMARY OF THE INVENTION

The present invention relates to 4-pyridinone compounds which are inhibitors of catechol O-methyltransferase (COMT) enzyme, and are useful in the treatment and prevention of neurological and psychiatric disorders and diseases in which COMT is involved.

The present invention also relates to pharmaceutical compositions comprising these compounds and the use of these compounds and compositions in the prevention or treatment of such diseases in which COMT enzyme is involved.

The present invention further relates to a method of treating symptoms associated with a psychiatric disorder, comprising administration of a pharmacologically effective dose of a composition comprising a 4-pyridinone COMT inhibitor or a pharmaceutically acceptable salt thereof to a patient.

Still, the present invention relates to improving negative symptoms and cognitive deficit associated with schizophrenia, augmentation of the effects of anti-psychotics in treatment of positive symptoms of schizophrenia, in treatment of major depression, the depressive phase of bipolar disorder, DA deficiency-related diseases such as ADD/ADHD, and substance dependency (combat cravings associated with and/or addictions to abuse of alcohol, opiates, cocaine, marijuana, amphetamines, tobacco). The present invention also relates to a method for the treatment of tobacco addiction and the weight gain/food cravings associated with quitting smoking or the use of antipsychotics.

The present invention also relates to a method of enhancing cognition in head injuries and dementias.

These and other aspects of the invention will be realized upon closer inspection of the specification as a whole.

DETAILED DESCRIPTION OF THE INVENTION

The present invention relates to novel COMT inhibitors of formula I

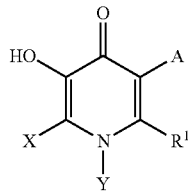

I or pharmaceutically acceptable salts and individual enantiomers and diastereomers thereof wherein:
A represents hydrogen, B(OH)$_2$, NO$_2$, halo, OH, C(O)NH (CH$_2$)$_n$C(O)N(R$^3$)$_2$, C$_{3-10}$ cycloalkyl, or C$_{1-6}$ alkyl;
X represents hydrogen, halo, C$_{1-6}$ alkyl, (CH$_2$)$_n$C$_{5-10}$ heterocyclyl, said alkyl, heterocyclyl optionally substituted with 1 to 3 groups of R$^a$;
Y represents phenyl, benzimidazolyl, benzthiazolyl, benzoxazolyl, benzpiperidinyl, quinolyl, indolyl, indazolyl, or pyridyl, any of which is optionally substituted with 1 to 3 groups of R$^a$;
R$^1$ represents hydrogen, NR$^2$R$^3$, Si(CH$_3$)$_3$, (CH$_2$)$_n$C$_{6-10}$ aryl, (CH$_2$)$_n$C$_{5-10}$ heterocyclyl, C$_{2-10}$ alkenyl, C$_{1-10}$ alkyl, said alkyl and alkenyl optionally substituted with 1 to 3 groups of halo, OH, C$_{1-6}$ alkyl, O—C$_{1-6}$ alkyl, NR$^2$R$^3$, SOR$^2$, NHSO$_2$R$^2$, CF$_3$, C$_{6-10}$ aryl, C$_{5-10}$ heterocyclyl, OC$_{6-10}$ aryl, C$_{1-6}$ alkenyl, C$_{3-6}$ cycloalkyl, C$_{1-6}$ alkynyl, —C≡C— C$_{6-10}$ aryl, C(O)NR$^2$R$^3$, NHSO$_2$C$_{6-10}$aryl, COOR$^2$, C(O) R$^2$, cyano, said aryl and heterocyclyl optionally substituted with 1 to 3 groups of R$^a$;
R$^2$ and R$^3$ independently represent H, OH, C$_{1-6}$ alkyl, N(CH$_3$)$_2$, (CH$_2$)$_n$C$_{5-10}$ heterocyclyl, (CH$_2$)$_n$C$_{6-10}$ aryl, said aryl and heterocyclyl optionally substituted with 1 to 3 groups of R$^a$;

R$^2$ and R$^3$ together with the nitrogen atom to which they are attached form a 5-10 membered ring that is optionally substituted with 1 to 3 groups of halo, OH, C2-6 alkenyl, (CH$_2$)$_n$C$_{5-10}$ heterocyclyl or (CH$_2$)$_n$C$_{6-10}$ aryl;
R$^a$ represents C$_{1-6}$ alkyl, halogen, hydroxyl, (CH$_2$)$_n$CF$_3$, OCHF$_2$, OCF$_3$, C$_{3-6}$ cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, (CH$_2$)$_n$C(O)OR$^2$, SO$_2$R$^2$, OR$^2$, (CH$_2$)$_n$C$_{5-10}$ heterocyclyl, NH(CH$_2$)$_n$C$_{5-10}$ heterocyclyl, (CH$_2$)$_n$C$_{6-10}$ aryl, O(CH$_2$)$_n$C$_{6-10}$ aryl, or O(CH$_2$)$_n$C$_{5-10}$ heterocyclyl, said cycloalkyl, heterocyclyl and aryl optionally substituted with 1 to 3 groups of R$^b$:
R$^b$ represents C$_{1-6}$ alkyl, halogen, CHF$_2$, —O—, N(R$^2$)$_2$, CH$_2$OH, S(O)$_2$NR$^2$R$^3$, (CH$_2$)$_n$C$_{6-10}$ aryl, (CH$_2$)$_n$C$_{5-10}$ heterocyclyl, C(O)(CH$_2$)$_n$C$_{5-10}$ heterocyclyl, NH(CH$_2$)$_n$C$_{5-10}$ heterocyclyl, C(O)NHC$_{3-6}$cycloalkyl, OR$^2$, C$_{3-6}$cycloalkyl, (CH$_2$)$_n$CF$_3$, or CN; and
n represents 0 to 5.

An embodiment of the present invention is realized when Y is phenyl, said phenyl optionally substituted with 1 to 3 groups of R$^a$ and all other variables are as previously described. A subembodiment of this invention is realized when at least one of R$^a$ is selected from the group consisting of C$_{6-10}$ aryl and C$_{5-10}$ heterocyclyl, said aryl and heterocyclyl optionally substituted with 1 to 3 groups of R$^b$. Another subembodiment of this invention is realized when the aryl and heterocyclyl of R$^a$ is selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of R$^b$. A further subembodiment of this invention is realized when R$^a$ is selected from the group consisting of indolyl, pyridyl, phenyl, and indazolyl any of which is optionally substituted with 1 to 3 groups of R$^b$. Still a further subembodiment of this invention is realized when R$^b$ is selected from the group consisting of C$_{1-6}$ alkyl, halogen, CHF$_2$, N(R$^2$)$_2$, CH$_2$OH, OR$^2$, C$_{3-6}$cycloalkyl, (CH$_2$)$_n$CF$_3$, or CN.

Another embodiment of this invention is realized when Y is pyridyl, said pyridyl optionally substituted with 1 to 3 groups of R$^a$ and all other variables are as previously described. A subembodiment of this invention is realized when at least one of R$^a$ is selected from the group consisting of C$_{6-10}$ aryl and C$_{5-10}$ heterocyclyl, said aryl and heterocyclyl optionally substituted with 1 to 3 groups of R$^b$. Another subembodiment of this invention is realized when the aryl and heterocyclyl of R$^a$ is selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1, 3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. A further subembodiment of this invention is realized when $R^a$ is selected from the group consisting of indolyl, pyridyl, phenyl, and indazolyl any of which is optionally substituted with 1 to 3 groups of $R^b$. Still a further subembodiment of this invention is realized when $R^b$ is selected from the group consisting of $C_{1-6}$ alkyl, halogen, $CHF_2$, $N(R^2)_2$, $CH_2OH$, $OR^2$, $C_{3-6}$cycloalkyl, $(CH_2)_nCF_3$, or CN.

Still another embodiment of this invention is realized when Y is indolyl, said indolyl optionally substituted with 1 to 3 groups of $R^a$ and all other variables are as previously described. A subembodiment of this invention is realized when at least one of $R^a$ is selected from the group consisting of $C_{6-10}$ aryl and $C_{5-10}$ heterocyclyl, said aryl and heterocyclyl optionally substituted with 1 to 3 groups of Rb. Another subembodiment of this invention is realized when the aryl and heterocyclyl of $R^a$ is selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. A further subembodiment of this invention is realized when $R^a$ is selected from the group consisting of indolyl, pyridyl, phenyl, and indazolyl any of which is optionally substituted with 1 to 3 groups of $R^b$. Still a further subembodiment of this invention is realized when $R^b$ is selected from the group consisting of $C_{1-6}$ alkyl, halogen, $CHF_2$, $N(R^2)_2$, $CH_2OH$, $OR^2$, $C_{3-6}$cycloalkyl, $(CH_2)_nCF_3$, or CN.

Another embodiment of this invention is realized when Y is benzimidazolyl, said benzimidazolyl optionally substituted with 1 to 3 groups of $R^a$ and all other variables are as previously described. A subembodiment of this invention is realized when at least one of $R^a$ is selected from the group consisting of $C_{6-10}$ aryl and $C_{5-10}$ heterocyclyl, said aryl and heterocyclyl optionally substituted with 1 to 3 groups of Rb. Another subembodiment of this invention is realized when the aryl and heterocyclyl of $R^a$ is selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. A further subembodiment of this invention is realized when $R^a$ is selected from the group consisting of indolyl, pyridyl, phenyl, and indazolyl any of which is optionally substituted with 1 to 3 groups of $R^b$. Still a further subembodiment of this invention is realized when $R^b$ is selected from the group consisting of $C_{1-6}$ alkyl, halogen, $CHF_2$, $N(R^2)_2$, $CH_2OH$, $OR^2$, $C_{3-6}$cycloalkyl, $(CH_2)_nCF_3$, or CN.

Yet another embodiment of this invention is realized when Y is indazolyl, said indazolyl optionally substituted with 1 to 3 groups of $R^a$ and all other variables are as previously described. A subembodiment of this invention is realized when at least one of $R^a$ is selected from the group consisting of $C_{6-10}$ aryl and $C_{5-10}$ heterocyclyl, said aryl and heterocyclyl optionally substituted with 1 to 3 groups of Rb. Another subembodiment of this invention is realized when the aryl and heterocyclyl of $R^a$ is selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. A further subembodiment of this invention is realized when $R^a$ is selected from the group consisting of indolyl, pyridyl, phenyl, and indazolyl any of which is optionally substituted with 1 to 3 groups of $R^b$. Still a further subembodiment of this invention is realized when $R^b$ is selected from the group consisting of $C_{1-6}$ alkyl, halogen, $CHF_2$, $N(R^2)_2$, $CH_2OH$, $OR^2$, $C_{3-6}$cycloalkyl, $(CH_2)_nCF_3$, and CN.

Another embodiment of this invention is realized when $R^1$ is hydrogen, and all other variables are as originally described.

Still another embodiment of this invention is realized when $R^1$ is $NR^2R^3$, and all other variables are as originally described.

Yet another embodiment of this invention is realized when $R^1C_{1-10}$ is alkyl, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$.

Another embodiment of this invention is realized when $R^1$ is hydrogen, $CH(OH)CH_3$, $NH_2$, $NHCH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of this invention is realized when $R^1$ is hydrogen or $CH(OH)CH_3$.

Another embodiment of this invention is realized when A is hydrogen and all other variables are as originally described.

Another embodiment of this invention is realized when X is hydrogen and all other variables are as originally described.

Still another embodiment of this invention is realized when X is halo and all other variables are as originally described.

Another embodiment of this invention is realized by structural formula II:

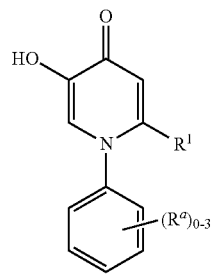

or pharmaceutically acceptable salts and individual enantiomers and diastereomers thereof wherein $R^1$ and $R^a$ are as originally described. A subembodiment of formula II is realized when $R^1$ is hydrogen, and all other variables are as originally described. Another subembodiment of formula II is realized when $R^1$ is $NR^2R^3$, and all other variables are as originally described. Still another subembodiment of formula II is realized when $R^1$ $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula II is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula II is realized when $R^1$ is hydrogen or $CH(OH)CH_3$. Yet another embodiment of the invention of formula II is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula II is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. Another subembodiment of the invention of formula II is reaized when at least one of $R^a$ is aryl or heterocyclyl optionally substituted with 1 to 3 groups of $R^b$.

Another embodiment of this invention is realized by structural formula III:

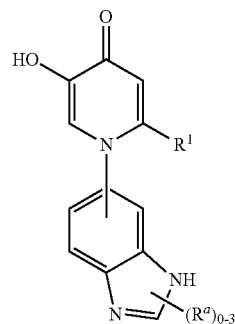

or pharmaceutically acceptable salts and individual enantiomers and diastereomers thereof wherein $R^1$ and $R^a$ are as originally described. A subembodiment of formula III is realized when $R^1$ is hydrogen, and all other variables are as originally described. Another subembodiment of formula III is realized when $R^1$ is $NR^2R^3$, and all other variables are as originally described. Still another subembodiment of formula III is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula III is realized when $R^1$ is hydrogen, $NH_2$, $NHCH_3$, and a substituted alkyl selected from $CH(OH)CH_3$, $(CHR^2)nC_{6-10}$ aryl, and $(CHR^2)nC_{6-10}$heterocyclyl, wherein said aryl and heteroaryl are optionally substituted with 1 to 3 groups of $R^a$. Another subembodiment of formula III is realized when $R^1$ is hydrogen or $CH(OH)CH_3$. Yet another embodiment of the invention of formula III is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula III is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

A sub-embodiment of formula III this invention is realized by structural formula IIIa and IIIb:

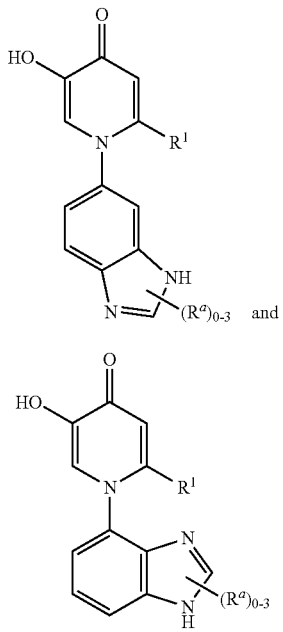

IIIa and

IIIb or pharmaceutically acceptable salts and individual enantiomers and diastereomers thereof wherein $R^1$ and $R^a$ are as originally described. Another subembodiment of formula IIIa and IIIb is realized when $R^1$ is hydrogen, and all other variables are as originally described. Still another subembodiment of formula IIIa and IIIb is realized when $R^1$ is $NR^2R^3$, and all other variables are as originally described. Yet another subembodiment of formula IIIa and IIIb is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—C6-10 aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula IIIa and IIIb is realized when $R^1$ is hydrogen, $NH_2$, $NHCH_3$, and a substituted alkyl selected from $CH(OH)CH_3$, $(CHR^2)_nC_{6-10}$aryl, and $(CHR^2)_nC_{6-10}$ heterocyclyl, wherein said aryl and heteroaryl are optionally substituted with 1 to 3 groups of $R^a$. Another subembodiment of formula IIIa and IIIb is realized when $R^1$ is hydrogen or $CH(OH)CH_3$. Yet another embodiment of the invention of formula IIIa and IIIb is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula IIIa and IIIb is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Another embodiment of this invention is realized by structural formula IV:

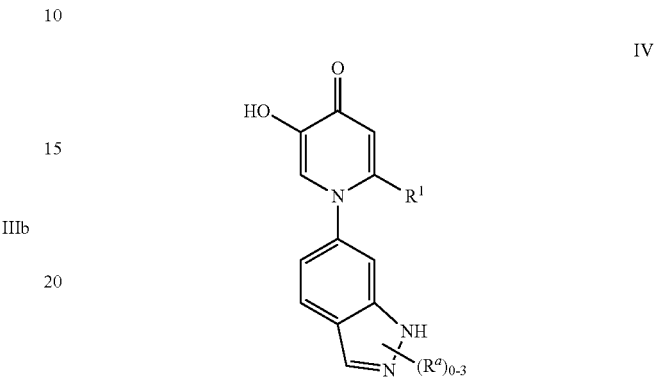

IV or pharmaceutically acceptable salts and individual enantiomers and diastereomers thereof wherein $R^1$ and $R^a$ are as originally described. A subembodiment of formula IV is realized when $R^1$ is hydrogen, and all other variables are as originally described. Another subembodiment of formula IV is realized when $R^1$ is $NR^2R^3$, and all other variables are as originally described. Still another subembodiment of formula IV is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—C6-10 aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula IV is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula IV is realized when $R^1$ is hydrogen or $CH(OH)CH_3$. Yet another embodiment of the invention of formula IV is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula IV is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Another embodiment of this invention is realized by structural formula V:

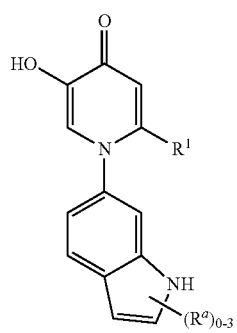

V or pharmaceutically acceptable salts and individual enantiomers and diastereomers thereof wherein $R^1$ and $R^a$ are as originally described. A subembodiment of formula V is realized when $R^1$ is hydrogen, and all other variables are as originally described. Another subembodiment of formula V is realized when $R^1$ is $NR^2R^3$, and all other variables are as originally described. Still another subembodiment of formula V is realized when $R^1$ is $C_{1-10}$ alkyl and all other variables are as originally described, said alkyl a optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula V is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula V is realized when $R^1$ is hydrogen or $CH(OH)CH_3$. Yet another embodiment of the invention of formula V is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula V is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Another embodiment of this invention is realized by structural formula VI:

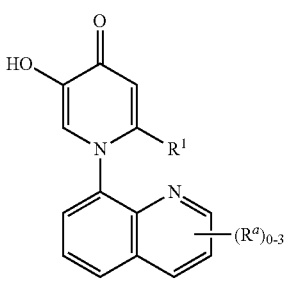

VI or pharmaceutically acceptable salts and individual enantiomers and diastereomers thereof wherein $R^1$ and $R^a$ are as originally described. A subembodiment of formula VI is realized when $R^1$ is hydrogen, and all other variables are as originally described. Another subembodiment of formula VI is realized when $R^1$ is $NR^2R^3$, and all other variables are as originally described. Still another subembodiment of formula VI is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula VI is realized when $R^1$ is hydrogen, $NH_2$, $NHCH_3$, and a substituted alkyl selected from $CH(OH)CH_3$, $(CHR^2)_nC_{6-10}$aryl, and $(CHR^2)_nC_{6-10}$heterocyclyl, wherein said aryl and heteroaryl are optionally substituted with 1 to 3 groups of $R^a$. Another subembodiment of formula VI is realized when $R^1$ is hydrogen or $CH(OH)CH_3$. Yet another embodiment of the invention of formula VI is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula VI is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. Another subembodiment of the invention of formula II is reaized when at least one of $R^a$ is aryl or heterocyclyl optionally substituted with 1 to 3 groups of $R^b$.

Another embodiment of this invention is realized by structural formula VII:

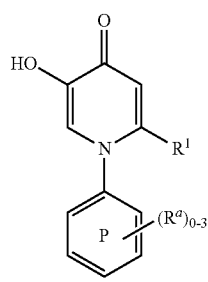

VII or pharmaceutically acceptable salts and individual enantiomers and diastereomers thereof wherein P represents pyridyl, and $R^1$ and $R^a$ are as originally described. A subembodiment of formula VII is realized when $R^1$ is hydrogen, and all other variables are as originally described. Another subembodiment of formula VII is realized when $R^1$ is $NR^2R^3$, and all other variables are as originally described. Still another subembodiment of formula VII is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula VII is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula VII is realized when $R^1$ is hydrogen or $CH(OH)CH_3$. Yet another embodiment of the invention of formula VII is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula VII is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$. Another subembodiment of the invention of formula VII is reaized when at least one of $R^a$ is aryl or heterocyclyl optionally substituted with 1 to 3 groups of $R^b$.

Another embodiment of this invention is realized by structural formula VIII:

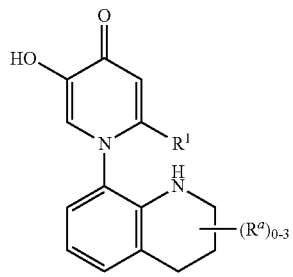

VIII or pharmaceutically acceptable salts and individual enantiomers and diastereomers thereof wherein $R^a$ can be attached to a carbon or nitrogen atom on the ring, and $R^1$ and $R^a$ are as originally described. A subembodiment of formula VIII is realized when $R^1$ is hydrogen, and all other variables are as originally described. Another subembodiment of formula VIII is realized when $R^1$ is $NR^2R^3$, and all other variables are as originally described. Still another subembodiment of formula VIII is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula VIII is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula VIII is realized when $R^1$ is hydrogen or $CH(OH)CH_3$. Yet another embodiment of the invention of formula VIII is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula VIII is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Another embodiment of this invention is realized by structural formula IX:

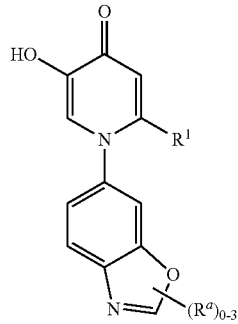

IX or pharmaceutically acceptable salts and individual enantiomers and diastereomers thereof wherein $R^a$ can be attached to a carbon or nitrogen atom on the ring, and $R^1$ and $R^a$ are as originally described. A subembodiment of formula IX is realized when $R^1$ is hydrogen, and all other variables are as originally described. Another subembodiment of formula IX is realized when $R^1$ is $NR^2R^3$, and all other variables are as originally described. Still another subembodiment of formula IX is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—C6-10 aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another subembodiment of formula IX is realized when $R^1$ is hydrogen, $NH_2$, $NHCH_3$, and a substituted alkyl selected from $CH(OH)CH_3$, $(CHR^2)nC_{6-10}$aryl, and $(CHR^2)nC_{6-10}$heterocyclyl, wherein said aryl and heteroaryl are optionally substituted with 1 to 3 groups of $R^a$. Another subembodiment of formula IX is realized when $R^1$ is hydrogen or $CH(OH)CH_3$. Yet another embodiment of the invention of formula IX is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula IX is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Another embodiment of this invention is realized by structural formula X:

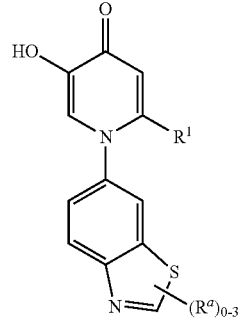

X or pharmaceutically acceptable salts and individual enantiomers and diastereomers thereof wherein $R^a$ can be attached to a carbon or nitrogen atom on the ring, and $R^1$ and $R^a$ are as originally described. A subembodiment of formula X is realized when $R^1$ is hydrogen, and all other variables are as originally described. Another subembodiment of formula X is realized when $R^1$ is $NR^2R^3$, and all other variables are as originally described. Still another subembodiment of formula X is realized when $R^1$ is $C_{1-10}$ alkyl and all other variables are as originally described, said alkyl optionally substituted with 1 to 3 groups of halo, OH, O—$C_{1-6}$ alkyl, $NR^2R^3$, $CF_3$, $C_{6-10}$ aryl, $C_{5-10}$ heterocyclyl, $OC_{6-10}$ aryl, $C_{1-6}$ alkenyl, $C_{3-6}$ cycloalkyl, $C_{1-6}$ alkynyl, —C≡C—$C_{6-10}$ aryl, $C(O)NR^2R^3$, $NHSO_2C_{6-10}$aryl, $COOR^2$, $C(O)R^2$, cyano, said aryl and heterocyclyl optionally substituted with 1 to 3 groups of $R^a$. Still another embodiment of formula X is realized when $R^1$ is hydrogen, $NH_2$, $NHCH_3$, and a substituted alkyl selected from $CH(OH)CH_3$, $(CHR^2)_nC_{6-10}$aryl, and $(CHR^2)_nC_{6-10}$heterocyclyl, wherein said aryl and heteroaryl are optionally substituted with 1 to 3 groups of $R^a$. Another subembodiment of formula X is realized when $R^1$ is hydrogen or $CH(OH)CH_3$. Yet another embodiment of the invention of formula X is realized when $R^a$ is $C_{1-6}$ alkyl, halogen, $(CH_2)_nCF_3$, $OR^2$, $(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, heterocyclyl and aryl optionally substituted with 1 to 3 groups of $R^b$. Still another embodiment of $R^a$ of formula X is realized when the aryl and heterocyclyl are selected from the group consisting of naphthyridine, indolyl, pyrazolyl, benzodioxaolyl, pyridyl, furopyridinyl, isoindolyl, pyridooxazinyl, imidazolyl, pyrrolyl, pyrrolopyridinyl, thiophenyl, isoxazolyl, pyrimidinyl, quinoxalinyl, quinazolinyl, quinolinyl, isoquinolinyl, phenyl, indazolyl, [1,2,4]triazolo[1,5-a]pyridine; 1,2,3,4-tetrahydroisoquinoline; 1,3-benzodioxole; 1-benzothiophene; 1H-indazole; 1H-pyrrolo[2,3-b]pyridine; 1H-pyrrolo[2,3-c]pyridine; 1H-pyrrolo[3,2-b]pyridine; 1H-pyrrolo[3,2-c]pyridine; 2,1,3-benzoxadiazole; 3,4-dihydro-2H-pyrido[3,2-b][1,4]oxazine; 3H-imidazo[4,5-b]pyridine; 4,5,6,7-tetrahydropyrazolo[1,5-a]pyridine; furo[2,3-c]pyridine; furo[3,2-b]pyridine; imidazo[1,2-a]pyridine; isoxazole; quinazoline; and thieno[3,2-c]pyridin-4(5H)-one, any of which is optionally substituted with 1 to 3 groups of $R^b$.

Examples of compounds of this invention are found in Table 1:

TABLE 1

| Structure | IUPAC Name | Exact Mass [M + H]+ |
|---|---|---|
| 1 | 5-hydroxy-2-(hydroxymethyl)-1-(4-morpholin-4-ylphenyl)pyridin-4(1H)-one | Calcd 303.1, Found 303.1 |
| 2 | 1-(3,5-dimethylphenyl)-5-hydroxy-2-(hydroxymethyl)pyridin-4(1H)-one | Calcd 246.1, Found 246.1 |
| 3 | 5-hydroxy-2-(hydroxymethyl)-1-(3-methoxyphenyl)pyridin-4(1H)-one | Calcd 248.0, Found 248.0 |
| 4 | 1-[3-(dimethylamino)phenyl]-5-hydroxy-2-(hydroxymethyl)pyridin-4(1H)-one | Calcd 261.1, Found 261.1 |

TABLE 1-continued

| | Structure | IUPAC Name | Exact Mass [M + H]+ |
|---|---|---|---|
| 5 | 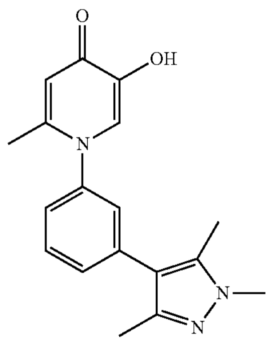 | 5-hydroxy-2-methyl-1-[3-(1,3,5-trimethyl-1H-pyrazol-4-yl)phenyl]pyridin-4(1H)-one | Calcd 310.1, Found 310.1 |
| 6 | 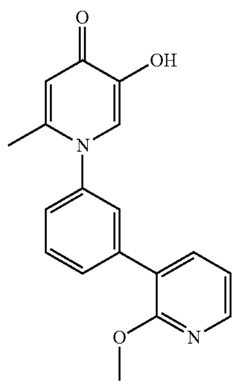 [SMILES: COc1ncccc1-c1cccc(-n2cc(O)c(=O)cc2C)c1] | 5-hydroxy-1-[3-(2-methoxypyridin-3-yl)phenyl]-2-methylpyridin-4(1H)-one | Calcd 309.1, Found 309.1 |
| 7 | 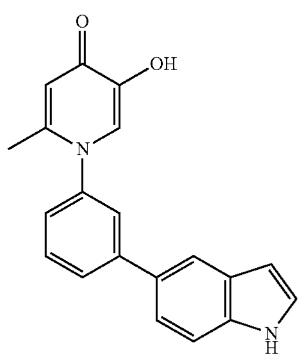 [SMILES: Cc1cc(=O)c(O)cn1-c1cccc(-c2ccc3[nH]ccc3c2)c1] | 5-hydroxy-1-[3-(1H-indol-5-yl)phenyl]-2-methylpyridin-4(1H)-one | Calcd 317.1, Found 317.1 |
| 8 | 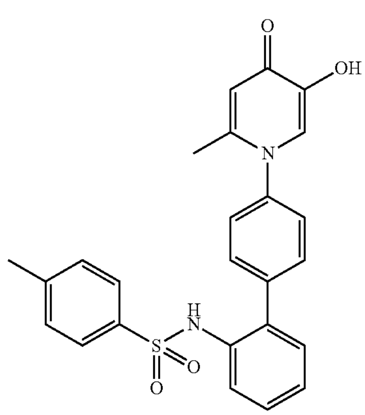 [SMILES: Cc1ccc(S(=O)(=O)Nc2ccccc2-c2ccc(-n3cc(O)c(=O)cc3C)cc2)cc1] | N-[4'-(5-hydroxy-2-methyl-4-oxopyridin-1(4H)-yl)biphenyl-2-yl]-4-methylbenzenesulfonamide | Calcd 447.1, Found 447.1 |

TABLE 1-continued
| Structure | IUPAC Name | Exact Mass [M + H]+ |
|---|---|---|
| 9 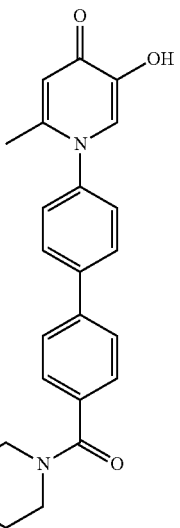 | 5-hydroxy-1-{4'-[(4-hydroxypiperidin-1-yl)carbonyl]biphenyl-4-yl}-2-methylpyridin-4(1H)-one | Calcd 405.1, Found 405.1 |
| 10 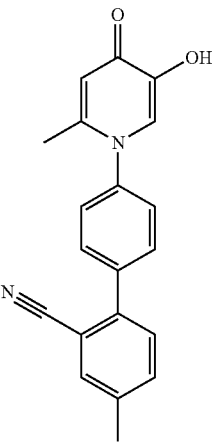 [SMILES: Cc1ccc(-c2ccc(-n3cc(O)c(=O)cc3C)cc2)c(C#N)c1] | 4'-(5-hydroxy-2-methyl-4-oxopyridin-1(4H)-yl)-4-methylbiphenyl-2-carbonitrile | Calcd 317.1, Found 317.1 |
| 11 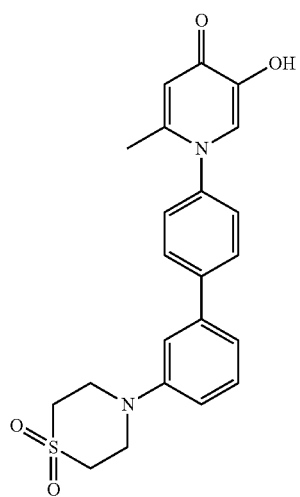 [SMILES: Cc1cc(=O)c(O)cn1-c1ccc(-c2cccc(N3CCS(=O)(=O)CC3)c2)cc1] | 1-[3'-(1,1-dioxidothiomorpholin-4-yl)biphenyl-4-yl]-5-hydroxy-2-methylpyridin-4(1H)-one | Calcd 411.1, Found 411.1 |

TABLE 1-continued

| Structure | IUPAC Name | Exact Mass [M + H]+ |
|---|---|---|
| 12 | 5-hydroxy-1-[3'-(3-hydroxypropyl)biphenyl-4-yl]-2-methylpyridin-4(1H)-one | Calcd 336.1, Found 336.1 |
| 13 | 1-[4-(4-fluorobenzyl)phenyl]-5-hydroxy-2-methylpyridin-4(1H)-one | Calcd 310.1, Found 310.1 |
| 14 | 1-[2'-(difluoromethoxy)biphenyl-4-yl]-5-hydroxy-2-methylpyridin-4(1H)-one | Calcd 344.1, Found 344.1 |
| 15 | 5-hydroxy-2-methyl-1-(3-[1,2,4]triazolo[1,5-a]pyridin-6-ylphenyl)pyridin-4(1H)-one | Calcd 319.1, Found 319.1 |

TABLE 1-continued

| Structure | IUPAC Name | Exact Mass [M + H]+ |
|---|---|---|
| 16 | 4-[3-(5-hydroxy-2-methyl-4-oxopyridin-1(4H)-yl)phenyl]-2,3-dihydro-1H-isoindol-1-one | Calcd 333.1, Found 333.1 |
| 17 | 5-hydroxy-1-{3-[2-(hydroxymethyl)pyridin-4-yl]phenyl}-2-methylpyridin-4(1H)-one | Calcd 309.1, Found 309.1 |
| 18 | 3-hydroxy-1-phenylpyridin-4(1H)-one | Calcd 188.0, Found 188.0 |
| 19 | 1-biphenyl-4-yl-3-hydroxypyridin-4(1H)-one | Calcd 264.1, Found 264.1 |

TABLE 1-continued

| | Structure | IUPAC Name | Exact Mass [M + H]+ |
|---|---|---|---|
| 20 | 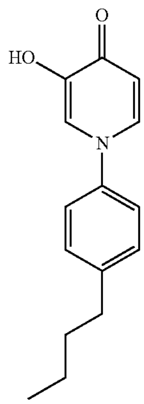 [SMILES: CCCCc1ccc(-n2ccc(=O)c(O)c2)cc1] | 1-(4-butylphenyl)-3-hydroxypyridin-4(1H)-one | Calcd 244.1, Found 244.1 |
| 21 | 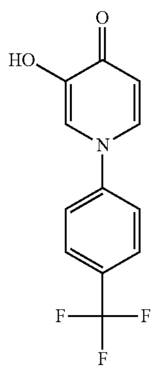 [SMILES: O=c1ccn(-c2ccc(C(F)(F)F)cc2)cc1O] | 3-hydroxy-1-[4-(trifluoromethyl)phenyl]pyridin-4(1H)-one | Calcd 256.2, Found 256.1 |
| 22 | 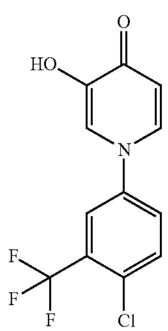 [SMILES: O=c1ccn(-c2ccc(Cl)c(C(F)(F)F)c2)cc1O] | 1-[4-chloro-3-(trifluoromethyl)phenyl]-3-hydroxypyridin-4(1H)-one | Calcd 290.0, Found 290.0 |
| 23 | 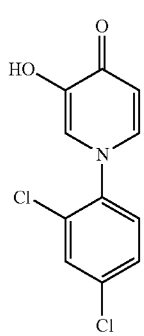 [SMILES: O=c1ccn(-c2ccc(Cl)cc2Cl)cc1O] | 1-(2,4-dichlorophenyl)-3-hydroxypyridin-4(1H)-one | Calcd 255.9, Found 255.9 |

TABLE 1-continued

| | Structure | IUPAC Name | Exact Mass [M + H]+ |
|---|---|---|---|
| 24 | 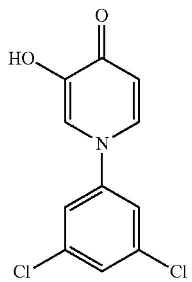 [SMILES: O=c1ccn(-c2cc(Cl)cc(Cl)c2)cc1O] | 1-(3,5-dichlorophenyl)-3-hydroxypyridin-4(1H)-one | Calcd 255.9, Found 255.9 |
| 25 | 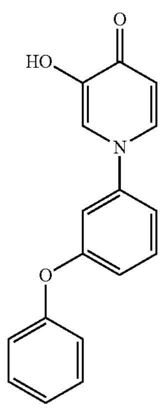 [SMILES: O=c1ccn(-c2cccc(Oc3ccccc3)c2)cc1O] | 3-hydroxy-1-(3-phenoxyphenyl)pyridin-4(1H)-one | Calcd 280.0, Found 280.0 |
| 26 | 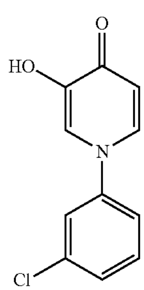 [SMILES: O=c1ccn(-c2cccc(Cl)c2)cc1O] | 1-(3-chlorophenyl)-3-hydroxypyridin-4(1H)-one | Calcd 222.0, Found 222.0 |
| 27 | 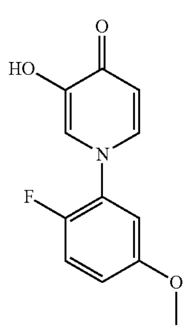 [SMILES: COc1ccc(F)c(-n2ccc(=O)c(O)c2)c1] | 1-(2-fluoro-5-methoxyphenyl)-3-hydroxypyridin-4(1H)-one | Calcd 236.0, Found 236.0 |

TABLE 1-continued

| | Structure | IUPAC Name | Exact Mass [M + H]+ |
|---|---|---|---|
| 28 | 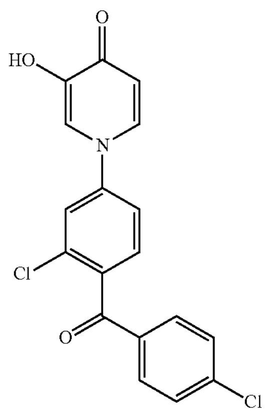 [SMILES: O=C(c1ccc(Cl)cc1)c1ccc(-n2ccc(=O)c(O)c2)cc1Cl] | 1-{3-chloro-4-[(4-chlorophenyl)carbonyl]phenyl}-3-hydroxypyridin-4(1H)-one | Calcd 360.0, Found 360.0 |
| 29 | 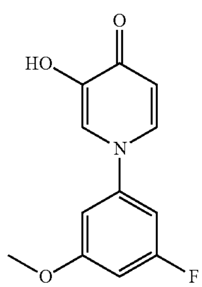 [SMILES: COc1cc(F)cc(-n2ccc(=O)c(O)c2)c1] | 1-(3-fluoro-5-methoxyphenyl)-3-hydroxypyridin-4(1H)-one | Calcd 236.0, Found 236.0 |
| 30 | 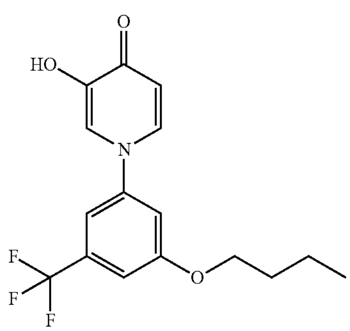 [SMILES: CCCCOc1cc(-n2ccc(=O)c(O)c2)cc(C(F)(F)F)c1] | 1-[3-butoxy-5-(trifluoromethyl)phenyl]-3-hydroxypyridin-4(1H)-one | Calcd 328.1, Found 328.1 |
| 31 | 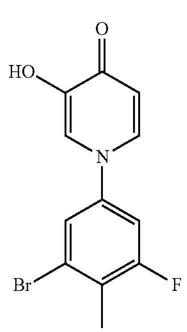 [SMILES: Cc1c(F)cc(-n2ccc(=O)c(O)c2)cc1Br] | 1-(3-bromo-5-fluoro-4-methylphenyl)-3-hydroxypyridin-4(1H)-one | Calcd 297.9, Found 297.9 |

TABLE 1-continued

| Structure | IUPAC Name | Exact Mass [M + H]+ |
|---|---|---|
| 32 | 2'-fluoro-5'-(3-hydroxy-4-oxopyridin-1(4H)-yl)-4-(trifluoromethyl)biphen-yl-2-carbonitrile | Calcd 375.0, Found 375.0 |
| 33 | 1-[4-(3-chlorophenoxy)-3-(trifluoromethyl)phen-yl]-3-hydroxypyridin-4(1H)-one | Calcd 382.0, Found 382.0 |
| 34 | N-[2-chloro-4-(3-hydroxy-4-oxopyridin-1(4H)-yl)phenyl]pentanamide | Calcd 321.1, Found 321.1 |
| 35 | 1-[3-fluoro-5-(pyridin-3-yloxy)phenyl]-3-hydroxypyridin-4(1H)-one | Calcd 299.0, Found 299.0 |

TABLE 1-continued

| | Structure | IUPAC Name | Exact Mass [M + H]+ |
|---|---|---|---|
| 36 | 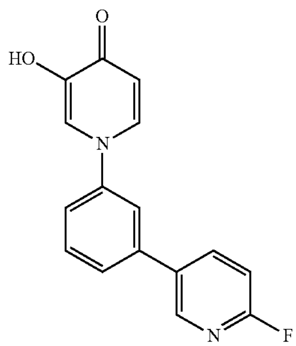 [SMILES: O=c1ccn(-c2cccc(-c3ccc(F)nc3)c2)cc1O] | 1-[3-(6-fluoropyridin-3-yl)phenyl]-3-hydroxypyridin-4(1H)-one | Calcd 283.0, Found 283.0 |
| 37 | 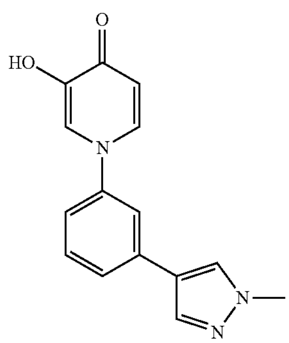 [SMILES: Cn1cc(-c2cccc(-n3ccc(=O)c(O)c3)c2)cn1] | 3-hydroxy-1-[3-(1-methyl-1H-pyrazol-4-yl)phenyl]pyridin-4(1H)-one | Calcd 268.1, Found 268.1 |
| 38 | 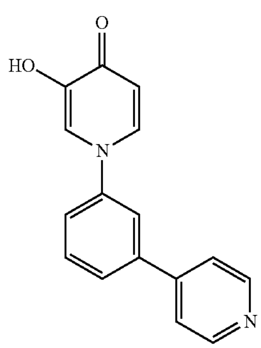 [SMILES: O=c1ccn(-c2cccc(-c3ccncc3)c2)cc1O] | 3-hydroxy-1-(3-pyridin-4-ylphenyl)pyridin-4(1H)-one | Calcd 265.0, Found 265.0 |
| 39 | 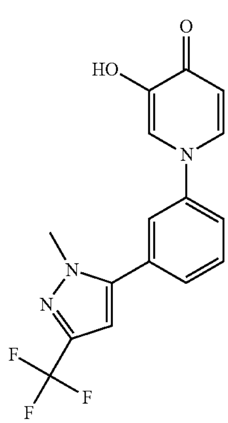 [SMILES: Cn1nc(C(F)(F)F)cc1-c1cccc(-n2ccc(=O)c(O)c2)c1] | 3-hydroxy-1-{3-[1-methyl-3-(trifluoromethyl)-1H-pyrazol-5-yl]phenyl}pyridin-4(1H)-one | Calcd 336.0, Found 336.0 |

TABLE 1-continued
| Structure | IUPAC Name | Exact Mass [M + H]+ |
|---|---|---|
| 40 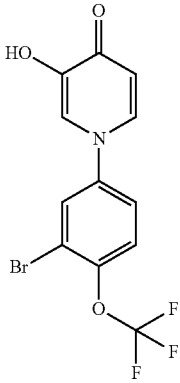 | 1-[3-bromo-4-(trifluoromethoxy)phenyl]-3-hydroxypyridin-4(1H)-one | Calcd 349.9, Found 349.9 |
| 41 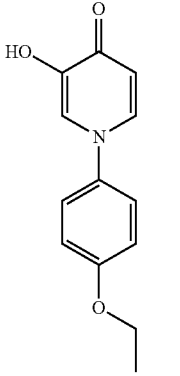 | 1-(4-ethoxyphenyl)-3-hydroxypyridin-4(1H)-one | Calcd 232.0, Found 232.0 |
| 42 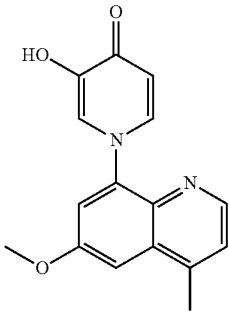 [SMILES: COc1cc(-n2ccc(=O)c(O)c2)c2nccc(C)c2c1] | 3-hydroxy-1-(6-methoxy-4-methylquinolin-8-yl)pyridin-4(1H)-one | Calcd 283.1, Found 283.1 |
| 43 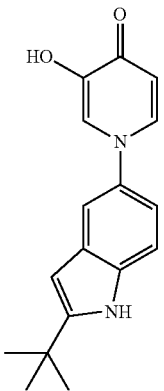 [SMILES: CC(C)(C)c1cc2cc(-n3ccc(=O)c(O)c3)ccc2[nH]1] | 1-(2-tert-butyl-1H-indol-5-yl)-3-hydroxypyridin-4(1H)-one | Calcd 283.1, Found 283.1 |

TABLE 1-continued

| Structure | IUPAC Name | Exact Mass [M + H]+ |
|---|---|---|
| 44 | 3-hydroxy-1-[4-methoxy-3-(1-methylethyl)phenyl]pyridin-4(1H)-one | Calcd 260.1, Found 260.1 |
| 45 | 1-[2-(3,4-difluorophenyl)-1,3-benzoxazol-5-yl]-3-hydroxypyridin-4(1H)-one | Calcd 341.0, Found 341.0 |
| 46 | 3-hydroxy-1-[4-(3-pyridin-4-ylpropoxy)phenyl]pyridin-4(1H)-one | Calcd 323.1, Found 323.1 |

TABLE 1-continued

| Structure | IUPAC Name | Exact Mass [M + H]+ |
|---|---|---|
| 47 | 3-hydroxy-1-[4-(2-morpholin-4-ylethoxy)phenyl]pyridin-4(1H)-one | Calcd 317.1, Found 317.1 |
| 48 | 1-[3-chloro-4-(diethylamino)phenyl]-3-hydroxypyridin-4(1H)-one | Calcd 293,1, Found 293.1 |
| 49 | 3-hydroxy-1-(4-{[4-(hydroxymethyl)cyclohexyl]methoxy}phenyl)pyridin-4(1H)-one | Calcd 330,1, Found 330.1 |

TABLE 1-continued
| Structure | IUPAC Name | Exact Mass [M + H]+ |
|---|---|---|
| 50 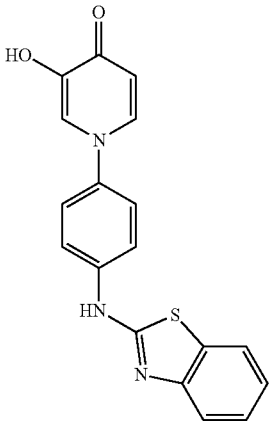 [SMILES: O=c1ccn(-c2ccc(Nc3nc4ccccc4s3)cc2)cc1O] | 1-[4-(1,3-benzothiazol-2-ylamino)phenyl]-3-hydroxypyridin-4(1H)-one | Calcd 336.0, Found 336.0 |
| 51 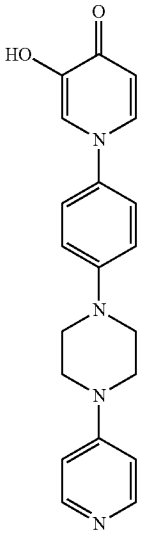 | 3-hydroxy-1-[4-(4-pyridin-4-ylpiperazin-1-yl)phenyl]pyridin-4(1H)-one | Calcd 349.1, Found 349.1 |
| 52 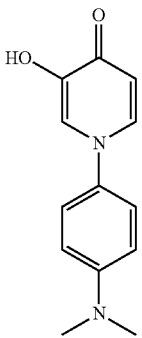 | 1-[4-(dimethylamino)phenyl]-3-hydroxypyridin-4(1H)-one | Calcd 231.1, Found 231.1 |

TABLE 1-continued

| Structure | IUPAC Name | Exact Mass [M + H]+ |
|---|---|---|
| 53 | 3-hydroxy-1-{4-[3-pyridin-3-yl-5-(trifluoromethyl)-1H-pyrazol-1-yl]phenyl}pyridin-4(1H)-one | Calcd 399.1, Found 399.1 |
| 54 | 1-[4-(cyclopentyloxy)phenyl]-3-hydroxypyridin-4(1H)-one | Calcd 272.1, Found 272.1 |
| 55 | 3-hydroxy-1-(4-morpholin-4-ylphenyl)pyridin-4(1H)-one | Calcd 273.1, Found 273.1 |

TABLE 1-continued
| Structure | IUPAC Name | Exact Mass [M + H]+ |
|---|---|---|
| 56 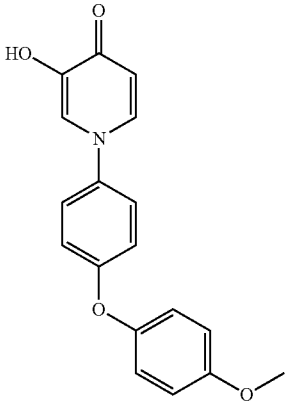 [SMILES: COc1ccc(Oc2ccc(-n3ccc(=O)c(O)c3)cc2)cc1] | 3-hydroxy-1-[4-(4-methoxyphenoxy)phenyl]pyridin-4(1H)-one | Calcd 310.1, Found 310.1 |
| 57 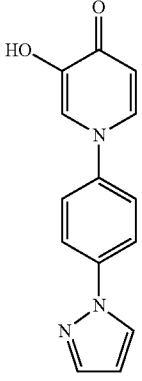 | 3-hydroxy-1-[4-(1H-pyrazol-1-yl)phenyl]pyridin-4(1H)-one | Calcd 254.0, Found 254.0 |
| 58 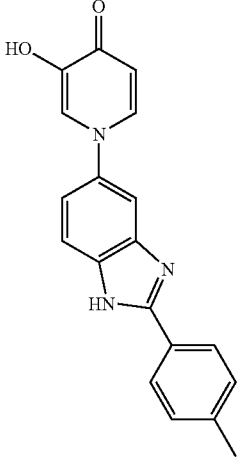 [SMILES: Cc1ccc(-c2nc3cc(-n4ccc(=O)c(O)c4)ccc3[nH]2)cc1] | 3-hydroxy-1-[2-(4-methylphenyl)-1H-benzimidazol-5-yl]pyridin-4(1H)-one | Calcd 318.1, Found 318.1 |
| 59 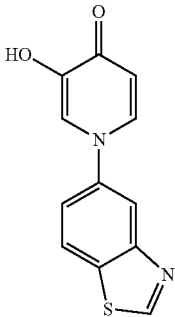 [SMILES: O=c1ccn(-c2ccc3scnc3c2)cc1O] | 1-(1,3-benzothiazol-5-yl)-3-hydroxypyridin-4(1H)-one | Calcd 245.0, Found 245.0 |

TABLE 1-continued

| | Structure | IUPAC Name | Exact Mass [M + H]+ |
|---|---|---|---|
| 60 | 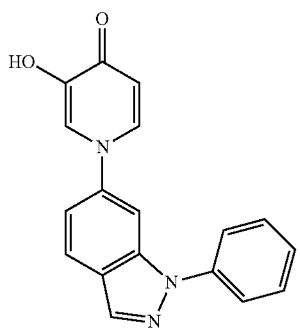 [SMILES: O=c1ccn(-c2ccc3cnn(-c4ccccc4)c3c2)cc1O] | 3-hydroxy-1-(1-phenyl-1H-indazol-6-yl)pyridin-4(1H)-one | Calcd 304.1, Found 304.1 |
| 61 | 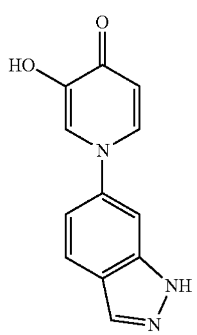 [SMILES: O=c1ccn(-c2ccc3cn[nH]c3c2)cc1O] | 3-hydroxy-1-(1H-indazol-6-yl)pyridin-4(1H)-one | Calcd 228.0, Found 228.0 |
| 62 | 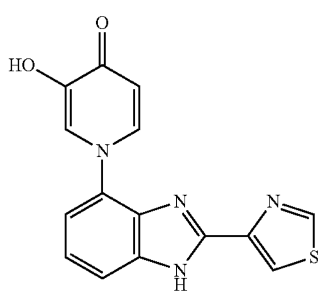 [SMILES: O=c1ccn(-c2cccc3[nH]c(-c4cscn4)nc23)cc1O] | 3-hydroxy-1-[2-(1,3-thiazol-4-yl)-1H-benzimidazol-4-yl]pyridin-4(1H)-one | Calcd 311.0, Found 311.0 |
| 63 | 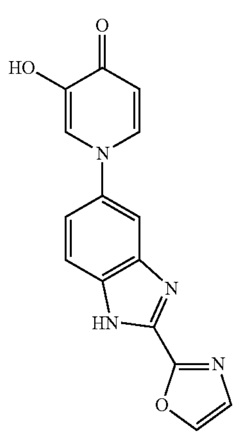 [SMILES: O=c1ccn(-c2ccc3[nH]c(-c4ncco4)nc3c2)cc1O] | 3-hydroxy-1-[2-(1,3-oxazol-2-yl)-1H-benzimidazol-5-yl]pyridin-4(1H)-one | Calcd 295.0, Found 295.0 |

TABLE 1-continued
| Structure | IUPAC Name | Exact Mass [M + H]+ |
|---|---|---|
| 64 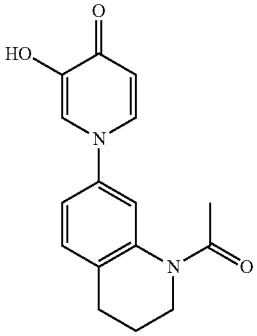 [SMILES: CC(=O)N1CCCc2ccc(-n3ccc(=O)c(O)c3)cc21] | 1-(1-acetyl-1,2,3,4-tetrahydroquinolin-7-yl)-3-hydroxypyridin-4(1H)-one | Calcd 285.1, Found 285.1 |
| 65 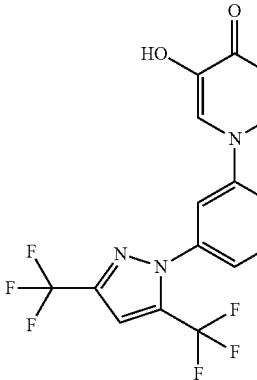 | 1-{3-[3,5-bis(trifluoromethyl)-1H-pyrazol-1-yl]phenyl}-3-hydroxypyridin-4(1H)-one | Calcd 390.0, Found 390.0 |
| 66 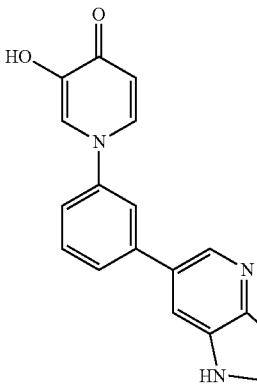 | 3-hydroxy-1-[3-(1H-pyrrolo[3,2-b]pyridin-6-yl)phenyl]pyridin-4(1H)-one | Calcd 304.3, Found 304.4 |
| 67 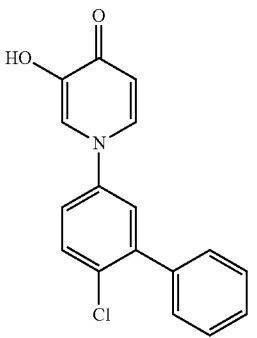 [SMILES: O=c1ccn(-c2ccc(Cl)c(-c3ccccc3)c2)cc1O] | 1-(6-chlorobiphenyl-3-yl)-3-hydroxypyridin-4(1H)-one | Calcd 298.7, Found 298.2 |

TABLE 1-continued

| | Structure | IUPAC Name | Exact Mass [M + H]+ |
|---|---|---|---|
| 68 | 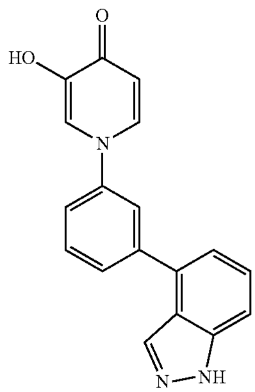 [SMILES: O=c1ccn(-c2cccc(-c3cccc4[nH]ncc34)c2)cc1O] | 3-hydroxy-1-[3-(1H-indazol-4-yl)phenyl]pyridin-4(1H)-one | Calcd 304.1, Found 304.1 |
| 69 | 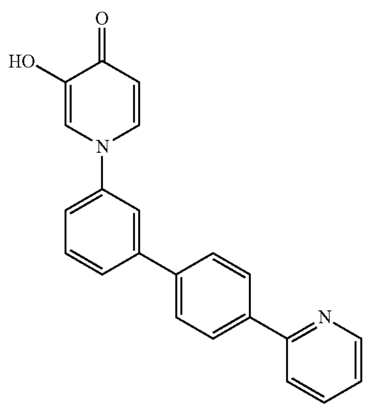 [SMILES: O=c1ccn(-c2cccc(-c3ccc(-c4ccccn4)cc3)c2)cc1O] | 3-hydroxy-1-(4'-pyridin-2-ylbiphenyl-3-yl)pyridin-4(1H)-one | Calcd 341.1, Found 341.1 |
| 70 | 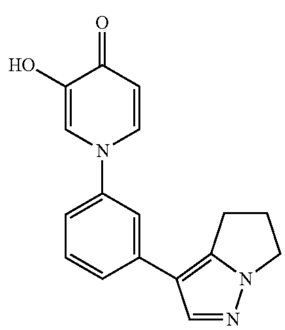 [SMILES: O=c1ccn(-c2cccc(-c3cnn4c3CCC4)c2)cc1O] | 1-[3-(5,6-dihydro-4H-pyrrolo[1,2-b]pyrazol-3-yl)phenyl]-3-hydroxypyridin-4(1H)-one | Calcd 294.1, Found 294.1 |
| 71 | 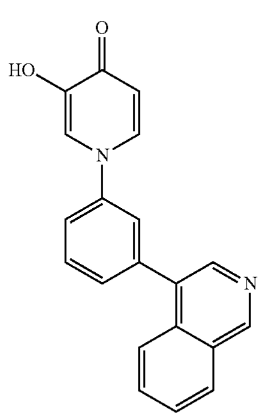 [SMILES: O=c1ccn(-c2cccc(-c3cncc4ccccc34)c2)cc1O] | 3-hydroxy-1-(3-isoquinolin-4-ylphenyl)pyridin-4(1H)-one | Calcd 315.1, Found 315.1 |

TABLE 1-continued

| Structure | IUPAC Name | Exact Mass [M + H]+ |
|---|---|---|
| 72 | 1-(2-biphenyl-4-yl-1H-benzimidazol-5-yl)-3-hydroxypyridin-4(1H)-one | Calcd 380.1, Found 380.1 |
| 73 | 5-(3-hydroxy-4-oxopyridin-1(4H)-yl)biphenyl-3-carboxylic acid | Calcd 308.3, Found 308.2 |
| 74 | 1-biphenyl-3-yl-2-(difluoromethyl)-5-hydroxypyridin-4(1H)-one | Calcd 314.3, Found 314.3 |
| 75 | 1-biphenyl-3-yl-3-bromo-5-hydroxy-2-(hydroxymethyl)pyridin-4(1H)-one | Calcd 372.0, Found 372.0 |

TABLE 1-continued

| | Structure | IUPAC Name | Exact Mass [M + H]+ |
|---|---|---|---|
| 76 | 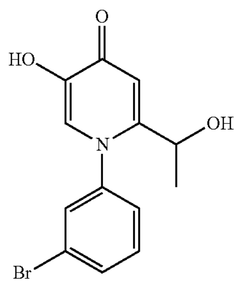 [SMILES: CC(O)c1cc(=O)c(O)cn1-c1cccc(Br)c1] | 1-(3-bromophenyl)-5-hydroxy-2-(1-hydroxyethyl)pyridin-4(1H)-one | Calcd 310.0, Found 310.0 |
| 77 | 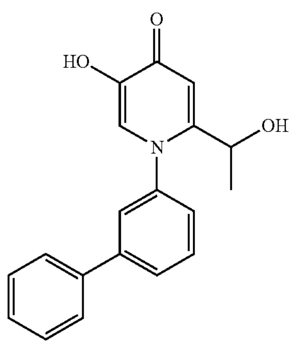 [SMILES: CC(O)c1cc(=O)c(O)cn1-c1cccc(-c2ccccc2)c1] | 1-biphenyl-3-yl-5-hydroxy-2-(1-hydroxyethyl)pyridin-4(1H)-one | Calcd 308.1, Found 308,1 |
| 78 | 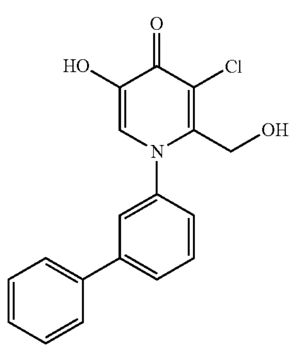 [SMILES: O=c1c(O)cn(-c2cccc(-c3ccccc3)c2)c(CO)c1Cl] | 1-biphenyl-3-yl-3-chloro-5-hydroxy-2-(hydroxymethyl)pyridin-4(1H)-one | Calcd 328.0, Found 328.0 |
| 79 | 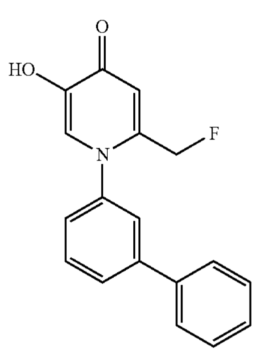 [SMILES: O=c1cc(CF)n(-c2cccc(-c3ccccc3)c2)cc1O] | 1-biphenyl-3-yl-2-(fluoromethyl)-5-hydroxypyridin-4(1H)-one | Calcd 296.1, Found 296.1 |

TABLE 1-continued
| | Structure | IUPAC Name | Exact Mass [M + H]+ |
|---|---|---|---|
| 80 | 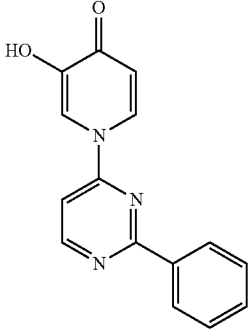 [SMILES: O=c1ccn(-c2ccnc(-c3ccccc3)n2)cc1O] | 3-hydroxy-1-(2-phenylpyrimidin-4-yl)pyridin-4(1H)-one | Calcd 266.0, Found 266.0 |
| 81 | 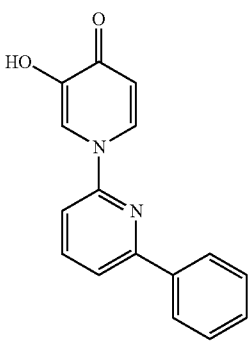 [SMILES: O=c1ccn(-c2cccc(-c3ccccc3)n2)cc1O] | 3-hydroxy-6'-phenyl-4H-1,2'-bipyridin-4-one | Calcd 265.0, Found 265.0 |
| 82 | 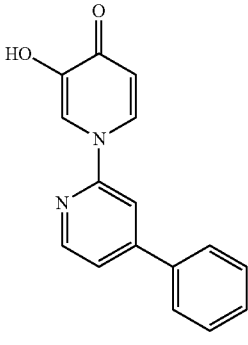 [SMILES: O=c1ccn(-c2cc(-c3ccccc3)ccn2)cc1O] | 3-hydroxy-4'-phenyl-4H-1,2'-bipyridin-4-one | Calcd 265.0, Found 265.0 |
| 83 | 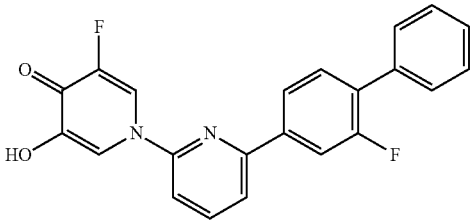 [SMILES: O=c1c(O)cn(-c2cccc(-c3ccc(-c4ccccc4)c(F)c3)n2)cc1F] | 3-fluoro-6'-(2-fluorobiphenyl-4-yl)-5-hydroxy-4H-1,2'-bipyridin-4-one | Calcd 377.4, Found 377.3 |
| 84 | 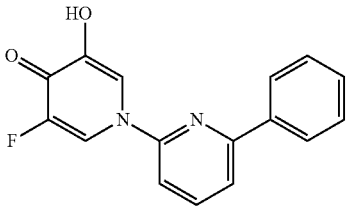 [SMILES: O=c1c(O)cn(-c2cccc(-c3ccccc3)n2)cc1F] | 3-fluoro-5-hydroxy-6'-phenyl-4H-1,2'-bipyridin-4-one | Calcd 283.3, Found 283.3 |

TABLE 1-continued
| | Structure | IUPAC Name | Exact Mass [M + H]+ |
|---|---|---|---|
| 85 | 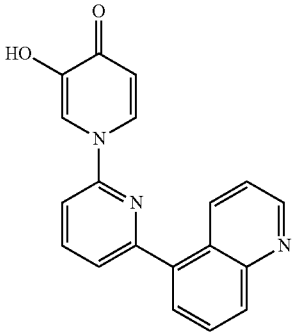 [SMILES: O=c1ccn(-c2cccc(-c3cccc4ncccc34)n2)cc1O] | 3-hydroxy-6'-quinolin-5-yl-4H-1,2'-bipyridin-4-one | Calcd 316.1, Found 316.1 |
| 86 | 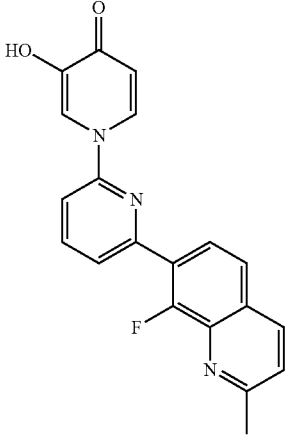 [SMILES: Cc1ccc2ccc(-c3cccc(-n4ccc(=O)c(O)c4)n3)c(F)c2n1] | 6'-(8-fluoro-2-methylquinolin-7-yl)-3-hydroxy-4H-1,2'-bipyridin-4-one | Calcd 348.1, Found 348.1 |
| 87 | 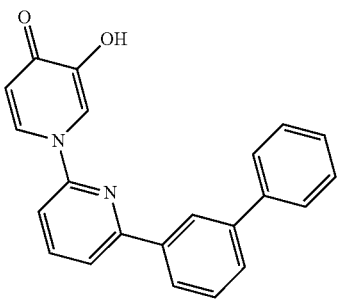 [SMILES: O=c1ccn(-c2cccc(-c3cccc(-c4ccccc4)c3)n2)cc1O] | 6'-biphenyl-3-yl-3-hydroxy-4H-1,2'-bipyridin-4-one | Calcd 341.1, Found 341.1 |
| 88 | 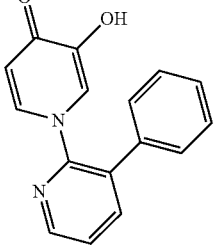 | 3-hydroxy-3'-phenyl-4H-1,2'-bipyridin-4-one | Calcd 265.3, Found 265.1 |

TABLE 1-continued
| Structure | IUPAC Name | Exact Mass [M + H]+ |
|---|---|---|
| 89 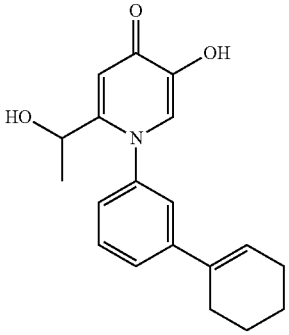 [SMILES: CC(O)c1cc(=O)c(O)cn1-c1cccc(C2=CCCCC2)c1] | 1-(3-cyclohex-1-en-1-ylphenyl)-5-hydroxy-2-(1-hydroxyethyl)pyridin-4(1H)-one | Calcd 312.1, Found 312.1 |
| 90 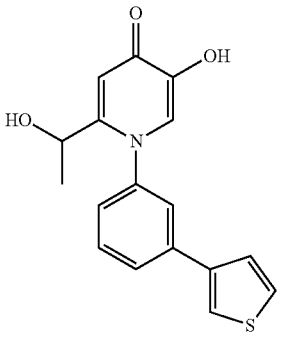 [SMILES: CC(O)c1cc(=O)c(O)cn1-c1cccc(-c2ccsc2)c1] | 5-hydroxy-2-(1-hydroxyethyl)-1-(3-thiophen-3-ylphenyl)pyridin-4(1H)-one | Calcd 314.0, Found 314.0 |
| 91 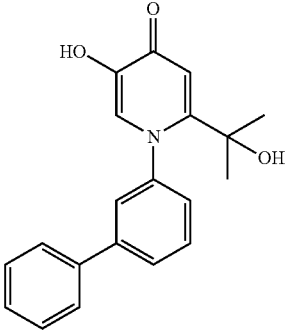 [SMILES: CC(C)(O)c1cc(=O)c(O)cn1-c1cccc(-c2ccccc2)c1] | 1-biphenyl-3-yl-5-hydroxy-2-(1-hydroxy-1-methylethyl)pyridin-4(1H)-one | Calcd 322.4, Found 322.1 |
| 92 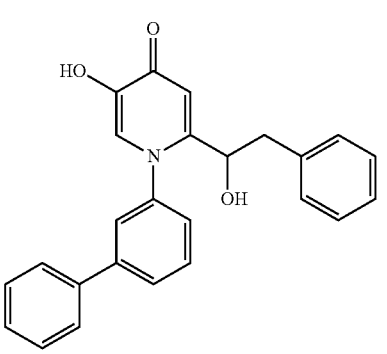 [SMILES: O=c1cc(C(O)Cc2ccccc2)n(-c2cccc(-c3ccccc3)c2)cc1O] | 1-biphenyl-3-yl-5-hydroxy-2-(1-hydroxy-2-phenylethyl)pyridin-4(1H)-one | Calcd 384.4, Found 384.2 |

TABLE 1-continued

| | Structure | IUPAC Name | Exact Mass [M + H]+ |
|---|---|---|---|
| 93 | 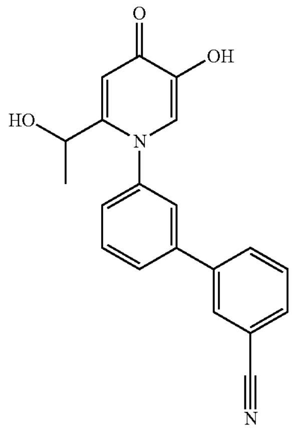 [SMILES: CC(O)c1cc(=O)c(O)cn1-c1cccc(-c2cccc(C#N)c2)c1] | 3'-[5-hydroxy-2-(1-hydroxyethyl)-4-oxopyridin-1(4H)-yl]biphenyl-3-carbonitrile | Calcd 333.1, Found 333.1 |
| 94 | 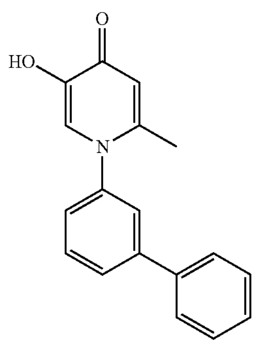 [SMILES: Cc1cc(=O)c(O)cn1-c1cccc(-c2ccccc2)c1] | 1-biphenyl-3-yl-5-hydroxy-2-methylpyridin-4(1H)-one | Calcd 278.3, Found 277.9 |
| 95 | 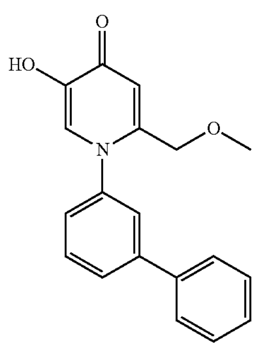 [SMILES: COCc1cc(=O)c(O)cn1-c1cccc(-c2ccccc2)c1] | 1-biphenyl-3-yl-5-hydroxy-2-(methoxymethyl)pyridin-4(1H)-one | Calcd 308.3, Found 308.1 |
| 96 | 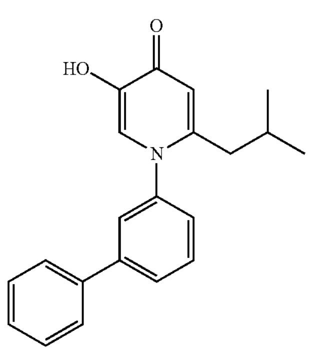 [SMILES: CC(C)Cc1cc(=O)c(O)cn1-c1cccc(-c2ccccc2)c1] | 1-biphenyl-3-yl-5-hydroxy-2-(2-methylpropyl)pyridin-4(1H)-one | Calcd 320.1, Found 320.1 |

TABLE 1-continued
| | Structure | IUPAC Name | Exact Mass [M + H]+ |
|---|---|---|---|
| 97 | 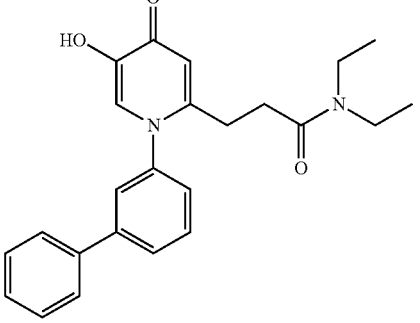 | 3-(1-biphenyl-3-yl-5-hydroxy-4-oxo-1,4-dihydropyridin-2-yl)-N,N-diethylpropanamide | Calcd 391.2, Found 391.2 |
| 98 | 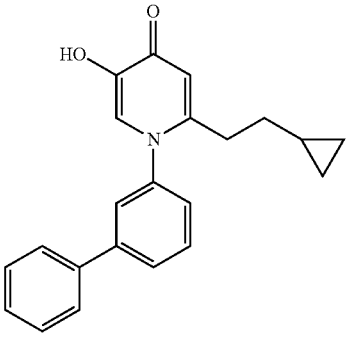 [SMILES: O=c1cc(CCC2CC2)n(-c2cccc(-c3ccccc3)c2)cc1O] | 1-biphenyl-3-yl-2-(2-cyclopropylethyl)-5-hydroxypyridin-4(1H)-one | Calcd 332.1, Found 332.1 |
| 99 | 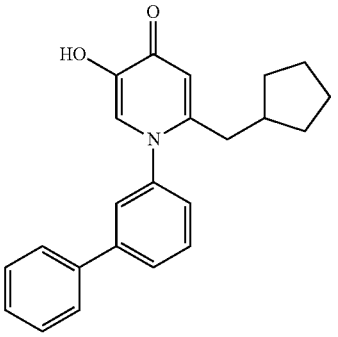 [SMILES: O=c1cc(CC2CCCC2)n(-c2cccc(-c3ccccc3)c2)cc1O] | 1-biphenyl-3-yl-2-(cyclopentylmethyl)-5-hydroxypyridin-4(1H)-one | Calcd 346.1, Found 346.1 |
| 100 | 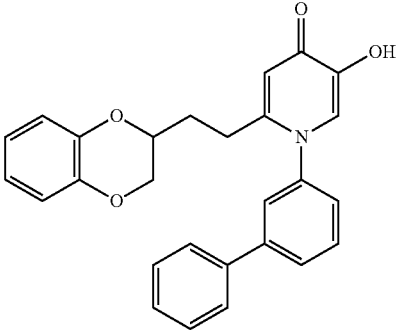 [SMILES: O=c1cc(CCC2COc3ccccc3O2)n(-c2cccc(-c3ccccc3)c2)cc1O] | 1-biphenyl-3-yl-2-[2-(2,3-dihydro-1,4-benzodioxin-2-yl)ethyl]-5-hydroxypyridin-4(1H)-one | Calcd 426.1, Found 426.1 |

TABLE 1-continued
| | Structure | IUPAC Name | Exact Mass [M + H]+ |
|---|---|---|---|
| 101 | 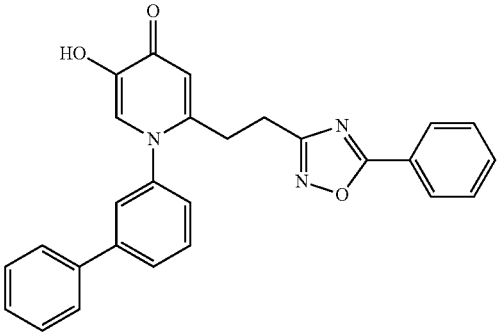 [SMILES: O=c1cc(CCc2noc(-c3ccccc3)n2)n(-c2cccc(-c3ccccc3)c2)cc1O] | 1-biphenyl-3-yl-5-hydroxy-2-[2-(5-phenyl-1,2,4-oxadiazol-3-yl)ethyl]pyridin-4(1H)-one | Calcd 436.1, Found 436.1 |
| 102 | 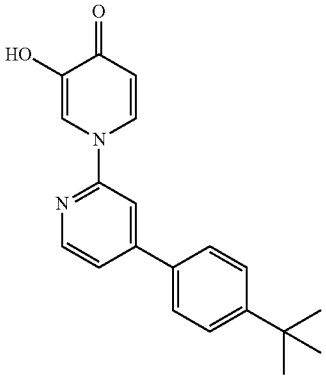 [SMILES: CC(C)(C)c1ccc(-c2ccnc(-n3ccc(=O)c(O)c3)c2)cc1] | 4'-(4-tert-butylphenyl)-3-hydroxy-4H-1,2'-bipyridin-4-one | Calcd 321.1, Found 321.1 |
| 103 | 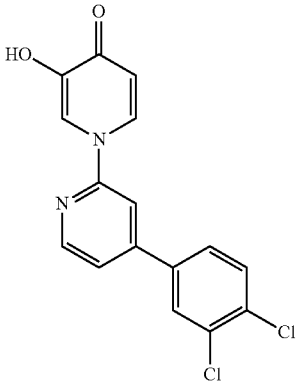 | 4'-(3,4-dichlorophenyl)-3-hydroxy-4H-1,2'-bipyridin-4-one | Calcd 333.0, Found 333.0 |
| 104 | 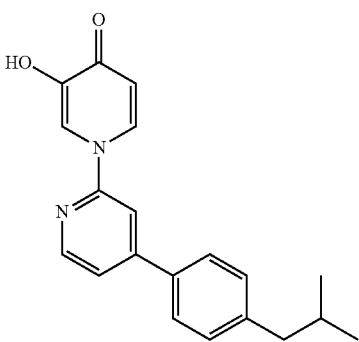 [SMILES: CC(C)Cc1ccc(-c2ccnc(-n3ccc(=O)c(O)c3)c2)cc1] | 3-hydroxy-4'-[4-(2-methylpropyl)phenyl]-4H-1,2'-bipyridin-4-one | Calcd 321.1, Found 321.1 |

TABLE 1-continued
| | Structure | IUPAC Name | Exact Mass [M + H]+ |
|---|---|---|---|
| 105 | 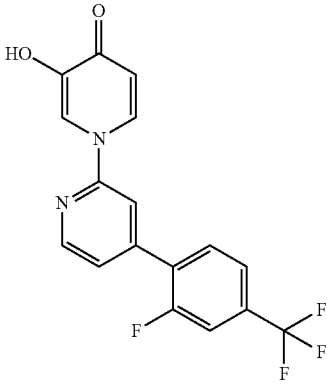 [SMILES: O=c1ccn(-c2cc(-c3ccc(C(F)(F)F)cc3F)ccn2)cc1O] | 4'-[2-fluoro-4-(trifluoromethyl)phenyl]-3-hydroxy-4H-1,2'-bipyridin-4-one | Calcd 351.0, Found 351.0 |
| 106 | 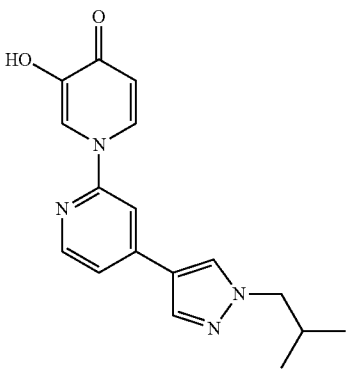 [SMILES: CC(C)Cn1cc(-c2ccnc(-n3ccc(=O)c(O)c3)c2)cn1] | 3-hydroxy-4'-(1-(2-methylpropyl)-1H-pyrazol-4-yl]-4H-1,2'-bipyridin-4-one | Calcd 311.1, Found 311.1 |
| 107 | 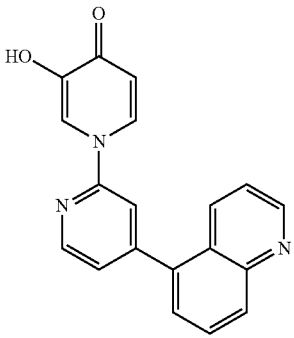 [SMILES: O=c1ccn(-c2cc(-c3cccc4ncccc34)ccn2)cc1O] | 3-hydroxy-4'-quinolin-5-yl-4H-1,2'-bipyridin-4-one | Calcd 316.1, Found 316.1 |
| 108 | 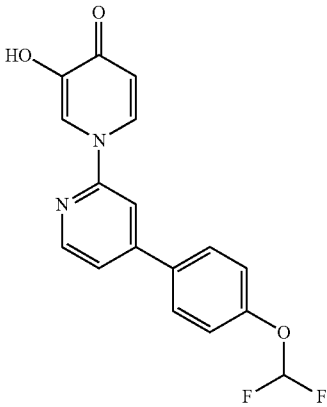 [SMILES: O=c1ccn(-c2cc(-c3ccc(OC(F)F)cc3)ccn2)cc1O] | 4'-[4-(difluoromethoxy)phenyl]-3-hydroxy-4H-1,2'-bipyridin-4-one | Calcd 331.0, Found 331.0 |

TABLE 1-continued

| | Structure | IUPAC Name | Exact Mass [M + H]+ |
|---|---|---|---|
| 109 | 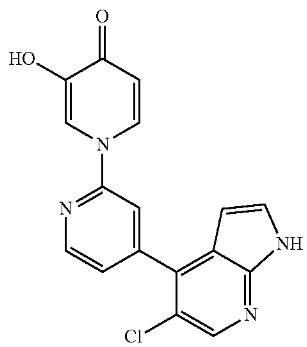 [SMILES: O=c1ccn(-c2cc(-c3c(Cl)cnc4[nH]ccc34)ccn2)cc1O] | 4'-(5-chloro-1H-pyrrolo[2,3-b]pyridin-4-yl)-3-hydroxy-4H-1,2'-bipyridin-4-one | Calcd 339.0, Found 339.0 |
| 110 | 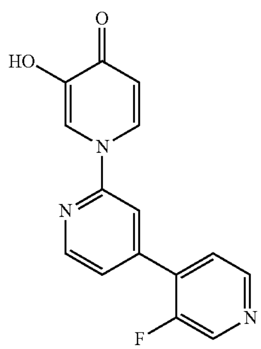 [SMILES: O=c1ccn(-c2cc(-c3ccncc3F)ccn2)cc1O] | 3"-fluoro-3-hydroxy-4H-1,2':4',4"-terpyridin-4-one | Calcd 284.0, Found 284.0 |
| 111 | 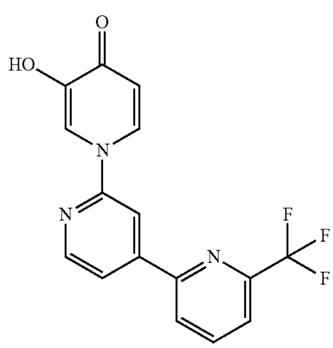 [SMILES: O=c1ccn(-c2cc(-c3cccc(C(F)(F)F)n3)ccn2)cc1O] | 3-hydroxy-6"-(trifluoromethyl)-4H-1,2':4',2"-terpyridin-4-one | Calcd 334.1, Found 334.1 |
| 112 | 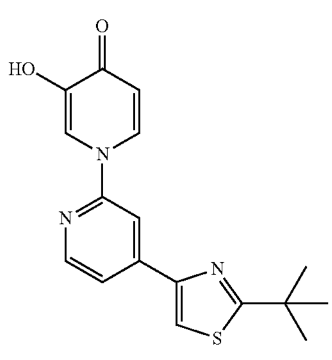 [SMILES: CC(C)(C)c1nc(-c2ccnc(-n3ccc(=O)c(O)c3)c2)cs1] | 4'-(2-tert-butyl-1,3-thiazol-4-yl)-3-hydroxy-4H-1,2'-bipyridin-4-one | Calcd 328.1, Found 328.1 |

TABLE 1-continued

| | Structure | IUPAC Name | Exact Mass [M + H]+ |
|---|---|---|---|
| 113 | 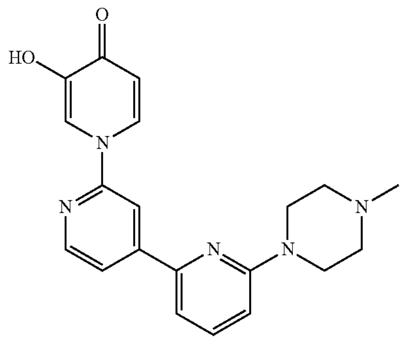 [SMILES: CN1CCN(c2cccc(-c3ccnc(-n4ccc(=O)c(O)c4)c3)n2)CC1] | 3-hydroxy-6''-(4-methylpiperazin-1-yl)-4H-1,2':4',2''-terpyridin-4-one | Calcd 364.1, Found 364.1 |
| 114 | 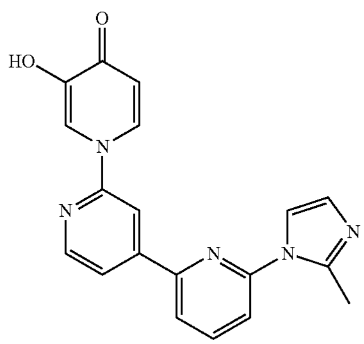 [SMILES: Cc1nccn1-c1cccc(-c2ccnc(-n3ccc(=O)c(O)c3)c2)n1] | 3-hydroxy-6''-(2-methyl-1H-imidazol-1-yl)-4H-1,2':4',2''-terpyridin-4-one | Calcd 346.1, Found 346.1 |
| 115 | 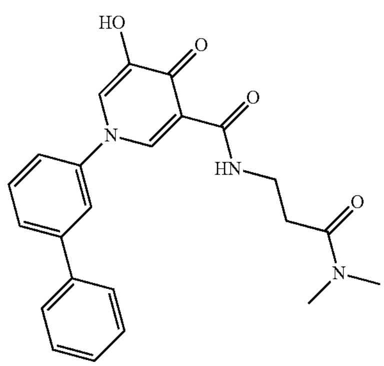 [SMILES: CN(C)C(=O)CCNC(=O)c1cn(-c2cccc(-c3ccccc3)c2)cc(O)c1=O] | 1-biphenyl-3-yl-N-[3-(dimethylamino)-3-oxopropyl]-5-hydroxy-4-oxo-1,4-dihydropyridine-3-carboxamide | Calcd 406.1, Found 406.1 |
| 116 | 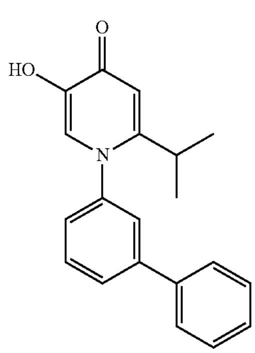 [SMILES: CC(C)c1cc(=O)c(O)cn1-c1cccc(-c2ccccc2)c1] | 1-biphenyl-3-yl-5-hydroxy-2-(1-methylethyl)pyridin-4(1H)-one | Calcd 306.1, Found 306.1 |

TABLE 1-continued

| Structure | IUPAC Name | Exact Mass [M + H]+ |
|---|---|---|
| 117 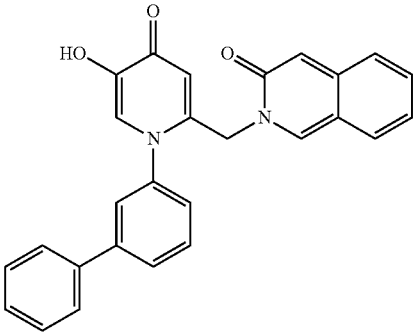 [SMILES: O=c1cc(Cn2cc3ccccc3cc2=O)n(-c2cccc(-c3ccccc3)c2)cc1O] | 2-[(1-biphenyl-3-yl-5-hydroxy-4-oxo-1,4-dihydropyridin-2-yl)methyl]isoquinolin-3(2H)-one | Calcd 421.1, Found 421.1 |
| 118 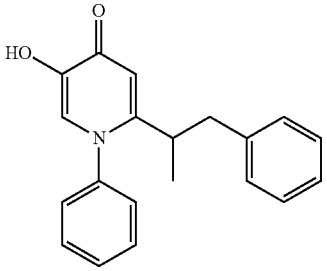 [SMILES: CC(Cc1ccccc1)c1cc(=O)c(O)cn1-c1ccccc1] | 5-hydroxy-2-(1-methyl-2-phenylethyl)-1-phenylpyridin-4(1H)-one | Calcd 306.1, Found 306.1 |
| 119 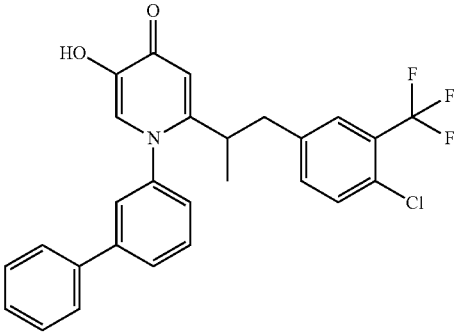 [SMILES: CC(Cc1ccc(Cl)c(C(F)(F)F)c1)c1cc(=O)c(O)cn1-c1cccc(-c2ccccc2)c1] | 1-biphenyl-3-yl-2-{2-[4-chloro-3-(trifluoromethyl)phenyl]-1-methylethyl}-5-hydroxypyridin-4(1H)-one | Calcd 484.1, Found 484.1 |
| 120 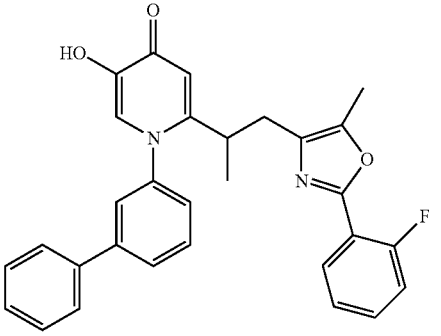 [SMILES: Cc1oc(-c2ccccc2F)nc1CC(C)c1cc(=O)c(O)cn1-c1cccc(-c2ccccc2)c1] | 1-biphenyl-3-yl-2-{2-[2-(2-fluorophenyl)-5-methyl-1,3-oxazol-4-yl]-1-methylethyl}-5-hydroxypyridin-4(1H)-one | Calcd 481.1, Found 481.1 |

TABLE 1-continued

| | Structure | IUPAC Name | Exact Mass [M + H]+ |
|---|---|---|---|
| 121 | 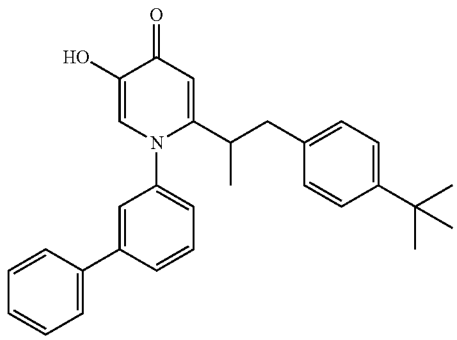 [SMILES: CC(Cc1ccc(C(C)(C)C)cc1)c1cc(=O)c(O)cn1-c1cccc(-c2ccccc2)c1] | 1-biphenyl-3-yl-2-[2-(4-tert-butylphenyl)-1-methylethyl]-5-hydroxypyridin-4(1H)-one | Calcd 438.2, Found 438.2 |
| 122 | 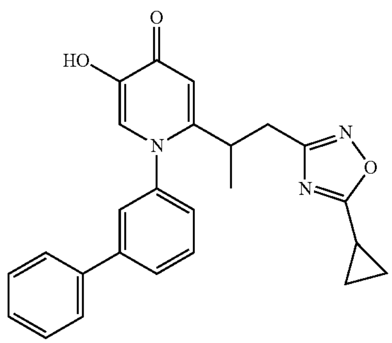 [SMILES: CC(Cc1noc(C2CC2)n1)c1cc(=O)c(O)cn1-c1cccc(-c2ccccc2)c1] | 1-biphenyl-3-yl-2-[2-(5-cyclopropyl-1,2,4-oxadiazol-3-yl)-1-methylethyl]-5-hydroxypyridin-4(1H)-one | Calcd 414.1, Found 414.1 |
| 123 | 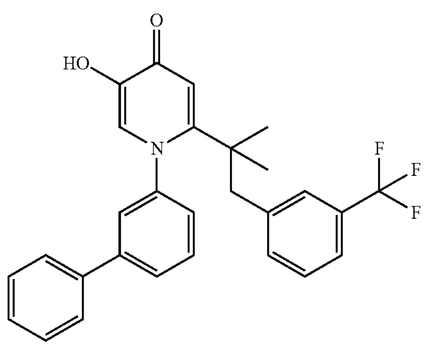 [SMILES: CC(C)(Cc1cccc(C(F)(F)F)c1)c1cc(=O)c(O)cn1-c1cccc(-c2ccccc2)c1] | 1-biphenyl-3-yl-2-{1,1-dimethyl-2-[3-(trifluoromethyl)phenyl]ethyl}-5-hydroxypyridin-4(1H)-one | Calcd 464.1, Found 464.1 |
| 124 | 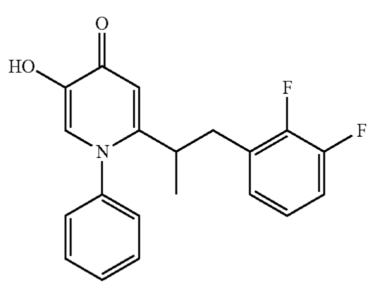 [SMILES: CC(Cc1cccc(F)c1F)c1cc(=O)c(O)cn1-c1ccccc1] | 2-[2-(2,3-difluorophenyl)-1-methylethyl]-5-hydroxy-1-phenylpyridin-4(1H)-one | Calcd 342.1, Found 342.1 |
| 125 | 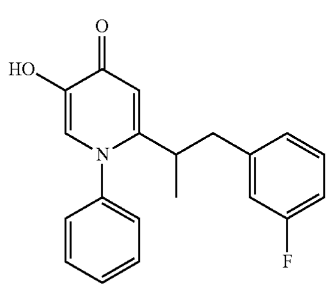 [SMILES: CC(Cc1cccc(F)c1)c1cc(=O)c(O)cn1-c1ccccc1] | 2-[2-(3-fluorophenyl)-1-methylethyl]-5-hydroxy-1-phenylpyridin-4(1H)-one | Calcd 324.1, Found 324.1 |

TABLE 1-continued

| | Structure | IUPAC Name | Exact Mass [M + H]+ |
|---|---|---|---|
| 126 | 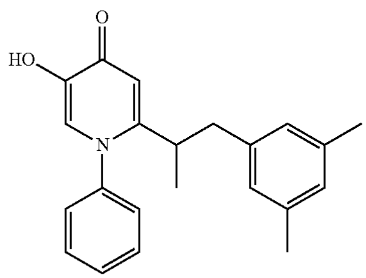 [SMILES: Cc1cc(C)cc(CC(C)c2cc(=O)c(O)cn2-c2ccccc2)c1] | 2-[2-(3,5-dimethylphenyl)-1-methylethyl]-5-hydroxy-1-phenylpyridin-4(1H)-one | Calcd 334.1, Found 334.1 |
| 127 | 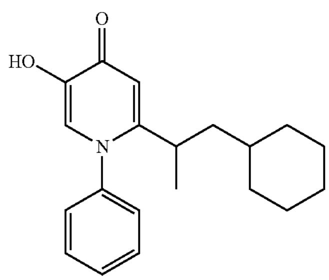 [SMILES: CC(CC1CCCCC1)c1cc(=O)c(O)cn1-c1ccccc1] | 2-(2-cyclohexyl-1-methylethyl)-5-hydroxy-1-phenylpyridin-4(1H)-one | Calcd 312.1, Found 312.1 |
| 128 | 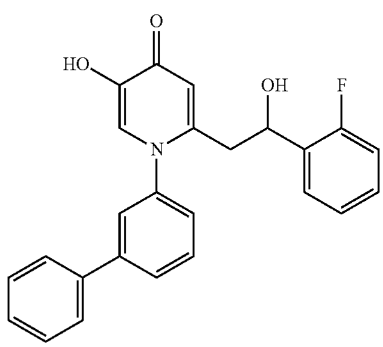 [SMILES: O=c1cc(CC(O)c2ccccc2F)n(-c2cccc(-c3ccccc3)c2)cc1O] | 1-biphenyl-3-yl-2-[2-(2-fluorophenyl)-2-hydroxyethyl]-5-hydroxypyridin-4(1H)-one | Calcd 402.1, Found 402.1 |
| 129 | 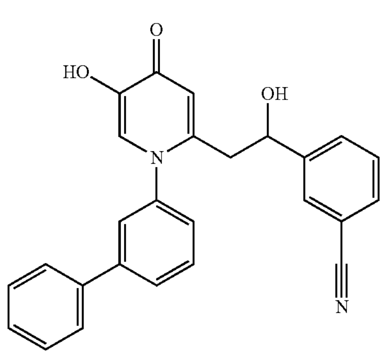 [SMILES: N#Cc1cccc(C(O)Cc2cc(=O)c(O)cn2-c2cccc(-c3ccccc3)c2)c1] | 3-[2-(1-biphenyl-3-yl-5-hydroxy-4-oxo-1,4-dihydropyridin-2-yl)-1-hydroxyethyl]benzonitrile | Calcd 409.1, Found 409.1 |

TABLE 1-continued

| Structure | IUPAC Name | Exact Mass [M + H]+ |
|---|---|---|
| 130 | 1-biphenyl-3-yl-2-(2-biphenyl-2-yl-2-hydroxyethyl)-5-hydroxypyridin-4(1H)-one | Calcd 460.1, Found 460.1 |
| 131 | 1-biphenyl-3-yl-5-hydroxy-2-[2-hydroxy-2-(1,3-thiazol-4-yl)ethyl]pyridin-4(1H)-one | Calcd 391.1, Found 391.1 |
| 132 | 1-biphenyl-3-yl-5-hydroxy-2-[2-hydroxy-2-(2-methoxypyrimidin-5-yl)ethyl]pyridin-4(1H)-one | Calcd 416.1, Found 416.1 |
| 133 | 1-biphenyl-3-yl-5-hydroxy-2-[2-hydroxy-2-(3-methoxyphenyl)ethyl]pyridin-4(1H)-one | Calcd 414.1, Found 414.1 |

TABLE 1-continued

| | Structure | IUPAC Name | Exact Mass [M + H]+ |
|---|---|---|---|
| 134 | 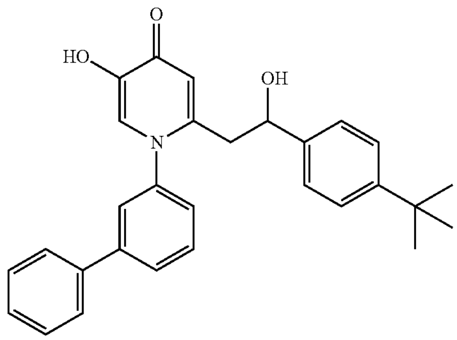 [SMILES: CC(C)(C)c1ccc(C(O)Cc2cc(=O)c(O)cn2-c2cccc(-c3ccccc3)c2)cc1] | 1-biphenyl-3-yl-2-[2-(4-tert-butylphenyl)-2-hydroxyethyl]-5-hydroxypyridin-4(1H)-one | Calcd 440.2, Found 440.2 |
| 135 | 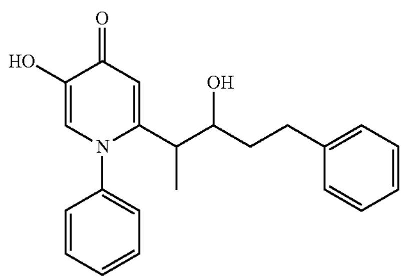 [SMILES: CC(c1cc(=O)c(O)cn1-c1ccccc1)C(O)CCc1ccccc1] | 5-hydroxy-2-(2-hydroxy-1-methyl-4-phenylbutyl)-1-phenylpyridin-4(1H)-one | Calcd 350.1, Found 350.1 |
| 136 | 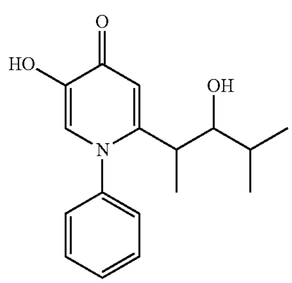 [SMILES: CC(C)C(O)C(C)c1cc(=O)c(O)cn1-c1ccccc1] | 5-hydroxy-2-(2-hydroxy-1,3-dimethylbutyl)-1-phenylpyridin-4(1H)-one | Calcd 288.1, Found 288.1 |
| 137 | 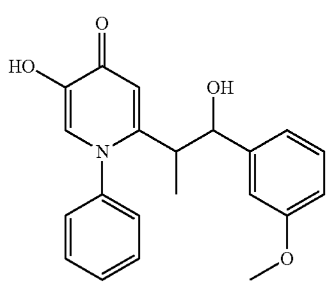 [SMILES: COc1cccc(C(O)C(C)c2cc(=O)c(O)cn2-c2ccccc2)c1] | 5-hydroxy-2-[2-hydroxy-2-(3-methoxyphenyl)-1-methylethyl]-1-phenylpyridin-4(1H)-one | Calcd 352.1, Found 352.1 |
| 138 | 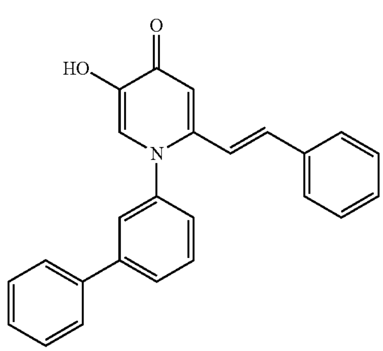 [SMILES: O=c1cc(/C=C/c2ccccc2)n(-c2cccc(-c3ccccc3)c2)cc1O] | 1-biphenyl-3-yl-5-hydroxy-2-[(E)-2-phenylethenyl]pyridin-4(1H)-one | Calcd 366.1, Found 366.1 |

TABLE 1-continued

| | Structure | IUPAC Name | Exact Mass [M + H]+ |
|---|---|---|---|
| 139 | 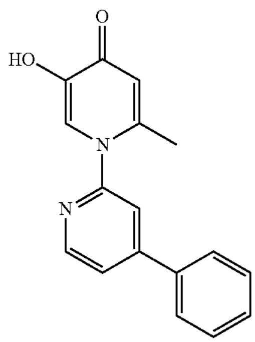 [SMILES: Cc1cc(=O)c(O)cn1-c1cc(-c2ccccc2)ccn1] | 5-hydroxy-2-methyl-4'-phenyl-4H-1,2'-bipyridin-4-one | Calcd 279.1, Found 279.1 |
| 140 | 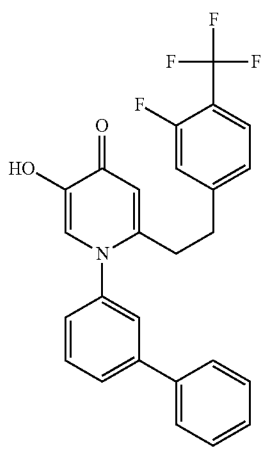 [SMILES: O=c1cc(CCc2ccc(C(F)(F)F)c(F)c2)n(-c2cccc(-c3ccccc3)c2)cc1O] | 1-biphenyl-3-yl-2-{2-[3-fluoro-4-(trifluoromethyl)phenyl]ethyl}-5-hydroxypyridin-4(1H)-one | Calcd 454.1, Found 454.1 |
| 141 | 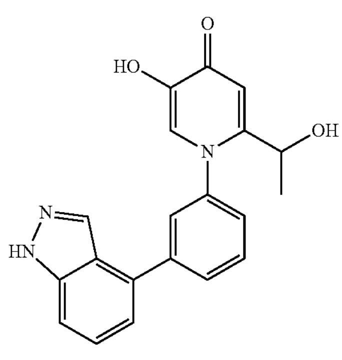 [SMILES: CC(O)c1cc(=O)c(O)cn1-c1cccc(-c2cccc3[nH]ncc23)c1] | 5-hydroxy-2-(1-hydroxyethyl)-1-[3-(1H-indazol-4-yl)phenyl]pyridin-4(1H)-one | Calcd 348.1, Found 348.1 |
| 142 | 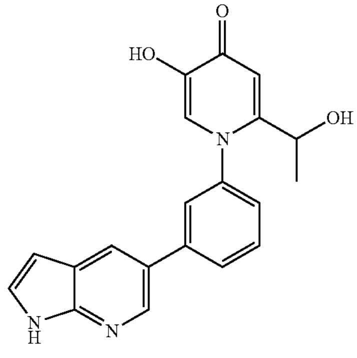 [SMILES: CC(O)c1cc(=O)c(O)cn1-c1cccc(-c2cnc3[nH]ccc3c2)c1] | 5-hydroxy-2-(1-hydroxyethyl)-1-[3-(1H-pyrrolo[2,3-b]pyridin-5-yl)phenyl]pyridin-4(1H)-one | Calcd 348.1, Found 348.1 |

TABLE 1-continued

| | Structure | IUPAC Name | Exact Mass [M + H]+ |
|---|---|---|---|
| 143 | 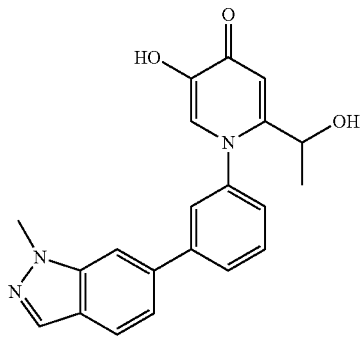 [SMILES: CC(O)c1cc(=O)c(O)cn1-c1cccc(-c2ccc3cnn(C)c3c2)c1] | 5-hydroxy-2-(1-hydroxyethyl)-1-[3-(1-methyl-1H-indazol-6-yl)phenyl]pyridin-4(1H)-one | Calcd 362.1, Found 362.1 |
| 144 | 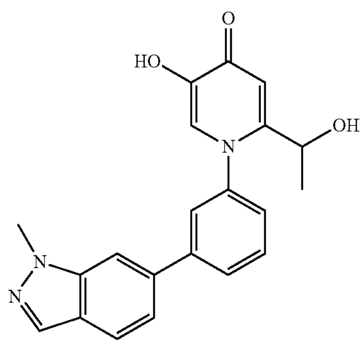 [SMILES: CC(O)c1cc(=O)c(O)cn1-c1cccc(-c2ccc3cnn(C)c3c2)c1] | 5-hydroxy-2-(1-hydroxyethyl)-1-[3-(1-methyl-1H-indazol-6-yl)phenyl]pyridin-4(1H)-one | Calcd 362.1, Found 362.1 |
| 145 | 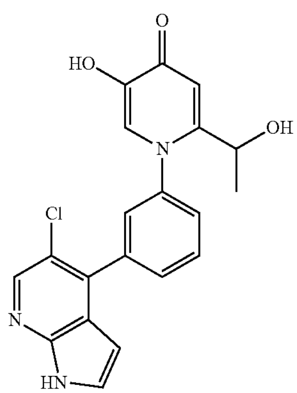 [SMILES: CC(O)c1cc(=O)c(O)cn1-c1cccc(-c2c(Cl)cnc3[nH]ccc23)c1] | 1-[3-(5-chloro-1H-pyrrolo[2,3-b]pyridin-4-yl)phenyl]-5-hydroxy-2-(1-hydroxyethyl)pyridin-4(1H)-one | Calcd 382.0, Found 382.0 |
| 146 | 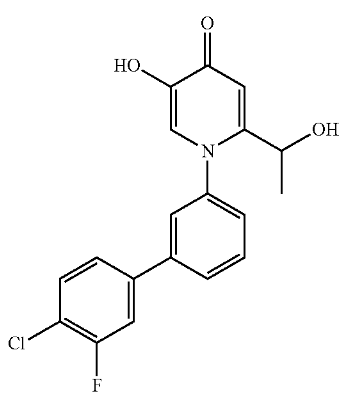 [SMILES: CC(O)c1cc(=O)c(O)cn1-c1cccc(-c2ccc(Cl)c(F)c2)c1] | 1-(4'-chloro-3'-fluorobiphenyl-3-yl)-5-hydroxy-2-(1-hydroxyethyl)pyridin-4(1H)-one | Calcd 360.0, Found 360.0 |

TABLE 1-continued
| Structure | IUPAC Name | Exact Mass [M + H]+ |
|---|---|---|
| 147 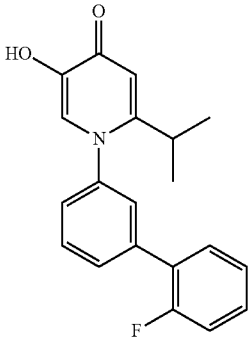 [SMILES: CC(C)c1cc(=O)c(O)cn1-c1cccc(-c2ccccc2F)c1] | 1-(2'-fluorobiphenyl-3-yl)-5-hydroxy-2-(1-methylethyl)pyridin-4(1H)-one | Calcd 324.1, Found 324.1 |
| 148 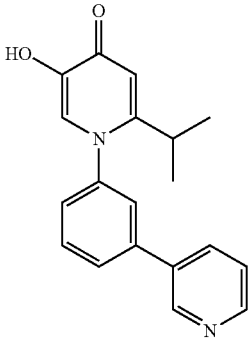 [SMILES: CC(C)c1cc(=O)c(O)cn1-c1cccc(-c2cccnc2)c1] | 5-hydroxy-2-(1-methylethyl)-1-(3-pyridin-3-ylphenyl)pyridin-4(1H)-one | Calcd 307.1, Found 307.1 |
| 149 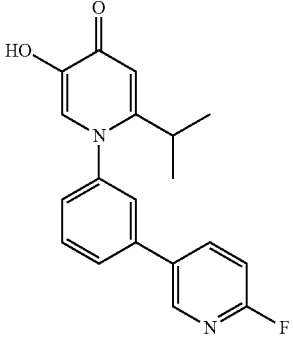 [SMILES: CC(C)c1cc(=O)c(O)cn1-c1cccc(-c2ccc(F)nc2)c1] | 1-[3-(6-fluoropyridin-3-yl)phenyl]-5-hydroxy-2-(1-methylethyl)pyridin-4(1H)-one | Calcd 325.1, Found 325,1 |
| 150 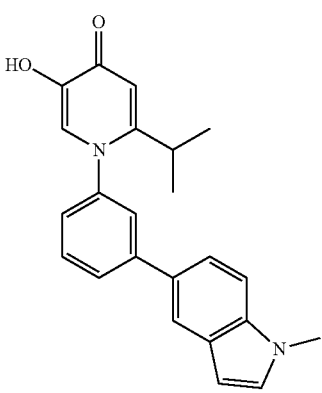 [SMILES: CC(C)c1cc(=O)c(O)cn1-c1cccc(-c2ccc3c(ccn3C)c2)c1] | 5-hydroxy-2-(1-methylethyl)-1-[3-(1-methyl-1H-indol-5-yl)phenyl]pyridin-4(1H)-one | Calcd 359.1, Found 359.1 |

TABLE 1-continued

| | Structure | IUPAC Name | Exact Mass [M + H]+ |
|---|---|---|---|
| 151 | 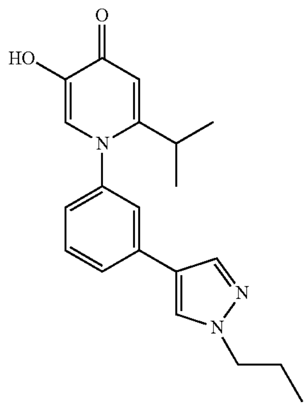 [SMILES: CCCn1cc(-c2cccc(-n3cc(O)c(=O)cc3C(C)C)c2)cn1] | 5-hydroxy-2-(1-methylethyl)-1-[3-(1-propyl-1H-pyrazol-4-yl)phenyl]pyridin-4(1H)-one | Calcd 338.1, Found 338.1 |
| 152 | 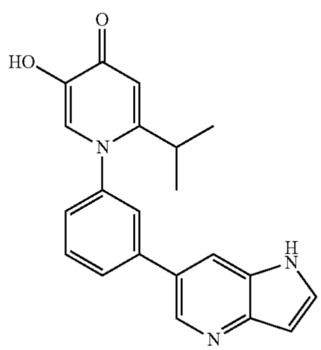 [SMILES: CC(C)c1cc(=O)c(O)cn1-c1cccc(-c2cnc3cc[nH]c3c2)c1] | 5-hydroxy-2-(1-methylethyl)-1-[3-(1H-pyrrolo[3,2-b]pyridin-6-yl)phenyl]pyridin-4(1H)-one | Calcd 346.1, Found 346.1 |
| 153 | 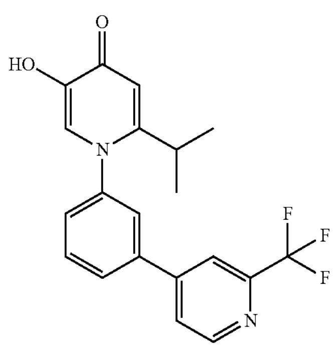 [SMILES: CC(C)c1cc(=O)c(O)cn1-c1cccc(-c2ccnc(C(F)(F)F)c2)c1] | 5-hydroxy-2-(1-methylethyl)-1-{3-[2-(trifluoromethyl)pyridin-4-yl]phenyl}pyridin-4(1H)-one | Calcd 375.1, Found 375.1 |
| 154 | 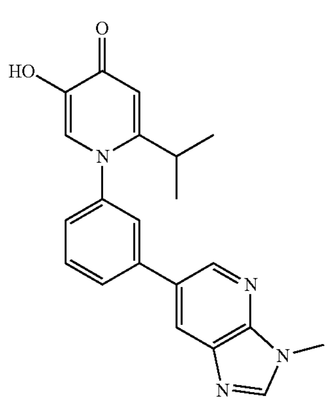 [SMILES: CC(C)c1cc(=O)c(O)cn1-c1cccc(-c2cnc3c(c2)ncn3C)c1] | 5-hydroxy-2-(1-methylethyl)-1-[3-(3-methyl-3H-imidazo[4,5-b]pyridin-6-yl)phenyl]pyridin-4(1H)-one | Calcd 361.1, Found 361.1 |

TABLE 1-continued

| Structure | IUPAC Name | Exact Mass [M + H]+ |
|---|---|---|
| 155 | 5-hydroxy-1-(3-imidazo[1,2-a]pyridin-6-ylphenyl)-2-(1-methylethyl)pyridin-4(1H)-one | Calcd 346.1, Found 346.1 |
| 156 | 1-[3-(2-fluoropyridin-4-yl)phenyl]-5-hydroxy-2-(1-methylethyl)pyridin-4(1H)-one | Calcd 325.1, Found 325.1 |
| 157 | 5-hydroxy-2-[2-hydroxy-2-(6-methylpyridin-2-yl)ethyl]-1-(4'-methylbiphenyl-3-yl)pyridin-4(1H)-one | Calcd 413.1, Found 413.1 |
| 158 | 1-[3-(6-fluoropyridin-3-yl)phenyl]-5-hydroxy-2-[2-hydroxy-2-(6-methylpyridin-2-yl)ethyl]pyridin-4(1H)-one | Calcd 418.1, Found 418.1 |

TABLE 1-continued

| Structure | IUPAC Name | Exact Mass [M + H]+ |
|---|---|---|
| 159 | 5-hydroxy-2-[2-hydroxy-2-(6-methylpyridin-2-yl)ethyl]-1-[3-(1-methyl-1H-indol-5-yl)phenyl]pyridin-4(1H)-one | Calcd 452.1, Found 452.1 |
| 160 | 1-[3'-(dimethylamino)biphenyl-3-yl]-5-hydroxy-2-[2-hydroxy-2-(6-methylpyridin-2-yl)ethyl]pyridin-4(1H)-one | Calcd 442.2, Found 442.2 |
| 161 | 5-hydroxy-2-[2-hydroxy-2-(6-methylpyridin-2-yl)ethyl]-1-(3-[1,2,4]triazolo[1,5-a]pyridin-6-ylphenyl)pyridin-4(1H)-one | Calcd 440.1, Found 440.1 |
| 162 | 5-hydroxy-2-[2-hydroxy-2-(6-methylpyridin-2-yl)ethyl]-1-[3-(1H-pyrrolo[2,3-b]pyridin-5-yl)phenyl]pyridin-4(1H)-one | Calcd 439.1, Found 439.1 |

TABLE 1-continued

| Structure | IUPAC Name | Exact Mass [M + H]+ |
|---|---|---|
| 163 | 1-biphenyl-3-yl-2-(2-hydroxy-4-phenylbutyl)-5-[(4-methoxybenzyl)oxy]pyridin-4(1H)-one | Calcd 532.2, Found 532.2 |
| 164 | 1-biphenyl-3-yl-2-{2-[3-fluoro-4-(trifluoromethyl)phenyl]-2-hydroxyethyl}-5-hydroxypyridin-4(1H)-one | Calcd 470.1, Found 470.1 |
| 165 | 4'-(4-cyclopropylphenyl)-3'-fluoro-3-hydroxy-4H-1,2'-bipyridin-4-one | Calcd 323.1, Found 323.1 |
| 166 | 3'-fluoro-3-hydroxy-4'-(1,2,3,4-tetrahydroisoquinolin-6-yl)-4H-1,2'-bipyridin-4-one | Calcd 338.1, Found 338.1 |

TABLE 1-continued

| | Structure | IUPAC Name | Exact Mass [M + H]+ |
|---|---|---|---|
| 167 | 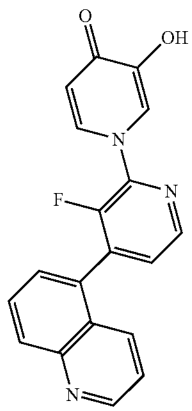 [SMILES: O=c1ccn(-c2nccc(-c3cccc4ncccc34)c2F)cc1O] | 3'-fluoro-3-hydroxy-4'-quinolin-5-yl-4H-1,2'-bipyridin-4-one | Calcd 334.0, Found 334.0 |
| 168 | 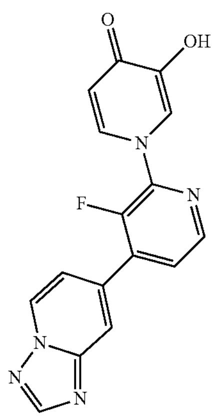 [SMILES: O=c1ccn(-c2nccc(-c3ccn4ncnc4c3)c2F)cc1O] | 3'-fluoro-3-hydroxy-4'-[1,2,4]triazolo[1,5-a]pyridin-7-yl-4H-1,2'-bipyridin-4-one | Calcd 324.0, Found 324.0 |
| 169 | 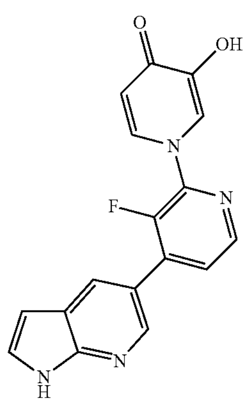 [SMILES: O=c1ccn(-c2nccc(-c3cnc4[nH]ccc4c3)c2F)cc1O] | 3'-fluoro-3-hydroxy-4'-(1H-pyrrolo[2,3-b]pyridin-5-yl)-4H-1,2'-bipyridin-4-one | Calcd 323.0, Found 323.0 |
| 170 | 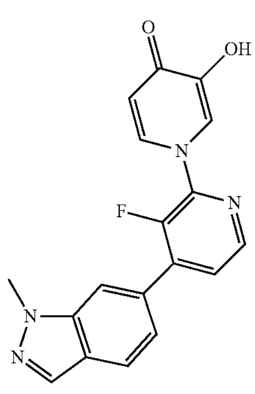 [SMILES: Cn1ncc2ccc(-c3ccnc(-n4ccc(=O)c(O)c4)c3F)cc21] | 3'-fluoro-3-hydroxy-4'-(1-methyl-1H-indazol-6-yl)-4H-1,2'-bipyridin-4-one | Calcd 337.1, Found 337.1 |

TABLE 1-continued
| Structure | IUPAC Name | Exact Mass [M + H]+ |
|---|---|---|
| 171 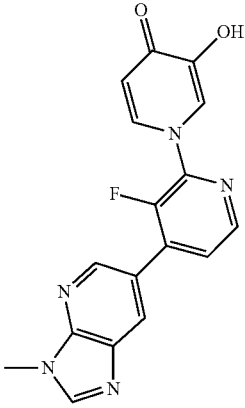 [SMILES: Cn1cnc2cc(-c3ccnc(-n4ccc(=O)c(O)c4)c3F)cnc21] | 3'-fluoro-3-hydroxy-4'-(3-methyl-3H-imidazo[4,5-b]pyridin-6-yl)-4H-1,2'-bipyridin-4-one | Calcd 338.1, Found 338.1 |
| 172 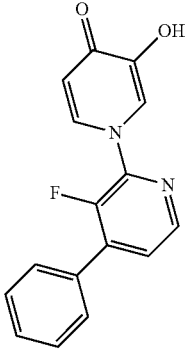 [SMILES: O=c1ccn(-c2nccc(-c3ccccc3)c2F)cc1O] | 3'-fluoro-3-hydroxy-4'-phenyl-4H-1,2'-bipyridin-4-one | Calcd 283.0, Found 283.0 |
| 173 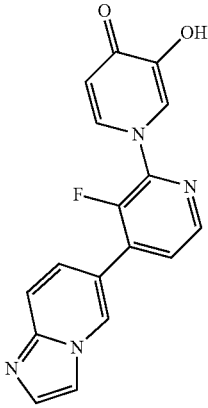 [SMILES: O=c1ccn(-c2nccc(-c3ccc4nccn4c3)c2F)cc1O] | 3'-fluoro-3-hydroxy-4'-imidazo[1,2-a]pyridin-6-yl-4H-1,2'-bipyridin-4-one | Calcd 323.0, Found 323.0 |

TABLE 1-continued

| | Structure | IUPAC Name | Exact Mass [M + H]+ |
|---|---|---|---|
| 174 | 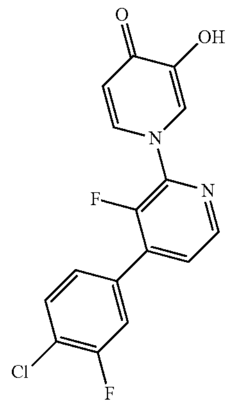 [SMILES: O=c1ccn(-c2nccc(-c3ccc(Cl)c(F)c3)c2F)cc1O] | 4'-(4-chloro-3-fluorophenyl)-3'-fluoro-3-hydroxy-4H-1,2'-bipyridin-4-one | Calcd 335.0, Found 335.0 |
| 175 | 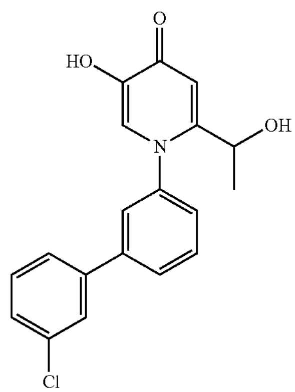 [SMILES: CC(O)c1cc(=O)c(O)cn1-c1cccc(-c2cccc(Cl)c2)c1] | 1-(3'-chlorobiphenyl-3-yl)-5-hydroxy-2-(1-hydroxyethyl)pyridin-4(1H)-one | Calcd 342.0, Found 342.0 |
| 176 | 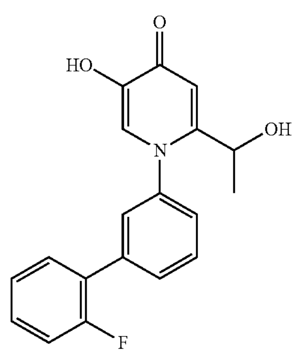 [SMILES: CC(O)c1cc(=O)c(O)cn1-c1cccc(-c2ccccc2F)c1] | 1-(2'-fluorobiphenyl-3-yl)-5-hydroxy-2-(1-hydroxyethyl)pyridin-4(1H)-one | Calcd 326.1, Found 326.1 |
| 177 | 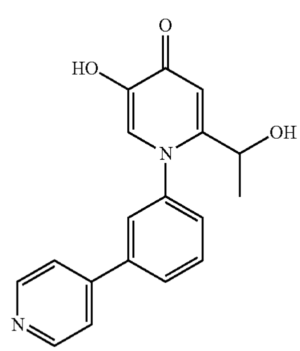 [SMILES: CC(O)c1cc(=O)c(O)cn1-c1cccc(-c2ccncc2)c1] | 5-hydroxy-2-(1-hydroxyethyl)-1-(3-pyridin-4-ylphenyl)pyridin-4(1H)-one | Calcd 309.1, Found 309.1 |

TABLE 1-continued

| | Structure | IUPAC Name | Exact Mass [M + H]+ |
|---|---|---|---|
| 178 | 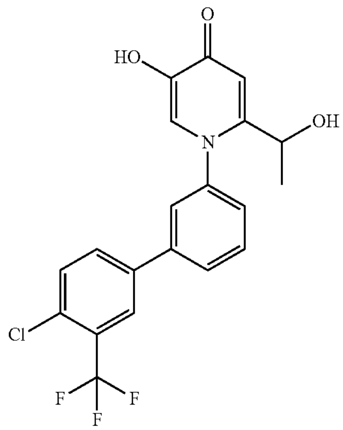 [SMILES: CC(O)c1cc(=O)c(O)cn1-c1cccc(-c2ccc(Cl)c(C(F)(F)F)c2)c1] | 1-[4'-chloro-3'-(trifluoromethyl)biphen-yl-3-yl]-5-hydroxy-2-(1-hydroxyethyl)pyridin-4(1H)-one | Calcd 410.0, Found 410.0 |
| 179 | 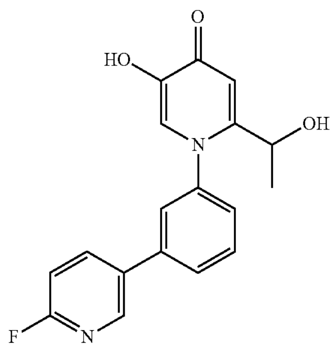 [SMILES: CC(O)c1cc(=O)c(O)cn1-c1cccc(-c2ccc(F)nc2)c1] | 1-[3-(6-fluoropyridin-3-yl)phenyl]-5-hydroxy-2-(1-hydroxyethyl)pyridin-4(1H)-one | Calcd 327.1, Found 327.1 |
| 180 | 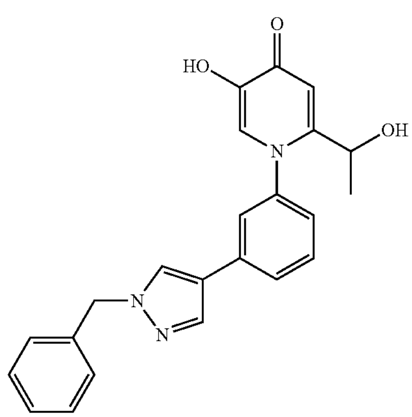 [SMILES: CC(O)c1cc(=O)c(O)cn1-c1cccc(-c2cnn(Cc3ccccc3)c2)c1] | 1-[3-(1-benzyl-1H-pyrazol-4-yl)phenyl]-5-hydroxy-2-(1-hydroxyethyl)pyridin-4(1H)-one | Calcd 388.1, Found 388.1 |
| 181 | 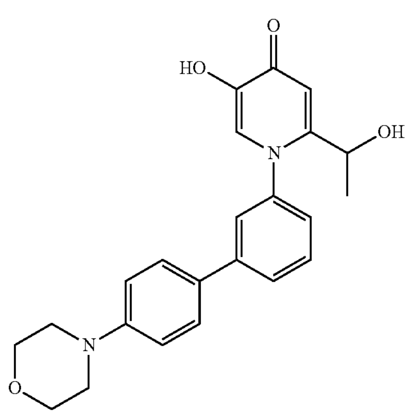 [SMILES: CC(O)c1cc(=O)c(O)cn1-c1cccc(-c2ccc(N3CCOCC3)cc2)c1] | 5-hydroxy-2-(1-hydroxyethyl)-1-(4'-morpholin-4-ylbiphenyl-3-yl)pyridin-4(1H)-one | Calcd 393.1, Found 393.1 |

TABLE 1-continued
| Structure | IUPAC Name | Exact Mass [M + H]+ |
|---|---|---|
| 182 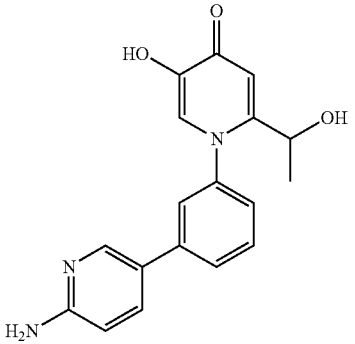 [SMILES: CC(O)c1cc(=O)c(O)cn1-c1cccc(-c2ccc(N)nc2)c1] | 1-[3-(6-aminopyridin-3-yl)phenyl]-5-hydroxy-2-(1-hydroxyethyl)pyridin-4(1H)-one | Calcd 324.1, Found 324.1 |
| 183 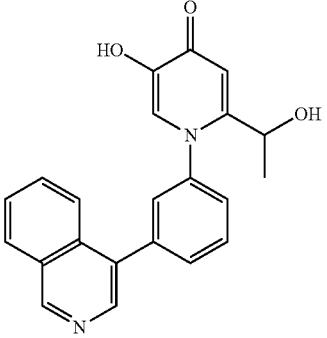 [SMILES: CC(O)c1cc(=O)c(O)cn1-c1cccc(-c2cncc3ccccc23)c1] | 5-hydroxy-2-(1-hydroxyethyl)-1-(3-isoquinolin-4-ylphenyl)pyridin-4(1H)-one | Calcd 359.1, Found 359.1 |
| 184 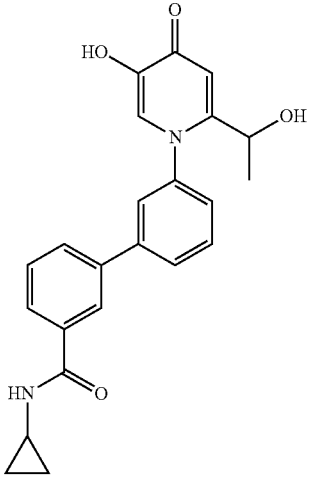 [SMILES: CC(O)c1cc(=O)c(O)cn1-c1cccc(-c2cccc(C(=O)NC3CC3)c2)c1] | N-cyclopropyl-3'-[5-hydroxy-2-(1-hydroxyethyl)-4-oxopyridin-1(4H)-yl]biphenyl-3-carboxamide | Calcd 391.1, Found 391.1 |

TABLE 1-continued

| Structure | IUPAC Name | Exact Mass [M + H]+ |
|---|---|---|
| 185 | 5-hydroxy-2-(1-hydroxyethyl)-1-(3-{6-[(2-morpholin-4-ylethyl)amino]pyridin-3-yl}phenyl)pyridin-4(1H)-one | Calcd 437.2, Found 437.2 |
| 186 | 5-hydroxy-2-(1-hydroxyethyl)-1-[3-(1H-pyrrolo[3,2-b]pyridin-6-yl)phenyl]pyridin-4(1H)-one | Calcd 348.1, Found 348.1 |
| 187 | 1-biphenyl-3-yl-5-hydroxy-2-{2-hydroxy-2-[1-(3-methylphenyl)-1H-imidazol-2-yl]ethyl}pyridin-4(1H)-one | Calcd 464.1, Found 464.1 |
| 188 | 1-biphenyl-3-yl-5-hydroxy-2-(2-hydroxy-2-pyrazolo[1,5-a]pyridin-7-ylethyl)pyridin-4(1H)-one | Calcd 424.1, Found 424.1 |

TABLE 1-continued

| Structure | IUPAC Name | Exact Mass [M + H]+ |
|---|---|---|
| 189 | 1-biphenyl-3-yl-5-hydroxy-2-[2-hydroxy-2-(1,6-naphthyridin-8-yl)ethyl]pyridin-4(1H)-one | Calcd 436.1, Found 436.1 |
| 190 | 1-biphenyl-3-yl-2-[2-(6-ethoxypyridin-2-yl)-2-hydroxyethyl]-5-hydroxypyridin-4(1H)-one | Calcd 429.1, Found 429.1 |
| 191 | 1-biphenyl-3-yl-5-hydroxy-2-[2-hydroxy-2-(5-methyl-1,2,4-oxadiazol-3-yl)ethyl]pyridin-4(1H)-one | Calcd 390.1, Found 390.1 |
| 192 | 1-biphenyl-3-yl-5-hydroxy-2-{2-hydroxy-2-[6-(trifluoromethyl)pyridin-3-yl]ethyl}pyridin-4(1H)-one | Calcd 453.1, Found 453.1 |

TABLE 1-continued

| | Structure | IUPAC Name | Exact Mass [M + H]+ |
|---|---|---|---|
| 193 | 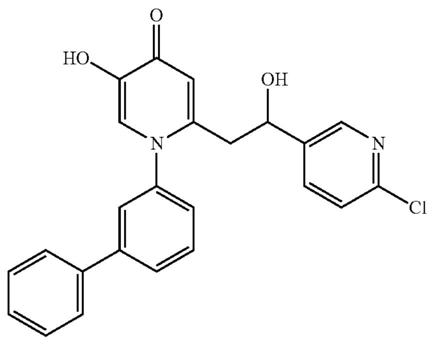 [SMILES: O=c1cc(CC(O)c2ccc(Cl)nc2)n(-c2cccc(-c3ccccc3)c2)cc1O] | 1-biphenyl-3-yl-2-[2-(6-chloropyridin-3-yl)-2-hydroxyethyl]-5-hydroxypyridin-4(1H)-one | Calcd 419.1, Found 419.1 |
| 194 | 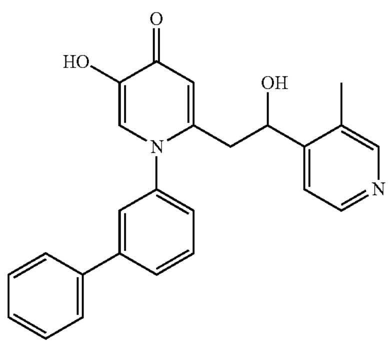 [SMILES: Cc1cnccc1C(O)Cc1cc(=O)c(O)cn1-c1cccc(-c2ccccc2)c1] | 1-biphenyl-3-yl-5-hydroxy-2-[2-hydroxy-2-(3-methylpyridin-4-yl)ethyl]pyridin-4(1H)-one | Calcd 399.1, Found 399.1 |
| 195 | 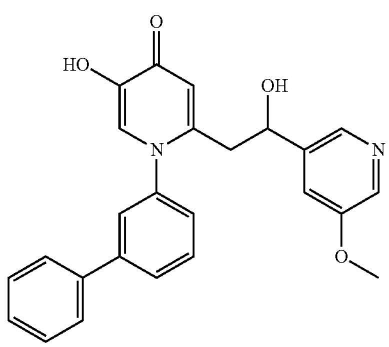 [SMILES: COc1cncc(C(O)Cc2cc(=O)c(O)cn2-c2cccc(-c3ccccc3)c2)c1] | 1-biphenyl-3-yl-5-hydroxy-2-[2-hydroxy-2-(5-methoxypyridin-3-yl)ethyl]pyridin-4(1H)-one | Calcd 415.1, Found 415.1 |
| 196 | 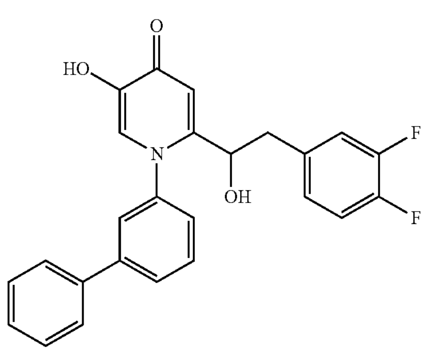 [SMILES: O=c1cc(C(O)Cc2ccc(F)c(F)c2)n(-c2cccc(-c3ccccc3)c2)cc1O] | 1-biphenyl-3-yl-2-[2-(3,4-difluorophenyl)-1-hydroxyethyl]-5-hydroxypyridin-4(1H)-one | Calcd 420.1, Found 420.1 |

TABLE 1-continued

| | Structure | IUPAC Name | Exact Mass [M + H]+ |
|---|---|---|---|
| 197 | 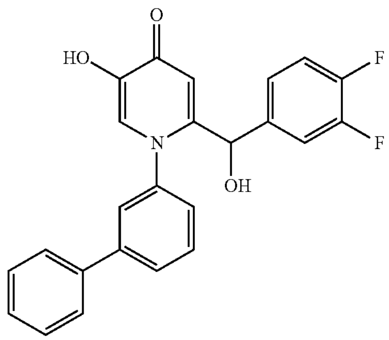 [SMILES: O=c1cc(C(O)c2ccc(F)c(F)c2)n(-c2cccc(-c3ccccc3)c2)cc1O] | 1-biphenyl-3-yl-2-[(3,4-difluorophenyl)(hydroxy)methyl]-5-hydroxypyridin-4(1H)-one | Calcd 406.1, Found 406.1 |
| 198 | 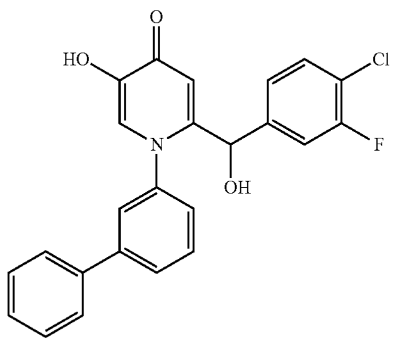 [SMILES: O=c1cc(C(O)c2ccc(Cl)c(F)c2)n(-c2cccc(-c3ccccc3)c2)cc1O] | 1-biphenyl-3-yl-2-[(4-chloro-3-fluorophenyl)(hydroxy)methyl]-5-hydroxypyridin-4(1H)-one | Calcd 422.0, Found 422.0 |
| 199 | 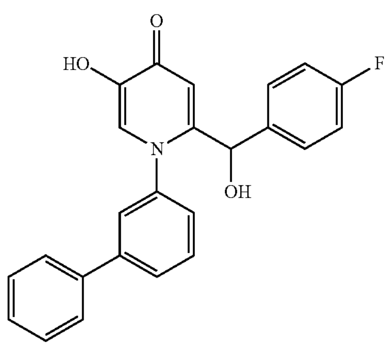 [SMILES: O=c1cc(C(O)c2ccc(F)cc2)n(-c2cccc(-c3ccccc3)c2)cc1O] | 1-biphenyl-3-yl-2-[(4-fluorophenyl)(hydroxy)methyl]-5-hydroxypyridin-4(1H)-one | Calcd 388.1, Found 388.1 |
| 200 | 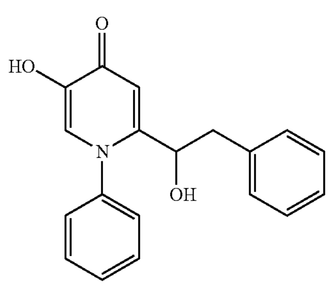 [SMILES: O=c1cc(C(O)Cc2ccccc2)n(-c2ccccc2)cc1O] | 5-hydroxy-2-(1-hydroxy-2-phenylethyl)-1-phenylpyridin-4(1H)-one | Calcd 308.1, Found 308.1 |
| 201 | 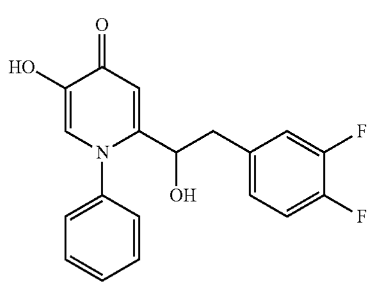 [SMILES: O=c1cc(C(O)Cc2ccc(F)c(F)c2)n(-c2ccccc2)cc1O] | 2-[2-(3,4-difluorophenyl)-1-hydroxyethyl]-5-hydroxy-1-phenylpyridin-4(1H)-one | Calcd 344.1, Found 344.1 |

TABLE 1-continued

| | Structure | IUPAC Name | Exact Mass [M + H]+ |
|---|---|---|---|
| 202 | 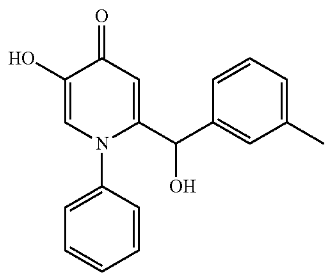 [SMILES: Cc1cccc(C(O)c2cc(=O)c(O)cn2-c2ccccc2)c1] | 5-hydroxy-2-[hydroxy(3-methylphenyl)methyl]-1-phenylpyridin-4(1H)-one | Calcd 308.1, Found 308.1 |
| 203 | 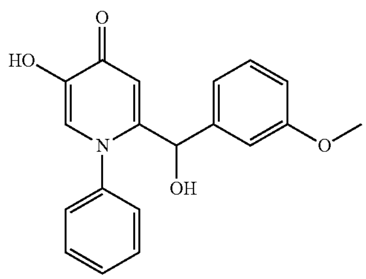 [SMILES: COc1cccc(C(O)c2cc(=O)c(O)cn2-c2ccccc2)c1] | 5-hydroxy-2-[hydroxy(3-methoxyphenyl)methyl]-1-phenylpyridin-4(1H)-one | Calcd 324.1, Found 324.1 |
| 204 | 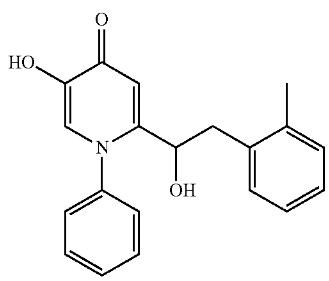 [SMILES: Cc1ccccc1CC(O)c1cc(=O)c(O)cn1-c1ccccc1] | 5-hydroxy-2-[1-hydroxy-2-(2-methylphenyl)ethyl]-1-phenylpyridin-4(1H)-one | Calcd 322.1, Found 322.1 |
| 205 | 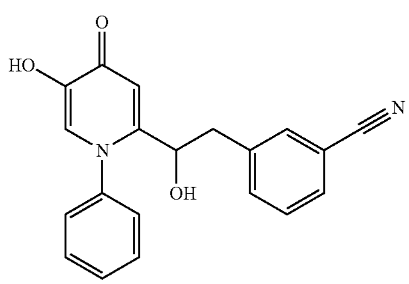 [SMILES: N#Cc1cccc(CC(O)c2cc(=O)c(O)cn2-c2ccccc2)c1] | 3-[2-hydroxy-2-(5-hydroxy-4-oxo-1-phenyl-1,4-dihydropyridin-2-yl)ethyl]benzonitrile | Calcd 333.1, Found 333.1 |
| 206 | 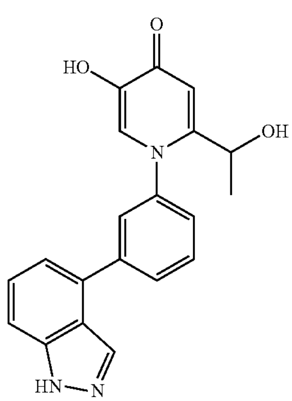 [SMILES: CC(O)c1cc(=O)c(O)cn1-c1cccc(-c2cccc3[nH]ncc23)c1] | 5-hydroxy-2-(1-hydroxyethyl)-1-[3-(1H-indazol-4-yl)phenyl]pyridin-4(1H)-one | Calcd 348.1, Found 348.1 |

TABLE 1-continued
| Structure | IUPAC Name | Exact Mass [M + H]+ |
|---|---|---|
| 207 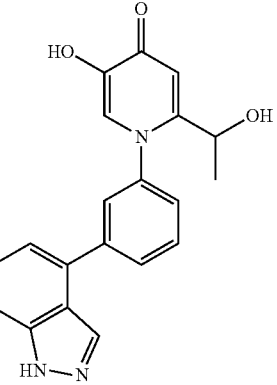 | 5-hydroxy-2-(1-hydroxyethyl)-1-[3-(1H-indazol-4-yl)phenyl]pyridin-4(1H)-one | Calcd 348.1, Found 348.1 |
| 208 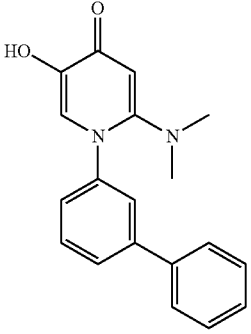 [SMILES: CN(C)c1cc(=O)c(O)cn1-c1cccc(-c2ccccc2)c1] | 1-biphenyl-3-yl-2-(dimethylamino)-5-hydroxypyridin-4(1H)-one | Calcd 307.4, Found 307.4 |
| 209 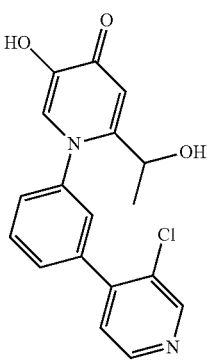 [SMILES: CC(O)c1cc(=O)c(O)cn1-c1cccc(-c2ccncc2Cl)c1] | 1-[3-(3-chloropyridin-4-yl)phenyl]-5-hydroxy-2-(1-hydroxyethyl)pyridin-4(1H)-one | Calcd 343.8, Found 343.0 |
| 210 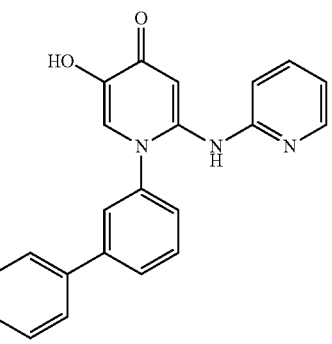 | 1-biphenyl-3-yl-5-hydroxy-2-(pyridin-2-ylamino)pyridin-4(1H)-one | Calcd 356.4, Found 356.4 |

TABLE 1-continued

| Structure | IUPAC Name | Exact Mass [M + H]+ |
|---|---|---|
| 211 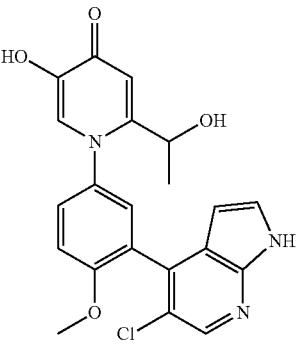 [SMILES: COc1ccc(-n2cc(O)c(=O)cc2C(C)O)cc1-c1c(Cl)cnc2[nH]ccc12] | 1-[3-(5-chloro-1H-pyrrolo[2,3-b]pyriclin-4-yl)-4-methoxyphenyl]-5-hydroxy-2-(1-hydroxyethyl)pyridin-4(1H)-one | Calcd 412.8, Found 412.4 |
| 212 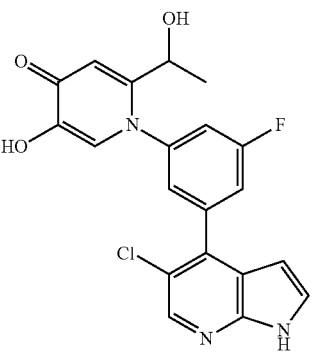 [SMILES: CC(O)c1cc(=O)c(O)cn1-c1cc(F)cc(-c2c(Cl)cnc3[nH]ccc23)c1] | 1-[3-(5-chloro-1H-pyrrolo[2,3-b]pyridin-4-yl)-5-fluorophenyl]-5-hydroxy-2-(1-hydroxyethyl)pyridin-4(1H)-one | Calcd 400.8, Found 400.0 |
| 213 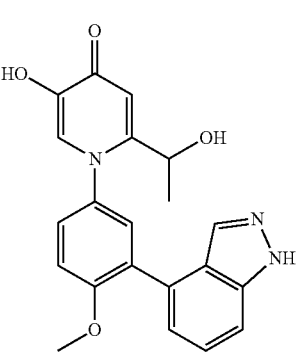 [SMILES: COc1ccc(-n2cc(O)c(=O)cc2C(C)O)cc1-c1cccc2[nH]ncc12] | 5-hydroxy-2-(1-hydroxyethyl)-1-[3-(1H-indazol-4-yl)-4-methoxyphenyl]pyridin-4(1H)-one | Calcd 378.4, Found 378.4 |
| 214 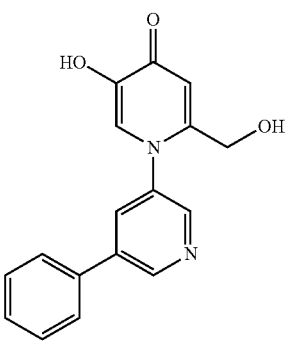 [SMILES: O=c1cc(CO)n(-c2cncc(-c3ccccc3)c2)cc1O] | 5-hydroxy-2-(hydroxymethyl)-5'-phenyl-4H-1,3'-bipyridin-4-one | Calcd 295.1, Found 295.1 |

TABLE 1-continued

| | Structure | IUPAC Name | Exact Mass [M + H]+ |
|---|---|---|---|
| 215 | 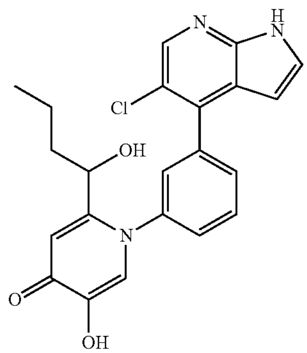 [SMILES: CCCC(O)c1cc(=O)c(O)cn1-c1cccc(-c2c(Cl)cnc3[nH]ccc23)c1] | 1-[3-(5-chloro-1H-pyrrolo[2,3-b]pyridin-4-yl)phenyl]-5-hydroxy-2-(1-hydroxybutyl)pyridin-4(1H)-one | Calcd 410.1, Found 410.1 |
| 216 | 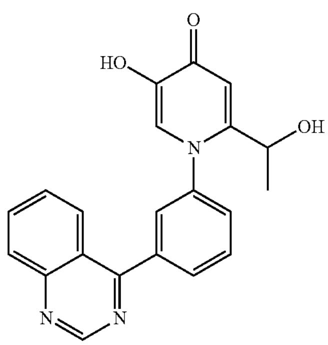 [SMILES: CC(O)c1cc(=O)c(O)cn1-c1cccc(-c2ncnc3ccccc23)c1] | 5-hydroxy-2-(1-hydroxyethyl)-1-(3-quinazolin-4-ylphenyl)pyridin-4(1H)-one | Calcd 360.1, Found 360.1 |
| 217 | 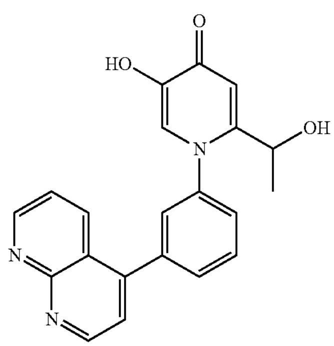 [SMILES: CC(O)c1cc(=O)c(O)cn1-c1cccc(-c2ccnc3ncccc23)c1] | 5-hydroxy-2-(1-hydroxyethyl)-1-[3-(1,8-naphthyridin-4-yl)phenyl]pyridin-4(1H)-one | Calcd 360.1, Found 360.1 |
| 218 | 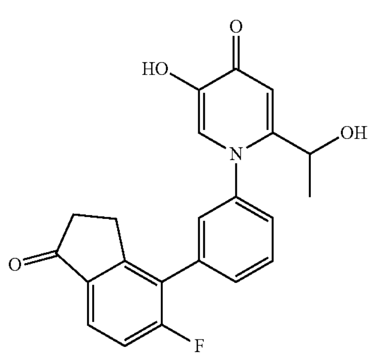 [SMILES: CC(O)c1cc(=O)c(O)cn1-c1cccc(-c2c(F)ccc3c2CCC3=O)c1] | 1-[3-(5-fluoro-1-oxo-2,3-dihydro-1H-inden-4-yl)phenyl]-5-hydroxy-2-(1-hydroxyethyl)pyridin-4(1H)-one | Calcd 380.1, Found 380.1 |

TABLE 1-continued
| Structure | IUPAC Name | Exact Mass [M + H]+ |
|---|---|---|
| 219 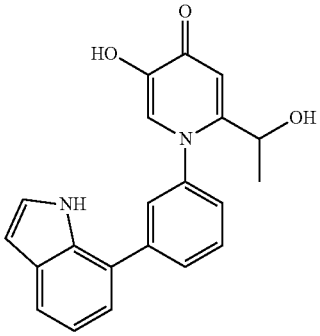 [SMILES: CC(O)c1cc(=O)c(O)cn1-c1cccc(-c2cccc3cc[nH]c23)c1] | 5-hydroxy-2-(1-hydroxyethyl)-1-[3-(1H-indol-7-yl)phenyl]pyridin-4(1H)-one | Calcd 347.1, Found 347.1 |
| 220 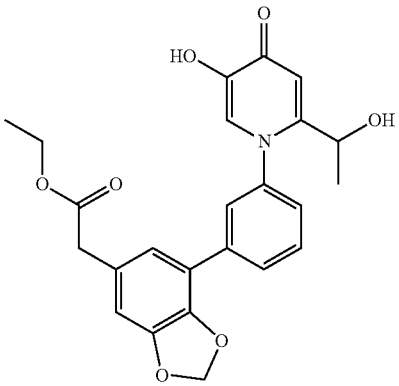 [SMILES: CCOC(=O)Cc1cc2c(c(-c3cccc(-n4cc(O)c(=O)cc4C(C)O)c3)c1)OCO2] | ethyl (7-{3-[5-hydroxy-2-(1-hydroxyethyl)-4-oxopyridin-1(4H)-yl]phenyl}-1,3-benzodioxol-5-yl)acetate | Calcd 438.1, Found 438.1 |
| 221 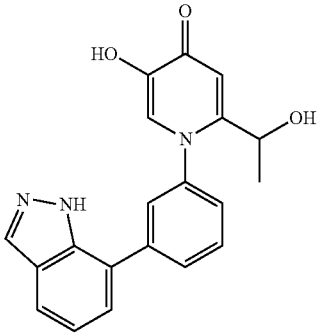 [SMILES: CC(O)c1cc(=O)c(O)cn1-c1cccc(-c2cccc3cn[nH]c23)c1] | 5-hydroxy-2-(1-hydroxyethyl)-1-[3-(1H-indazol-7-yl)phenyl]pyridin-4(1H)-one | Calcd 348.1, Found 348.1 |
| 222 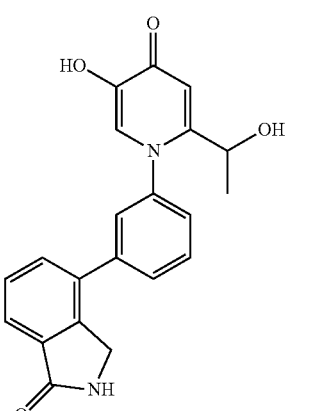 | 4-{3-[5-hydroxy-2-(1-hydroxyethyl)-4-oxopyridin-1(4H)-yl]phenyl}-2,3-dihydro-1H-isoindol-1-one | Calcd 363.1, Found 363.1 |

TABLE 1-continued

| | Structure | IUPAC Name | Exact Mass [M + H]+ |
|---|---|---|---|
| 223 | 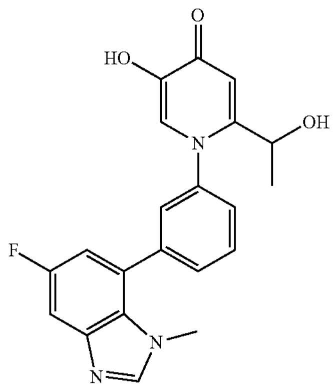 [SMILES: CC(O)c1cc(=O)c(O)cn1-c1cccc(-c2cc(F)cc3ncn(C)c23)c1] | 1-[3-(5-fluoro-1-methyl-1H-benzimidazol-7-yl)phenyl]-5-hydroxy-2-(1-hydroxyethyl)pyridin-4(1H)-one | Calcd 380.1, Found 380.1 |
| 224 | 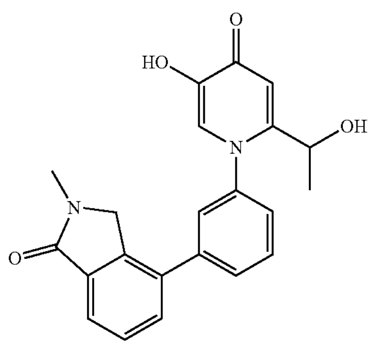 [SMILES: CC(O)c1cc(=O)c(O)cn1-c1cccc(-c2cccc3c2CN(C)C3=O)c1] | 4-{3-[5-hydroxy-2-(1-hydroxyethyl)-4-oxopyridin-1(4H)-yl]phenyl}-2-methyl-2,3-dihydro-1H-isoindol-1-one | Calcd 377.1, Found 377.1 |
| 225 | 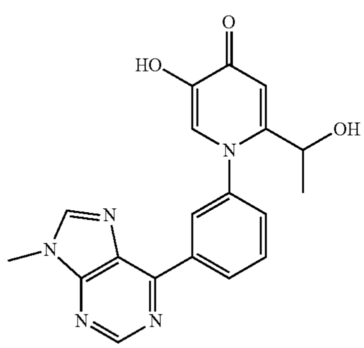 [SMILES: CC(O)c1cc(=O)c(O)cn1-c1cccc(-c2ncnc3c2ncn3C)c1] | 5-hydroxy-2-(1-hydroxyethyl)-1-[3-(9-methyl-9H-purin-6-yl)phenyl]pyridin-4(1H)-one | Calcd 364.1, Found 364.1 |
| 226 | 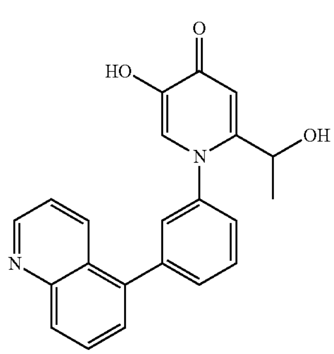 [SMILES: CC(O)c1cc(=O)c(O)cn1-c1cccc(-c2cccc3ncccc23)c1] | 5-hydroxy-2-(1-hydroxyethyl)-1-(3-quinolin-5-ylphenyl)pyridin-4(1H)-one | Calcd 359.4, Found 359.4 |

TABLE 1-continued

| Structure | IUPAC Name | Exact Mass [M + H]+ |
|---|---|---|
| 227 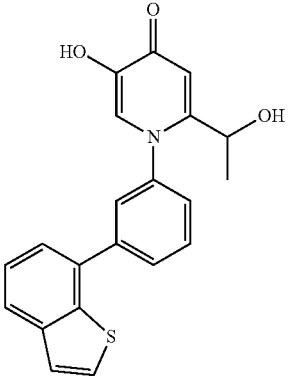 [SMILES: CC(O)c1cc(=O)c(O)cn1-c1cccc(-c2cccc3ccsc23)c1] | 1-[3-(1-benzothiophen-7-yl)phenyl]-5-hydroxy-2-(1-hydroxyethyl)pyridin-4(1H)-one | Calcd 364.1, Found 364.1 |
| 228 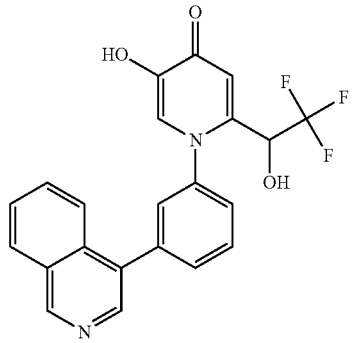 [SMILES: O=c1cc(C(O)C(F)(F)F)n(-c2cccc(-c3cncc4ccccc34)c2)cc1O] | 5-hydroxy-1-(3-isoquinolin-4-ylphenyl)-2-(2,2,2-trifluoro-1-hydroxyethyl)pyridin-4(1H)-one | Calcd 413.4, Found 413.3 |
| 229 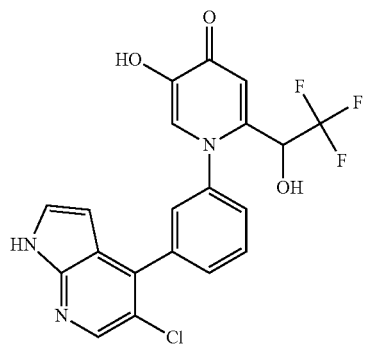 [SMILES: O=c1cc(C(O)C(F)(F)F)n(-c2cccc(-c3c(Cl)cnc4[nH]ccc34)c2)cc1O] | 1-[3-(5-chloro-1H-pyrrolo[2,3-b]pyridin-4-yl)phenyl]-5-hydroxy-2-(2,2,2-trifluoro-1-hydroxyethyl)pyridin-4(1H)-one | Calcd 436.8, Found 436.2 |
| 230 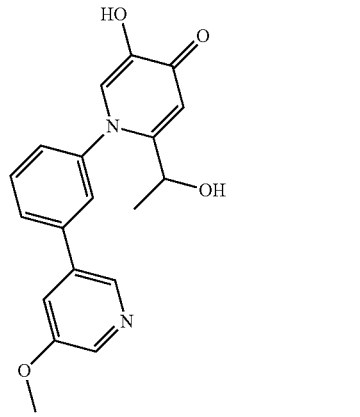 [SMILES: COc1cncc(-c2cccc(-n3cc(O)c(=O)cc3C(C)O)c2)c1] | 5-hydroxy-2-(1-hydroxyethyl)-1-[3-(5-methoxypyridin-3-yl)phenyl]pyridin-4(1H)-one | Calcd 339.1, Found 339.1 |

TABLE 1-continued

| | Structure | IUPAC Name | Exact Mass [M + H]+ |
|---|---|---|---|
| 231 | 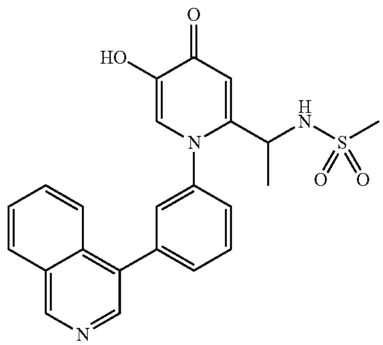 [SMILES: CC(NS(C)(=O)=O)c1cc(=O)c(O)cn1-c1cccc(-c2cncc3ccccc23)c1] | N-{1-[5-hydroxy-1-(3-isoquinolin-4-ylphenyl)-4-oxo-1,4-dihydropyridin-2-yl]ethyl}methanesulfonamide | Calcd 436.1, Found 436.1 |
| 232 | 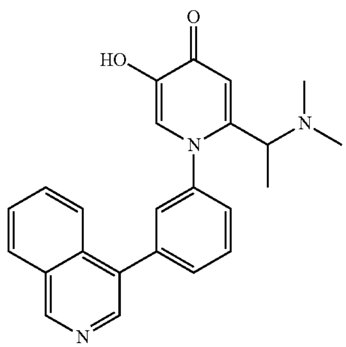 [SMILES: CC(c1cc(=O)c(O)cn1-c1cccc(-c2cncc3ccccc23)c1)N(C)C] | 2-[1-(dimethylamino)ethyl]-5-hydroxy-1-(3-isoquinolin-4-ylphenyl)pyridin-4(1H)-one | Calcd 386.1, Found 386.1 |
| 233 | 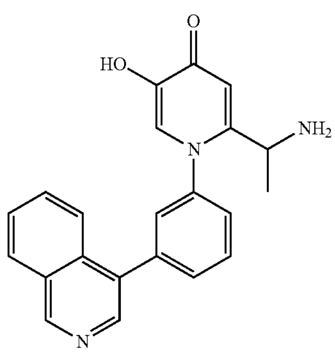 [SMILES: CC(N)c1cc(=O)c(O)cn1-c1cccc(-c2cncc3ccccc23)c1] | 2-(1-aminoethyl)-5-hydroxy-1-(3-isoquinolin-4-ylphenyl)pyridin-4(1H)-one | Calcd 358.1, Found 358.1 |
| 234 | 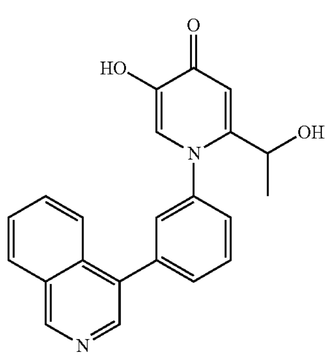 [SMILES: CC(O)c1cc(=O)c(O)cn1-c1cccc(-c2cncc3ccccc23)c1] | 5-hydroxy-2-(1-hydroxyethyl)-1-(3-isoquinolin-4-ylphenyl)pyridin-4(1H)-one | Calcd 359.4, Found 359.4 |

TABLE 1-continued

| Structure | IUPAC Name | Exact Mass [M + H]+ |
|---|---|---|
| 235 | 5-hydroxy-2-(1-hydroxyethyl)-1-[3-(1-methyl-1H-indazol-4-yl)phenyl]pyridin-4(1H)-one | Calcd 362.1, Found 362.1 |
| 236 | 5-hydroxy-2-(1-hydroxyethyl)-1-[3-(2-methyl-2H-indazol-4-yl)phenyl]pyridin-4(1H)-one | Calcd 362.1, Found 362.1 |
| 237 | 2-amino-1-(2'-cyclopropylbiphenyl-3-yl)-5-hydroxypyridin-4(1H)-one | Calcd 319.1, Found 319.1 |
| 238 | 2-amino-5-hydroxy-1-[3-(1H-indazol-4-yl)phenyl]pyridin-4(1H)-one | Calcd 319.1, Found 319.1 |

TABLE 1-continued
| | Structure | IUPAC Name | Exact Mass [M + H]+ |
|---|---|---|---|
| 239 | 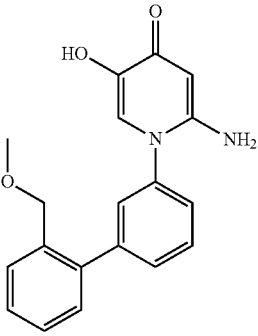 [SMILES: COCc1ccccc1-c1cccc(-n2cc(O)c(=O)cc2N)c1] | 2-amino-5-hydroxy-1-[2'-(methoxymethyl)biphenyl-3-yl]pyridin-4(1H)-one | Calcd 323.1, Found 323.1 |
| 240 | 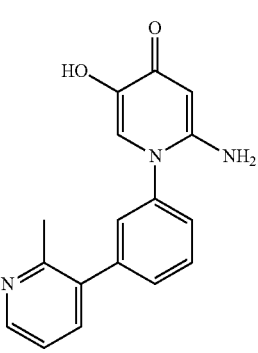 [SMILES: Cc1ncccc1-c1cccc(-n2cc(O)c(=O)cc2N)c1] | 2-amino-5-hydroxy-1-[3-(2-methylpyridin-3-yl)phenyl]pyridin-4(1H)-one | Calcd 294.1, Found 294.1 |
| 241 | 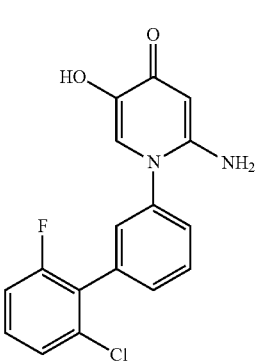 [SMILES: Nc1cc(=O)c(O)cn1-c1cccc(-c2c(F)cccc2Cl)c1] | 2-amino-1-(2'-chloro-6'-fluorobiphenyl-3-yl)-5-hydroxypyridin-4(1H)-one | Calcd 331.0, Found 331.0 |
| 242 | 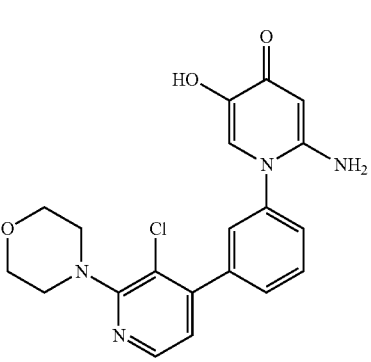 [SMILES: Nc1cc(=O)c(O)cn1-c1cccc(-c2ccnc(N3CCOCC3)c2Cl)c1] | 2-amino-1-[3-(3-chloro-2-morpholin-4-ylpyridin-4-yl)phenyl]-5-hydroxypyridin-4(1H)-one | Calcd 399.1, Found 399.1 |

TABLE 1-continued
| Structure | IUPAC Name | Exact Mass [M + H]+ |
|---|---|---|
| 243 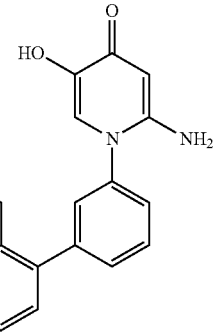 | 2-amino-5-hydroxy-1-(3-isoquinolin-5-ylphenyl)pyridin-4(1H)-one | Calcd 330.4, Found 330.4 |
| 244 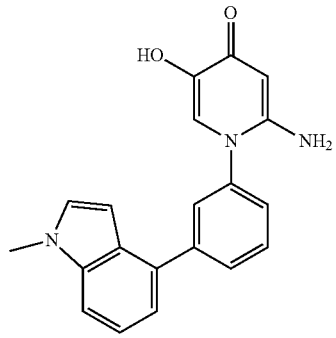 [SMILES: Cn1ccc2c(-c3cccc(-n4cc(O)c(=O)cc4N)c3)cccc21] | 2-amino-5-hydroxy-1-[3-(1-methyl-1H-indol-4-yl)phenyl]pyridin-4(1H)-one | Calcd 332.1, Found 332.1 |
| 245 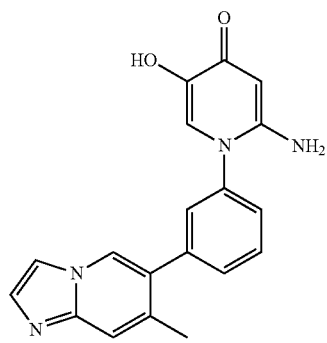 [SMILES: Cc1cc2nccn2cc1-c1cccc(-n2cc(O)c(=O)cc2N)c1] | 2-amino-5-hydroxy-1-[3-(7-methylimidazo[1,2-a]pyridin-6-yl)phenyl]pyridin-4(1H)-one | Calcd 333.1, Found 333.1 |
| 246 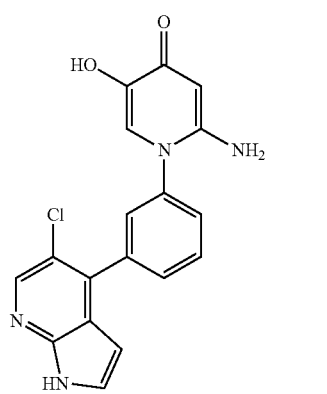 [SMILES: Nc1cc(=O)c(O)cn1-c1cccc(-c2c(Cl)cnc3[nH]ccc23)c1] | 2-amino-1-[3-(5-chloro-1H-pyrrolo[2,3-b]pyridin-4-yl)phenyl]-5-hydroxypyridin-4(1H)-one | Calcd 353.0, Found 353.0 |

TABLE 1-continued

| | Structure | IUPAC Name | Exact Mass [M + H]+ |
|---|---|---|---|
| 247 | | 2-amino-5-hydroxy-1-[3-(1-methyl-1H-indazol-4-yl)phenyl]pyridin-4(1H)-one | Calcd 333.1, Found 333.1 |
| 248 | | 2-amino-5-hydroxy-1-[3-(1-methyl-1H-indazol-6-yl)phenyl]pyridin-4(1H)-one | Calcd 333.1, Found 333.1 |
| 249 | | 2-amino-1-[3-(6-fluoropyridin-3-yl)phenyl]-5-hydroxypyridin-4(1H)-one | Calcd 298.0, Found 298.0 |
| 250 | | 2-amino-5-hydroxy-1-(3-pyridin-3-ylphenyl)pyridin-4(1H)-one | Calcd 280.1, Found 280.1 |

TABLE 1-continued
| Structure | IUPAC Name | Exact Mass [M + H]+ |
|---|---|---|
| 251 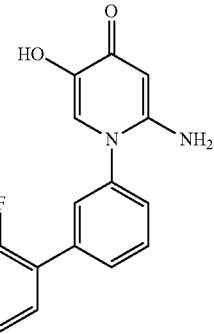 | 2-amino-1-(2',4'-difluorobiphenyl-3-yl)-5-hydroxypyridin-4(1H)-one | Calcd 315.0, Found 315.0 |
| 252 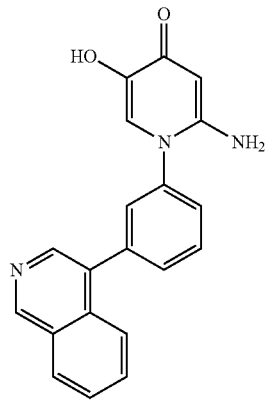 [SMILES: Nc1cc(=O)c(O)cn1-c1cccc(-c2cncc3ccccc23)c1] | 2-amino-5-hydroxy-1-(3-isoquinolin-4-ylphenyl)pyridin-4(1H)-one | Calcd 330.1, Found 330.1 |
| 253 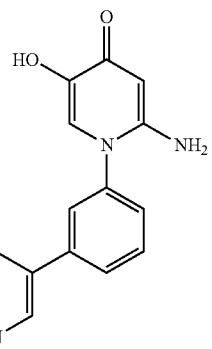 | 2-amino-1-[3-(6-aminopyridin-3-yl)phenyl]-5-hydroxypyridin-4(1H)-one | Calcd 295.1, Found 295.1 |
| 254 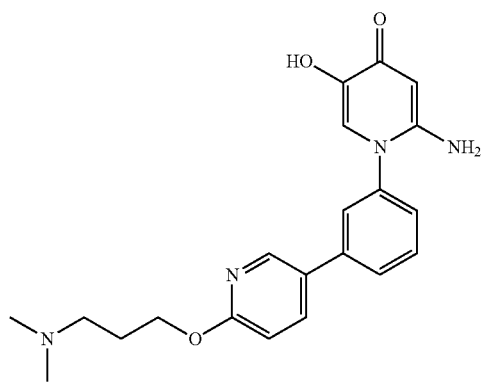 [SMILES: CN(C)CCCOc1ccc(-c2cccc(-n3cc(O)c(=O)cc3N)c2)cn1] | 2-amino-1-(3-{6-[3-(dimethylamino)propoxy]pyridin-3-yl}phenyl)-5-hydroxypyridin-4(1H)-one | Calcd 381.1, Found 381.1 |

TABLE 1-continued

| Structure | IUPAC Name | Exact Mass [M + H]+ |
|---|---|---|
| 255 | 2-amino-1-[3-(2,2-difluoro-1,3-benzodioxol-4-yl)phenyl]-5-hydroxypyridin-4(1H)-one | Calcd 359.0, Found 359.0 |
| 256 | 2-amino-5-hydroxy-1-[3-(1H-pyrrolo[3,2-b]pyridin-6-yl)phenyl]pyridin-4(1H)-one | Calcd 319.1, Found 319.1 |
| 257 | 5-hydroxy-2-(2,2,2-trifluoro-1-hydroxyethyl)-1-{3-[6-(trifluoromethyl)pyridin-2-yl]phenyl}pyridin-4(1H)-one | Calcd 431.0, Found 431.0 |
| 258 | 5-hydroxy-2-(1-hydroxyethyl)-1-[3-(8-methylquinolin-5-yl)phenyl]pyridin-4(1H)-one | Calcd 373.1, Found 373.1 |

TABLE 1-continued

| | Structure | IUPAC Name | Exact Mass [M + H]+ |
|---|---|---|---|
| 259 | 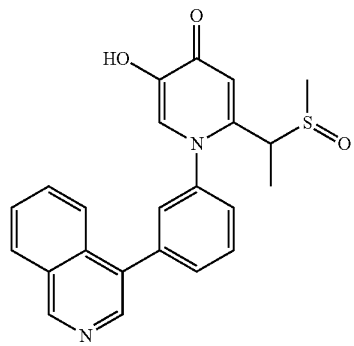 [SMILES: CC(c1cc(=O)c(O)cn1-c1cccc(-c2cncc3ccccc23)c1)S(C)=O] | 5-hydroxy-1-(3-isoquinolin-4-ylphenyl)-2-[1-(methylsulfinyl)ethyl]pyridin-4(1H)-one | Calcd 405.1, Found 405.1 |
| 260 | 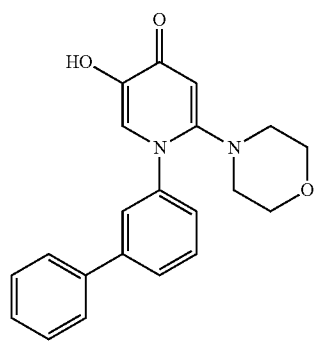 [SMILES: O=c1cc(N2CCOCC2)n(-c2cccc(-c3ccccc3)c2)cc1O] | 1-biphenyl-3-yl-5-hydroxy-2-morpholin-4-ylpyridin-4(1H)-one | Calcd 348.4, Found 349.0 |
| 261 | 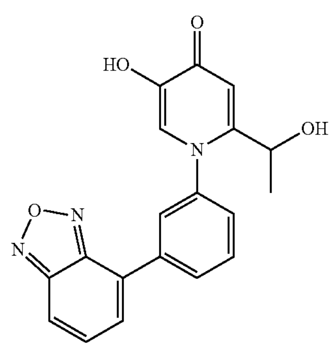 [SMILES: CC(O)c1cc(=O)c(O)cn1-c1cccc(-c2cccc3nonc23)c1] | 1-[3-(2,1,3-benzoxadiazol-4-yl)phenyl]-5-hydroxy-2-(1-hydroxyethyl)pyridin-4(1H)-one | Calcd 350.1, Found 350.1 |
| 262 | 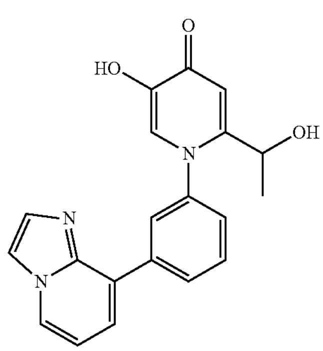 [SMILES: CC(O)c1cc(=O)c(O)cn1-c1cccc(-c2cccn3ccnc23)c1] | 5-hydroxy-2-(1-hydroxyethyl)-1-(3-imidazo[1,2-a]pyridin-8-ylphenyl)pyridin-4(1H)-one | Calcd 348.1, Found 348.1 |

TABLE 1-continued

| | Structure | IUPAC Name | Exact Mass [M + H]+ |
|---|---|---|---|
| 263 | 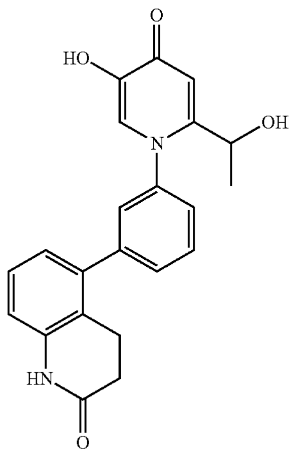 [SMILES: CC(O)c1cc(=O)c(O)cn1-c1cccc(-c2cccc3c2CCC(=O)N3)c1] | 5-{3-[5-hydroxy-2-(1-hydroxyethyl)-4-oxopyridin-1(4H)-yl]phenyl}-3,4-dihydroquinolin-2(1H)-one | Calcd 377.1, Found 377.1 |
| 264 | 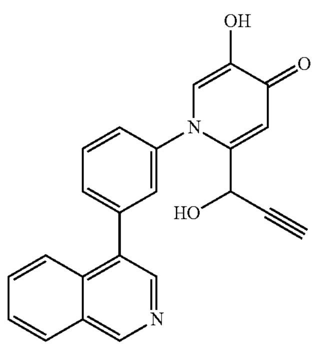 [SMILES: C#CC(O)c1cc(=O)c(O)cn1-c1cccc(-c2cncc3ccccc23)c1] | 5-hydroxy-2-(1-hydroxyprop-2-yn-1-yl)-1-(3-isoquinolin-4-ylphenyl)pyridin-4(1H)-one | Calcd 369.1, Found 369.1 |
| 265 | 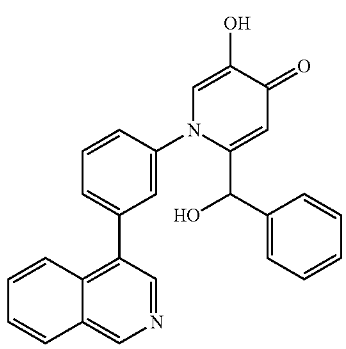 [SMILES: O=c1cc(C(O)c2ccccc2)n(-c2cccc(-c3cncc4ccccc34)c2)cc1O] | 5-hydroxy-2-[hydroxy(phenyl)methyl]-1-(3-isoquinolin-4-ylphenyl)pyridin-4(1H)-one | Calcd 421.1, Found 421.1 |
| 266 | 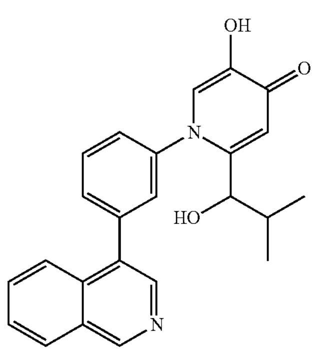 [SMILES: CC(C)C(O)c1cc(=O)c(O)cn1-c1cccc(-c2cncc3ccccc23)c1] | 5-hydroxy-2-(1-hydroxy-2-methylpropyl)-1-(3-isoquinolin-4-ylphenyl)pyridin-4(1H)-one | Calcd 387.1, Found 387.1 |

TABLE 1-continued

| | Structure | IUPAC Name | Exact Mass [M + H]+ |
|---|---|---|---|
| 267 | | 2-[cyclohexyl(hydroxy)methyl]-5-hydroxy-1-(3-isoquinolin-4-ylphenyl)pyridin-4(1H)-one | Calcd 427.2, Found 427.2 |
| 268 | | 2-[cyclopropyl(hydroxy)methyl]-5-hydroxy-1-(3-isoquinolin-4-ylphenyl)pyridin-4(1H)-one | Calcd 385.1, Found 385.1 |
| 269 | | 5-hydroxy-2-(1-hydroxy-2-phenylethyl)-1-(3-isoquinolin-4-ylphenyl)pyridin-4(1H)-one | Calcd 435.1, Found 435.1 |
| 270 | | 5-hydroxy-2-(1-hydroxyethyl)-1-(6-methoxybiphenyl-3-yl)pyridin-4(1H)-one | Calcd 338.1, Found 338.1 |

TABLE 1-continued

| Structure | IUPAC Name | Exact Mass [M + H]+ |
|---|---|---|
| 271 | 5-hydroxy-2-(1-hydroxyethyl)-1-(3-isoquinolin-4-yl-4-methoxyphenyl)pyridin-4(1H)-one | Calcd 389.1, Found 389.1 |
| 272 | 5-hydroxy-1-[2-methyl-3-(1H-pyrrolo[2,3-b]pyridin-5-yl)phenyl]-2-(2,2,2-trifluoro-1-hydroxyethyl)pyridin-4(1H)-one | Calcd 416.1, Found 416.1 |
| 273 | 5-hydroxy-1-[2-methyl-3-(6-morpholin-4-ylpyridin-3-yl)phenyl]-2-(2,2,2-trifluoro-1-hydroxyethyl)pyridin-4(1H)-one | Calcd 462.1, Found 462.1 |

TABLE 1-continued
| Structure | IUPAC Name | Exact Mass [M + H]+ |
|---|---|---|
| 274 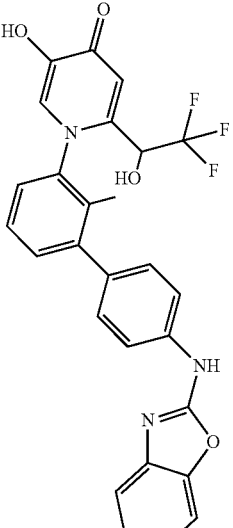 | 1-[4'-(1,3-benzoxazol-2-ylamino)-2-methylbiphenyl-3-yl]-5-hydroxy-2-(2,2,2-trifluoro-1-hydroxyethyl)pyridin-4(1H)-one | Calcd 508.1, Found 508.1 |
| 275 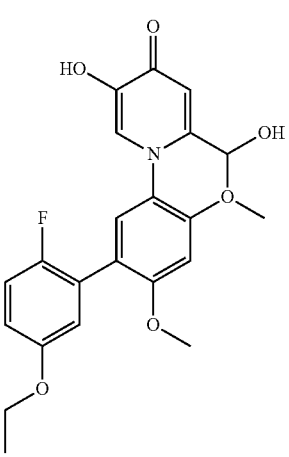 | 1-(5'-ethoxy-2'-fluoro-4,6-dimethoxybiphenyl-3-yl)-5-hydroxy-2-(1-hydroxyethyl)pyridin-4(1H)-one | Calcd 430.2, Found 430.2 |
| 276 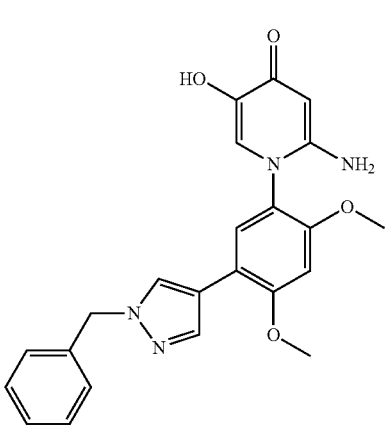 [SMILES: COc1cc(OC)c(-n2cc(O)c(=O)cc2N)cc1-c1cnn(Cc2ccccc2)c1] | 2-amino-1-[5-(1-benzyl-1H-pyrazol-4-yl)-2,4-dimethoxyphenyl]-5-hydroxypyridin-4(1H)-one | Calcd 419.1, Found 419.1 |

TABLE 1-continued

| Structure | IUPAC Name | Exact Mass [M + H]+ |
|---|---|---|
| 277 | 2-amino-5-hydroxy-1-(5-isoquinolin-5-yl-2,4-dimethoxyphenyl)pyridin-4(1H)-one | Calcd 390.1, Found 390.1 |
| 278 | 2-amino-1-[4,6-dimethoxy-2'-(trifluoromethoxy)biphenyl-3-yl]-5-hydroxypyridin-4(1H)-one | Calcd 423.1, Found 423.1 |
| 279 | 2-amino-1-{3-[6-(difluoromethyl)pyridin-2-yl]phenyl}-5-hydroxypyridin-4(1H)-one | Calcd 330.1, Found 330.1 |
| 280 | 2-amino-5-hydroxy-1-{3-[6-(2-hydroxy-1,1-dimethylethyl)pyridin-2-yl]phenyl}pyridin-4(1H)-one | Calcd 352.1, Found 352.1 |

TABLE 1-continued

| Structure | IUPAC Name | Exact Mass [M + H]+ |
|---|---|---|
| 281 | 2-amino-5-hydroxy-1-{3-[6-(trifluoromethyl)-1,5-naphthyridin-2-yl]phenyl}pyridin-4(1H)-one | Calcd 399.1, Found 399.1 |
| 282 | 2-[3-(2-amino-5-hydroxy-4-oxopyridin-1(4H)-yl)phenyl]pyridine-3-carbonitrile | Calcd 305.1, Found 305.1 |
| 283 | 2-amino-5-hydroxy-1-[3-(6-methoxyquinolin-2-yl)phenyl]pyridin-4(1H)-one | Calcd 360.1, Found 360.1 |
| 284 | 5-hydroxy-2-(1-hydroxyethyl)-1-(2-methylbiphenyl-3-yl)pyridin-4(1H)-one | Calcd 322.1, Found 322.1 |

TABLE 1-continued
| Structure | IUPAC Name | Exact Mass [M + H]+ |
|---|---|---|
| 285 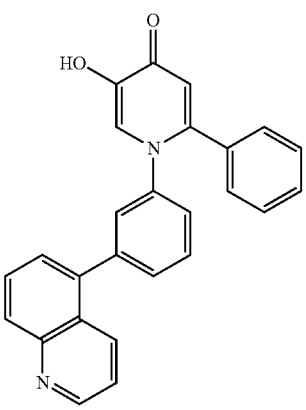 [SMILES: O=c1cc(-c2ccccc2)n(-c2cccc(-c3cccc4ncccc34)c2)cc1O] | 5-hydroxy-2-phenyl-1-(3-quinolin-5-ylphenyl)pyridin-4(1H)-one | Calcd 391.1, Found 391.1 |
| 286 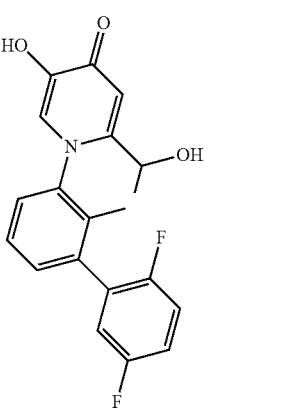 [SMILES: Cc1c(-c2cc(F)ccc2F)cccc1-n1cc(O)c(=O)cc1C(C)O] | 1-(2',5'-difluoro-2-methylbiphenyl-3-yl)-5-hydroxy-2-(1-hydroxyethyl)pyridin-4(1H)-one | Calcd 358.1, Found 358.1 |
| 287 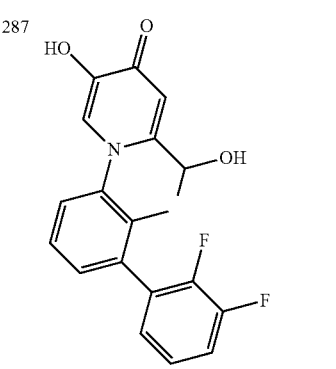 | 1-(2',3'-difluoro-2-methylbiphenyl-3-yl)-5-hydroxy-2-(1-hydroxyethyl)pyridin-4(1H)-one | Calcd 358.1, Found 358.1 |
| 288 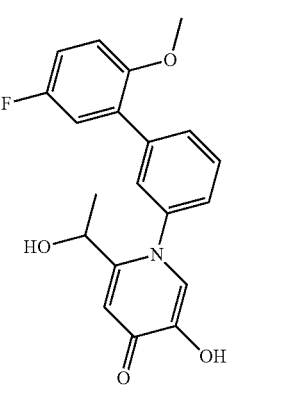 [SMILES: COc1ccc(F)cc1-c1cccc(-n2cc(O)c(=O)cc2C(C)O)c1] | 1-(5'-fluoro-2'-methoxy-6-methylbiphenyl-3-yl)-5-hydroxy-2-(1-hydroxyethyl)pyridin-4(1H)-one | Calcd 370.1, Found 370.1 |

TABLE 1-continued

| | Structure | IUPAC Name | Exact Mass [M + H]+ |
|---|---|---|---|
| 289 | 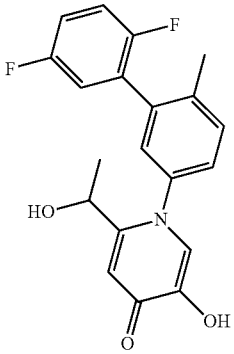 [SMILES: Cc1ccc(-n2cc(O)c(=O)cc2C(C)O)cc1-c1cc(F)ccc1F] | 1-(2',5'-difluoro-6-methylbiphenyl-3-yl)-5-hydroxy-2-(1-hydroxyethyl)pyridin-4(1H)-one | Calcd 358.1, Found 358.1 |
| 290 | 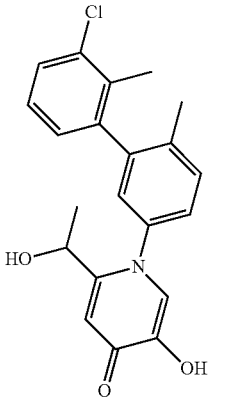 [SMILES: Cc1ccc(-n2cc(O)c(=O)cc2C(C)O)cc1-c1cccc(Cl)c1C] | 1-(3'-chloro-2',6-dimethylbiphenyl-3-yl)-5-hydroxy-2-(1-hydroxyethyl)pyridin-4(1H)-one | Calcd 370.1, Found 370.1 |
| 291 | 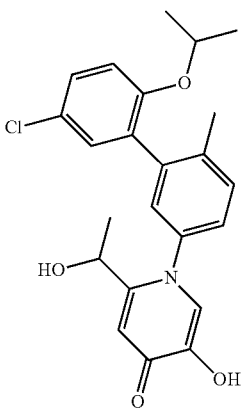 [SMILES: Cc1ccc(-n2cc(O)c(=O)cc2C(C)O)cc1-c1cc(Cl)ccc1OC(C)C] | 1-[5'-chloro-6-methyl-2'-(1-methylethoxy)biphenyl-3-yl]-5-hydroxy-2-(1-hydroxyethyl)pyridin-4(1H)-one | Calcd 414.1, Found 414.1 |
| 292 | 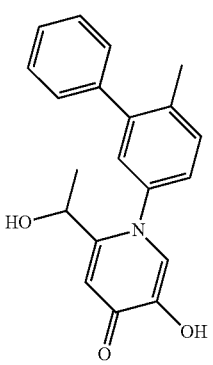 [SMILES: Cc1ccc(-n2cc(O)c(=O)cc2C(C)O)cc1-c1ccccc1] | 5-hydroxy-2-(1-hydroxyethyl)-1-(6-methylbiphenyl-3-yl)pyridin-4(1H)-one | Calcd 322.1, Found 322.1 |

TABLE 1-continued

| | Structure | IUPAC Name | Exact Mass [M + H]+ |
|---|---|---|---|
| 293 | 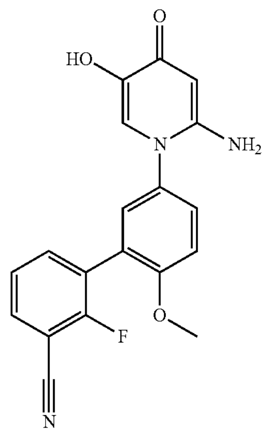 [SMILES: COc1ccc(-n2cc(O)c(=O)cc2N)cc1-c1cccc(C#N)c1F] | 5'-(2-amino-5-hydroxy-4-oxopyridin-1(4H)-yl)-2-fluoro-2'-methoxybiphenyl-3-carbonitrile | Calcd 352.1, Found 352.1 |
| 294 | 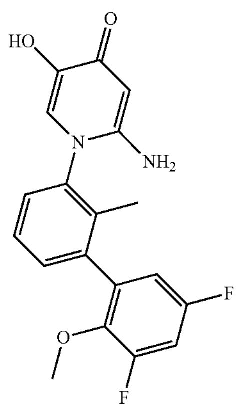 [SMILES: COc1c(F)cc(F)cc1-c1cccc(-n2cc(O)c(=O)cc2N)c1C] | 2-amino-1-(3',5'-difluoro-2'-methoxy-2-methylbiphenyl-3-yl)-5-hydroxypyridin-4(1H)-one | Calcd 359.1, Found 359.1 |
| 295 | 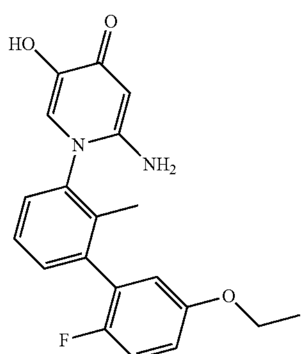 | 2-amino-1-(5'-ethoxy-2'-fluoro-2-methylbiphenyl-3-yl)-5-hydroxypyridin-4(1H)-one | Calcd 355.1, Found 355.1 |
| 296 | 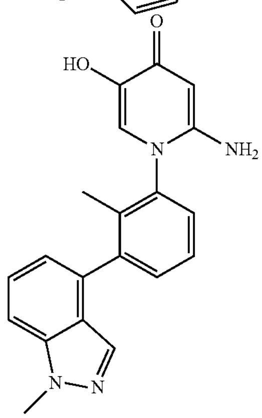 | 2-amino-5-hydroxy-1-[2-methyl-3-(1-methyl-1H-indazol-4-yl)phenyl]pyridin-4(1H)-one | Calcd 347.1, Found 347.1 |

TABLE 1-continued
| Structure | IUPAC Name | Exact Mass [M + H]+ |
|---|---|---|
| 297 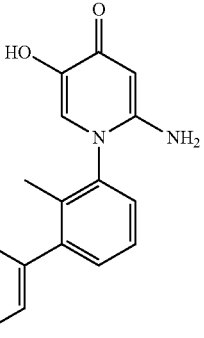 | 2-amino-5-hydroxy-1-[3-(1H-indazol-5-yl)-2-methylphenyl]pyridin-4(1H)-one | Calcd 333.1, Found 333.1 |
| 298 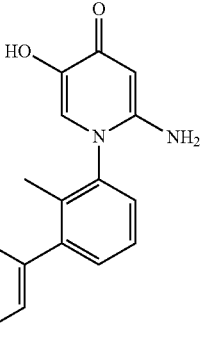 | 2-amino-5-hydroxy-1-[2-methyl-3-(1-methyl-1H-indazol-5-yl)phenyl]pyridin-4(1H)-one | Calcd 347.1, Found 347.1 |
| 299 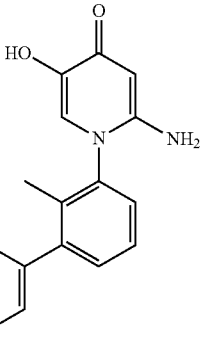 | 2-amino-5-hydroxy-1-[2-methyl-3-(1-methyl-1H-indazol-6-yl)phenyl]pyridin-4(1H)-one | Calcd 347.1, Found 347.1 |
| 300 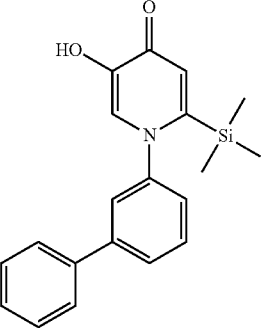 [SMILES: C[Si](C)(C)c1cc(=O)c(O)cn1-c1cccc(-c2ccccc2)c1] | 1-biphenyl-3-yl-5-hydroxy-2-(trimethylsilyl)pyridin-4(1H)-one | Calcd 336.1, Found 336.1 |

TABLE 1-continued

| Structure | IUPAC Name | Exact Mass [M + H]+ |
|---|---|---|
| 301 | 1-(2',5'-difluoro-6-methoxybiphenyl-3-yl)-5-hydroxy-2-(1-hydroxyethyl)pyridin-4(1H)-one | Calcd 374.1, Found 374.1 |
| 302 | 1-(2'-chloro-5',6-dimethoxybiphenyl-3-yl)-5-hydroxy-2-(1-hydroxyethyl)pyridin-4(1H)-one | Calcd 402.1, Found 402.1 |
| 303 | 5-hydroxy-2-(1-hydroxyethyl)-1-(6-methoxy-2',3'-dimethylbiphenyl-3-yl)pyridin-4(1H)-one | Calcd 366.1, Found 366.1 |
| 304 | 1-(5'-tert-butyl-2',6-dimethoxybiphenyl-3-yl)-5-hydroxy-2-(1-hydroxyethyl)pyridin-4(1H)-one | Calcd 424.2, Found 424.2 |

TABLE 1-continued

| | Structure | IUPAC Name | Exact Mass [M + H]+ |
|---|---|---|---|
| 305 | 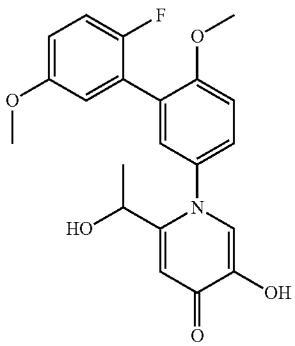 [SMILES: COc1ccc(F)c(-c2cc(-n3cc(O)c(=O)cc3C(C)O)ccc2OC)c1] | 1-(2'-fluoro-5',6-dimethoxybiphenyl-3-yl)-5-hydroxy-2-(1-hydroxyethyl)pyridin-4(1H)-one | Calcd 386.1, Found 386.1 |
| 306 | 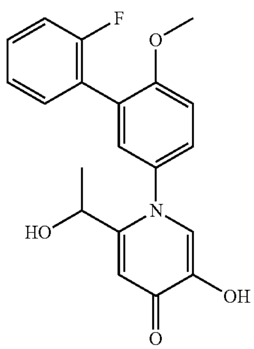 [SMILES: COc1ccc(-n2cc(O)c(=O)cc2C(C)O)cc1-c1ccccc1F] | 1-(2'-fluoro-6-methoxybiphenyl-3-yl)-5-hydroxy-2-(1-hydroxyethyl)pyridin-4(1H)-one | Calcd 356.1, Found 356.1 |
| 307 | 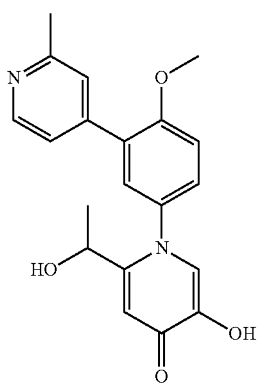 [SMILES: COc1ccc(-n2cc(O)c(=O)cc2C(C)O)cc1-c1ccnc(C)c1] | 5-hydroxy-2-(1-hydroxyethyl)-1-[4-methoxy-3-(2-methylpyridin-4-yl)phenyl]pyridin-4(1H)-one | Calcd 353.1, Found 353.1 |
| 308 | 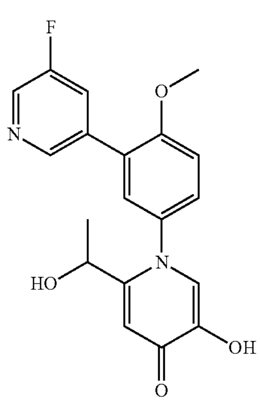 [SMILES: COc1ccc(-n2cc(O)c(=O)cc2C(C)O)cc1-c1cncc(F)c1] | 1-[3-(5-fluoropyridin-3-yl)-4-methoxyphenyl]-5-hydroxy-2-(1-hydroxyethyl)pyridin-4(1H)-one | Calcd 357.1, Found 357.1 |

TABLE 1-continued

| | Structure | IUPAC Name | Exact Mass [M + H]+ |
|---|---|---|---|
| 309 | 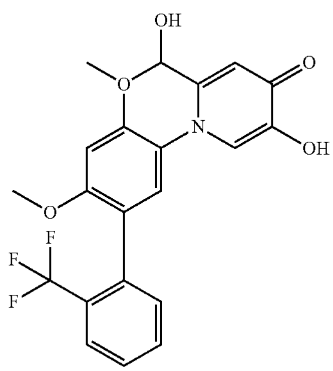 | 1-[4,6-dimethoxy-2'-(trifluoromethyl)biphen-yl-3-yl]-5-hydroxy-2-(1-hydroxyethyl)pyridin-4(1H)-one | Calcd 436.1, Found 436.1 |
| 310 | 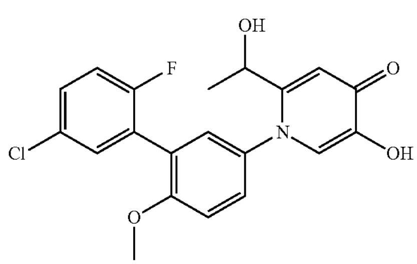 [SMILES: COc1ccc(-n2cc(O)c(=O)cc2C(C)O)cc1-c1cc(Cl)ccc1F] | 1-(5'-chloro-2'-fluoro-6-methoxybiphenyl-3-yl)-5-hydroxy-2-(1-hydroxyethyl)pyridin-4(1H)-one | Calcd 390.0, Found 390.0 |
| 311 | 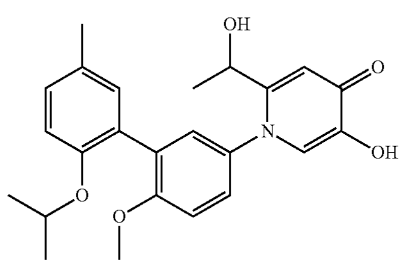 [SMILES: COc1ccc(-n2cc(O)c(=O)cc2C(C)O)cc1-c1cc(C)ccc1OC(C)C] | 5-hydroxy-2-(1-hydroxyethyl)-1-[6-methoxy-5'-methyl-2'-(1-methylethoxy)biphenyl-3-yl]pyridin-4(1H)-one | Calcd 410.1, Found 410.1 |
| 312 | 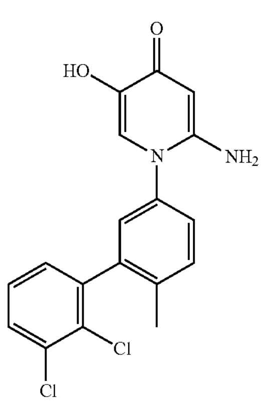 [SMILES: Cc1ccc(-n2cc(O)c(=O)cc2N)cc1-c1cccc(Cl)c1Cl] | 2-amino-1-(2',3'-dichloro-6-methylbiphenyl-3-yl)-5-hydroxypyridin-4(1H)-one | Calcd 361.0, Found 361.0 |

TABLE 1-continued

| | Structure | IUPAC Name | Exact Mass [M + H]+ |
|---|---|---|---|
| 313 | 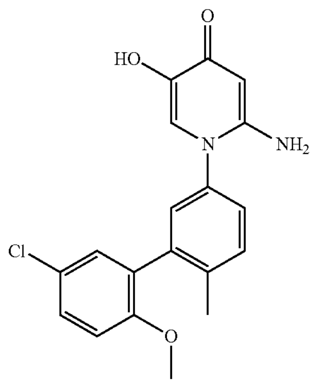 [SMILES: COc1ccc(Cl)cc1-c1cc(-n2cc(O)c(=O)cc2N)ccc1C] | 2-amino-1-(5'-chloro-2'-methoxy-6-methylbiphenyl-3-yl)-5-hydroxypyridin-4(1H)-one | Calcd 357.1, Found 357.0 |
| 314 | 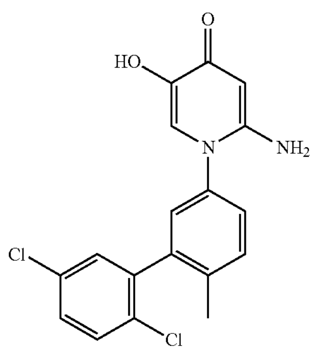 [SMILES: Cc1ccc(-n2cc(O)c(=O)cc2N)cc1-c1cc(Cl)ccc1Cl] | 2-amino-1-(2',5'-dichloro-6-methylbiphenyl-3-yl)-5-hydroxypyridin-4(1H)-one | Calcd 361.0, Found 361.0 |
| 315 | 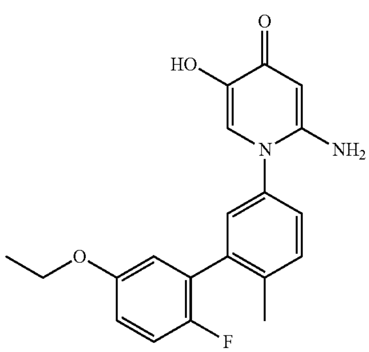 [SMILES: CCOc1ccc(F)c(-c2cc(-n3cc(O)c(=O)cc3N)ccc2C)c1] | 2-amino-1-(5'-ethoxy-2'-fluoro-6-methylbiphenyl-3-yl)-5-hydroxypyridin-4(1H)-one | Calcd 355.1, Found 355.1 |
| 316 | 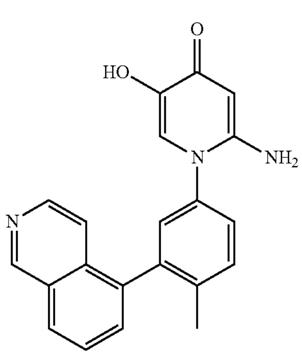 [SMILES: Cc1ccc(-n2cc(O)c(=O)cc2N)cc1-c1cccc2cnccc12] | 2-amino-5-hydroxy-1-(3-isoquinolin-5-yl-4-methylphenyl)pyridin-4(1H)-one | Calcd 344.1, Found 344.1 |

TABLE 1-continued
| Structure | IUPAC Name | Exact Mass [M + H]+ |
|---|---|---|
| 317 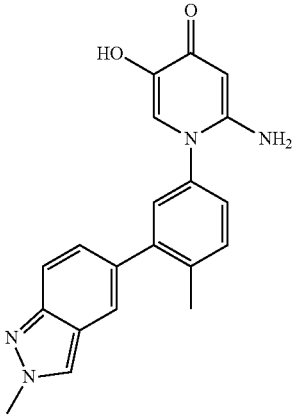 [SMILES: Cc1ccc(-n2cc(O)c(=O)cc2N)cc1-c1ccc2nn(C)cc2c1] | 2-amino-5-hydroxy-1-[4-methyl-3-(2-methyl-2H-indazol-5-yl)phenyl]pyridin-4(1H)-one | Calcd 347.1, Found 347.1 |
| 318 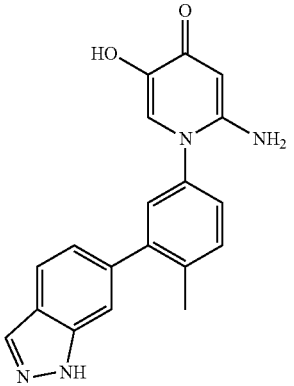 [SMILES: Cc1ccc(-n2cc(O)c(=O)cc2N)cc1-c1ccc2cn[nH]c2c1] | 2-amino-5-hydroxy-1-[3-(1H-indazol-6-yl)-4-methylphenyl]pyridin-4(1H)-one | Calcd 333.1, Found 333.1 |
| 319 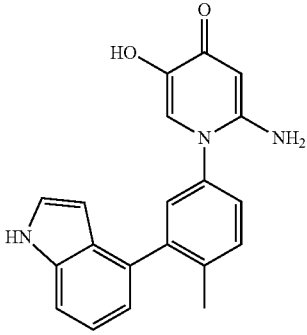 [SMILES: Cc1ccc(-n2cc(O)c(=O)cc2N)cc1-c1cccc2[nH]ccc12] | 2-amino-5-hydroxy-1-[3-(1H-indol-4-yl)-4-methylphenyl]pyridin-4(1H)-one | Calcd 332.1, Found 332.1 |
| 320 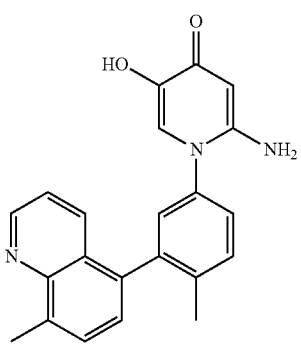 [SMILES: Cc1ccc(-n2cc(O)c(=O)cc2N)cc1-c1ccc(C)c2ncccc12] | 2-amino-5-hydroxy-1-[4-methyl-3-(8-methylquinolin-5-yl)phenyl]pyridin-4(1H)-one | Calcd 358.1, Found 358.1 |

TABLE 1-continued

| Structure | IUPAC Name | Exact Mass [M + H]+ |
|---|---|---|
| 321 | 5-hydroxy-2-(1-hydroxyethyl)-1-[3-(6-hydroxypyridin-3-yl)phenyl]pyridin-4(1H)-one | Calcd 325.1, Found 325.1 |
| 322 | 2-amino-1-[3-(2-chloro-5-methylphenoxy)-4-methylphenyl]-5-hydroxypyridin-4(1H)-one | Calcd 357.1, Found 357.0 |
| 323 | 5-hydroxy-2-(1-hydroxyethyl)-1-(3-thieno[2,3-b]pyridin-3-ylphenyl)pyridin-4(1H)-one | Calcd 365.0, Found 365.0 |
| 324 | 1-(3'-cyclopropylbiphenyl-3-yl)-5-hydroxy-2-(1-hydroxyethyl)pyridin-4(1H)-one | Calcd 348.1, Found 348.1 |

TABLE 1-continued

| Structure | IUPAC Name | Exact Mass [M + H]+ |
|---|---|---|
| 325 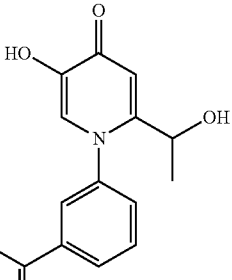 | 1-[3-(3-chloroquinolin-7-yl)phenyl]-5-hydroxy-2-(1-hydroxyethyl)pyridin-4(1H)-one | Calcd 393.1, Found 393.1 |
| 326 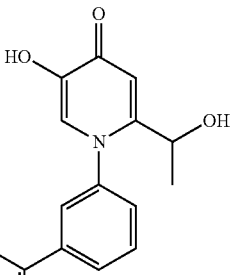 | 1-[3-(3-chloroisoquinolin-7-yl)phenyl]-5-hydroxy-2-(1-hydroxyethyl)pyridin-4(1H)-one | Calcd 393.1, Found 393.0 |
| 327 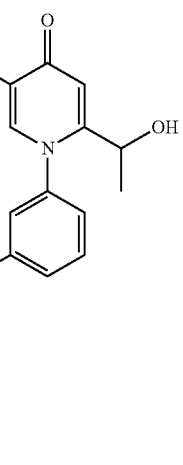 | 5-hydroxy-2-(1-hydroxyethyl)-1-[4'-(pyridin-2-ylmethyl)biphenyl-3-yl]pyridin-4(1H)-one | Calcd 399.1, Found 399.1 |
| 328 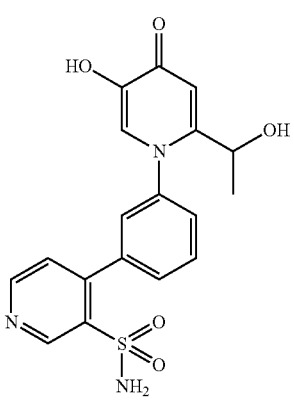 [SMILES: CC(O)c1cc(=O)c(O)cn1-c1cccc(-c2ccncc2S(N)(=O)=O)c1] | 4-{3-[5-hydroxy-2-(1-hydroxyethyl)-4-oxopyridin-1(4H)-yl]phenyl}pyridine-3-sulfonamide | Calcd 388.0, Found 388.0 |

TABLE 1-continued

| Structure | IUPAC Name | Exact Mass [M + H]+ |
| --- | --- | --- |
| 329 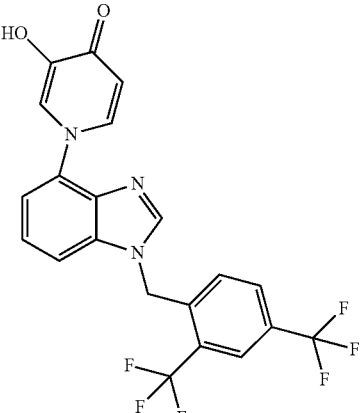 | 1-{1-[2,4-bis(trifluoromethyl)benzyl]-1H-benzimidazol-4-yl}-3-hydroxypyridin-4(1H)-one | Calcd 454.0, Found 454.0 | or pharmaceutically acceptable salts and individual enantiomers and diastereomers thereof.

Particular compounds of the invention are:
1-biphenyl-3-yl-3-hydroxypyridin-4(1H)-one;
3-hydroxy-1-[2-(4-methoxyphenyl)-1H-benzimidazol-5-yl]pyridin-4(1H)-one;
3-hydroxy-1-[2-(4-methylphenyl)-1H-benzimidazol-5-yl]pyridin-4(1H)-one;
(1-biphenyl-3-yl-5-hydroxy-4-oxo-1,4-dihydropyridin-3-yl)boronic acid;
3-hydroxy-1-[3-(1H-pyrrolo[3,2-b]pyridin-6-yl)phenyl]pyridin-4(1H)-one;
3-hydroxy-1-[3-(1H-indazol-4-yl)phenyl]pyridin-4(1H)-one;
1-biphenyl-3-yl-5-hydroxy-2-(1-hydroxyethyl)pyridin-4(H)-one;
3-hydroxy-6'-phenyl-4H-1,2'-bipyridin-4-one;
3-hydroxy-4'-phenyl-4H-1,2'-bipyridin-4-one;
1-biphenyl-3-yl-5-hydroxy-2-(1-hydroxy-2-phenylethyl)pyridin-4(1H)-one;
4'-(5-chloro-1H-pyrrolo[2,3-b]pyridin-4-yl)-3-hydroxy-4H-1,2'-bipyridin-4-one;
3-hydroxy-6''-(trifluoromethyl)-4H-1,2':4',2''-terpyridin-4-one;
2-amino-1-biphenyl-3-yl-5-hydroxypyridin-4(1H)-one;
1-biphenyl-3-yl-5-hydroxy-2-(methylamino)pyridin-4(1H)-one;
1-[3-(5-chloro-1H-pyrrolo[2,3-b]pyridin-4-yl)phenyl]-5-hydroxy-2-(1-hydroxyethyl)pyridin-4(1H)-one;
5-hydroxy-2-(1-hydroxyethyl)-1-[3-(1H-indazol-4-yl)phenyl]pyridin-4(1H)-one;
1-[3-(5-chloro-1H-pyrrolo[2,3-b]pyridin-4-yl)-4-methoxyphenyl]-5-hydroxy-2-(1-hydroxyethyl)pyridin-4(1H)-one;
1-[3-(5-chloro-1H-pyrrolo[2,3-b]pyridin-4-yl)-5-fluorophenyl]-5-hydroxy-2-(1-hydroxyethyl)pyridin-4(1H)-one;
5-hydroxy-2-(1-hydroxyethyl)-1-[3-(1H-indazol-4-yl)-4-methoxyphenyl]pyridin-4(1H)-one;
5-hydroxy-2-(1-hydroxyethyl)-1-(3-isoquinolin-4-ylphenyl)pyridin-4(1H)-one;
5-hydroxy-2-(1-hydroxyethyl)-1-(3-quinolin-5-ylphenyl)pyridin-4(1H)-one;
5-hydroxy-1-(3-isoquinolin-4-ylphenyl)-2-(2,2,2-trifluoro-1-hydroxyethyl)pyridin-4(1H)-one;
1-[3-(5-chloro-1H-pyrrolo[2,3-b]pyridin-4-yl)phenyl]-5-hydroxy-2-(2,2,2-trifluoro-1-hydroxyethyl)pyridin-4(1H)-one;
2-amino-5-hydroxy-1-(3-isoquinolin-5-ylphenyl)pyridin-4(1H)-one;
5-hydroxy-1-(3-quinolin-5-ylphenyl)-2-(2,2,2-trifluoro-1-hydroxyethyl)pyridin-4(1H)-one;
1-(5'-ethoxy-2'-fluoro-4,6-dimethoxybiphenyl-3-yl)-5-hydroxy-2-(1-hydroxyethyl)pyridin-4(1H)-one;
2-amino-5-hydroxy-1-(5-isoquinolin-5-yl-2,4-dimethoxyphenyl)pyridin-4(1H)-one;
1-[1-(2-chlorobenzyl)-1H-benzimidazol-4-yl]-3-hydroxypyridin-4(1H)-one;
or pharmaceutically acceptable salts and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

When an Rgroup is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "fluoroalkyl" refers to an alkyl group as described herin containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S which may be saturated, such as piperidinyl, partially saturated, or unsaturated, such as pyridinyl, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

In certain other embodiments, the heterocyclic group is fused to an aryl or heteroaryl group. Examples of such fused heterocycles include, without limitation, tetrahydroquinolinyl and dihydrobenzofuranyl.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, C1-$C_9$ alkoxy, $C_1$-$C_8$ alkoxycarbonyl, aryloxycarbonyl, $C_2$-$C_8$ acyl, $C_2$-$C_8$acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" and "halo" refer to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of COMT enzyme complex modulator sufficient to inhibit or enhance the effect of the COMT enzyme complex.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders. In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain. In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The subject compounds are further useful in a method for the prevention, treatment, control, amelioration, or reduction of risk of the diseases, disorders and conditions noted herein.

In another specific embodiment, compounds of the present invention provide a method for treating Parkinson's disease when co-administered with L-DOPA, with or without a aromatic L-amino acid decarboxylase inhibitor (AADC) such as carbidopa, by preventing COMT—mediated metabolism of L-DOPA The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, other COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with thesubject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

COMT inhibitor drugs have a beneficial effect in ill individuals if the principle or minor cause of illness is due to frontal lobe hypodopaminergia for multiple reasons, including, but not limited to, COMT over activity. COMT inhibitors are expected to be more useful in individuals with hypomethylated MB-COMT promoter and/or Val/Val and Val/Met genotype than those with Met/Met genotype.

The medicinal products which are useful in the treatment of these diseases consist of COMT inhibitor drugs or MB-COMT inhibitors or a pharmaceutical salt thereof either alone or in the form of a composition in which it is combined with any other pharmaceutically compatible product, which may be inert or physiologically active. These medicinal products may be used orally, topically, parenterally or rectally.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

Further, it is understood that compounds of this invention can be administered at prophylactically effective dosage levels to prevent the above-recited conditions and disorders, as well as to prevent other conditions and disorders associated with calcium channel activity.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, DBU (1,8-diazabicyclo[5.4.0] undec-7-ene), LHMDS (lithium hexamethyldisilyl amide), DMSO (methyl sulfoxide), PPTS (pridinium p-toluenesulfonate), PD/C (palladium on carbon), HRMS high resolution mass spectrometry, DCM (dichloromethane), LDA (lithium diisopropylamide), HPLC (high performance liquid chromatography) DIPEA (diisopropylethyl amine), DMAP (4-(dimethylamino)pyridine), NMR (nuclear magnetic resonance); DMF (N,N-dimethylformamide), EDC (1-(3-dimethylaminopropyl)-3-ethylcarbodiimide hydrochloride), $Et_3N$ (triethylamine), GST (glutathione transferase), HOBt (1-hydroxybenzotriazole), LAH (lithium aluminum hydride), Ms (methanesulfonyl; mesyl; or $SO_2$ Me), MsO (methanesulfonate or mesylate), NaHMDS (sodium hexamethyldisilazane), NBS (N-bromosuccinimide), NCS(N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or $SO_2NH_2$), SPA (scintillation proximity assay), Th (2- or 3-thienyl), TFA (trifluoroacetic acid), THF (Tetrahydrofuran), TLC (thin layer chromatography), Tr or trityl (N-triphenylmethyl), $C_3H_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the procedures provided in the Examples. The following Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t, triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter (s)), mL (milliliters), g (gram(s)), mg (milligrams(s)), mol (moles), mmol (millimoles), eq (equivalent(s)).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1H$ and $^{13}C$ NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnaesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the examples below can be further manipulated, when appropriate, using the standard functional group transformation techniques available to those skilled in the art, to provide desired compounds described in this invention.

It is also understood that compounds of this invention contain one or more stereocenters that may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Several methods for preparing the compounds of this invention are illustrated in the following Schemes and Examples. Starting materials are made according to procedures known in the art or as illustrated herein.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

General Reaction Schemes

Scheme 1

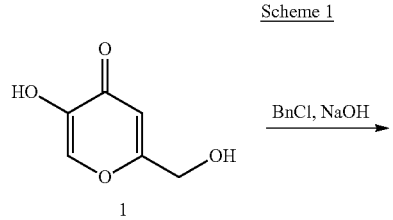

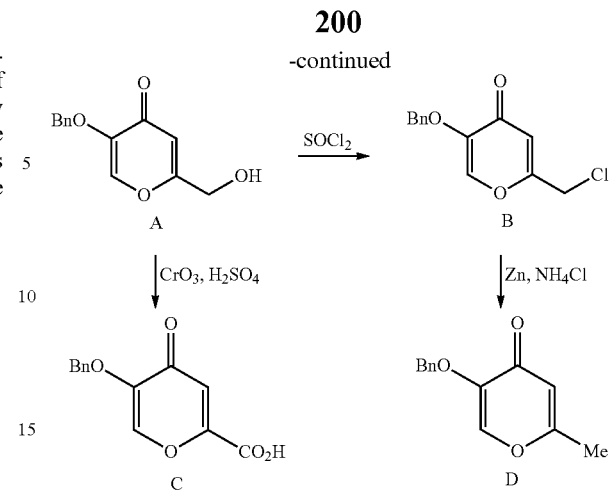

Compounds of the invention may be prepared as outlined in Schemes 1-6. Preparation of key intermediates is described in Scheme 1. Kojic acid (1) is protected as its benzyl ether, followed either by oxidation to provide the carboxylic acid C or, alternatively, conversion to chloromethyl derivative B and reduction to generate D.

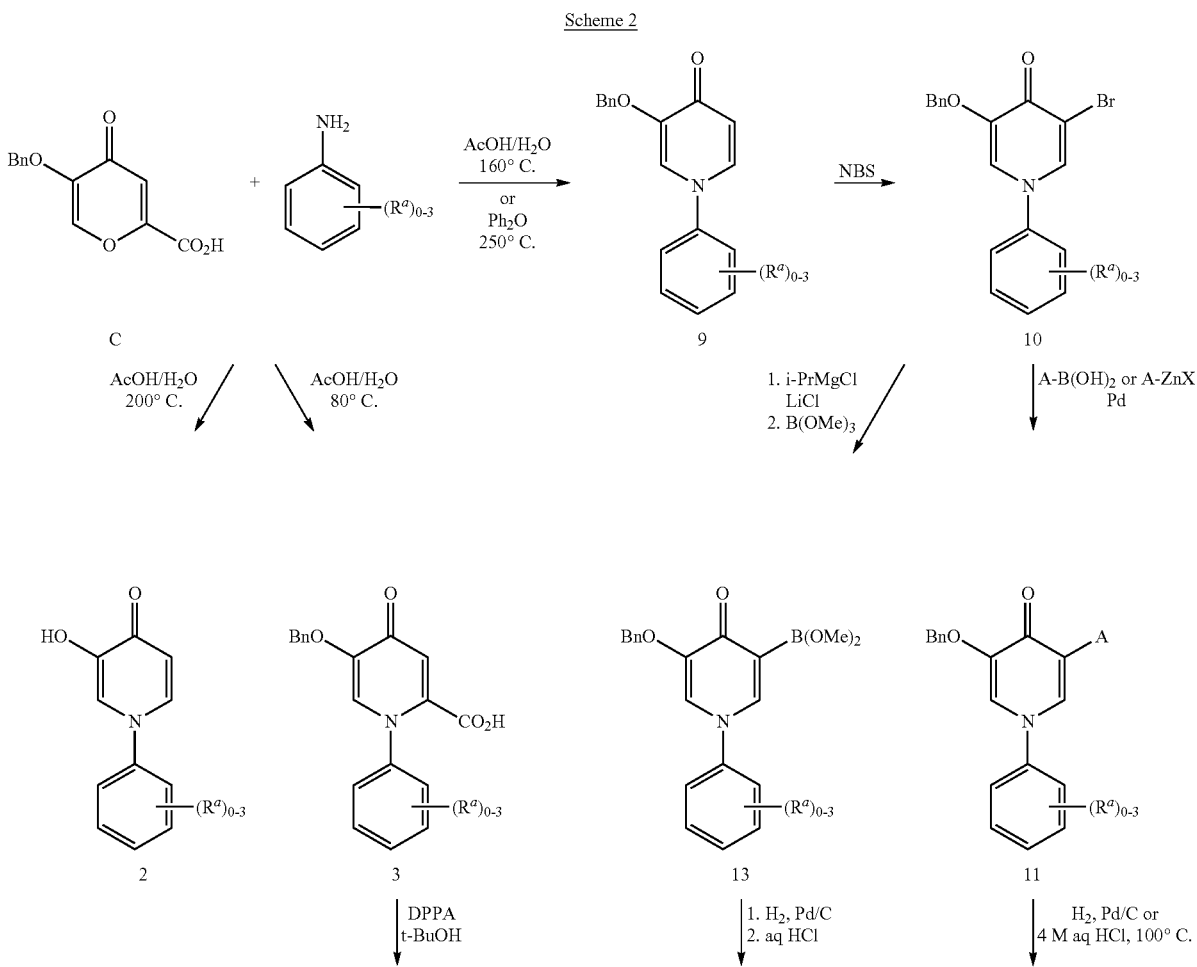

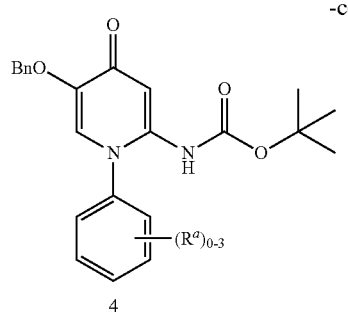
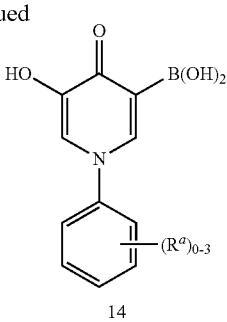
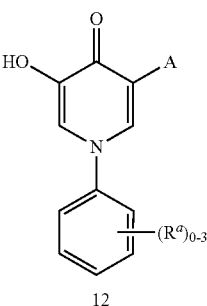

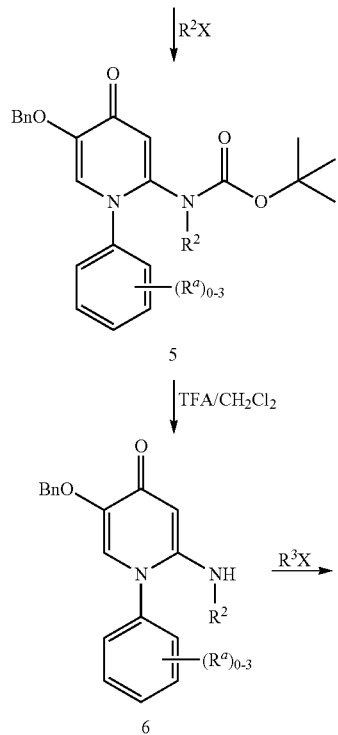

Key intermediate C is elaborated to compounds of the invention as described in Scheme 2. Reaction at high temperature (200° C.) with substituted anilines mediated by acetic acid provides target compounds 2.

The same conditions at reduced temperature (80° C.) provide the pyridinones 3 which can be converted to the N—BOC protected amines 4 via Curtius rearrangement in t-BuOH, Alkylation introduces the $R^2$ substituent (→5) and deprotection, and a second alkylation reaction introduces $R^3$ and provides benzyl protected dialkylamines 7. Target compounds 8 are prepared via catalytic hydrogenation.

Reaction of key intermediate C with substituted anilines and acetic acid at intermediate temperature (160° C.) provides compounds 9 which are brominated to provide 10. Suzuki and Negishi reactions of 10 with organoboron and organozinc reagents, followed by deprotection provide target compounds 12. Alternatively, compounds 10 are magnesiated, converted to methyl borate 13, and deprotected to afford target compounds 14.

Compounds 2-9 and 11 of Scheme 2 can be further modified by manipulation of the substitutent groups by general methods known in the art, including (but not limited to) cross coupling, oxidation, reduction, dealkylation, alkylation, acylation, and the like, and this modification may occur prior to or after deprotection.

Scheme 3

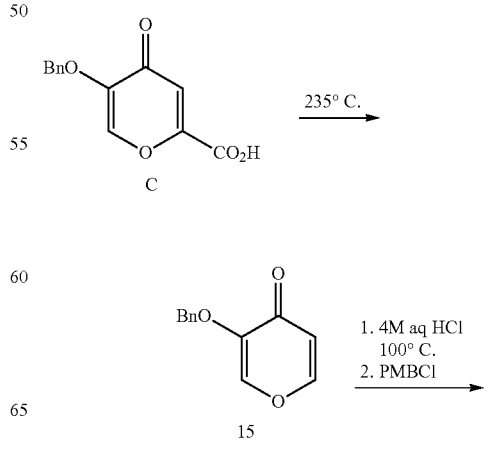

203
-continued

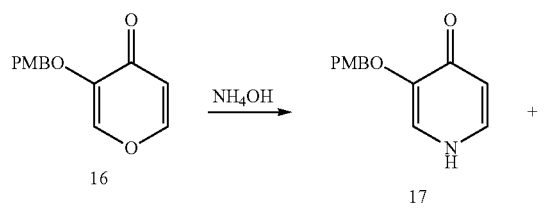

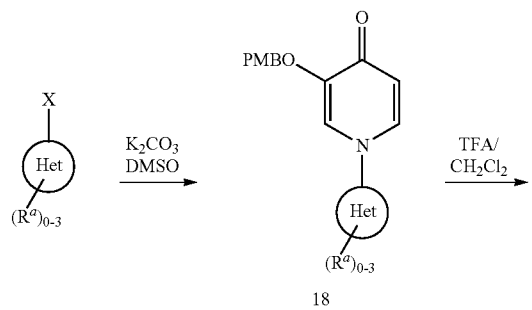

204
-continued

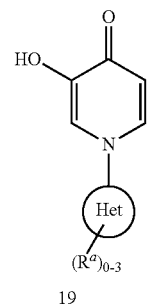

Key intermediate C is converted to compounds of the invention as described in Scheme 3. Decarboxylation and protecting group switch provides compound 16 which upon treatment with ammonia affords pyridinone 17, Nucleophilic aromatic substitution reaction with halogenated heterocycles generates compounds 18 which, when deprotected provide target compounds 19, Compounds 18 of Scheme 3 can be further modified by manipulation of the substitutent groups by general methods known in the art, including (but not limited to) cross coupling, oxidation, reduction, dealkylation, alkylation, acylation, and the like, and this modification may occur prior to or after deprotection.

Scheme 4

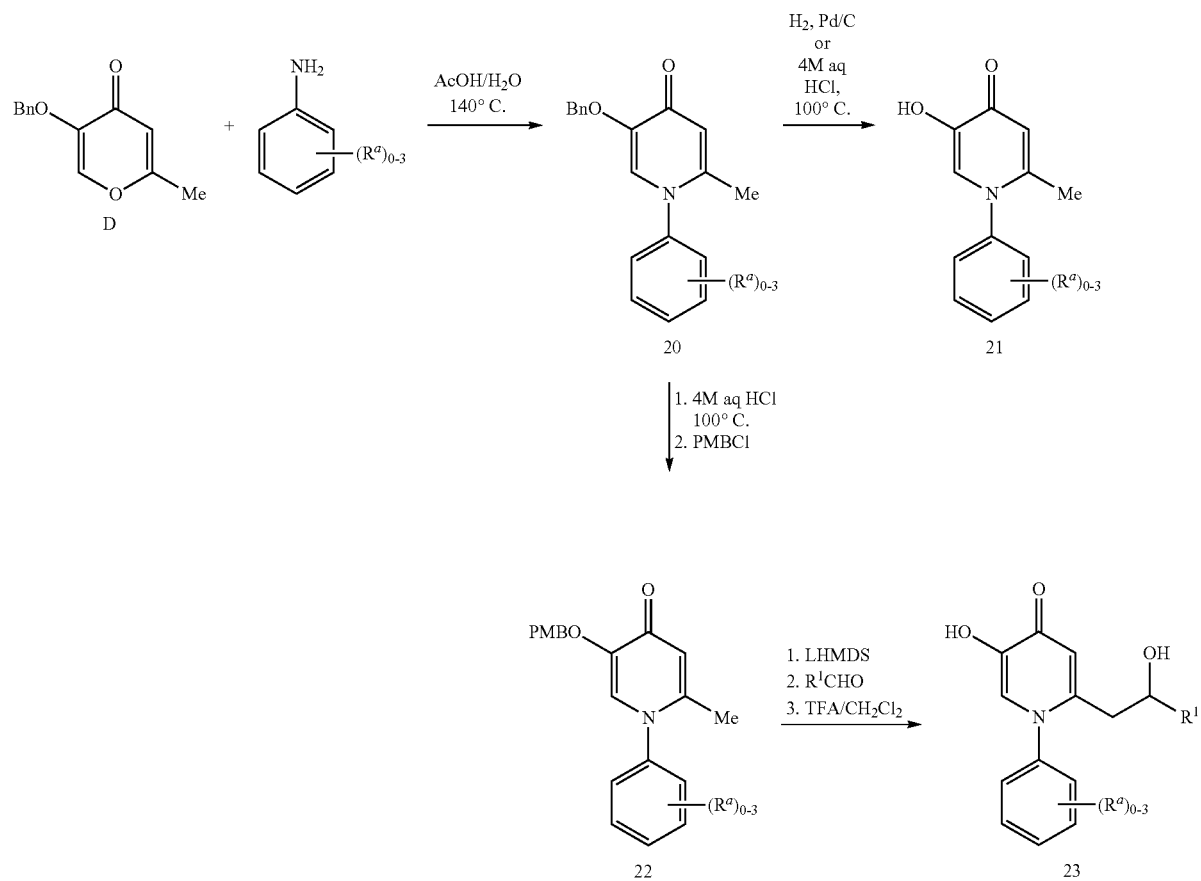

Key intermediate D is converted to compounds of the invention as described in Scheme 4. Reaction at intermediate temperature (140° C.) with substituted anilines mediated by acetic acid provides 20 which is deprotected to provide target compounds 21. Alternatively, 20 is subjected to a protecting group switch followed by lithiation and reaction with carbonyl compounds to introduce the $R^1$ substitutent. Deprotection affords target compounds 23. Compounds 20-23 of Scheme 4 can be further modified by manipulation of the substituent groups by general methods known in the art, including (but not limited to) cross coupling, oxidation, reduction, dealkylation, alkylation, acylation, and the like, and this modification may occur prior to or after deprotection.

Key intermediate A is converted to compounds of the invention as described in Scheme 5. Reaction at 100° C. with substituted anilines mediated by acetic acid or HC provides 24 which is deprotected to provide target compounds 25. Compounds 25 are protected and oxidized to furnish aldehydes 27 which are treated with organometallic reagents to introduce $R^1$; deprotection provides target compounds 29. Alternatively, 27 is treated with trimethyl(trifluoromethyl)silane and TBAF, followed by deprotection, to afford target compounds 31. Compounds 24-29 of Scheme 5 can be further modified by manipulation of the substitutent groups by general methods known in the art, including (but not limited to)

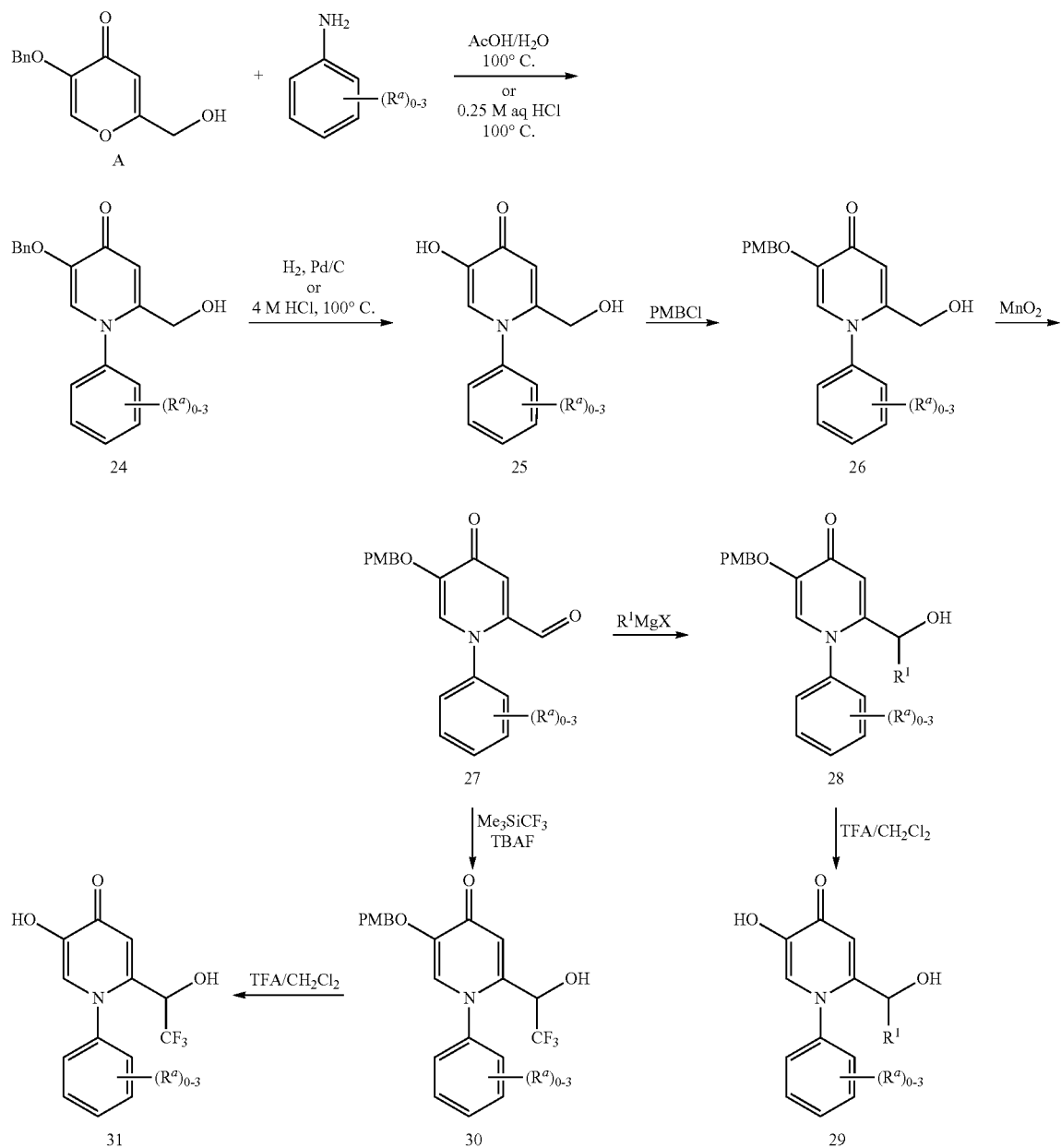

Scheme 5 cross coupling, oxidation, reduction, dealkylation, alkylation, acylation, and the like, and this modification may occur prior to or after deprotection.

Scheme 6

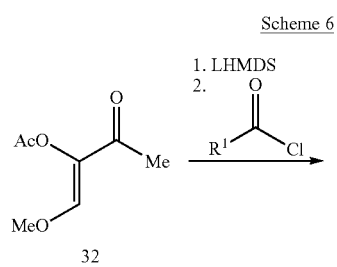

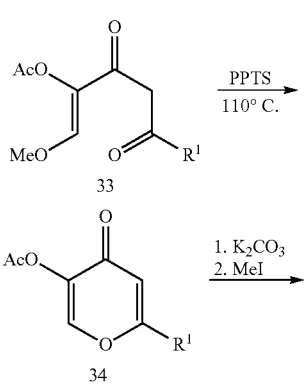

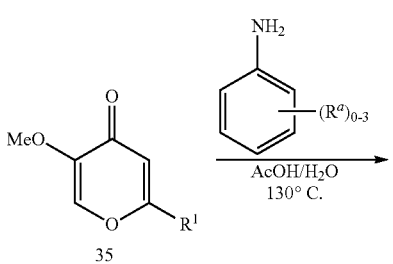

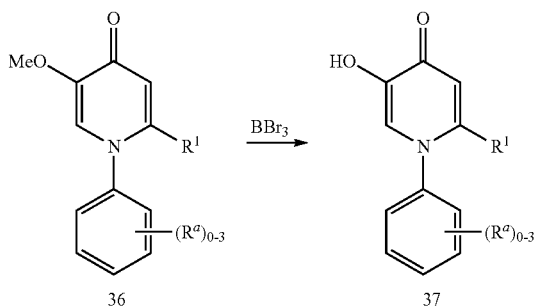

Compounds of the invention are prepared as described in Scheme 6. Lithiation of 32 and reaction with appropriate acid chlorides introduces $R^1$ and provides diketones 33 which upon warming with PPTS cyclize to generate 34. After a protecting group switch compounds 35 are reacted at 130° C. with substituted anilines to provide 36 which are deprotected to provide target compounds 37. Compounds 34-37 of Scheme 6 can be further modified by manipulation of the substituent groups by general methods known in the art, including (but not limited to) cross coupling, oxidation, reduction, dealkylation, alkylation, acylation, and the like, and this modification may occur prior to or after deprotection.

EXAMPLES

The following examples are provided so that the invention might be more fully understood. These examples are illustrative only and should not be construed as limiting the invention in any way.

Example 1

1-(Biphenyl-3-yl)-5-hydroxy-2-(methylamino)pyridin-4(1H)-one (1)

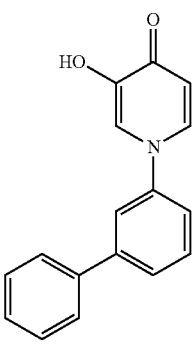 [SMILES: O=c1ccn(-c2cccc(-c3ccccc3)c2)cc1O]

5-(Benzyloxy)-2-(hydroxymethyl)-4H-pyran-4-one

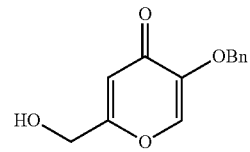 [SMILES: O=c1cc(CO)occ1OCc1ccccc1]

To a stirred solution of kojic acid (71.05 g, 0.5 mmol) and sodium hydroxide (22 g, 0.55 mol) in 750 mL of MeOH and 75 mL of water was added benzylchloride (73 g, 0.575 mmol) drop-wise. The resulting mixture was heated at reflux for 4.5 h with stirring. The mixture was then allowed to cool and concentrated to half of the starting volume. The mixture was poured into water, the resultant solid was collected, washed with water, and dried to give 110 g crude compound. The crude compound was re-crystallized from EtOAc to give 5-(benzyloxy)-2-(hydroxymethyl)-4H-pyran-4-one. $^1$H NMR δ (400 MHz, $d_6$-DMSO): 8.14 (s, 1H), 7.40-7.30 (m, 5H), 6.29(s, 1H), 5.68 (t, J=6.0 Hz, 1H), 4.91 (s, 2H), 4.26 (d, J=6.0 Hz,1H).

5-(Benzyloxy)-4-oxo-4H-pyran-2-carboxylic acid

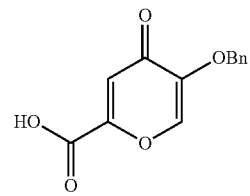 [SMILES: O=C(O)c1cc(=O)c(OCc2ccccc2)co1]

To a solution of 5-(benzyloxy)-2-(hydroxymethyl)-4H-pyran-4-one (93.4 g, 401 mmol) in 2.6 L of acetone was added 400 mL of Jone's reagent (2.45 M) at 0° C. The reaction was warmed to room temperature, and the mixture was stirred overnight. The solid was removed by filtration, and the filtrate was concentrated. The concentrated residue was poured into water. The resulting white solid was collected and washed with water and dried to obtain 5-(benzyloxy)-4-oxo-4H-pyran-2-carboxylic acid. $^1$H NMR δ (400 MHz, d$_6$-DMSO): 8.34 (s, 1H), 7.42-7.33 (m, 5H), 6.91(s, 1H), 4.95 (s, 2H).

3-(Benzyloxy)-1-(biphenyl-3-yl)pyridin-4(1H)-one

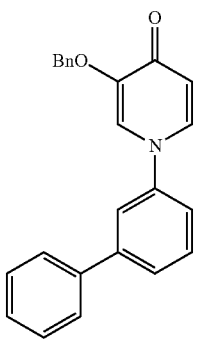 [SMILES: O=c1ccn(-c2cccc(-c3ccccc3)c2)cc1OCc1ccccc1]

5-(Benzyloxy)-4-oxo-4H-pyran-2-carboxylic acid (36.9 g, 150 mmol) and 3-aminobiphenyl (25.35 g, 150 mmol) were combined in diphenyl ether (110 ml). The mixture was heated to 250° C. (pre-heated block) in an open flask. After 10 min, the mixture was cooled to room temperature. The residue was purified by silica gel chromatography to provide 3-(benzyloxy)-1-(biphenyl-3-yl)pyridin-4(1H)-one. $^1$H NMR δ (400 MHz, d$_6$-DMSO): 7.55 (d, J=7.6 Hz, 1H), 7.46 (m, 4H), 7.44-7.31 (m, 5H), 7.29-7.11 (m, 4H), 6.51 (d, J=7.2 Hz, 1H), 5.17 (s, 2H). MS (M+H)$^+$ 354.

1-(Biphenyl-3-yl)-5-hydroxy-2-(methylamino)pyridin-4(1H)-one (1)

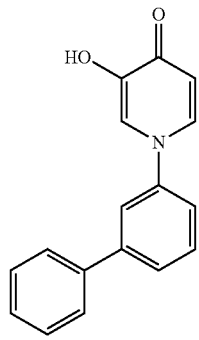

3-(Benzyloxy)-1-(biphenyl-3-yl)pyridin-4(H)-one (3.53 g, 10 mmol) and 10% Pd/C (306 mg) in MeOH (300 mL) was stirred under an H$_2$ balloon for 2 h. After this time, LC/MS indicated that the reaction was complete. After evacuation and purge with N$_2$ (3×), the MeOH solution was filtered and the catalyst was washed with MeOH (4×50 mL). The combined MeOH solution was concentrated to give 1-(Biphenyl-3-yl)-5-hydroxy-2-(methylamino)pyridin-4(1H)-one as a slightly yellow solid. $^1$H NMR (500 MHz, DMSO): ä 8.02 (dd, J=7.3, 2.5 Hz, 1 H); 7.89 (d, J=2.4 Hz, 1 H); 7.81 (m, 3 H); 7.73 (d, J=7.7 Hz, 1 H); 7.62 (t, J=7.8 Hz, 1 H); 7.58-7.47 (m, 3 H); 7.42 (t, J=7.3 Hz, 1 H); 6.34 (d, J=7.3 Hz, 1 H); LC/MS (M+H)$^+$ 264; HRMS Calcd for (C$_{17}$H$_{13}$NO$_2$+H)$^+$ 264.1019. Found 264.1021.

Example 2

3-hydroxy-1-[2-(4-methoxyphenyl)-1H-benzimidazol-5-yl]pyridin-4(1H)-one (2)

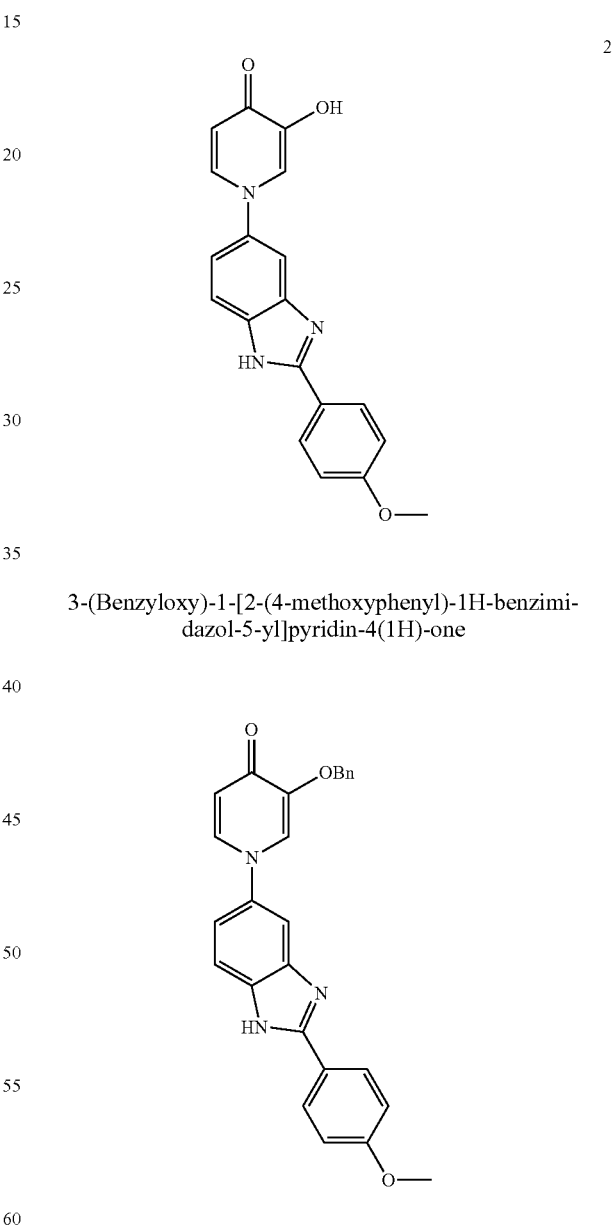

3-(Benzyloxy)-1-[2-(4-methoxyphenyl)-1H-benzimidazol-5-yl]pyridin-4(1H)-one

A mixture of 5-(benzyloxy)-4-oxo-4H-pyran-2-carboxylic acid (492 mg, 2 mmol) and 2-(4-methoxyphenyl)-1H-benzimidazol-5-amine (574 mg, 2.4 mmol) in 50% aq. HOAc was heated under microwave irradiation at 160° C. for 1.5 h. The aq. HOAc solution was then concentrated and the crude product was purified by LCMS. The pure LCMS fraction was concentrated to give the TFA salt of the product as white solid.

The solid of the TFA salt was stirred overnight in aq. NaHCO₃ at rt, filtered, washed with water (5×), dried under vacuum over weekend to provide 3-(Benzyloxy)-1-[2-(4-methoxyphenyl)-1H-benzimidazol-5-yl]pyridin-4(1H)-one as its free base. LC/MS (M+H)⁺ 424.

3-Hydroxy-1-[2-(4-methoxyphenyl)-1H-benzimidazol-5-yl]pyridin-4(1H)-one (2)

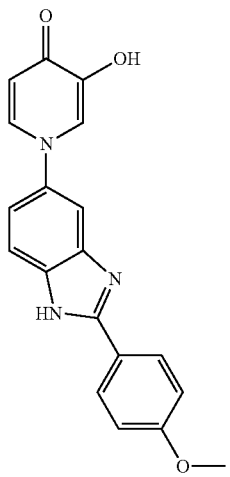 [SMILES: COc1ccc(-c2nc3cc(-n4ccc(=O)c(OCc5ccccc5)c4)ccc3[nH]2)cc1]

3-(Benzyloxy)-1-[2-(4-methoxyphenyl)-1H-benzimidazol-5-yl]pyridin-4(1H)-one (912 mg, 10 mmol) and 10% Pd/C (100 mg) in EtOH (300 mL) was stirred under an H₂ balloon for 3 hours. After this time, LCMS indicated that the reaction was complete. After evacuation and purge with N₂ (3×), the EtOH solution was heated at 60° C. for 1 h, filtered, and the catalyst was washed with EtOH (4×50 mL). The combined EtOH solution was concentrated to provide the desired product 3-hydroxy-1-[2-(4-methoxyphenyl)-1H-benzimidazol-5-yl]pyridin-4(1H)-one as a slightly yellow solid. ¹H NMR (500 MHz, DMSO): δ 13.05 (s, broad, 1 H); 8.15 (d, J=8.3 Hz, 2 H); 7.89 (d, J=6.9 Hz, 1 H); 7.71 (m, 3 H); 7.34 (d, J=7.9 Hz, 1 H); 7.13 (d, J=8.6 Hz, 2 H); 6.32 (d, J=7.3 Hz, 1 H); 3.85 (s, 3 H); LCMS (M+H)⁺ 334; HRMS Calcd for (C₁₉H₁₅N₃O₃+H)⁺ 334.1186. Found 334.1188.

Example 3

2-Amino-1-(biphenyl-3-yl)-5-hydroxypyridin-4(1H)-one (3)

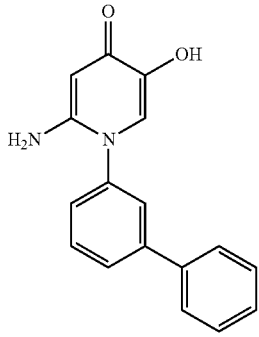

5-(Benzyloxy)-1-(biphenyl-3-yl)-2-(hydroxymethyl)pyridin-4(1H)-one

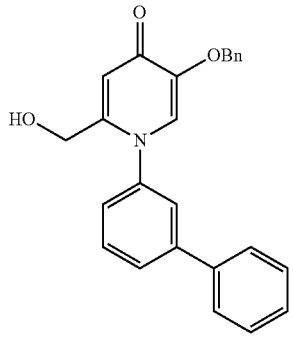 [SMILES: O=c1cc(CO)n(-c2cccc(-c3ccccc3)c2)cc1OCc1ccccc1]

To a suspension of 5-(benzyloxy)-2-(hydroxymethyl)-4H-pyran-4-one (92.9 g, 0.40 mol) in dilute aq hydrochloric acid (0.5 N, 800 mL) was added biphenyl-3-amine (74.4 g, 0.44 mol). The resulting mixture was heated under refluxed for 16 h. Concentration of the solvent gave a residue which was purified by silica gel chromatography (EtOAc:MeOH/20:1) to afford 5-(benzyloxy)-1-(biphenyl-3-yl)-2-(hydroxymethyl)pyridin-4(1H)-one as pale solid MS (ESI) (M+H)⁺384.

5-(Benzyloxy)-1-(biphenyl-3-yl)-4-oxo-1,4-dihydropyridine-2-carbaldehyde

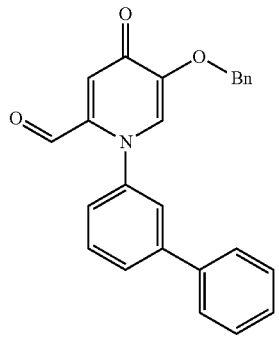 [SMILES: O=Cc1cc(=O)c(OCc2ccccc2)cn1-c1cccc(-c2ccccc2)c1]

5-(Benzyloxy)-1-(biphenyl-3-yl)-2-(hydroxymethyl)pyridin-4(1H)-one (112 g, 292 mmol) was dissolved in 2.2 L of anhydrous THF and active manganese dioxide (407 g, 4.68 mol) was added. The reaction mixture was heated under reflux for 3 hours. The insoluble part was filtered off and the filtrate was concentrated to give crude 5-(benzyloxy)-1-(biphenyl-3-yl)-4-oxo-1,4-dihydropyridine-2-carbaldehyde, which was used in next step without further purification.

5-(Benzyloxy)-1-(biphenyl-3-yl)-4-oxo-1,4-dihydropyridine-2-carboxylic acid

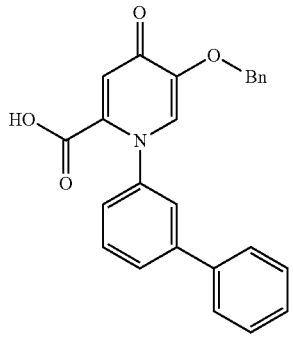 [SMILES: O=C(O)c1cc(=O)c(OCc2ccccc2)cn1-c1cccc(-c2ccccc2)c1]

NaClO$_2$ (28.3 g, 315 mmol) was added portion-wise to a mixture of 5-(benzyloxy)-1-(biphenyl-3-yl)-4-oxo-1,4-dihydropyridine-2-carbaldehyde (80 g, 210 mmol) in 800 mL of acetone and 800 mL of water at room temperature. The resulting mixture was stirred at room temperature for 3 h. The solvent was removed to give a residue which was washed with water and MeOH and dried to give 5-(benzyloxy)-1-(biphenyl-3-yl)-4-oxo-1,4-dihydropyridine-2-carboxylic acid. $^1$H NMR δ (400 MHz, d$_6$-DMSO): 7.79 (s, 1H), 7.77~7.68 (m, 4H), 7.57 (t, J=8.0 Hz, 1H), 7.48 (t,=7.6 Hz, 2H), 7.42-7.31 (m, 7H), 6.66 (s, 1H), 5.04 (s, 2H).

Tert-butyl[5-(benzyloxy)-1-(biphenyl-3-yl)-4-oxo-1,4-dihydropyridin-2-yl]carbamate

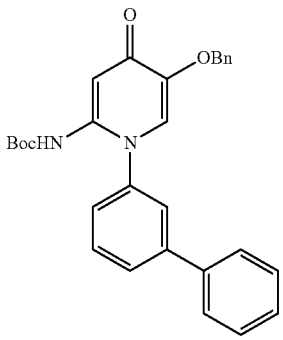 [SMILES: CC(C)(C)OC(=O)Nc1cc(=O)c(OCc2ccccc2)cn1-c1cccc(-c2ccccc2)c1]

5-(Benzyloxy)-1-(biphenyl-3-yl)-4-oxo-1,4-dihydropyridine-2-carboxylic acid (48.0 g, 121 mmol), DIPEA (31.25 g, 242 mmol), and DPPA (49.9 g, 91.2 mmol) were added to t-BuOH (500 mL) at room temperature. The resulting solution was heated to at 80° C. for 16 h. After cooling to room temperature, the mixture was concentrated to give a residue which was purified by silica gel chromatography to afford tert-butyl[5-(benzyloxy)-1-(biphenyl-3-yl)-4-oxo-1,4-dihydropyridin-2-yl]carbamate. $^1$H NMR δ (400 MHz, CDCl$_3$): 7.70 (d, J=7.6Hz, 1H), 7.58-7.53 (m, 3H), 7.47 (m, 2H), 7.42-7.37 (m, 4H), 7.33-7.20 (m, 3H), 7.18 (d, J=7.2 Hz, 1H), 6.94 (s, 1H), 6.87 (s, 1H), 6.09 (s, 1H), 5.12 (s, 2H), 1.34 (s, 9H). MS (ESI) (M+H)$^+$ 469.

2-Amino-5-(benzyloxy)-1-(biphenyl-3-yl)pyridin-4(1H)-one

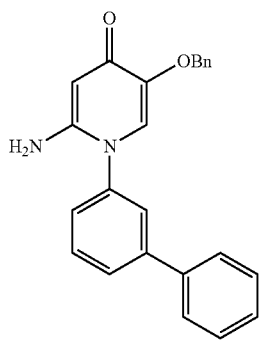 [SMILES: Nc1cc(=O)c(OCc2ccccc2)cn1-c1cccc(-c2ccccc2)c1]

To tert-butyl[5-(benzyloxy)-1-(biphenyl-3-yl)-4-oxo-1,4-dihydropyridin-2-yl]carbamate (4.68 g, 10 mmol) was added TFA-DCM (1:1, 60 mL), and the resulting solution was stirred for 1 h at rt. The solution was then concentrated and treated with saturated aq. NaHCO$_3$-EtOAc. The organic layer was separated, washed with brine, dried (Na$_2$SO$_4$), filtered, and concentrated to give 2-amino-5-(benzyloxy)-1-(biphenyl-3-yl)pyridin-4(1H)-one as a slightly yellow solid $^1$H NMR (500 MHz, DMSO): ä 7.82 (ddd, J=7.8, 1.8, 1.0 Hz, 1 H); 7.76-7.73 (m, 2 H); 7.67-7.61 (m, 2 H); 7.53-7.47 (m, 2 H); 7.43-7.34 (m, 6 H); 7.33-7.29 (m, 1 H); 7.04 (s, 1 H); 5.65 (s, 2 H); 5.49 (s, 1 H); 4.89 (s, 2 H).

2-Amino-1-(biphenyl-3-yl)-5-hydroxypyridin-4(1H)-one (3)

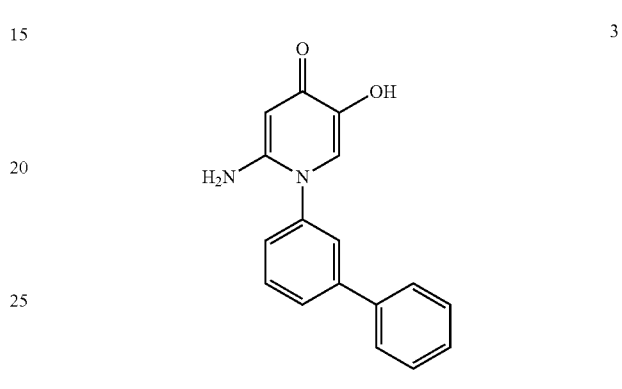

A mixture of 2-amino-5-(benzyloxy)-1-(biphenyl-3-yl)pyridin-4(1H)-one (2.65 g, 7.19 mmol) and 10% Pd/C (230 mg) in EtOH (300 mL) was stirred under an H$_2$ balloon for 2 h. After this time, LCMS indicated that the reaction was complete. After evacuation and purge with N$_2$ (3×), the EtOH solution was warmed to 50° C. and stirred 1 h at 50° C. The warmed EtOH solution was filtered and the catalyst was washed with warmed EtOH (4×50 mL). The combined EtOH solution was concentrated to give 2-amino-1-(biphenyl-3-yl)-5-hydroxypyridin-4(1H)-one as slightly yellow solid. $^1$H NMR (500 MHz, DMSO): δ 7.81 (d, J=7.9 Hz, 1 H); 7.76 (d, J=7.7 Hz, 2 H); 7.71-7.59 (m, 2 H); 7.49 (t, J=7.6 Hz, 2 H); 7.43-7.37 (m, 2 H); 6.91 (s, 1 H); 5.66 (s, 2 H); 5.54 (s, 1 H). HRMS Calcd for (C$_{17}$H$_{14}$N$_2$O$_2$+H)$^+$ 279.1128. Found 279.1128.

Example 4

1-(Biphenyl-3-yl)-5-hydroxy-2-(methylamino)pyridin-4(1H)-one (4)

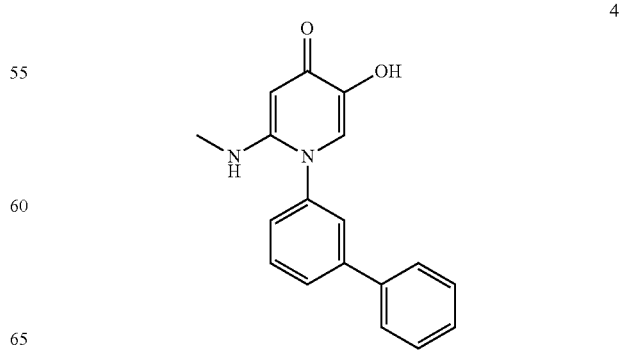

215

Tert-butyl[5-(benzyloxy)-1-(biphenyl-3-yl)-4-oxo-1,4-dihydropyridin-2-yl]methylcarbamate

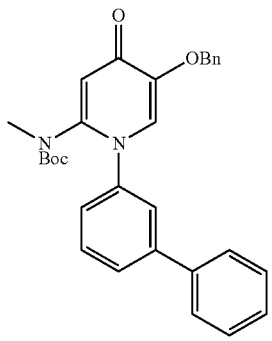 [SMILES: CN(C(=O)OC(C)(C)C)c1cc(=O)c(OCc2ccccc2)cn1-c1cccc(-c2ccccc2)c1]

To a mixture of tert-butyl[5-(benzyloxy)-1-(biphenyl-3-yl)-4-oxo-1,4-dihydropyridin-2-yl]carbamate (2.39 g, 5.1 mmol) and cesium carbonate (3.32 g, 10.20 mmol) in DMF was added iodomethane (0.478 ml, 7.65 mmol). The resulting mixture was heated at 65° C. After 18 h, the reaction was cooled to rt, and the mixture was diluted with EtOAc, washed with water, brine (3×), dried ($Na_2SO_4$), filtered, and concentrated to afford the crude product which was purified by flash chromatography to give Tert-butyl[5-(benzyloxy)-1-(biphenyl-3-yl)-4-oxo-1,4-dihydropyridin-2-yl]methylcarbamate as a slightly yellow solid. LC/MS $(M+H)^+$ 483.

5-(Benzyloxy)-1-(biphenyl-3-yl)-2-(methylamino)pyridin-4(1H)-one

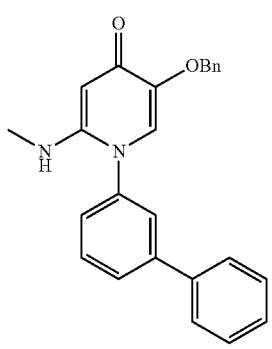 [SMILES: CNc1cc(=O)c(OCc2ccccc2)cn1-c1cccc(-c2ccccc2)c1]

Tert-butyl[5-(benzyloxy)-1-(biphenyl-3-yl)-4-oxo-1,4-dihydropyridin-2-yl]methylcarbamate (1.84 g, 3.81 mmol) was dissolved in DCM-TFA (1:1) and stirred for 1 h at rt. The reaction solution was concentrated and treated with saturated aq. $NaHCO_3$-EtOAc. The organic layer was separated, washed with saturated $NaHCO_3$, brine, dried ($Na_2SO_4$), filtered, and concentrated to give 5-(benzyloxy)-1-(biphenyl-3-yl)-2-(methylamino)pyridin-4(1H)-one as a slightly yellow solid. LC/MS $(M+H)^+$ 383.

216

1-(Biphenyl-3-yl)-5-hydroxy-2-(methylamino)pyridin-4(1H)-one (4)

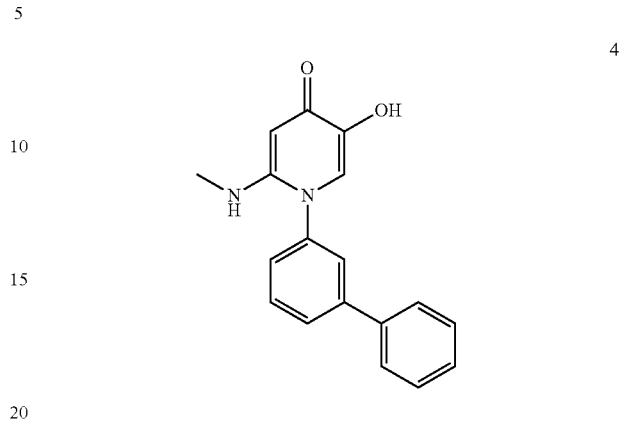

A mixture of 5-(benzyloxy)-1-(biphenyl-3-yl)-2-(methylamino)pyridin-4(1H)-one (1.31 g, 3.43 mmol) 10% Pd/C (150 mg) in MeOH (200 mL) was stirred under an $H_2$ balloon for 2 h. After this time, LCMS indicated that the reaction was complete. The catalyst was filtered and washed with MeOH (4×50). The combined MeOH solution was concentrated to give 1-(biphenyl-3-yl)-5-hydroxy-2-(methylamino)pyridin-4(1)-one as slightly yellow solid. $^1$H NMR (500 MHz, DMSO): δ 7.84-7.81 (m, 1 H); 7.78-7.74 (m, 2 H); 7.70-7.62 (m, 2 H); 7.52-7.46 (m, 2 H); 7.42-7.36 (m, 2 H); 6.93 (s, 1 H); 5.42-5.32 (m, 2 H); 2.58 (d, J=4.7 Hz, 3 H). LC/MS (M+H), 293. HRMS Calculated for $(C_{18}H_{16} N_2O_2+H)^+$ 293.1285. Found 293.1285.

Example 5

1-(4-Butylphenyl)-3-cyclopropyl-5-hydroxypyridin-4(1H)-one (5)

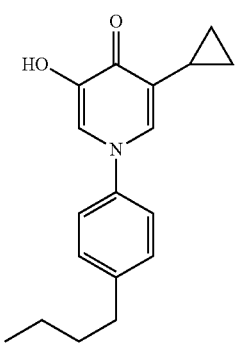

217
3-(Benzyloxy)-1-(4-butylphenyl)pyridin-4(1H)-one

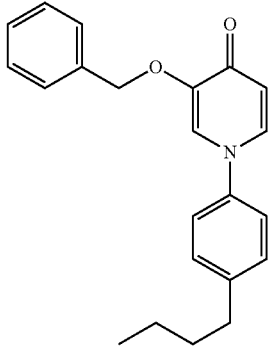 [SMILES: CCCCc1ccc(-n2ccc(=O)c(OCc3ccccc3)c2)cc1]

A suspension of 4-butylaniline (0.6 g, 4.1 mmol) and 5-(benzyloxy)-4-oxo-4H-pyran-2-carboxylic acid (1.0 g, 4.1 mmol) in a 1:1 mixture of AcOH:water (4 mL) was heated in a sealed reaction vessel at 120° C. for 72 h. After cooling to room temperature, the reaction mixture was concentrated under reduced pressure, diluted with 10 mL 10% aq. NaOH, and extracted with EtOAc (3×10 mL). The organic fractions were pooled, dried (Na$_2$SO$_4$), and concentrated under reduced pressure to provide 3-(benzyloxy)-1-(4-butylphenyl)pyridin-4(1H)-one, which was used in the subsequent step without further purification. LC/MS (M+H)$^+$ 334.

3-(Benzyloxy)-5-bromo-1-(4-butylphenyl)pyridin-4(1H)-one

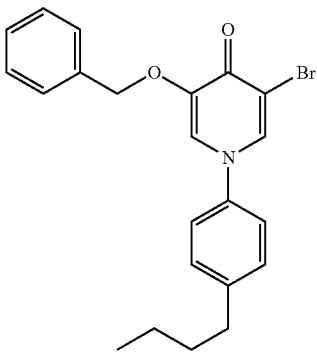 [SMILES: CCCCc1ccc(-n2cc(Br)c(=O)c(OCc3ccccc3)c2)cc1]

To a solution of 3-(benzyloxy)-1-(4-butylphenyl)pyridin-4(1H)-one (705 mg, 2.1 mmol) in AcOH (21 mL) was added N-bromosuccinimide (414 mg, 2.3 mmol) and the reaction mixture was stirred at room temperature. After 1 h, the mixture was concentrated under reduced pressure and purified by flash chromatography (50 g SiO$_2$, 0-70% ethyl acetate/hexanes) to provide 3-(benzyloxy)-5-bromo-1-(4-butylphenyl)pyridin-4(1H)-one. LC/MS (M+H)$^+$ 412/414.

218
3-(Benzyloxy)-1-(4-butylphenyl)-5-cyclopropylpyridin-4(1H)-one

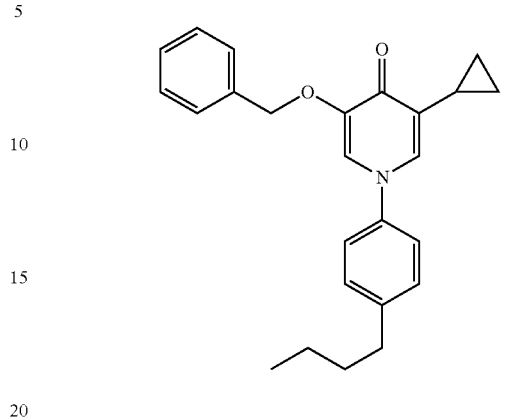

3-(Benzyloxy)-5-bromo-1-(4-butylphenyl)pyridin-4(1H)-one (37 mg, 0.09 mmol) was treated with 1,1'-bis(diphenylphosphino)ferrocene dichloro palladium(II) dichloromethane complex (6.6 mg, 0.009 mmol) and cyclopropylzinc bromide (0.54 mL of a 0.5 M solution in THF, 0.27 mmol). The reaction vessel was purged with N$_2$, sealed, and heated at 60° C. for 1 h, after which it was concentrated under a stream of N$_2$ and purified by flash chromatography (4 g SiO$_2$, 0-55% ethyl acetate/hexanes) to provide 3-(benzyloxy)-1-(4-butylphenyl)-5-cyclopropylpyridin-4(1H)-one. LC/MS (M+H)$^+$ 374.

1-(4-Butylphenyl)-3-cyclopropyl-5-hydroxypyridin-4(1H)-one (5)

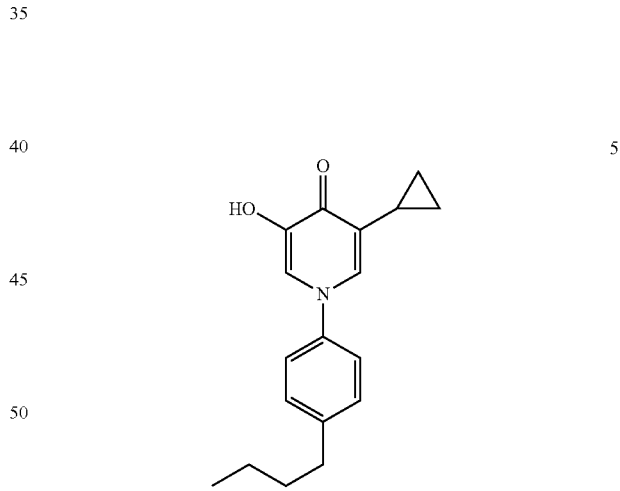

A suspension of 3-(benzyloxy)-1-(4-butylphenyl)-5-cyclopropylpyridin-4(1H)-one (27 mg, 0.07 mmol) and 10% Pd/C (1 mg, 0.001 mmol) in a 1:50 mixture of AcOH:MeOH was stirred under H$_2$ (1 atm) for 18 h. The reaction mixture was filtered (0.5μ), concentrated under reduced pressure and purified by reversed phase HPLC (2 cm×5 cm C18, acetonitrile-water gradient, 0.05% TFA added) to provide 1-(4-butylphenyl)-3-cyclopropyl-5-hydroxypyridin-4(1H)-one. $^1$H NMR (499 MHz, DMSO): δ 7.73 (s, 1 H); 7.55 (d, J=2.7 Hz, 1 H); 7.48 (d, J=8.1 Hz, 2 H); 7.35 (d, J=8.1 Hz, 2 H); 2.64 (t, J=7.7 Hz, 2 H); 2.04-1.95 (m, 1 H); 1.61-1.52 (m, 2 H); 1.37-1.27 (m, 2 H); 0.94-0.87 (m, 3 H); 0.84-0.75 (m, 4 H). HRMS (ES) Calc (M+H)$^+$=284.1645. Found 284.1643.

Example 6

[1-(biphenyl-3-yl)-5-hydroxy-4-oxo-1,4-dihydropyridin-3-yl]boronic acid (6)

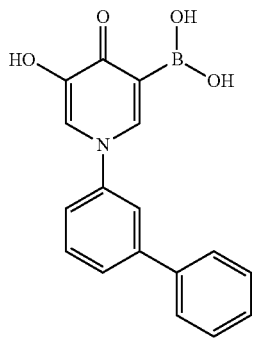

3-(Benzyloxy)-1-(biphenyl-3-yl)-5-bromopyridin-4(1H)-one

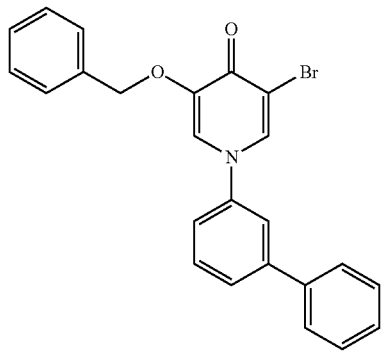 [SMILES: O=c1c(Br)cn(-c2cccc(-c3ccccc3)c2)cc1OCc1ccccc1]

To a solution of 3-(benzyloxy)-1-(biphenyl-3-yl)pyridin-4(1H)-one (2.41 g, 6.8 mmol) in AcOH (68 mL) was added N-bromosuccinamide (2.67 g, 15 mmol) and the reaction mixture was stirred at room temperature. After 1 h, the mixture was concentrated under reduced pressure and purified by flash chromatography (80 g SiO$_2$, 0-100% ethyl acetate/hexanes) to provide 3-(benzyloxy)-1-(biphenyl-3-yl)-5-bromopyridin-4(1H)-one. LC/MS (M+H)$^+$ 432/434.

[1-(biphenyl-3-yl)-5-hydroxy-4-oxo-1,4-dihydropyridin-3-yl]boronic acid (6)

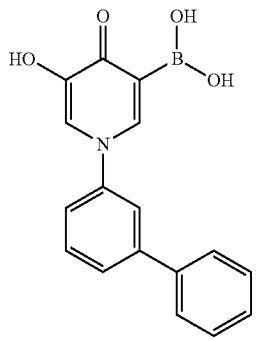

Lithium chloride (515 mg, 12.1 mmol) in a 25 mL round bottom flask under high vacuum was heated with a heat gun until a free flowing granular solid was obtained (~5 min). The flask was cooled to room temperature, purged with N$_2$, and treated with isopropylmagnesium chloride (6.1 mL of a 2 M solution in THF). After stirring at room temperature for 1 h, the mixture was cooled to −10° C. and treated with 3-(benzyloxy)-1-(biphenyl-3-yl)-5-bromopyridin-4(1H)-one (1.05 g, 2.4 mmol) as a suspension in 3.5 mL of THF. After stirring for 0.5 h, trimethylborate (1.35 mL, 12.1 mmol) was added dropwise and the reaction mixture was stirred an additional 3.5 h, before being quenched with the addition of MeOH (12 mL) to provide a solution of crude dimethyl[5-(benzyloxy)-1-(biphenyl-3-yl)-4-oxo-1,4-dihydropyridin-3-yl]boronate which was used directly in the subsequent step. LC/MS (M+H)$^+$ 398.

The solution of crude dimethyl[5-(benzyloxy)-1-(biphenyl-3-yl)-4-oxo-1,4-dihydropyridin-3-yl]boronate (2.4 mmol) in THF/MeOH from the preceeding step and 10% Pd/C (52 mg, 0.49 mmol) was stirred under H$_2$ (1 atm) for 18 h. The reaction mixture was diluted with MeOH (20 mL), filtered through a pad of Celite (MeOH wash), and concentrated under reduced pressure. The residue was diluted with DMF (10 mL) and 0.5 M aq. HCl (0.4 mL) and purified by reversed phase HPLC (2 cm×5 cm C18, acetonitrile-water gradient, 0.05% TFA added, fractions were lypholized) to provide [1-(biphenyl-3-yl)-5-hydroxy-4-oxo-1,4-dihydropyridin-3-yl]boronic acid. $^1$H NMR (599 MHz, DMSO, 75° C.): δ 8.19 (d, J=2.3 Hz, 1 H); 7.89 (d, J=2.3 Hz, 1 H); 7.83 (s, 1 H); 7.79-7.74 (m, 3 H); 7.67-7.61 (m, 1 H); 7.56 (d, J=8.1 Hz, 1 H); 7.49 (t, J=7.6 Hz, 2 H); 7.46-7.38 (m, 1 H). HRMS (ES) Calc (M+H)$^+$ 308.1089. Found 308.1092.

Example 7

2-chloro-3-hydroxy-4'-phenyl-4H-1,2'-bipyridin-4-one (7)

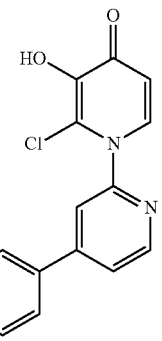

3-(benzyloxy)-4H-pyran-4-one

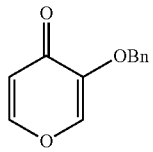

5-(Benzyloxy)-4-oxo-4H-pyran-2-carboxylic acid (68.9 g, 280 mmol) was added to 300 mL of quinoline at 235° C. and the mixture was heated at reflux for 30 min. The mixture was cooled to room temperature and concentrated to give a residue which was purified by silica gel chromatography to give 3-(benzyloxy)-4H-pyran-4-one, ¹H-NMR (CDCl₃, 400 MHz) δ 7.64 (dd, J=5.6, 0.8 Hz, 1H), 7.53 (d, J=0.4 Hz, 1H), 7.39-7.28 (m, 5H), 6.40(d, J=5.6 Hz, 1H), 5.06 (s, 2H). MS (M+H)⁺ 203.0.

3-hydroxy-4H-pyran-4-one

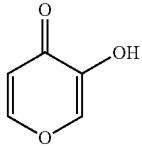

A suspension of 3-(benzyloxy)-4H-pyran-4-one (35.8 g, 177 mmol) in 350 mL of 4 N aq HCl was stirred at reflux for 2 h. After cooling to room temperature, the mixture was concentrated to give crude 3-hydroxy-4H-pyran-4-one, which was used in the next step without further purification. ¹H-NMR (DMSO, 400 MHz) 8.04 (m, 2H), 6.35(d, J=5.6 Hz, 1H).

3-[(4-methoxybenzyl)oxy]-4H-pyran-4-one

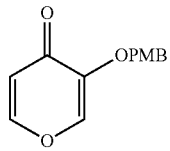

A mixture of 3-hydroxy-4H-pyran-4-one (19.8 g, 177 mmol), PMBCl (33.26 g, 212 mmol), K₂CO₃ (48.9 g, 354 mmol) and 200 mL of DMF was stirred at 100° C. for 2 h. After cooling the room temperature, the mixture was poured into 600 mL of water and extracted with EtOAc (3×100 mL). The combined organic layers were washed with water, brine, and dried over anhydrous MgSO₄ to give 50 g of a dark oil which was purified by silica gel chromatography to give 3-[(4-methoxybenzyl)oxy]-4H-pyran-4-one. ¹H-NMR (CDCl₃, 400 MHz) δ 7.64 (dd, J=5.6, 0.8 Hz, 1H), 7.52 (d, J=0.8 Hz, 1H), 7.29 (m, 2H), 6.86 (m, 2H), 6.40 (d, J=5.6 Hz, 1H), 4.99 (s, 2H), 3.78 (s, 3H). MS (M+H)⁺ 233.0.

3-[(4-methoxybenzyl)oxy]pyridin-4(1H)-one

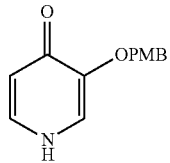

A suspension of 3-[(4-methoxybenzyl)oxy]-4H-pyran-4-one (6.2 g, 26.7 mmol) and 120 mL of NH₃.H₂O was sealed in a glass tube, and the mixture was stirred at 100° C. After 18 h, the reaction mixture was filtered and the collected solid was washed with MeOH to give 3-[(4-methoxybenzyl)oxy]pyridin-4(1H)-one. ¹H-NMR (DMSO, 400 MHz) δ 11.27 (s, 1H), 7.50 (s, 1H), 7.41 (s, 1H), 7.30 (dd, J=8.4, 2.8 Hz, 2H), 6.90 (m, 2H), 6.13 (s, 1H), 4.8(s, 2H), 3.72 (s, 3H). MS (M+H)⁺ 232.0.

2-Fluoro-3-iodopyridine

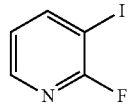

2-Fluoropyridine (48.5 g, 0.5 mol) in THF (200 mL) was slowly added to −78° C. solution of LDA (0.50 mol) in dry THF (800 mL). The resulting mixture was stirred for 4 h at −78° C., before addition of iodine (127 g, 0.50 mol) in THF (40 mL). Stirring was continued for 2 h at −78° C. before the reaction was quenched by the addition of water (20 mL). After warming to 0° C., additional water (150 mL) was added and the mixture was subjected to a reductive workup with solid sodium thiosulfate. The mixture was extracted with Et₂O, dried over MgSO₄, concentrated under reduced pressure, and purified by silica gel chromatography to give 2-fluoro-3-iodopyridine. ¹H-NMR (CDCl₃, 400 MHz) δ 8.10(m, 2H), 6.90 (m, 1H). MS (M+H)⁺ 223.9.

2-Fluoro-4-iodopyridine

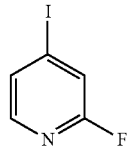

n-BuLi (122 mL, 305 mmol) was added to a solution of diisopropylamine (30.81 g, 305 mmol) in 600 mL of dry THF at −78° C. under an nitrogen atmosphere. After stirring for 30 min, a solution of 2-fluoro-3-iodopyridine (68.02 g, 305 mmol) in THF (150 mL) was added dropwise. The resulting mixture was stirred for 1 h at −78° C. Water was added (50 mL) to quench the reaction at −78° C. and after warming to room temperature an additional 100 mL of water was added. The mixture was extracted with Et₂O (2×), and the combined organic layers were dried over Na₂SO₄, concentrated, and purified by silica gel chromatography to give of 2-fluoro-4-iodopyridine. ¹H-NMR (CDCl₃, 400 MHz) δ 7.91 (d, J=1.2 Hz, 1H), 7.53 (m, 1H), 7.35 (m, 1H). MS (M+H)⁺ 223.9.

4'-iodo-3-[(4-methoxybenzyl)oxy]-4H-1,2'-bipyridin-4-one

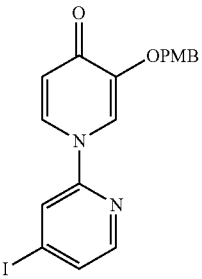

A mixture of 3-[(4-methoxybenzyl)oxy]pyridin-4(1H)-one (7.30 g, 31.6 mmol), 2-fluoro-4-iodopyridine (10.56 g, 47.35 mmol), and K₂CO₃ (10.9 g, 79 mmol) in DMSO (80 mL) was heated at 80° C. overnight. The reaction mixture was cooled to room temperature, diluted with EtOAc, washed with water and brine, dried (Na$_2$SO$_4$), filtered and concentrated. The residue was washed with EtOAc and filtered, and the collected solid dried to give 4'-iodo-3-[(4-methoxybenzyl)oxy]-4H-1,2'-bipyridin-4-one. $^1$H-NMR (DMSO, 400 MHz) δ 8.41 (dd, J=8.0, 2.4 Hz, 1H), 8.30 (s, 1H), 8.20 (m, 2H), 7.81 (dd, J=4.0, 0.8 Hz, 1H), 7.35 (d, J=8.4 Hz, 2H), 6.92 (d, J=8.4 Hz, 2H), 6.28 (d, J=7.6 Hz, 1H), 4.96 (s, 2H), 3.72 (s, 3H). MS (M+H)$^+$ 435.1.

{3-[(4-methoxybenzyl)oxy]-4-oxo-4H-1,2'-bipyridin-4'-yl}boronic acid

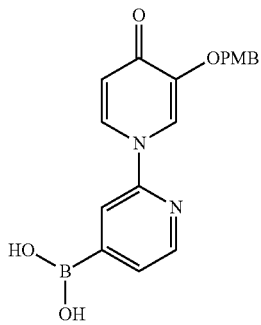

A mixture of 4'-iodo-3-[(4-methoxybenzyl)oxy]-4H-1,2'-bipyridin-4-one (5.6 g, 12.9 mmol), bis(pinacolato)diboron (4.91 g, 19.3 mmol), KOAc (2.53 g, 25.8 mmol), and Pd(dppf)Cl$_2$ (0.6 g) in 1,4-dioxane (100 mL) was heated to 100° C. overnight. After cooling to room temperature, the reaction mixture was concentrated to give a residue which was purified by Prep-HPLC to give {3-[(4-methoxybenzyl)oxy]-4-oxo-4H-1,2'-bipyridin-4'-yl}boronic acid. $^1$H NMR (DMSO, 400 MHz) δ 8.61(s, 1H), 8.51 (d, J=4.4 Hz, 1H), 8.437 (dd, J=8.0, 2.0 Hz, 1H), 8.21 (d, J=2.4 Hz, 1H), 8.00 (s, 1H), 7.65 (d, J=4.8 Hz, 1H), 7.36 (d, J=8.4 Hz, 2H), 6.92 (d, J=8.4 Hz, 2H), 6.34(d, J=7.6 Hz, 1H), 4.98 (s, 2H), 3.72 (s, 3H). MS (M+H)$^+$ 353.2.

3-(4-Methoxy-benzyloxy)-4'-phenyl-[1,2']bipyridinyl-4-one

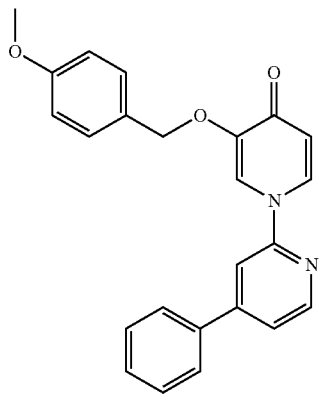 [SMILES: COc1ccc(COc2cn(-c3cc(-c4ccccc4)ccn3)ccc2=O)cc1]

To a 20 mL microwave vial (Biotage) was added {3-[(4-methoxybenzyl)oxy]-4-oxo-4H-1,2'-bipyridin-4'-yl}boronic acid (300 mg, 0.85 mmol), iodobenzene (348 mg, 1.70 mmol), cesium carbonate (6 mL of a 1.0 M aq solution, 6.0 mmol), and 69.6 mg (0.085 mmol) 1,1'-bis(diphenylphosphino)ferrocene-palladium(II)dichloride dichloromethane complex. The vial was sealed and the reaction mixture was heated at 135° C. under microwave irradiation for 15 minutes, then cooled. The organic layer was separated, washed with 5 mL water, dried over Na$_2$SO$_4$, filtered, and concentrated in vacuo. Purification by flash chromatography (silica gel, 0-10% MeOH in EtOAc gradient) afforded 3-[(4-methoxybenzyl)oxy]-4'-phenyl-4H-1,2'-bipyridin-4-one. LCMS (M+H)$^+$=385.4.

2-chloro-3-hydroxy-4'-phenyl-4H-1,2'-bipyridin-4-one (7)

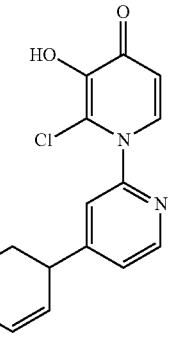

7

To a solution of 2,2,6,6,-tetramethylpiperidine (0.5 mL, 2.96 mmol) in 14.5 mL THF at 0° C. was added n-butyllithium (1.19 mL of a 2.5 M solution in hexanes, 2.97 mmol). After complete addition, the reaction mixture was allowed to warm to room temperature and 5 mL of the resulting solution was transferred to a new flask via syringe. After cooling to −78° C., a solution of 3-(4-methoxy-benzyloxy)-4'-phenyl-[1,2']bipyridinyl-4-one (0.12 g, 0.31 mmol) in a minimum volume of THF was added and the resulting mixture was allowed to warm to 0° C. for 5 minutes, at which point roughly half of the reaction mixture was removed by syringe, and added to a stirring suspension of N-chlorosuccinimide (0.05 g, 0.37 mmol) in THF at −78° C. After addition, the resulting mixture was allowed to warm to room temperature before being diluted with ethyl acetate (10 mL), washed with sat. aq. sodium thiosulfate (4 mL), water (4 mL), and concentrated. The resulting residue was dissolved in 1 mL of TFA and allowed to stand for 5 minutes before concentration in vacuo. Purification by automated mass-guided HPLC afforded 2-chloro-3-hydroxy-4'-phenyl-4H-1,2'-bipyridin-4-one as its TFA salt. $^1$H NMR (499 MHz, DMSO-d$_6$) δ 8.68 (d, J=5.25 Hz, 1 H); 8.08 (d, J=1.55 Hz, 1 H); 7.99-7.91 (m, 4 H); 7.59-7.52 (m, 3 H); 6.33 (d, J=7.46 Hz, 1 H). HRMS (FT/ICR) Calc (M+H)$^+$ 299.0582 found 299.0585.

Example 8

3-Hydroxy-6'-(1H-indazol-4-yl)-4H-1,2'-bipyridin-4-one (8)

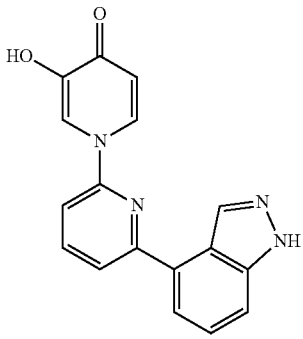

6'-Bromo-3-[(4-methoxybenzyl)oxy]-4H-1,2'-bipyridin-4-one

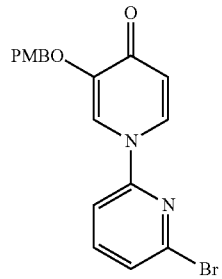

A mixture of 3-[(4-methoxybenzyl)oxy]pyridin-4(1H)-one (2.31 g, 10 mmol), 2,6-dibromopyridine (4.74 g, 20 mmol), and $K_2CO_3$ (3.45 g, 25 mmol) in DMSO was heated at 120° C. overnight. After cooling to rt, the solid was removed by filtration and the DMSO solution was purified by flash chromatography to give 6'-bromo-3-[(4-methoxybenzyl)oxy]-4H-1,2'-bipyridin-4-one. $^1$H NMR (600 MHz, DMSO): δ 8.42 (dd, J=7.7, 2.4 Hz, 1 H); 8.22 (d, J=2.4 Hz, 1 H); 8.03-7.96 (m, 1 H); 7.96-7.89 (m, 1 H); 7.71 (t, J=7.7 Hz, 1 H); 7.40 (d, J=8.4 Hz, 2 H); 6.96 (d, J=8.4 Hz, 2 H); 6.42 (d, J=7.7 Hz, 1 H); 5.03 (s, 2 H); 3.76 (s, 3 H); 264.1; MS (M+H)$^+$ 387.

3-Hydroxy-6'-(1H-indazol-4-yl)-4H-1,2'-bipyridin-4-one (8)

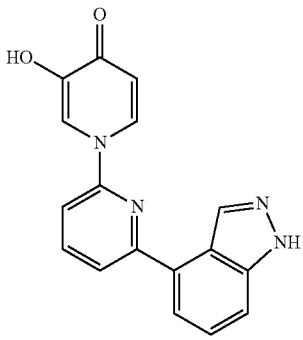

A mixture of 6'-bromo-3-[(4-methoxybenzyl)oxy]-4H-1,2'-bipyridin-4-one (40 mg, 0.1 mmol), 1H-indazol-4-ylboronic acid (32.5 mg, 0.2 mmol), and 1,1'-bis(diphenylphosphino)ferrocene-palladium(II)dichloride dichchloromethane complex (4 mg) in THF (2 mL) and 1 M aq. $Cs_2CO_3$ (1 mL) was heated under microwave irradiation at 160° C. for 10 min. After cooling to rt, the THF and aq. layers were separated and the aq. solution was extracted with THF (2×2 mL). The combined THF solution was treated with QuadraPure TU resin (Aldrich) for 1 h and filtered. The collected THF solution was concentrated. The concentrated residue was dissolved in TFA-DCM (1:1, 1 mL) and stirred for 1 h. The TFA-DCM solution was concentrated and the residue was purified by LCMS to give 3-Hydroxy-6'-(1H-indazol-4-yl)-4H-1,2'-bipyridin-4-one (TFA salt,). $^1$H NMR (499 MHz, DMSO): δ 8.60-8.55 (m, 2 H); 8.39 (d, J=2.4 Hz, 1 H); 8.18 (t, J=7.9 Hz, 1 H); 8.10 (d, J=7.7 Hz, 1 H); 7.87 (d, J=8.1 Hz, 1 H); 7.82 (d, J=7.2 Hz, 1 H); 7.70 (d, J=8.3 Hz, 1 H); 7.52 (t, J=7.7 Hz, 1 H); 6.50 (d, J=7.6 Hz, 1 H); LC/MS (M+H)$^+$ 305; HRMS Calcd for $(C_{17}H_{12}N_4O_2+H)^+$ 305.1033 found 305.1032.

Example 9

4'-(5-chloro-1H-pyrrolo[2,3-b]pyridin-4-yl)-3'-fluoro-3-hydroxy-4H-1,2'-bipyridin-4-one (9)

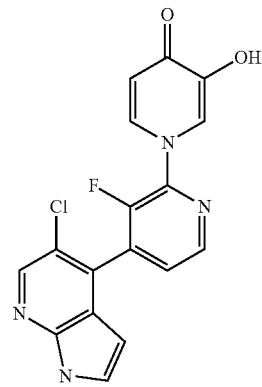

3'-fluoro-4'-iodo-3-[(4-methoxybenzyl)oxy]-4H-1,2'-bipyridin-4-one

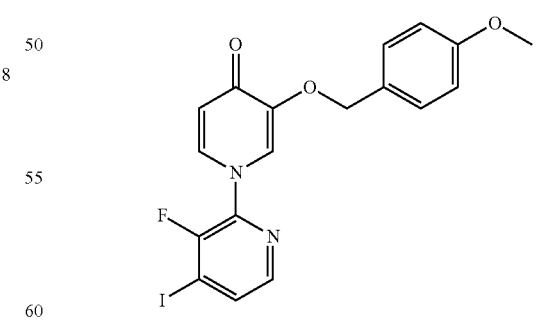

To a 20 mL microwave vial (Biotage) was added 0.70 g (3.03 mmol) 3-[(4-methoxybenzyl)oxy]pyridin-4(1H)-one, 1.26 g (9.08 mmol) potassium carbonate, 1.10 g (4.54 mmol) 2,3-difluoro-4-iodopyridine and 15 mL DMSO. A yellow suspension formed and the vial was sealed and heated at 85° C. for 48 h on a heat block. The suspension was cooled, diluted with ethyl acetate, and washed twice with 10 mL brine. The organic layer was dried over sodium sulfate, filtered, and evaporated onto silica gel. Purification by flash chromatography (silica gel 0-100% hexanes/EtOAc gradient, followed by 10% MeOH in EtOAc) afforded 3'-fluoro-4'-iodo-3-[(4-methoxybenzyl)oxy]-4H-1,2'-bipyridin-4-one as a yellow solid. LCMS (M+H)+ 453.3.

4'-(5-chloro-1H-pyrrolo[2,3-b]pyridin-4-yl)-3'-fluoro-3-[(4-methoxybenzyl)oxy]-4H-1,2'-bipyridin-4-one

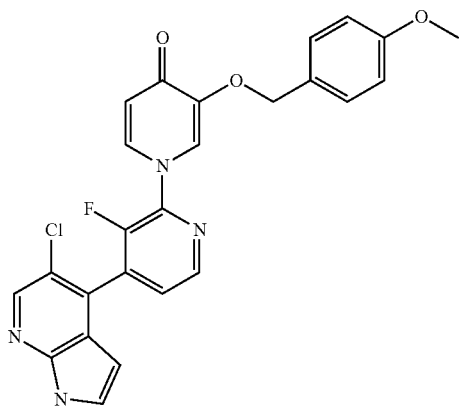 [SMILES: COc1ccc(COc2cn(-c3nccc(-c4c(Cl)cnc5[nH]ccc45)c3F)ccc2=O)cc1]

To a room temperature solution of 132 mg (0.292 mmol) 3'-fluoro-4'-iodo-3-[(4-methoxybenzyl)oxy]-4H-1,2'-bipyridin-4-one in 2 mL THF in a 5 mL microwave vial (Biotage) were added 253 mg (0.584 mmol) 5-chloro-4-(4,4,5,5-tetramethyl-1,3,2-dioxaborolan-2-yl)-1-(triisopropylsilyl)-1H-pyrrolo[2,3-b]pyridine, 1 mL 1.0 M cesium carbonate (1.0 mmol), and 23.8 mg (0.029 mmol) 1,1'-bis(diphenylphosphino)ferrocene-palladium(II)dichloride dichloromethane complex. The vial was sealed and the reaction mixture was heated at 135° C. under microwave irradiation for 15 minutes, then cooled. The organic layer was separated, washed with 1 mL water, dried over Na₂SO₄, filtered, stirred over Quadrapure TU resin (Aldrich), concentrated in vacuo, and used without further purification.

4'-(5-chloro-1H-pyrrolo[2,3-b]pyridin-4-yl)-3'-fluoro-3-hydroxy-4H-1,2'-bipyridin-4-one (9)

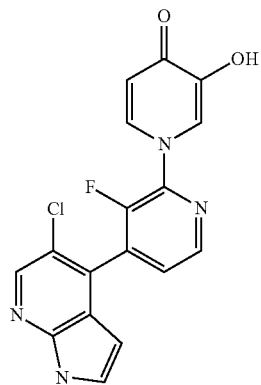

To a 10 mL round bottom flask containing 4'-(5-chloro-1H-pyrrolo[2,3-b]pyridin-4-yl)-3'-fluoro-3-hydroxy-4H-1,2'-bipyridin-4-one was added 2 mL 1:1 (v/v) dichloromethane:trifluoroacetic acid and solution stirred at room temperature for 30 min. Concentration under nitrogen stream and purification by reversed phase HPLC (2 cm×5 cm C18, acetonitrile-water gradient, 0.05% TFA added) afforded 4'-(5-chloro-1H-pyrrolo[2,3-b]pyridin-4-yl)-3'-fluoro-3-hydroxy-4H-1,2'-bipyridin-4-one. ¹H NMR (499 MHz, DMSO): δ 8.59 (d, J=4.9 Hz, 1 H); 8.43 (s, 1 H); 8.09-8.04 (m, 1 H); 7.75 (dd, J=4.9, 4.5 Hz, 1 H); 7.69 (m, 2 H); 6.40 (d, J=3.3 Hz, 1 H); 6.38 (d, J=7.5 Hz, 1 H). HRMS (FT/ICR) Calc 357.0549 (M+H)+=357.0551 found.

Example 10

1-[1-(2-Chloro-6-fluorobenzyl)-1H-benzimidazol-4-yl]-5-hydroxy-2-methylpyridin-4(1H)-one (10)

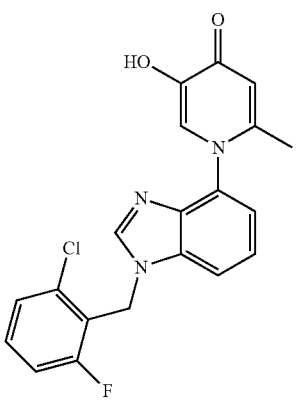

1H-Benzimidazol-4-amine

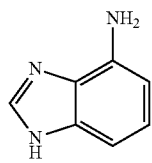

4-Nitro-1H-benzimidazole was hydrogenated (48 psi) with 1 g 10% Pd/C in HOAc (100 mL) for 3 h. The crude mixture was filtered through a pad of Celite, washing with MeOH, and concentrated. The residue was taken up in 2 M aq HCl and applied to a Phenomenex Strata-X—C ion exchange column (5 g). The column was washed with H₂O and MeOH. The washings contained additional material and were applied to another Strata X—C ion exchange column (5 g). The columns were washed with H₂O and MeOH. Each of the columns containing product were washed separately with 10% concentrated NH₄OH in MeOH and the product collected in fractions. The collected fractions were concentrated to give 1H-Benzimidazol-4-amine as a deep red solid. ¹H NMR (500 MHz, d6-DMSO) δ 12.10 (bs, 1 H), 7.98 (s, 1 H), 6.87 (t, J=7.81 Hz, 1 H), 6.72 (d, J=7.82 Hz, 1 H), 6.34 (d, J=7.57 Hz, 1 H), 5.16 (bs, 2 H).

5-(benzyloxy)-2-(chloromethyl)-4H-pyran-4-one

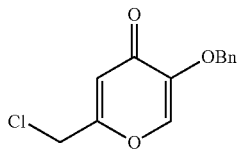 [SMILES: O=c1cc(CCl)occ1OCc1ccccc1]

To a suspension of 5-(benzyloxy)-2-(hydroxymethyl)-4H-pyran-4-one (18.5 g, 80 mmol) in Et$_2$O (130 mL) was added SOCl$_2$ (18 mL, 110 mmol) at r.t. and the mixture was stirred for 1 h. The reaction mixture was poured onto ice-water and more Et$_2$O was added. Then the Et$_2$O phase was collected and water phase was extracted by Et$_2$O twice, the combined Et$_2$O layer was washed with brine, dried over Na$_2$SO$_4$, and concentrated. The residue was purified by silica gel chromatography to give 5-(benzyloxy)-2-(chloromethyl)-4H-pyran-4-one $^1$HNMR (DMSO, 400 MHZ) δ 8.27 (s, 1H), 7.32-7.41 (m, 5H), 6.55 (s, 1H), 4.92 (s, 2H), 4.65 (s, 2H). MS (M+H)$^+$ 250.1/252.1.

5-(benzyloxy)-2-methyl-4H-pyran-4-one

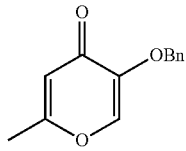 [SMILES: Cc1cc(=O)c(OCc2ccccc2)co1]

To a suspension of 5-(benzyloxy)-2-(chloromethyl)-4H-pyran-4-one (110 g, 0.44 mol) in saturated aqueous NH$_4$Cl (1 L) was added Zn powder (58.5 g, 0.9 mol) at r.t. and the mixture was stirred at 70° C. for 2 h. The mixture was partitioned between water and EtOAc, the EtOAc phase was collected and water phase was extracted with EtOAc twice. The combined EtOAc layer was washed with brine, dried over Na$_2$SO$_4$, and concentrated. The residue was purified by silica gel chromatography to give 40 g (42%) of 5-(benzyloxy)-2-methyl-4H-pyran-4-one.

1-(1H-Benzimidazol-4-yl)-5-(benzyloxy)-2-methylpyridin-4(1H)-one and 1-(1H-Benzimidazol-4-yl)-5-hydroxy-2-methylpyridin-4(11)-one

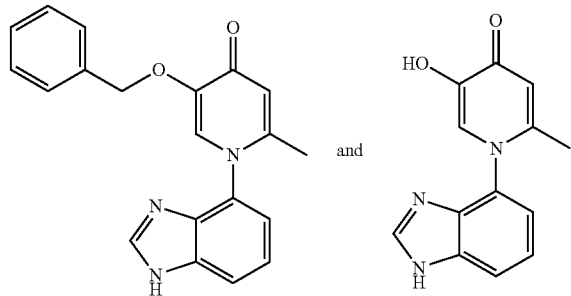 [SMILES: Cc1cc(=O)c(OCc2ccccc2)cn1-c1cccc2[nH]cnc12 ; Cc1cc(=O)c(O)cn1-c1cccc2[nH]cnc12]

5-(Benzyloxy)-2-methyl-4H-pyran-4-one (450 mg, 2.081 mmol) and 1H-benzimidazol-4-amine (279 mg, 2.095 mmol) were taken up in 40% HOAc/H$_2$O (10 ml) in a microwave vial. The vial was sealed and the mixture heated to 140° C. for 30 min by microwave irradiation. The reaction was incomplete by LC/MS. The mixture was heated to 200° C. for 30 min by microwave irradiation. The reaction was incomplete by LC/MS. The mixture was heated to 170° C. for 1 h by microwave irradiation. The mixture was concentrated. The crude material was purified by preparative reversed-phase HPLC (30×150 mm Waters Sunfire (0.1% TFA), 5-35% ACN/water over 20 min at 50 mL/min, 2 injections). Fractions containing each compound were pooled separately then applied to separate Phenomenex Strata-X—C ion exchange columns (5 g). Each column was washed with H$_2$O and MeOH (discard) then with 10% concentrated NH$_4$OH in MeOH (collect). The collected fractions for each were concentrated separately to give the title compounds below:

1-(1H-benzimidazol-4-yl)-5-(benzyloxy)-2-methylpyridin-4(1H)-one: tan solid LC/MS rt=1.24 min, $^1$H NMR (500 MHz, d6-DMSO) δ 12.90 (bs, 1 H), 8.33 (s, 1 H), 7.72 (bs, 1 H), 7.49 (bs, 1 H), 7.41-7.25 (m, 7 H), 6.26 (s, 1 H), 4.94 (s, 2 H), 1.92 (s, 3 H).

1-(1H-benzimidazol-4-yl)-5-hydroxy-2-methylpyridin-4(1H)-one: tan solid, LC/MS rt=0.47 min, $^1$H NMR (500 MHz, d6-DMSO) δ 12.88 (bs, 1 H), 8.32 (s, 1 H), 7.70 (d, J=8.06 Hz, 1 H), 7.38-7.25 (m, 3 H), 6.25 (s, 1 H), 1.92 (s, 3 H).

1-[1-(2-Chloro-6-fluorobenzyl)-1H-benzimidazol-4-yl]-5-hydroxy-2-methylpyridin-4(1H)-one

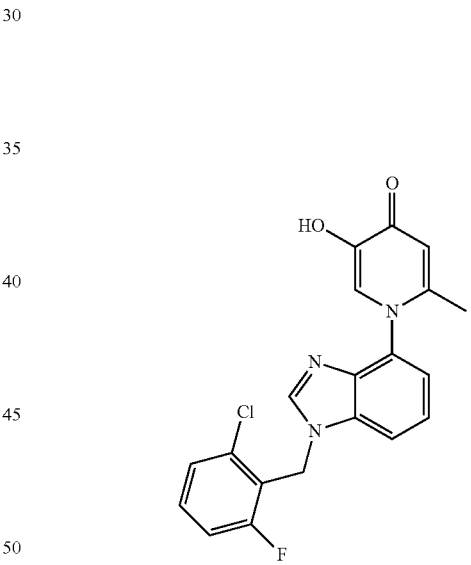

1-(1H-Benzimidazol-4-yl)-5-hydroxy-2-methylpyridin-4(1H)-one (30 mg, 0.124 mmol) and 2-chloro-6-fluorobenzyl bromide (20 μl, 0.146 mmol) were combined in DMF (0.5 ml) then heated to 100° C. After 3 h LC/MS indicated the reaction was incomplete. The mixture was cooled to RT and 10 μL of 2-chloro-6-fluorobenzyl bromide was added. The mixture was heated to 100° C. After 1 hr the mixture was cooled to RT and purified directly by preparative reversed-phase HPLC (20×150 mm Waters Sunfire (0.1% TFA), 5-40% ACN/water over 20 min at 20 mL/min). Fractions containing the product were pooled then applied to a Phenomenex Strata-X—C ion exchange column. The column was washed with H$_2$O and MeOH (discard) then with 10% concentrated NH$_4$OH in MeOH (collect). The collected fraction was concentrated to give 1-[1-(2-Chloro-6-fluorobenzyl)-1H-benzimidazol-4-yl]-5-hydroxy-2-methylpyridin-4(1H)-one as an off-white solid. $^1$H NMR (500 MHz, d6-DMSO) δ 8.43 (s, 1 H), 7.66 (d, J=8.3 Hz, 1 H), 7.52-7.29 (m, 6 H), 6.24 (s, 1 H), 5.70 (s, 2 H), 1.90 (s, 3 H). HRMS (ESI) Calc (M+H)=384.0910. Found 384.0913.

Example 11

1-biphenyl-3-yl-2-[2-(5-fluoro-2-methoxypyridin-3-yl)-2-hydroxyethyl]-5-hydroxypyridin-4(1H)-one (11)

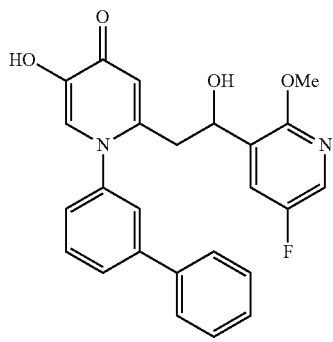

11

5-(benzyloxy)-1-biphenyl-3-yl-2-methylpyridin-4(1)-one

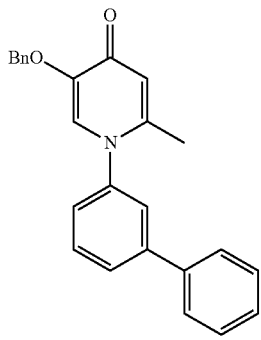 [SMILES: Cc1cc(=O)c(OCc2ccccc2)cn1-c1cccc(-c2ccccc2)c1]

To a suspension of 6.6 g (30.5 mmol) 5-(benzyloxy)-2-methyl-4H-pyran-4-one in 150 ml 30% AcOH was added 7.5 g (45.8 mmol) m-aminobiphenyl. The reaction mixture was heated at 160° C. for 18 h, then cooled to rt, extracted with 300 ml EtOAc, washed with brine, and concentrated in vacuo. Purification by flash chromatography (330 g silica gel, 0-20% MeOH:EtOAc) afforded 5-(benzyloxy)-1-biphenyl-3-yl-2-methylpyridin-4(1H)-one. LCMS (M+H)$^+$=368.3.

1-biphenyl-3-yl-5-hydroxy-2-methylpyridin-4(1H)-one

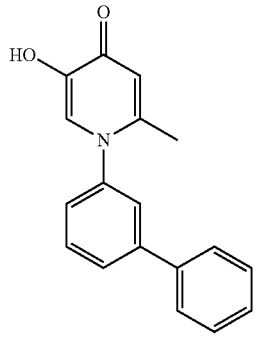

6.0 g (16.3 mmol) 5-(benzyloxy)-1-biphenyl-3-yl-2-methylpyridin-4(1H)-one was suspended in 150 ml 4 N aq HCl. The reaction mixture was heated at 140° C. for 18 h, then cooled to rt, concentrated in vacuo, suspended in CH$_2$Cl$_2$, and collected by filtration to give 1-biphenyl-3-yl-5-hydroxy-2-methylpyridin-4(1H)-one. LCMS (M+H)$^+$=278.2.

1-biphenyl-3-yl-5-[(4-methoxybenzyl)oxy]-2-methylpyridin-4(1/H)-one

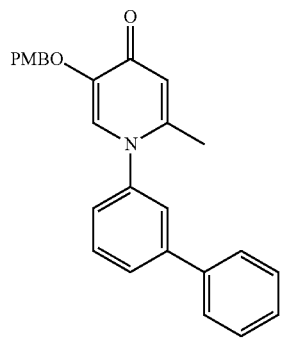

To a solution of 4.8 g (17.4 mmol) 1-biphenyl-3-yl-5-hydroxy-2-methylpyridin-4(1H)-one in 150 ml of DMF was added 4.1 g (26.1 mmol) PMBCl, and 12.0 g (87.0 mmol) K$_2$CO$_3$. The reaction was stirred at rt for 2 h, after which time water was added and a precipitate formed. The solid was collected by filtration and purified by flash chromatography (100 g silica gel, 0-20% MeOH:EtOAc) to afford 1-biphenyl-3-yl-5-[(4-methoxybenzyl)oxy]-2-methylpyridin-4(1H)-one. $^1$H NMR δ (ppm) (DMSO-d$_6$): 7.84 (1 H, d, J=7.86 Hz), 7.77 (2 H, d, J=7.71 Hz), 7.73 (1 H, s), 7.64 (1 H, t, J=7.84 Hz), 7.53-7.47 (3 H, m), 7.46-7.39 (2 H, m), 7.38-7.30 (3 H, m), 6.93 (2 H, d, J=8.32 Hz), 6.23 (1 H, s), 4.89 (2 H, s), 3.77-3.70 (3 H, m), 2.03 (3 H, s). LCMS (M+H)$^+$=398.3.

1-biphenyl-3-yl-2-[2-(5-fluoro-2-methoxypyridin-3-yl)-2-hydroxyethyl]-5-hydroxypyridin-4(1H)-one (11)

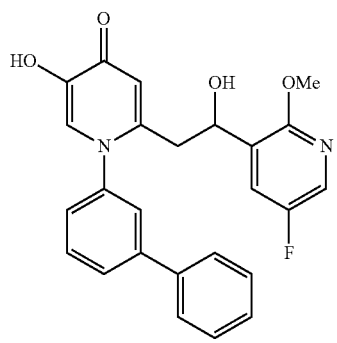

To a solution of 25 mg (0.063 mmol) 1-biphenyl-3-yl-5-[(4-methoxybenzyl)oxy]-2-methylpyridin-4(1H)-one in 1.2 ml of THF was added 94 μl (0.094 mmol) 1 M LiHMDS in THF. After 30 seconds, 9.8 mg (0.063 mmol) 5-fluoro-2-methoxynicotinaldehyde was added. The reaction was quenched with 2 ml of water, extracted with 6 ml of EtOAc, and the organic layer was concentrated in vacuo. The residue was dissolved in 1 ml $CH_2Cl_2$ and 1 ml TFA was added. The solution was concentrated in vacuo and purified by reverse phase HPLC to yield 1-biphenyl-3-yl-2-[2-(5-fluoro-2-methoxypyridin-3-yl)-2-hydroxyethyl]-5-hydroxypyridin-4(H)-one. $^1$H NMR δ (ppm) (DMSO-$d_6$): 8.00-7.90 (2 H, m), 7.86 (1 H, s), 7.78 (3 H, d, J=8.48 Hz), 7.71 (1 H, d, J=8.95 Hz), 7.52 (3 H, t, J=7.96 Hz), 7.47-7.39 (2 H, m), 6.79 (1 H, s), 4.73 (1 H, s), 2.94 (2 H, d, J=16.33 Hz), 2.73 (1 H, d, J=10.74 Hz), 2.54 (3 H, s). HRMS (ESI positive) Calc (M+H)$^+$ 433.1558. Found 433.1562.

Example 12

1-[3-(5-chloro-1H-pyrrolo[2,3-b]pyridin-4-yl)phenyl]-5-hydroxy-2(1-hydroxy-3-phenylprop-2-yn-1-yl)pyridin-4(1H)-one (12)

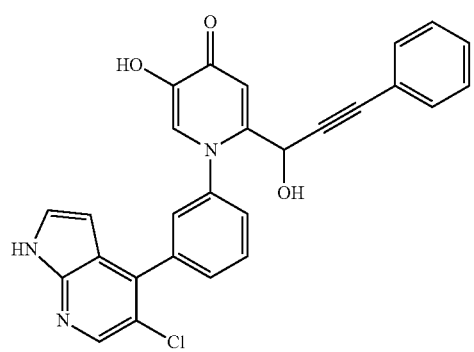

5-Benzyloxy-1-(3-bromo-phenyl)-2-hydroxymethyl-1H-pyridin-4-one

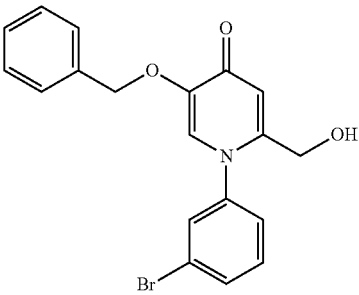 [SMILES: O=c1cc(CO)n(-c2cccc(Br)c2)cc1OCc1ccccc1]

To a suspension of compound 5-benzyloxy-2-hydroxymethyl-pyran-4-one (46.5 g, 0.2 mol) in aq HCl (0.25 N, 500 mL) was added 3-bromophenylamine (37.8 g, 0.22 mol). The resulting mixture was heated under refluxed for 16 h. The reaction mixture was cooled and concentrated to give a residue which was purified by silica gel chromatography elute with EtOAc: MeOH/20:1 to obtained benzyloxy-1-(3-bromo-phenyl)-2-hydroxymethyl-1H-pyridin-4-one as pale solid. $^1$H NMR (400 MHz, DMSO-d): δ 8.22 (s, 1H), 7.87 (t, J=2.0 Hz, 1H), 7.81(m, 1H), 7.60-7.52 (m, 2H), 7.41-7.32 (m, 5H), 7.18 (s, 1H), 5.07 (s, 2H), 4.14 (s, 2H). ESI (M+H)$^+$ 386.0/388.0.

1-(3-Bromo-phenyl)-5-hydroxy-2-hydroxymethyl-1H-pyridin-4-one

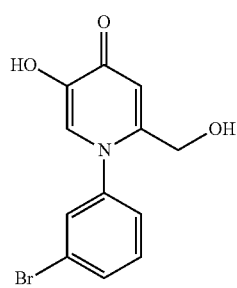

A suspension of benzyloxy-1-(3-bromo-phenyl)-2-hydroxymethyl-1H-pyridin-4-one (44 g, 114 mmol) in 800 mL of aq HCl (4N) was stirred at reflux for 2 h. After cooling to room temperature, the mixture was extracted with EtOAc three times. The aqueous solution was concentrated to give 28.5 g of 1-(3-bromo-phenyl)-5-hydroxy-2-hydroxymethyl-1H-pyridin-4-one (75.2%).

$^1$H NMR (400 MHz, DMSO-d): δ 8.16 (s, 1H), 7.97 (t, J=2.0 Hz, 1H), 7.84 (m, 1H), 7.64 (m, 1H), 7.56 (t, J=8.0 Hz, 1H), 7.49 (s, 1H), 4.16 (s, 2H). ESI (M+H)$^+$ 295.9/297.9.

1-(3-Bromo-phenyl)-2-hydroxymethyl-5-(4-methoxy-benzyloxy)-1H-pyridin-4-one

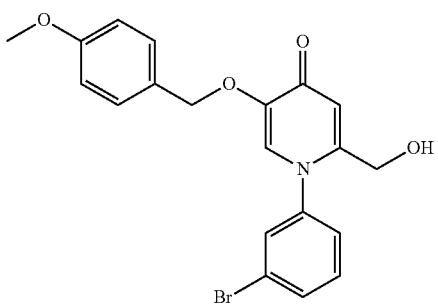 [SMILES: COc1ccc(COc2cn(-c3cccc(Br)c3)c(CO)cc2=O)cc1]

To a mixture of 1-(3-bromo-phenyl)-5-hydroxy-2-hydroxymethyl-1H-pyridin-4-one and $K_2CO_3$ (5.17 g, 37.5 mmol) in 50 mL of DMF was added 2.35 g of PMBCl (15 mmol) dropwise, and the reaction mixture was stirred at 80° C. for 3 h. After cooling to room temperature, the mixture was poured into 200 mL of water and extracted with EtOAc (50 mL) three times. The combined organic layers were washed with water, brine, and dried over anhydrous $MgSO_4$. Most of the volatiles were removed in vacuo and the resulting solid was collected and washed with EtOAc to obtain 1-(3-bromophenyl)-2-hydroxymethyl-5-(4-methoxy-benzyloxy)-1H-pyridin-4-one. $^1$H NMR (400 MHz, DMSO-$d_6$): δ 7.75 (d, J=8.0 Hz, 2H), 7.49 (d, J=4.0 Hz, 2H), 7.46 (s, 1H), 7.31 (d, J=7.6 Hz, 2H), 6.92 (d, J=7.6 Hz, 2H), 6.32 (s, 1H), 5.46 (s, 1H), 4.86 (s, 2H), 3.74 (s, 3H). ESI (M+H)$^+$ 415.9/417.9

1-[3-(5-Chloro-1H-pyrrolo[2,3-b]pyridin-4-yl)-phenyl]-2-hydroxymethyl-5-(4-methoxy-benzyloxy)-1H-pyridin-4-one

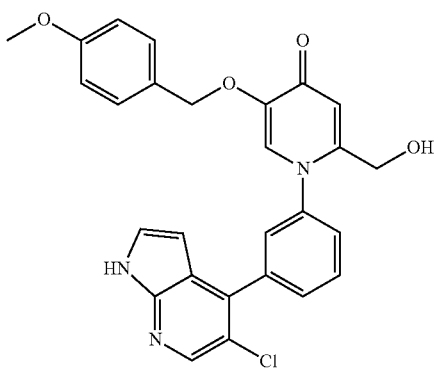 [SMILES: COc1ccc(COc2cn(-c3cccc(-c4c(Cl)cnc5[nH]ccc45)c3)c(CO)cc2=O)cc1]

To each of three 20 mL microwave tubes was added 0.5 g (1.2 mmol) 1-(3-bromo-phenyl)-2-hydroxymethyl-5-(4-methoxy-benzyloxy)-1H-pyridin-4-one, 0.33 g (0.45 mmol) dichloro 1,1'-bis(diphenylphosphino)ferrocene palladium (II) dichloromethane adduct, 0.51 g (1.44 mmol) 5-chloro-4-(4,4,5,5-tetramethyl-1,3,2-dioxaborolan-2-yl)-1-(triisopropylsilyl)-1H-pyrrolo[2,3-b]pyridine, 3.6 mL (3.6 mmol) 1 M aq. $Cs_2CO_3$, and 10 mL THF. The vials were then capped and heated by microwave to 150° C. for 12 minutes each. After cooling, the aqueous layer was removed and the organics were concentrated in vacuo. Purification by automated flash chromatography (40 g silica gel cartridge 0-10% MeOH/EtOAc over 30 min) afforded 1-[3-(5-chloro-1H-pyrrolo[2,3-b]pyridin-4-yl)-phenyl]-2-hydroxymethyl-5-(4-methoxy-benzyloxy)-1H-pyridin-4-one. LCMS (M+H)$^+$ 488.4.

1-[3-(5-Chloro-1H-pyrrolo[2,3-b]pyridin-4-yl)-phenyl]-5-(4-methoxy-benzyloxy)-4-oxo-1,4-dihydro-pyridine-2-carbaldehyde

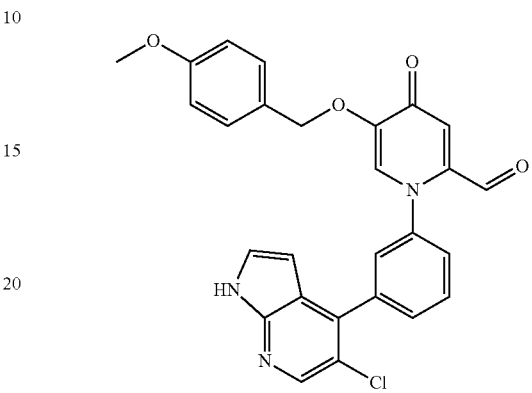

To a solution of 1.44 g (2.95 mmol) 1-[3-(5-chloro-1H-pyrrolo[2,3-b]pyridin-4-yl)-phenyl]-2-hydroxymethyl-5-(4-methoxy-benzyloxy)-1H-pyridin-4-one in 14.5 mL DMSO was added 1.67 g (5.90 mmol) o-iodoxybenzoic acid (99%). The mixture was stirred for 4 h at room temperature, then slowly diluted with 30 mL of a 1:1:1 mixture of sat. aq. sodium thiosulfate, sat. aq. $NaHCO_3$, and water. The crude product precipitated and was collected by filtration and dried in vacuo. Purification by automated flash chromatography (40 g silica gel cartridge 0-10% MeOH/EtOAc over 30 min) afforded 1-[3-(5-chloro-1H-pyrrolo[2,3-b]pyridin-4-yl)-phenyl]-5-(4-methoxy-benzyloxy)-4-oxo-1,4-dihydro-pyridine-2-carbaldehyde. $^1$H NMR (300 MHz, DMSO-d): δ 9.56 (s, 1 H); 8.36 (s, 1 H); 7.81-7.59 (m, 6 H); 7.35 (d, J=8.35 Hz, 2 H); 6.93 (d, J=8.32 Hz, 2 H); 6.87 (s, 1 H); 6.32 (d, J=3.42 Hz, 1 H); 5.00 (s, 2 H); 3.74 (s, 3 H).

1-[3-(5-chloro-1H-pyrrolo[2,3-b]pyridin-4-yl)phenyl]-5-hydroxy-2-(1-hydroxy-3-phenylprop-2-yn-1-yl)pyridin-4(1H)-one (12)

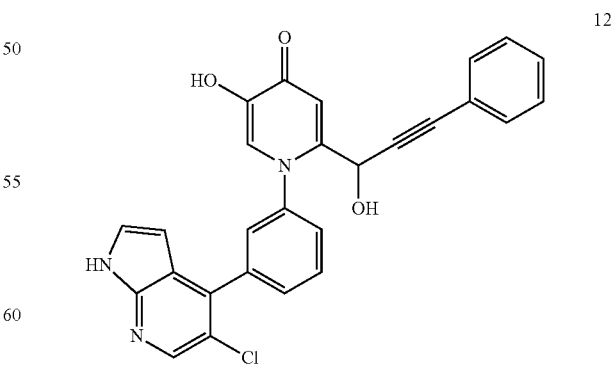

12

To a solution of 0.05 g (0.01 mmol) 1-[3-(5-chloro-1H-pyrrolo[2,3-b]pyridin-4-yl)-phenyl]-5-(4-methoxy-benzyloxy)-4-oxo-1,4-dihydro-pyridine-2-carbaldehyde in 3 mL THF at −40° C. was added 1 mL phenylethynylmagnesium bromide (1.0 M in THF). The reaction mixture was stirred at −40° C. for 30 min before 1 mL of water was added. The reaction was gravity filtered through an Isolute HM-N tube, which was rinsed with 4 mL EtOAc and the combined organics were concentrated. The resulting residue was dissolved in 1 mL TFA and allowed to stand at room temperature for 5 min before being concentrated. Purification by automated mass-guided HPLC afforded 1-[3-(5-chloro-1H-pyrrolo[2,3-b]pyridin-4-yl)phenyl]-5-hydroxy-2-(1-hydroxy-3-phenylprop-2-yn-1-yl)pyridin-4(1H)-one. Compound exhibits equilibrating rotational isomerism in solution. Reported NMR data correlates to the major rotational isomer. $^1$H NMR (500 MHz, CD$_3$OD, 0° C.): δ 8.26 (s, 1H); 7.96 (s, 1H); 7.89-7.78 (m, 3H); 7.71 (t, J=8.59 Hz, 1H); 7.50 (d, J=3.49 Hz, 1H); 7.41-7.36 (m, 5H); 6.34 (d, J=3.46 Hz, 1H); 5.45 (s, 1H). HRMS (FT/ICR) Calc (M+H)$^+$ 468.1109. Found 468.1109.

Example 13

1-[3-(5-chloro-1H-pyrrolo[2,3-b]pyridin-4-yl)phenyl]-5-hydroxy-2-(1-hydroxyethyl)-pyridin-4(1H)-one (13)

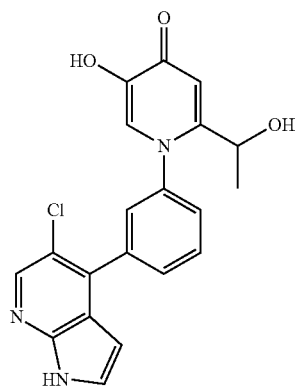

(R)-1-(3-bromophenyl)-2-(1-hydroxyethyl)-5-[(4-methoxybenzyl)oxy]pyridin-4(1H)-one and (S)-1-(3-bromophenyl)-2-(1-hydroxyethyl)-5-[(4-methoxybenzyl)oxy]pyridin-4(1H)-one

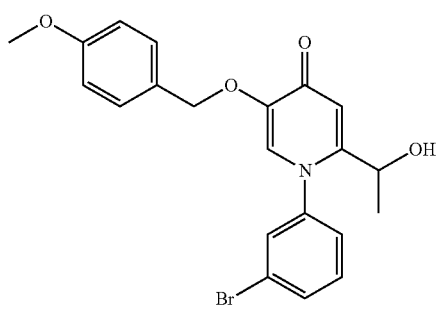 [SMILES: COc1ccc(COc2cn(-c3cccc(Br)c3)c(C(C)O)cc2=O)cc1]

To a solution of 1-(3-bromophenyl)-5-[(4-methoxybenzyl)oxy]-4-oxo-1,4-dihydropyridine-2-carbaldehyde (3.0 g, 7.25 mmol), in dry THF (50 mL) was added MeMgBr (7.25 mL of a 3 M solution in THF, 21.8 mmol) dropwise at −30° C., and the reaction mixture was stirred at −30° C. then warmed to room temperature and stirred for another 2 h. The reaction mixture was cooled to 0° C., 2 mL water was added, and the mixture was diluted with ethyl acetate. The layers were separated, and the organic fraction was dried (MgSO$_4$), concentrated under reduced pressure, and purified by Prep-HPLC to give 1.8 g (58%) of 1-(3-bromophenyl)-2-(1-hydroxyethyl)-5-[(4-methoxybenzyl)oxy]pyridin-4(1H)-one. Chiral resolution of 12.0 g 1-(3-bromophenyl)-2-(1-hydroxyethyl)-5-[(4-methoxybenzyl)oxy]pyridin-4(1H)-one was accomplished by SFC of racemic material using a Chiral Technologies ChiralPak AD-H column (25% MeOH in CO$_2$, 3 cm diameter×25 cm length, 70 mL/min flow, 200 mg per injection), and afforded (80%) of the first eluting enantiomer and (79%) of the second eluting enantiomer. $^1$H-NMR (CD$_3$OD, 400 MHz) δ 7.76 (d, J=8.0 Hz, 1H), 7.64 (s, 1H), 7.51-7.41(m, 2H), 7.38-7.35 (m, 2H), 7.33-7.31 (m, 2H), 6.88-6.86 (m, 2H), 6.76 (s, 1H), 4.95 (s, 2H), 4.39-4.34 (m, 1H), 3.76 (s, 3H), 1.26 (d, J=6.0 Hz, 2H). MS (ESI) m/z (M+H)$^+$ 430.1/432.1.

1-[3-(5-chloro-1H-pyrrolo[2,3-b]pyridin-4-yl)phenyl]-2-(1-hydroxyethyl)-5-[(4-methoxybenzyl)-oxy]pyridin-4(1H)-one

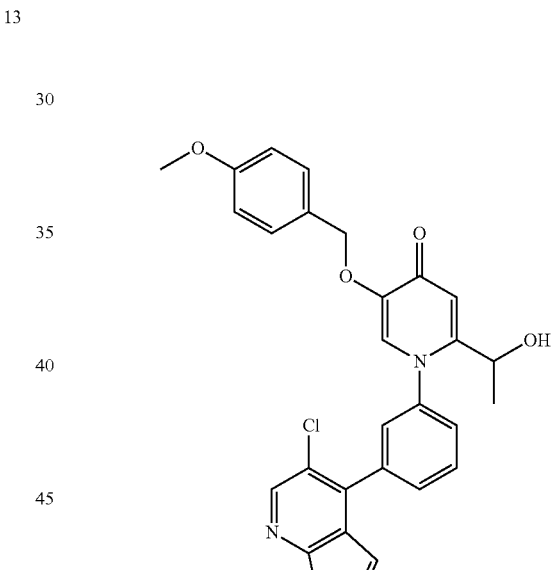

To a 250 mL round-bottom flask were added 2.25 g (5.23 mmol) of the first eluting enantiomer of 1-(3-bromophenyl)-2-(1-hydroxyethyl)-5-[(4-methoxybenzyl)oxy]pyridin-4(1H)-one, 4.55 g (10.46 mmol) 5-chloro-4-(4,4,5,5-tetramethyl-1,3,2-dioxaborolan-2-yl)-1-(triisopropylsilyl)-1H-pyrrolo[2,3-b]pyridine, and 0.427 g (0.523 mmol) 1,1'-bis(diphenylphosphino)ferrocene-palladium(II)dichloride dichloromethane complex. The flask was equipped with a condenser, evacuated, and purged with nitrogen. Evacuation was repeated three times and 50 mL THF and 25 mL 1 M aq cesium carbonate were added. The reaction mixture was heated at 85° C. for 15 h. Upon cooling, the organic layer was separated, washed with 10 mL water, dried over Na$_2$SO$_4$, filtered, and concentrated in vacuo. Purification by flash chromatography (silica gel, 0-100% hexane-ethyl acetate gradient, followed by 10% methanol wash) afforded 1-[3-(5- chloro-1H-pyrrolo[2,3-b]pyridin-4-yl)phenyl]-2-(1-hydroxyethyl)-5-[(4-methoxybenzyl)oxy]pyridin-4(1H)-one. LCMS (M+H)+ 502.4.

1-[3-(5-chloro-1H-pyrrolo[2,3-b]pyridin-4-yl)phenyl]-5-hydroxy-2-(1-hydroxyethyl)-pyridin-4(1H)-one (13)

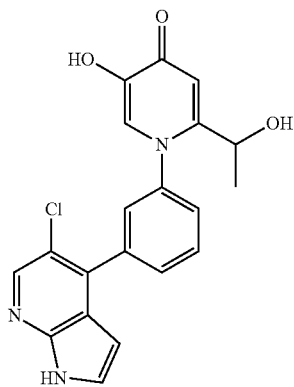

To a 100 mL round-bottom flask containing 2.34 g (4.66 mmol) 1-[3-(5-chloro-1H-pyrrolo[2,3-b]pyridin-4-yl)phenyl]-2-(1-hydroxyethyl)-5-[(4-methoxybenzyl)oxy]pyridin-4(1H)-one was added 25 mL 1:1 (v/v) dichloromethane:trifluoroacetic acid and the solution stirred at room temperature for 30 min. Concentration in vacuo, purification by reversed phase HPLC (2 cm×5 cm C18, acetonitrile-water gradient, 0.05% TFA added), and elution from an SCX column (50 g, sulfonic acid, rinsed with MeOH, eluted with 1 N NH$_3$ in MeOH) afforded 1-[3-(5-chloro-1H-pyrrolo[2,3-b]pyridin-4-yl)phenyl]-5-hydroxy-2-(1-hydroxyethyl)pyridin-4(1H)-one. $^1$H NMR (600 MHz, DMSO, 50° C.): δ 11.96 (s, 1 H); 8.35 (s, 1 H); 7.75 (dd, J=7.9, 7.7 Hz, 1 H); 7.70 (d, J=7.8 Hz, 1 H); 7.60-7.55 (m, 3 H); 7.34 (s, 1 H); 6.46 (s, 1 H); 6.29 (s, 1 H); 4.41 (q, J=6.4 Hz, 1 H); 1.20 (d, J=6.4 Hz, 3 H). HRMS (FT/ICR) Calc (M+H)+ 382.0953 found 382.0955.

Example 14

5-hydroxy-2-(1-hydroxyethyl)-1-[3-(isoquinolin-4-yl)phenyl]pyridin-4(1H)-one (14)

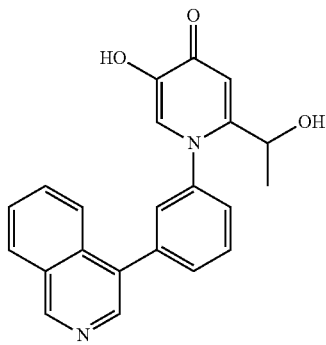

2-(1-hydroxyethyl)-1-[3-(isoquinolin-4-yl)phenyl]-5-[(4-methoxybenzyl)oxy]pyridin-4(1H)-one

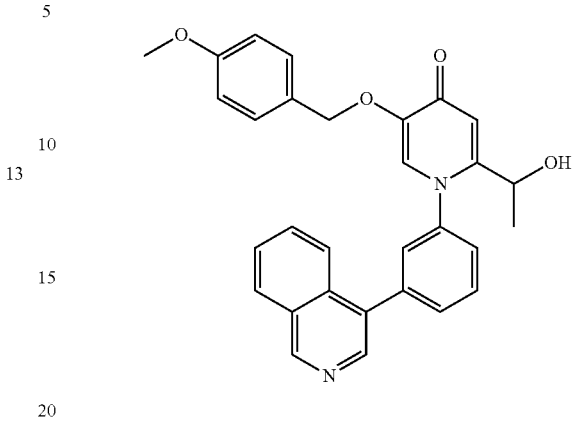

To a 100 mL round-bottom flask were added 4.20 g (9.76 mmol) of 2-(1-hydroxyethyl)-1-[3-bromophenyl]-5-[(4-methoxybenzyl)oxy]pyridin-4(1)-one, 3.38 g (19.52 mmol) isoquinolin-4-ylboronic acid, 0.75 g (0.97 mmol) 1,1'-bis(diphenylphosphino)ferrocene-palladium(II)dichloride dichloromethane complex. The flask was equipped with a condenser, evacuated, and purged with nitrogen. Evacuation was repeated three times and 50 mL THF and 40 mL 1 M aq cesium carbonate were added. The reaction mixture was heated at 80° C. for 3 h. Upon cooling, the organic layer was separated, washed with 15 mL water, dried over Na$_2$SO$_4$, filtered, stirred over Quadrapure TU resin (Aldrich), concentrated in vacuo, and used without further purification. LCMS (M+H)+ 479.5.

5-hydroxy-2-(1-hydroxyethyl)-1-[3-(isoquinolin-4-yl)phenyl]pyridin-4(1H)-one (14)

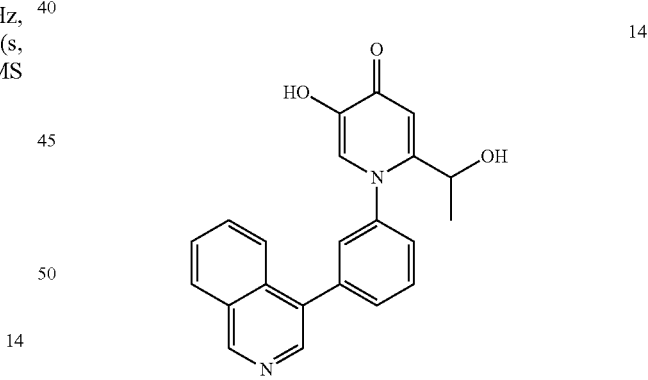

To a 25 mL round bottom flask containing 2-(1-hydroxyethyl)-1-[3-(isoquinolin-4-yl)phenyl]-5-[(4-methoxybenzyl)oxy]pyridin-4(1)-one was added 5 mL 1:1 (v/v) dichloromethane:trifluoroacetic acid and the solution was stirred at room temperature for 30 minutes and turned deep red. Concentration under nitrogen stream, purification by reversed phase HPLC (2 cm×5 cm C18, acetonitrile-water gradient, 0.05% TFA added), and elution from an SCX column (50 g, sulfonic acid, rinsed with MeOH, eluted with 1 N NH$_3$ in MeOH) afforded 5-hydroxy-2-(1-hydroxyethyl)-1-[3-(isoquinolin-4-yl)phenyl]pyridin-4(1H)-one. $^1$H NMR (599 MHz, DMSO, 75° C.): δ 9.35 (s, 1 H); 8.51 (s, 1 H); 8.22 (d, J=8.2 Hz, 1 H); 7.90 (d, J=8.5 Hz, 1 H); 7.81 (t, J=7.7 Hz, 1 H); 7.77-7.69 (m, 3 H); 7.61 (s, 1 H); 7.58 (d, J=7.8 Hz, 1 H); 7.39 (s, 1 H); 6.48 (s, 1 H); 4.44 (q, J=6.4 Hz, 1 H); 1.24 (d, J=6.4 Hz, 3 H). HRMS (FT/ICR) Calc 359.1390 (M+H)+ 359.1395 found.

Example 15

5-hydroxy-1-[3-(quinolin-5-yl)phenyl]-2-(2,2,2-trifluoro-1-hydroxyethyl)pyridin-4(1H)-one (15)

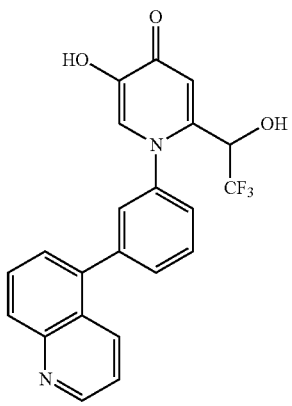

1-(3-bromophenyl)-5-[(4-methoxybenzyl)oxy]-2-(2,2,2-trifluoro-1-hydroxyethyl)pyridin-4(1H)-one

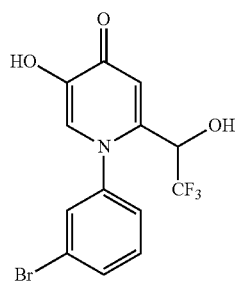 [SMILES: O=c1cc(C(O)C(F)(F)F)n(-c2cccc(Br)c2)cc1O]

To a semi-suspension of 1-(3-bromophenyl)-5-[(4-methoxybenzyl)oxy]-4-oxo-1,4-dihydropyridine-2-carbaldehyde (500 mg, 1.21 mmol) in THF (5 mL) at 0° C. was added (trifluoromethyl)trimethylsilane solution (5.3 mL of 0.5 mL solution in THF) followed by tetrabutylammonium fluoride solution (0.1 mL of a 1 M solution in THF). The reaction mixture was stirred at 0° C. for 1 h and then quenched by adding water. The quenched reaction mixture was then diluted with dichloromethane, washed with brine (1×), dried over $Na_2SO_4$, filtered, and concentrated in vacuo. Purification by flash chromatography (24 g silica gel, linear gradient of 0 to 5% methanol in dichloromethane) afforded 1-(3-bromophenyl)-5-[(4-methoxybenzyl)oxy]-2-(2,2,2-trifluoro-1-hydroxyethyl)pyridin-4(1H)-one.

5-hydroxy-1-[3-(quinolin-5-yl)phenyl]-2-(2,2,2-trifluoro-1-hydroxyethyl)pyridin-4(1H)-one (15)

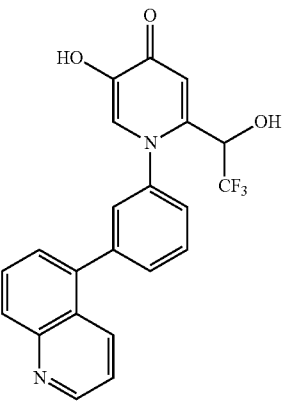

To a mixture of 1-(3-bromophenyl)-5-[(4-methoxybenzyl)oxy]-2-(2,2,2-trifluoro-1-hydroxyethyl)pyridin-4(1H)-one (400 mg, 0.826 mmol), quinolin-5-ylboronic acid (171 mg, 0.991 mmol), tris(3-sulfonatophenyl)phosphine hydrate sodium salt (79 mg, 0.124 mmol) and palladium(II)acetate (9.27 mg, 0.041 mmol), under nitrogen, were added DMF (6 mL), diisopropylamine (0.353 mL, 2.478 mmol) and water (1 mL). The reaction mixture was stirred at 60° C. under nitrogen for 1.5 h. After cooling to room temperature the reaction mixture was partitioned between half-saturated aqueous $NH_4Cl$ and EtOAc. Layers were separated and the aqueous solution was extracted with EtOAc (3×). Combined organic solutions were dried over $Na_2SO_4$, filtered and concentrated in vacuo. The resulting residue was dissolved in $CH_2Cl_2$-TFA (1:1, 6 mL), allowed to stand at room temperature for 10 min and then concentrated. Purification was done by preparative HPLC (5-95% $CH_3CN/H_2O$ over 20 min, 0.05% added TFA, C18 OBD Sunfire 30×150 mm). The desired fractions were loaded onto a Strata-X—C cation exchange column. After washing the column with water and MeOH, the column was eluted with 5% $NH_4OH$ in MeOH to give 5-hydroxy-1-[3-(quinolin-5-yl)phenyl]-2-(2,2,2-trifluoro-1-hydroxyethyl)pyridin-4(1H)-one as tan solid (277 mg, 81%). $^1$H NMR (DMSO-$d_6$, 400 MHz) □ 8.97-8.96 (m, 1H), 8.27 (dd, J=28.8, 8.4 Hz, 1H), 8.12 (d, J=8.4 Hz, 1H), 7.87 (t, J=7.5 Hz, 1H), 7.81-7.69 (m, 2H), 7.63-7.53 (m, 4H), 7.28 (br m, 1H), 6.54 (d, J=12.1 Hz, 1H), 4.84-4.73 (m, 1H). HRMS Calc (M+H)+ 413.1035. Found 413.1102.

Example 16

1-(Biphenyl-3-yl)-5-hydroxy-2-phenylpyridin-4(1H)-one (16)

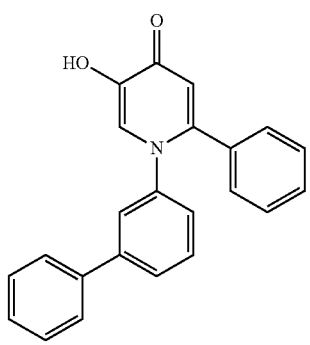

4-Oxo-6-phenyl-4H-pyran-3-yl acetate

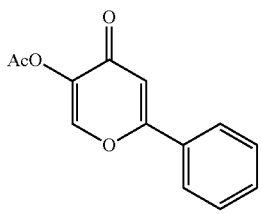

To a solution of 545 mg (3.5 mmol) of 1-methoxy-3-oxobut-1-en-2-yl acetate in THF (14.2 mL) at −78° C. was added LHMDS (3.45 mL of a 1 M solution in toluene) dropwise. After stirring for min at −78° C., the reaction mixture was treated with 0.4 mL (3.5 mmol) of benzoyl chloride dropwise, then removed from the cold bath and allowed to warm to room temperature and continue stirring for 18 h. The reaction was quenched with 10 mL 10% aq HCl and extracted with diethyl ether (3×10 mL). The organic fractions were combined, washed with sat. aq. NaCl, dried ($Na_2SO_4$), and concentrated under reduced pressure to provide 1-methoxy-3,5-dioxo-5-phenylpent-1-en-2-yl acetate which was used the subsequent step without further purification.

To a solution of crude 1-methoxy-3,5-dioxo-5-phenylpent-1-en-2-yl acetate (3.5 mmol) in toluene (35 mL) was added pyridinium p-toluenesulfonate (130 mg, 0.5 mmol). The reaction mixture was heated at reflux under a nitrogen atmosphere for 1 h before being cooled and concentrated under reduced pressure and purified by flash chromatography (80 g $SiO_2$, 0-100% ethyl acetate/hexanes gradient elution) to provide 4-oxo-6-phenyl-4H-pyran-3-yl acetate. LC/MS (M+H)$^+$ 231.

5-Methoxy-2-phenyl-4H-pyran-4-one

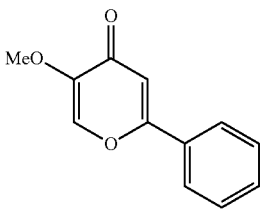 [SMILES: CC(=O)Oc1coc(-c2ccccc2)cc1=O]

To a solution of 4-oxo-6-phenyl-4H-pyran-3-yl acetate (100 mg, 0.4 mmol) in MeOH (10.9 mL) is added $K_2CO_3$ (180 mg, 1.3 mmol) and the reaction was stirred for 15 min at room temperature. The reaction mixture was concentrated under reduced pressure to provide 5-hydroxy-2-phenyl-4H-pyran-4-one which was used in the subsequent step without further purification.

To a solution of crude 5-hydroxy-2-phenyl-4H-pyran-4-one (0.4 mmol) in acetone (10.9 mL) is added iodomethane (0.7 mL, 11.3 mmol) and the reaction mixture was heated at 60° C. for 2 h. After being cooled to room temperature, the reaction was concentrated under reduced pressure and diluted with $CHCl_3$ (10 mL) and water (10 mL). The layers were separated and the organic fraction washed with sat. aq. NaCl, dried ($Na_2SO_4$), and concentrated under reduced pressure to provide (93%) of 5-methoxy-2-phenyl-4H-pyran-4-one as tan crystals which were used in the subsequent step without further purification. LC/MS (M+H)$^+$ 203.

1-(Biphenyl-3-yl)-5-methoxy-2-phenylpyridin-4(1H)-one

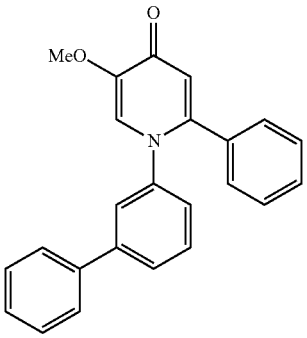

To a solution of 5-methoxy-2-phenyl-4H-pyran-4-one (35 mg, 0.17 mmol) in a 1:1 mixture of AcOH:water (0.6 mL) was added 3-aminobiphenyl (59 mg, 0.35 mmol). The reaction vessel was sealed and heated at 130° C. for 3 h before being cooled to room temperature and purified by reversed phase HPLC (2 cm×5 cm C18, acetonitrile-water gradient, 0.05% TFA added) to provide (44%) 1-(biphenyl-3-yl)-5-methoxy-2-phenylpyridin-4(1H)-one. LC/MS (M+H)$^+$ 354.

1-(Biphenyl-3-yl)-5-hydroxy-2-phenylpyridin-4(1H)-one (16)

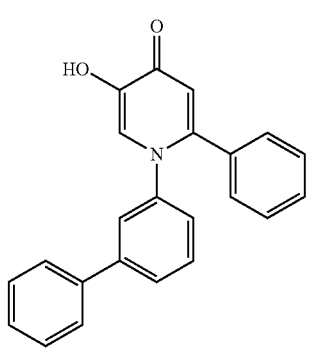 [SMILES: COc1cn(-c2cccc(-c3ccccc3)c2)c(-c2ccccc2)cc1=O]

16

1-(Biphenyl-3-yl)-5-methoxy-2-phenylpyridin-4(1H)-one (20 mg, 0.056 mmol) was treated with $BBr_3$ (0.5 mL of a 1 M solution in $CH_2Cl_2$) and stirred at room temperature. After 1 h, the reaction mixture was cooled to 0° C. and quenched with dropwise addition of MeOH (0.1 mL), before being concentrated under a stream of $N_2$, diluted with MeOH (0.8 mL) and purified by reversed phase HPLC (2 cm×5 cm C18, acetonitrile-water gradient, 0.05% TFA added) to provide (99%) of 1-(biphenyl-3-yl)-5-hydroxy-2-phenylpyridin-4(1H)-one.
$^1$H NMR (499 MHz, DMSO): δ 7.88 (s, 1 H); 7.64-7.60 (m, 2 H); 7.53 (d, J=7.7 Hz, 2 H); 7.46-7.40 (m, 3 H); 7.40-7.36 (m, 1 H); 7.30-7.26 (m, 6 H); 6.58 (s, 1 H). HRMS (ES) Calc (M+H)$^+$ 340.1332 found 340.

Example 17

1-[1-(2-chlorobenzyl)-1H-benzimidazol-4-yl]-3-hydroxypyridin-4(1H)-one (17)

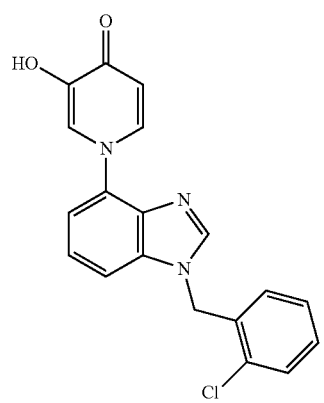

3-(benzyloxy)-1-[1-(2-chlorobenzyl)-1H-benzimidazol-4-yl]pyridin-4(1H)-one

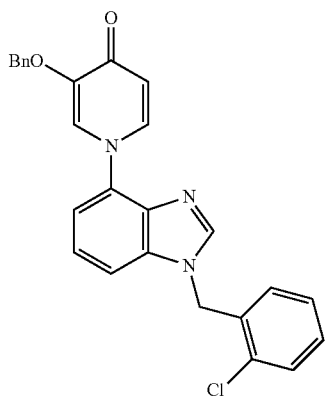 [SMILES: O=c1ccn(-c2cccc3c2ncn3Cc2ccccc2Cl)cc1OCc1ccccc1]

To a solution of 5-(benzyloxy)-4-oxo-4H-pyran-2-carboxylic acid (1.06 g, 4.5 mmol) in EtOH (20 mL) and H$_2$O (20 mL) was added 1H-benzimidazol-4-amine (0.6 g, 4.5 mmol) and the mixture was heated at reflux overnight. The reaction mixture was concentrated, then dissolved in DMF (20 mL) and the mixture was stirred at 80° C. for 2 h. After cooling to r.t. 1-chloro-2-(chloromethyl)benzene (725 mg, 4.5 mmol) and K$_2$CO$_3$ (620 mg, 4.5 mmol) were added and the mixture was stirred at 80° C. for another 2 h. The mixture was filtered, concentrated under reduced pressure, and the residue was purified by prep-HPLC to give 0.6 g (30%) of 3-(benzyloxy)-1-[1-(2-chlorobenzyl)-1H-benzimidazol-4-yl]pyridin-4(1)-one. MS (ESI) (M+H)$^+$ 442.1/444.1.

1-[1-(2-chlorobenzyl)-1H-benzimidazol-4-yl]-3-hydroxypyridin-4(1H)-one (17)

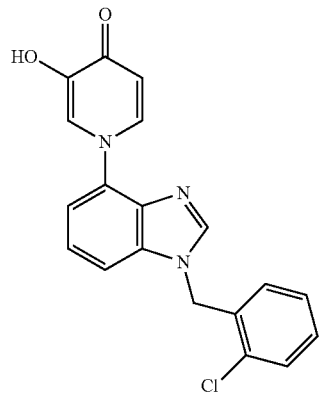

To a solution of 3-(benzyloxy)-1-[1-(2-chlorobenzyl)-1H-benzimidazol-4-yl]pyridin-4(H)-one (2.6 g, 5.9 mmol) in DCM (40 mL) was added ethanethiol (4 mL) and BF$_3$.Et$_{20}$ (4 mL) and the mixture was stirred at r.t. for 4 h. The mixture was diluted with MeOH, stirred for 10 min, then concentrated. The residue obtained was purified by prep-HPLC to give 1.2 g (58%) of 1-[1-(2-chlorobenzyl)-1H-benzimidazol-4-yl]-3-hydroxypyridin-4(1H)-one. $^1$H-NMR (CD$_3$OD, 400 MHz) δ 8.48-8.44 (m, 3H), 7.78 (d, J=7.6 Hz, 1H), 7.58-7.51 (m, 3H), 7.41-7.25 (m, 4H), 5.75 (s, 2H). MS (ESI) (M+H)$^+$ 352.1/354.1.

Assays

The activity of the compounds in accordance with the present invention as COMT inhibitors may be readily determined without undue experimentation using a fluorescence or fluorescence polarization (FP) methodology that is well known in the art (Kurkela M et al., Anal Biochem (331) 2004, 198-200 and Graves, T L et al., Anal Biochem (373) 2008, 296-306). Assays utilized purified human COMT enzyme of the Val158 variant (membrane-bound MB-COMT or soluble S-COMT) containing a C-terminal 6 or 10-histidine tag. Compounds of the following examples had activity in reference assays by exhibiting the ability to inhibit the methylation of esculetin and/or inhibit the production of S-adenosyl-homocysteine (SAH). Any compound exhibiting an IC$_{50}$ below 1 μM would be considered a COMT inhibitor as defined herein.

In a typical experiment the COMT inhibitory activity of the compounds of the present invention was determined in accordance with the following experimental methods detailed below. The fluorescence assay was based on methylation of a substrate (6,7-dihydroxycoumarin or 'esculetin') by COMT to produce a highly fluorescent product (7-hydroxy-6-methoxycoumarin or 'scopoletin'). The reaction requires the presence of magnesium ions and a methyl donor, in this case S-adenosylmethionine (SAM). A 10 mM compound stock in DMSO was used to prepare 10 point 3-fold dilution series and 1 μL of appropriate dilution was plated into assay wells (black 96 well round bottom polystyrene plates from Costar; catalog #3792). Recombinant enzyme was diluted in assay buffer (100 mM Na$_2$HPO$_4$ pH 7.4, 1 mM DTT, 0.005% Tween-20) and 35 μL was added to assay wells containing 1 μL of compound. Preincubation of COMT enzyme and compound proceeded for 2 hours at room temperature. Enzyme assays were initiated with 5 uL of a mixture containing 40 μM SAM (USB catalog #US10601), 4 μM esculetin (substrate) and 40 mM MgCl$_2$. The formation of product (scopoletin) was monitored over time by fluorescence (excitation 340 nm, emission 460 nm, no lag, 100 μs integration time, 5 flashes, top read) using a Tecan Safire$^2$ plate reader. Assays were monitored over time until a signal to background of 4 to 1 was achieved. Titration curves and IC$_{50}$ values were calculated using standard procedures. Briefly, data were calculated as (mean of test wells)–(mean of no-enzyme controls)/(mean of total enzyme controls)–(mean of no-enzyme controls), then expressed as a percentage and subtracted from 100 to give percent inhibition of COMT activity. In some cases, compounds were not preincubated with MB-COMT for 2 hours at room temperature prior to starting the enzyme assays.

To determine IC$_{50}$ values in the fluorescence polarization assay, solutions of test compounds were prepared and preincubated with COMT enzyme as stated above. Enzyme reactions were initiated upon the addition of 5 μL of an 8× mix prepared in assay buffer containing 8 μM SAM (USB catalog #US10601), 16 μM dopamine (Sigma catalog #H8502) and 40 mM MgCl$_2$. After 25 minutes incubation at room temperature, reactions were quenched with 5 μL 250 mM EDTA, pH 8.2. To quenched reactions, 20 μL of a preformed complex containing S-adenosyl-L-cysteine (SAC) TAMRA tracer (2 mM from Anaspec diluted 1:80,000) and a 1:20 dilution of anti-S-adenosyl-L-homocysteine antibody (mouse monoclonal from Abbott Homocysteine detection kit, catalog #7D29-20) was prepared in assay buffer II (Na$_2$HPO$_4$ pH 7.2). Prior to combining with quenched enzyme assays, the SAH antibody/SAC TAMRA tracer complex was preformed at room temperature for 30 minutes while protected from light. Therefore, the final concentration of the SAH antibody/SAC TAMRA mix was 1:60 and 1:240,000, respectively. After a 2.5 hour incubation at room temperature, protected from light, fluorescence polarization was measured using a Tecan Safire$^2$ plate reader (excitation 530 nm, emission 595 nm). Titration curves and IC$_{50}$ values were calculated using standard protocols.

The compounds of formula I have an IC$_{50}$ activity of 100 μM or less for COMT. Many of the compounds of formula I have an IC50 of less than 200 nM. For example, the compounds below have IC$_{50}$<250 nM in the "Esculetin or Fluorescence Polarization assay". In particular, the compounds of Examples 1-4, 6, and 8-16 exhibited the following IC$_{50}$ (nM) values:

| Example# | MB-COMT IC50-(nM) |
| --- | --- |
| 1 | 46 |
| 2 | 64 |
| 3 | 75 |
| 4 | 100 |
| 6 | 203 |
| 8 | 21 |
| 9 | 8 |
| 10 | 191 |
| 11 | 87 |
| 12 | 26 |
| 13 | 41 |
| 14 | 226 |
| 15 | 70 |
| 16 | 88 |

What is claimed:
1. A compound of structural formula I:

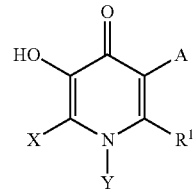

or a pharmaceutically acceptable salt, enantiomer or diastereomer thereof, wherein:
A represents hydrogen, B(OH)$_2$, halo, OH, C$_{3-10}$ cycloalkyl, or C$_{1-6}$ alkyl;
X represents hydrogen, or C$_{1-6}$ alkyl;
Y represents phenyl or pyridyl, any of which is optionally substituted with 1 to 3 groups of R$^a$;
R$^1$ represents CH(OH)CH$_3$, NH$_2$NHCH$_3$,(CHR$^2$)$_n$C$_{6-10}$aryl, or (CHR$^2$)$_n$C$_{6-10}$heterocyclyl, wherein said aryl and heterocyclyl are optionally substituted with 1 to 3 groups of R$^a$;
each R$^2$ independently represents H, OH, or C$_{1-6}$ alkyl;
each R$^a$ independently represents C$_{1-6}$ alkyl, halogen, (CH$_2$)$_n$CF$_3$, OCHF$_2$, OCF$_3$, C$_{3-6}$cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, C(O)OR$^2$SO$_2$R$^2$, OR$^2$, (CH$_2$)$_n$C$_{5-10}$ heterocyclyl, NH(CH$_2$)$_n$C$_{5-10}$ heterocyclyl, (CH$_2$)$_n$C$_{6-10}$ aryl, O(CH$_2$)$_n$C$_{6-10}$ aryl, or O(CH$_2$)$_n$C$_{5-10}$ heterocyclyl, said cycloalkyl, heterocyclyl and aryl optionally substituted with 1 to 3 groups of R$^b$;
each R$^b$ independently represents C$_{1-6}$ alkyl, halogen, CHF$_2$, N(R$^2$)$_2$, CH$_2$OH, (CH$_2$)$_n$CF$_3$, —O—, OR$^2$, or CN; and
n represents 0 to 5; and
provided that no more than one of said R$^a$ is (CH$_2$)$_n$C$_{5-10}$ heterocyclyl, (CH$_2$)$_n$C$_{6-10}$aryl, O(CH$_2$)$_n$C$_{6-10}$ aryl, or O(CH$_2$)nC$_{5-10}$ heterocyclyl.

2. The compound according to claim 1 represented by structural formula II:

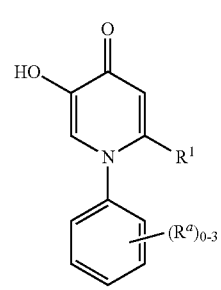

or a pharmaceutically acceptable salt, enantiomer or diastereomer thereof, wherein:
R$^1$ represents (CHR$^2$)$_n$C$_{6-10}$aryl, said aryl optionally substituted with 1 to 3 groups of R$^a$;
each R$^2$ independently represents H or OH;
each R$^a$ is independently selected from C$_{1-6}$ alkyl, halogen, (CH$_2$)$_n$CF$_3$, OR$^2$, (CH$_2$)$_n$C$_{5-10}$ heterocyclyl, (CH$_2$)$_n$C$_{6-10}$aryl, O(CH$_2$)$_n$C$_{6-10}$ aryl, or O(CH$_2$)$_n$C$_{5-10}$ heterocyclyl, said alkyl, heterocyclyl and aryl are optionally substituted with 1 to 3 groups of $R^b$;

each $R^b$ is independently selected from $C_{1-6}$ alkyl, halogen, $CHF_2$, $N(R^2)_2$, $CH_2OH$, $OR^2$, $(CH_2)_nCF_3$, and CN.

3. The compound according to claim 2 wherein:
$R^1$ represents $(CHR^2)_nC_{6-10}$aryl, and said aryl is phenyl.

4. The compound according to claim 2 wherein
at least one of said 1 to 3 groups of $R^a$ is selected from $(CH_2)_nC_{5-10}$heterocyclyl and $(CH_2)_nC_{6-10}$aryl, said aryl and heterocyclyl optionally substituted with 1 to 3 groups of $R^b$.

5. The compound according to claim 2 wherein
at least one of said 1 to 3 groups of $R^a$ is selected from $C_{6-10}$ aryl and $C_{5-10}$ heterocyclyl, and said aryl and heterocyclyl are optionally substituted with 1 to 3 groups of $R^b$.

6. The compound according to claim 4 or 5, wherein
said aryl and heterocyclyl are selected from naphthyridine, indolyl, benzodioxaolyl, pyridyl, furopyridinyl, isoindolyl, pyridooxazinyl, pyrrolopyridinyl, quinoxalinyl, quinazolinyl, quinolinyl, isoquinolinyl, phenyl, indazolyl, [1,2,4]triazolo[1,5-a]pyridine, 1,2,3,4-tetrahydroisoquinoline, 1,3-benzodioxole, 1-benzothiophene, 1H-indazole, 1H-pyrrolo[2,3-b]pyridine, 1H-pyrrolo[2,3-c]pyridine, 1H-pyrrolo[3,2-b]pyridine, 1H-pyrrolo[3,2-c]pyridine, 2,1,3-benzoxadiazole, 3,4-dihydro-2H-pyrido[3,2-b][1,4]oxazine, 3H-imidazo[4,5-b]pyridine, 4,5,6,7-tetrahydropyrazolo [1,5-a]pyridine, furo[2,3-c]pyridine, furo[3,2-b]pyridine, imidazo [1,2-a]pyridine, quinazoline, and thieno[3,2-c]pyridin-4(5H)-one, any of which is optionally substituted with 1 to 3 groups of $R^b$.

7. The compound according to claim 1, wherein the compound is represented by structural formula II:

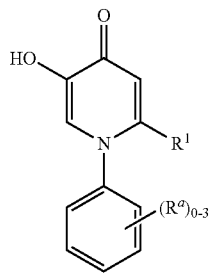

II or a pharmaceutically acceptable salt, enantiomer or diastereomer thereof, wherein:
$R^1$ represents $CH(OH)CH_3$;
$R^2$ and $R^3$ are independently selected from H and $C_{1-6}$ alkyl;
each $R^a$ is independently selected from $C_{1-6}$ alkyl, halogen, $(CH_2)_nCF_3$, $OR^2$, $(CH_2)_nC_{5-10}$ heterocyclyl, $(CH_2)_nC_{6-10}$aryl, $O(CH_2)_nC_{6-10}$ aryl, or $O(CH_2)_nC_{5-10}$ heterocyclyl, said alkyl, heterocyclyl and aryl are optionally substituted with 1 to 3 groups of $R^b$;
each $R^b$ is independently selected from $C_{1-6}$ alkyl, halogen, $CHF_2$, $N(R^2)_2$, $CH_2OH$, $OR^2$, $(CH_2)_nCF_3$, and CN; and
n represents 0 to 5.

8. The compound according to claim 7 wherein at least one of said 1 to 3 groups of $R^a$ is selected form $C_{6-10}$ aryl and $C_{5-10}$ heterocyclyl and said ary and heterocyclyl are selected from naphthyridine, indolyl, benzodioxaolyl, pyridyl, furopyridinyl, isoindolyl, pyridooxazinyl, pyrrolopyridinyl, quinoxalinyl, quinazolinyl, quinolinyl, isoquinolinyl, phenyl, indazolyl, [1,2,4]triazolo[1,5-a]pyridine, 1,2,3,4-tetrahydroisoquinoline, 1,3-benzodioxole, 1-benzothiophene, 1H-indazole, 1H-pyrrolo[2,3-b]pyridine, 1H-pyrrolo[2,3-c]pyridine, 1H-pyrrolo[3,2-b]pyridine, 1H-pyrrolo[3,2-c]pyridine, 2,1,3-benzoxadiazole, 3,4-dihydro-2H-pyrido[3,2-b][1,4]oxazine, 3H-imidazo[4,5-b]pyridine, 4,5,6,7-tetrahydropyrazolo[1,5-a]pyridine, furo[2,3-c]pyridine, furo[3,2-b]pyridine, imidazo [1,2-a]pyridine, quinazoline, and thieno[3,2-c]pyridin-4(5H)-one, any of which is optionally substituted with 1 to 3 groups of $R^b$.

9. The compound according to claim 1, wherein $R^1$ is hydrogen;
X is hydrogen;
Y is phenyl optionally substituted with 1 to 3 groups of $R^a$;
A is $B(OH)_2$, halo, or $C_{1-6}$ alkyl;
$R^2$ is selected from H and $C_{1-6}$ alkyl;
each $R^a$ is independently selected from $C_{1-6}$ alkyl, halogen, $(CH_2)_nCF_3$, $OR^2$, $(CHC_2)_nC_{5-10}$heterocyclyl, $(CH_2)_nC_{6-10}$aryl, $O(CH_2)_nC_{6-10}$ aryl, and $O(CH_2)nC_{5-10}$ heterocyclyl, said alkyl, heterocyclyl and aryl are optionally substituted with 1 to 3 groups of $R^b$;
each $R^b$ is independently selected from $C_{1-6}$ alkyl, halogen, $CHF_2$, $N(R^2)_2$, $CH_2OH$, $OR^2$, $(CH_2)_nCF_3$, and CN;
n represents 0 to 5; and
provided that no more than one of said $R^a$ is $(CH_2)_n C_{5-10}$heterocyclyl, $(CH_2)_nC_{6-10}$aryl, $O(CH_2)_nC_{6-10}$ aryl, or $O(CH_2)_nC_{5-10}$ heterocyclyl.

10. The compound according to claim 1, wherein the compound is represented by structural formula II:

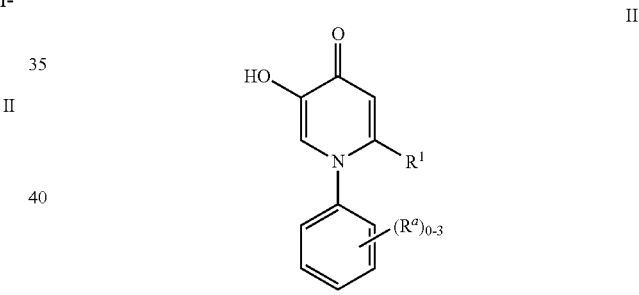

II or a pharmaceutically acceptable salt, enantiomer or diastereomer thereof, wherein $R^1$ is $NHCH_3$.

11. A compound according to claim 1 represented by structural formula VII:

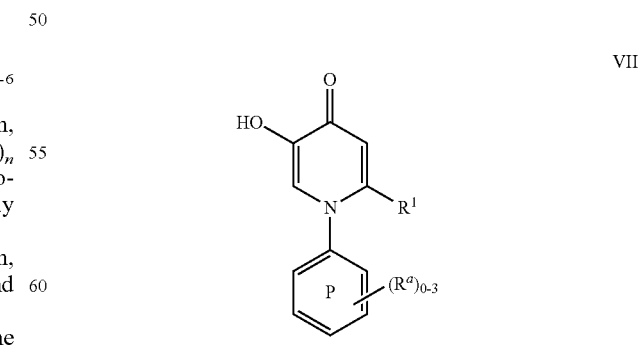

VII wherein P represents pyridyl;
R1 is hydrogen;
each $R^2$ is independently selected from hydrogen and $C_{1-6}$ alkyl;

each $R^a$ is independently selected from $C_{1-6}$ alkyl, halogen, $(CH_2)_nCF_3$, $OR^2$, $(CH_2)_nC_{5-10}$heterocyclyl, $(CH_2)_nC_{6-10}$aryl, $O(CH_2)_nC_{6-10}$ aryl, or $O(CH_2)nC_{5-10}$ heterocyclyl, said alkyl, heterocyclyl and aryl are optionally substituted with 1 to 3 groups of $R^b$;

each $R^b$ is independently selected from $C_{1-6}$ alkyl, halogen, $CHF_2$, $N(R^2)_2$, $CH_2OH$, $OR^2$, $(CH_2)_nCF_3$, and CN; and n represents 0 to 5.

12. A pharmaceutical composition comprising an inert carrier and an effective amount of a compound according to claim 1.

13. A method of treating neurological and psychiatric disorders and diseases comprising administering to said patient a therapeutically effective amount of a compound according to formula I in claim 1 or a pharmaceutically acceptable salt thereof, said neurological and psychiatric disorders and diseases selected from schizophrenia, augmentation of effect of anti-psychotics in treatment of positive symptoms of schizophrenia, major depressive disorder, the depressive phase of bipolar disorder, substance dependency, ADD/ADHD, and cognitive deficit associated with said neurological and psychiatric disorders and diseases.

14. The composition according to claim 12 further comprising one or more therapeutically active compounds selected from the group consisting of opiate agonists or antagonists, calcium channel antagonists, 5HT, 5-HT~A complete or partial receptor agonists or antagonists, sodium channel antagonists, N-methyl-D-aspartate (NMDA) receptor agonists or antagonists, COX-2 selective inhibitors, neurokinin receptor 1 (NKI) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical antidepressants, benzodiazepines, corticotropin releasing factor (CRF) antagonists, typical antipsychotics, atypical antipsychotics, neurontin (gabapentin) and pregabalin.

15. The compound of claim 1 or a pharmaceutically acceptable salt, enantiomer, or diastereomer thereof, wherein:

A represents hydrogen;

Y represents phenyl optionally substituted with 1 to 3 groups of $R^a$;

X represents hydrogen;

at least one of said 1 to 3 groups of $R^a$ represents indolyl, pyridyl, phenyl or indazolyl optionally substituted with 1 to 3 groups of $R^b$; and each $R^b$ independently represents $C_{1-6}$ alkyl, halogen, $CHF_2$, $N(R^2)_2$, $CH_2OH$, $OR^2$, $C_{3-6}$ cycloalkyl, $(CH_2)_nCF_3$, or CN.

16. The compound according to claim 15 or a pharmaceutically acceptable salt, enantiomer or diastereomer thereof, wherein $R^1$ represents $NH_2$.

17. The compound of claim 15 or a pharmaceutically acceptable salt, enantiomer, or and diastereomer thereof, wherein $R^1$ represents $NHCH_3$.

18. The compound of claim 1 having the structure of formula II

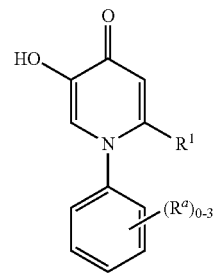

or a pharmaceutically acceptable salt, enantiomer, or diastereomer thereof, wherein $R^1$ represents $—CH(OH)CH_2$-phenyl;

$R^2$ and $R^3$ are independently selected from H and $C_{1-6}$ alkyl;

each $R^a$ is independently selected from $C_{1-6}$ alkyl, halogen, $(CH_2)_nCF_3$, $OR^2$, $(CH_2)_nC_{5-10}$ heterocyclyl, $(CH_2)_nC_{6-10}$aryl, $O(CH_2)_nC_{6-10}$ aryl, or $O(CH_2)_nC_{5-10}$ heterocyclyl, said alkyl, heterocyclyl and aryl are optionally substituted with 1 to 3 groups of $R^b$;

each $R^b$ is independently selected from $C_{1-6}$ alkyl, halogen, $CHF_2$, $N(R^2)_2$, $CH_2OH$, $OR^2$, $(CH_2)_nCF_3$, and CN; and n represents 0 to 5;

provided that no more than one of said $R^a$ is $(CH_2)_nC_{5-10}$ heterocyclyl, $(CH_2)_nC_{6-10}$aryl, $O(CH_2)_nC_{6-10}$ aryl, or $O(CH_2)nC_{5-10}$heterocyclyl.

19. The compound according to claim 1 which is:

5-hydroxy-1-[3-(quinolin-5-yl)phenyl]-2-(2,2,2-trifluoro-1-hydroxyethyl)pyridin-4(1H)-one;

1-[3-(5-chloro-1H-pyrrolo[2,3-b]pyridin-4-yl)phenyl]-5-hydroxy-2-(1-hydroxybutyl)pyridin-4(1H)-one;

1-(3-bromophenyl)-5-hydroxy-2-(1-hydroxyethyl)pyridin-4(1H)-one;

1-biphenyl-3-yl-5-hydroxy-2-(1-hydroxyethyl)pyridin-4(1H)-one;

1-(3-cyclohex-1-en-1-ylphenyl)-5-hydroxy-2-(1-hydroxyethyl)pyridin-4(1H)-one;

5-hydroxy-2-(1-hydroxyethyl)-1-(3-thiophen-3-ylphenyl)pyridin-4(1H)-one;

1-biphenyl-3-yl-5-hydroxy-2-(1-hydroxy-2-phenylethyl)pyridin-4(1H)-one;

5-hydroxy-2-(1-hydroxyethyl)-1-[3-(1H-indazol-4-yl)phenyl]pyridin-4(1H)-one;

5-hydroxy-2-(1-hydroxyethyl)-1-[3-(1H-pyrrolo[2,3-b]pyridin-5-yl)phenyl]pyridin-4(1H)-one;

5-hydroxy-2-(1-hydroxyethyl)-1-[3-(1-methyl-1H-indazol-6-yl)phenyl]pyridin-4(1H)-one;

5-hydroxy-2-(1-hydroxyethyl)-1-[3-(1-methyl-1H-indazol-6-yl)phenyl]pyridin-4(1H)-one;

1-[3-(5-chloro-1H-pyrrolo[2,3-b]pyridin-4-yl)phenyl]-5-hydroxy-2-(1-hydroxyethyl)pyridin-4(1H)-one;

1-(4'-chloro-3'-fluorobiphenyl-3-yl)-5-hydroxy-2-(1-hydroxyethyl)pyridin-4(1H)-one;

1-(3'-chlorobiphenyl-3-yl)-5-hydroxy-2-(1-hydroxyethyl)pyridin-4(1H)-one;

1-(2'-fluorobiphenyl-3-yl)-5-hydroxy-2-(1-hydroxyethyl)pyridin-4(1H)-one;

5-hydroxy-2-(1-hydroxyethyl)-1-(3-pyridin-4-ylphenyl)pyridin-4(1H)-one;

1-[4'-chloro-3'-(trifluoromethyl)biphenyl-3-yl]-5-hydroxy-2-(1-hydroxyethyl)pyridin-4(1H)-one;

1-[3-(6-fluoropyridin-3-yl)phenyl]-5-hydroxy-2-(1-hydroxyethyl)pyridin-4(1H)-one;

1-[3-(1-benzyl-1H-pyrazol-4-yl)phenyl]-5-hydroxy-2-(1-hydroxyethyl)pyridin-4(1H)-one;

5-hydroxy-2-(1-hydroxyethyl)-1-(4'-morpholin-4-ylbiphenyl-3-yl)pyridin-4(1H)-one;

1-[3-(6-aminopyridin-3-yl)phenyl]-5-hydroxy-2-(1-hydroxyethyl)pyridin-4(1H)-one;

5-hydroxy-2-(1-hydroxyethyl)-1-(3-isoquinolin-4-ylphenyl)pyridin-4(1H)-one;

5-hydroxy-2-(1-hydroxyethyl)-1-[3-(1H-pyrrolo[3,2-b]pyridin-6-yl)phenyl]pyridin-4(1H)-one;

5-hydroxy-2-(1-hydroxyethyl)-1-[3-(1H-indazol-4-yl)phenyl]pyridin-4(1H)-one;

5-hydroxy-2-(1-hydroxyethyl)-1-[3-(1H-indazol-4-yl)phenyl]pyridin-4(1H)-one;

1-[3-(3-chloropyridin-4-yl)phenyl]-5-hydroxy-2-(1-hydroxyethyl)pyridin-4(1H)-one;

1-[3-(5-chloro-1H-pyrrolo[2,3-b]pyridin-4-yl)-4-methoxyphenyl]-5-hydroxy-2-(1-hydroxyethyl)pyridin-4(1H)-one;

1-[3-(5-chloro-1H-pyrrolo[2,3-b]pyridin-4-yl)-5-fluorophenyl]-5-hydroxy-2-(1-hydroxyethyl)pyridin-4(1H)-one;

5-hydroxy-2-(1-hydroxyethyl)-1-[3-(1H-indazol-4-yl)-4-methoxyphenyl]pyridin-4(1H)-one;

5-hydroxy-2-(1-hydroxyethyl)-1-(3-quinazolin-4-ylphenyl)pyridin-4(1H)-one;

5-hydroxy-2-(1-hydroxyethyl)-1-[3-(1,8-naphthyridin-4-yl)phenyl]pyridin-4(1H)-one;

1-[3-(5-fluoro-1-oxo-2,3-dihydro-1H-inden-4-yl)phenyl]-5-hydroxy-2-(1-hydroxyethyl)pyridin-4(1H)-one;

5-hydroxy-2-(1-hydroxyethyl)-1-[3-(1H-indol-7-yl)phenyl]pyridin-4(1H)-one;

5-hydroxy-2-(1-hydroxyethyl)-1-[3-(1H-indazol-7-yl)phenyl]pyridin-4(1H)-one;

1-[3-(5-fluoro-1-methyl-1H-benzimidazol-7-yl)phenyl]-5-hydroxy-2-(1-hydroxyethyl)pyridin-4(1H)-one;

5-hydroxy-2-(1-hydroxyethyl)-1-[3-(9-methyl-9H-purin-6-yl)phenyl]pyridin-4(1H)-one;

5-hydroxy-2-(1-hydroxyethyl)-1-(3-quinolin-5-ylphenyl)pyridin-4(1H)-one;

1-[3-(1-benzothiophen-7-yl)phenyl]-5-hydroxy-2-(1-hydroxyethyl)pyridin-4(1H)-one;

5-hydroxy-1-(3-isoquinolin-4-ylphenyl)-2-(2,2,2-trifluoro-1-hydroxyethyl)pyridin-4(1H)-one;

1-[3-(5-chloro-1H-pyrrolo[2,3-b]pyridin-4-yl)phenyl]-5-hydroxy-2-(2,2,2-trifluoro-1-hydroxyethyl)pyridin-4(1H)-one;

5-hydroxy-2-(1-hydroxyethyl)-1-[3-(5-methoxypyridin-3-yl)phenyl]pyridin-4(1H)-one;

5-hydroxy-2-(1-hydroxyethyl)-1-(3-isoquinolin-4-ylphenyl)pyridin-4(1H)-one;

5-hydroxy-2-(1-hydroxyethyl)-1-[3-(1-methyl-1H-indazol-4-yl)phenyl]pyrdin-4(1H)-one;

5-hydroxy-2-(1-hydroxyethyl)-1-[3-(2-methyl-2H-indazol-4-yl)phenyl]pyrdin-4(1H)-one;

5-hydroxy-2-(2,2,2-trifluoro-1-hydroxyethyl)-1-{3[6-(trifluoromethyl)pyridin-2-yl]phenyl}pyridin-4(1H)-one;

5-hydroxy-2-(1-hydroxyethyl)-1-[3-(8-methylquinolin-5-yl)phenyl]pyridin-4(1H)-one;

1-[3-(2,1,3-benzoxadiazol-4-yl)phenyl]-5-hydroxy-2-hydroxyethyl)pyridin-4(1H)-one;

5-hydroxy-2-(1-hydroxyethyl)-1-(3-imidazo[1,2-a]pyridin-8-ylphenyl)pyridin-4(1H)-one;

5-hydroxy-2-(1-hydroxyethyl)-1-(6-methoxybiphenyl-3-yl)pyridin-4(1H)-one;

5-hydroxy-2-(1-hydroxyethyl)-1-(3-isoquinolin-4-yl-4-methoxyphenyl)pyridin-4(1H)-one;

5-hydroxy-1[2-methyl-3-(1H-pyrrolo[2,3-b]pyridin-5-yl)phenyl]-2-(2,2,2-trifluoro-1-hydroxyethyl)pyridin-4(1H)-one;

5-hydroxy-1[2-methyl-3-(6-morpholin-4-ylpyridin-3-yl)phenyl]-2-(2,2,2-trifluoro-1-hydroxyethyl)pyridin-4(1H)-one;

1-[4'-(1,3-benzoxazol-2-ylamino)-2-methylbiphenyl-3-yl]-5-hydroxy-2-(2,2,2-trifluoro-1-hydroxyethyl)pyridin-4(1H)-one;

1-(5'-ethoxy-2'-fluoro-4,6-dimethoxybiphenyl-3-yl)-5-hydroxy-2-(1-hydroxyethyl)pyridin-4(1H)-one;

5-hydroxy-2-(1-hydroxyethyl)-1-(2-methylbiphenyl-3-yl)pyridin-4(1H)-one;

5-hydroxy-2-phenyl-1-(3-quinolin-5-ylphenyl)pyridin-4(1H)-one;

1-(2',3'-difluoro-2-methylbiphenyl-3-yl)-5-hydroxy-2-hydroxyethyl)pyridin-4(1H)-one;

1-(5'-fluoro-2'-methoxy-6-methylbiphenyl-3-yl)-5-hydroxy-2-(1-hydroxyethyl)pyridin-4(1H)-one;

1-(2',5'-difluoro-6-methylbiphenyl-3-yl)-5-hydroxy-2(1-hydroxyethyl)pyridin-4(1H)-one;

1-(3'-chloro-2',6-dimethylbiphenyl-3-yl)-5-hydroxy-2-(1-hydroxyethyl)pyridin-4(1H)-one;

1-[5'-chloro-6-methyl-2'-(1-methylethoxy)biphenyl-3-yl]-5-hydroxy-2-(1-hydroxyethyl)pyridin-4(1H)-one;

5-hydroxy-2-(1-hydroxyethyl)-1-(6-methylbiphenyl-3-yl)pyridin-4(1H)-one;

1-(2',5'-difluoro-6-methoxybiphenyl-3-yl)-5-hydroxy-2-(1-hydroxyethyl)pyridin-4(1H)-one;

1-(2'-chloro-5',6-dimethoxybiphenyl-3-yl)-5-hydroxy-2-(1-hydroxyethyl)pyridin-4(1H)-one;

5-hydroxy-2-(1-hydroxyethyl)-1-(6-methoxy-2',3'-dimethylbiphenyl-3-yl)pyridin-4(1H)-one;

1-(5'-tert-butyl-2',6-dimethoxybiphenyl-3-yl)-5-hydroxy-2-(1-hydroxyethyl)pyridin-4(1H)-one;

1-(2'-fluoro-5',6-dimethoxybiphenyl-3-yl)-5-hydroxy-2-(1-hydroxyethyl)pyridin-4(1H)-one;

1-(2'-fluoro-6-methoxybiphenyl-3-yl)-5-hydroxy-2-(1-hydroxyethyl)pyridin-4(1H)-one;

5-hydroxy-2-(1-hydroxyethyl)-1-[4-methoxy-3-(2-methylpyridin-4-yl)phenyl]pyridin-4(1H)-one;

1-[3-(5-fluoropyridin-3-yl)-4-methoxyphenyl]-5-hydroxy-2-(1-hydroxyethyl)pyridin-4(1H)-one;

1-[4,6-dimethoxy-2'-(trifluoromethyl)biphenyl-3-yl]-5-hydroxy-2-(1-hydroxyethyl)pyridin-4(1H)-one;

1-(5'-chloro-2'-fluoro-6-methoxybiphenyl-3-yl)-5-hydroxy-2-(1-hydroxyethyl)pyridin-4(1H)-one;

5-hydroxy-2-(1-hydroxyethyl)-1-[6-methoxy-5'-methyl-2'-(1-methylethoxy)biphenyl-3-yl]pyridin-4(1H)-one;

5-hydroxy-2-(1-hydroxyethyl)-1-[3-(6-hydroxypyridin-3-yl)phenyl]pyridin-4(1H)-one;

5-hydroxy-2-(1-hydroxyethyl)-1-(3-thieno[2,3-b]pyridin-3-ylphenyl)pyridin-4(1H)-one;

1-(3'-cyclopropylbiphenyl-3-yl)-5-hydroxy-2-(1-hydroxyethyl)pyridin-4(1H)-one;

1-[3-(3-chloroquinolin-7-yl)phenyl]-5-hydroxy-2-(1-hydroxyethyl)pyridin-4(1H)-one;

1-[3-(3-chloroisoquinolin-7-yl)phenyl]-5-hydroxy-2-(1-hydroxyethyl)pyridin-4(1H)-one;

5-hydroxy-2-(1-hydroxyethyl)-1-[4'-(pyridin-2-ylmethyl)biphenyl-3-yl]pyridin-4(1H)-one;

1-biphenyl-3-yl-5-hydroxy-2-(2-hydroxy-2-pyrazolo[1,5-a]pyridin-7-ylethyl)pyridin-4(1H)-one;

1-biphenyl-3-yl-5-hydroxy-2-[2-hydroxy-2-(1,6-naphthyridin-8-yl)ethyl]pyridin-4(1H)-one;

1-biphenyl-3-yl-5-hydroxy-2-[2-hydroxy-2-(5-methyl-1,2,4-oxadiazol-3-yl)ethyl]pyridin-4(1H)-one;
5-hydroxy-2-[2-hydroxy-2-(6-methylpyridin-2-yl)ethyl]-1-(4'-methylbiphenyl-3-yl)pyridin-4(1H)-one;
1-[3-(6-fluoropyridin-3-yl)phenyl]-5-hydroxy-2-[2-hydroxy-2-(6-methylpyridin-2-yl)ethyl]pyridin-4(1H)-one;
5-hydroxy-2-[2-hydroxy-2-(6-methylpyridin-2-yl)ethyl]-1-[3-(1-methyl-1H-indol-5-yl)phenyl]pyridin-4(1H)-one;
1-[3'-(dimethylamino)biphenyl-3-yl]-5-hydroxy-2-[2-hydroxy-2-(6-methylpyridin-2-yl)ethyl]pyridin-4(1H)-one;
5-hydroxy-2-[2-hydroxy-2-(6-methylpyridin-2-yl)ethyl]-1-(3-[1,2,4]triazolo[1,5-a]pyridin-6-ylphenyl)pyridin-4(1H)-one;
5-hydroxy-2-[2-hydroxy-2-(6-methylpyridin-2-yl)ethyl]-1-[3-(1H-pyrrolo[2,3-b]pyridin-5-yl)phenyl]pyridin-4(1H)-one;
1-biphenyl-3-yl-5-hydroxy-2-{2-hydroxy-2-[6-(trifluoromethyl)pyridin-3-yl]ethyl}pyridin-4(1H)-one;
1-biphenyl-3-yl-2-[2-(6-chloropyridin-3-yl)-2-hydroxyethyl]-5-hydroxypyridin-4(1H)-one;
1-biphenyl-3-yl-5-hydroxy-2-[2-hydroxy-2-(3-methylpyridin-4-yl)ethyl]pyridin-4(1H)-one;
1-biphenyl-3-yl-5-hydroxy-2-[2-hydroxy-2-(5-methoxypyridin-3-yl)ethyl]pyridin-4(1H)-one;
1-biphenyl-3-yl-2-[2-(6-ethoxypyridin-2-yl)-2-hydroxyethyl]-5-hydroxypyridin-4(1H)-one;
1-biphenyl-3-yl-5-hydroxy-2-(1-hydroxy-1-methylethyl)pyridin-4(1H)-one;
1-biphenyl-3-yl-5-hydroxy-2-(1-hydroxy-2-phenylethyl)pyridin-4(1H)-one;
1-biphenyl-3-yl-3-bromo-5-hydroxy-2-(hydroxymethyl)pyridin-4(1H)-one;
5-hydroxy-2-[hydroxy(phenyl)methyl]-1-(3-isoquinolin-4-ylphenyl)pyridin-4(1H)-one;
5-hydroxy-2-(1-hydroxy-2-methylpropyl)-1-(3-isoquinolin-4-ylphenyl)pyridin-4(1H)-one;
5-hydroxy-2-(1-hydroxy-2-phenylethyl)-1-(3-isoquinolin-4-ylphenyl)pyridin-4(1H)-one;
or a pharmaceutically acceptable salt, enantiomer, or diastereomer thereof.

20. A compound which is:
2-amino-1-(2'-cyclopropylbiphenyl-3-yl)-5-hydroxypyridin-4(1H)-one;
2-amino-5-hydroxy-1-[3-(1H-indazol-4-yl)phenyl]pyridin-4(1H)-one;
2-amino-5-hydroxy-1-[2'-(methoxymethyl)biphenyl-3-yl]pyridin-4(1H)-one;
2-amino-5-hydroxy-1-[3-(2-methylpyridin-3-yl)phenyl]pyridin-4(1H)-one;
2-amino-1-(2'-chloro-6'-fluorobiphenyl-3-yl)-5-hydroxypyridin-4(1H)-one;
2-amino-1-[3-(3-chloro-2-morpholin-4-ylpyridin-4-yl)phenyl]-5-hydroxypyridin-4(1H)-one;
2-amino-5-hydroxy-1-(3-isoquinolin-5-ylphenyl)pyridin-4(1H)-one;
2-amino-5-hydroxy-1-[3-(1-methyl-1H-indol-4-yl)phenyl]pyridin-4(1H)-one;
2-amino-5-hydroxy-1-[3-(7-methylimidazo[1,2-a]pyridin-6-yl)phenyl]pyridin-4(1H)-one;
2-amino-1-[3-(5-chloro-1H-pyrrolo[2,3-b]pyridin-4-yl)phenyl]-5-hydroxypyridin-4(1H)-one;
2-amino-5-hydroxy-1-[3-(1-methyl-1H-indazol-4-yl)phenyl]pyridin-4(1H)-one;
2-amino-5-hydroxy-1-[3-(1-methyl-1H-indazol-6-yl)phenyl]pyridin-4(1H)-one;
2-amino-1-[3-(6-fluoropyridin-3-yl)phenyl]-5-hydroxypyridin-4(1H)-one;
2-amino-5-hydroxy-1-(3-pyridin-3-ylphenyl)pyridin-4(1H)-one;
2-amino-1-(2',4'-difluorobiphenyl-3-yl)-5-hydroxypyridin-4(1H)-one;
2-amino-5-hydroxy-1-(3-isoquinolin-4-ylphenyl)pyridin-4(1H)-one;
2-amino-1-[3-(6-aminopyridin-3-yl)phenyl]-5-hydroxypyridin-4(1H)-one;
2-amino-1-(3-{6-[3-(dimethylamino)propoxy]pyridin-3-yl}phenyl)-5-hydroxypyridin-4(1H)-one;
2-amino-1-[3-(2,2-difluoro-1,3-benzodioxol-4-yl)phenyl]-5-hydroxypyridin-4(1H)-one;
2-amino-5-hydroxy-1-[3-(1H-pyrrolo[3,2-b]pyridin-6-yl)phenyl]pyridin-4(1H)-one;
2-amino-1-[5-(1-benzyl-1H-pyrazol-4-yl)-2,4-dimethoxyphenyl]-5-hydroxypyridin-4(1H)-one;
2-amino-5-hydroxy-1-(5-isoquinolin-5-yl-2,4-dimethoxyphenyl)pyridin-4(1H)-one;
2-amino-1-[4,6-dimethoxy-2'-(trifluoromethoxy)biphenyl-3-yl]-5-hydroxypyridin-4(1H)-one;
2-amino-1-{3-[6-(difluoromethyl)pyridin-2-yl]phenyl}-5-hydroxypyridin-4(1H)-one;
2-amino-5-hydroxy-1-{3-[6-(2-hydroxy-1,1-dimethylethyl)pyridin-2-yl]phenyl}pyridin-4(1H)-one;
2-amino-5-hydroxy-1-{3-[6-(trifluoromethyl)-1,5-naphthyridin-2-yl]phenyl}pyridin-4(1H)-one;
2-[3-(2-amino-5-hydroxy-4-oxopyridin-1(4H)-yl)phenyl]pyridine-3-carbonitrile;
2-amino-5-hydroxy-1-[3-(6-methoxyquinolin-2-yl)phenyl]pyridin-4(1H)-one;
5'-(2-amino-5-hydroxy-4-oxopyridin-1(4H)-yl)-2-fluoro-2'-methoxybiphenyl-3-carbonitrile;
2-amino-1-(3',5'-difluoro-2'-methoxy-2-methylbiphenyl-3-yl)-5-hydroxypyridin-4(1H)-one;
2-amino-1-(5'-ethoxy-2'-fluoro-2-methylbiphenyl-3-yl)-5-hydroxypyridin-4(1H)-one;
2-amino-5-hydroxy-1-[2-methyl-3-(1-methyl-1H-indazol-4-yl)phenyl]pyridin-4(1H)-one;
2-amino-5-hydroxy-1-[3-(1H-indazol-5-yl)-2-methylphenyl]pyridin-4(1H)-one;
2-amino-5-hydroxy-1-[2-methyl-3-(1-methyl-1H-indazol-5-yl)phenyl]pyridin-4(1H)-one;
2-amino-5-hydroxy-1-[2-methyl-3-(1-methyl-1H-indazol-6-yl)phenyl]pyridin-4(1H)-one;
2-amino-1-(2',3'-dichloro-6-methylbiphenyl-3-yl)-5-hydroxypyridin-4(1H)-one;
2-amino-1-(5'-chloro-2'-methoxy-6-methylbiphenyl-3-yl)-5-hydroxypyridin-4(1H)-one;
2-amino-1-(2',5'-dichloro-6-methylbiphenyl-3-yl)-5-hydroxypyridin-4(1H)-one;
2-amino-1-(5'-ethoxy-2'-fluoro-6-methylbiphenyl-3-yl)-5-hydroxypyridin-4(1H)-one;
2-amino-5-hydroxy-1-(3-isoquinolin-5-yl-4-methylphenyl)pyridin-4(1H)-one;
2-amino-5-hydroxy-1-[4-methyl-3-(2-methyl-2H-indazol-5-yl)phenyl]pyridin-4(1H)-one;
2-amino-5-hydroxy-1-[3-(1H-indazol-6-yl)-4-methylphenyl]pyridin-4(1H)-one;
2-amino-5-hydroxy-1-[3-(1H-indol-4-yl)-4-methylphenyl]pyridin-4(1H)-one;
2-amino-5-hydroxy-1-[4-methyl-3-(8-methylquinolin-5-yl)phenyl]pyridin-4(1H)-one;

2-amino-1-[3-(2-chloro-5-methylphenoxy)-4-methylphenyl]-5-hydroxypyridin-4(1H)-one;

N-{1-[5-hydroxy-1-(3-isoquinolin-4-ylphenyl)-4-oxo-1,4-dihydropyridin-2-yl]ethyl}methanesulfonamide;

2-[1-(dimethylamino)ethyl]-5-hydroxy-1-(3-isoquinolin-4-ylphenyl)pyridin-4(1H)-one;

2-(1-aminoethyl)-5-hydroxy-1-(3-isoquinolin-4-ylphenyl)pyridin-4(1H)-one;

1-biphenyl-3-yl-5-hydroxy-2-(pyridin-2-ylamino)pyridin-4(1H)-one;

1-(Biphenyl-3-yl)-5-hydroxy-2-(methylamino)pyridin-4(1H)-one(4);

2-Amino-1-(biphenyl-3-yl)-5-hydroxypyridin-4(1H)-one (3);

or a pharmaceutically acceptable salt, enantiomer, or diastereomer thereof.

21. The compound according to claim 7, 9, 10, or 11 or a pharmaceutically acceptable salt, enantiomer or diastereomer thereof, wherein:
at least one of said 1 to 3 groups of $R^a$ is selected from $C_{6-10}$aryl and $C_{5-10}$heterocyclyl, wherein said aryl and heterocyclyl are optionally substituted with 1 to 3 groups of $R^b$.

22. The compound according to claim 7, 9, 10, or 11 or a pharmaceutically acceptable salt, enantiomer or diastereomer thereof, wherein at least one of said 1 to 3 groups of $R^a$ is $C_{6-10}$aryl optionally substituted with 1 to 3 groups of $R^b$.

23. The compound according to claim 7, 9, 10, or 11 or a pharmaceutically acceptable salt, enantiomer or diastereomer thereof, wherein at least one of said 1 to 3 groups of $R^a$ is phenyl optionally substituted with 1 to 3 groups of $R^b$.

24. The compound according to claim 7, 9, 10, or 11 or a pharmaceutically acceptable salt, enantiomer or diastereomer thereof, wherein at least one of said 1 to 3 groups of $R^a$ is phenyl substituted with 1 to 3 groups of $R^b$.

25. The compound according to claim 7, 9, 10, or 11 or a pharmaceutically acceptable salt, enantiomer or diastereomer thereof, wherein at least one of said 1 to 3 groups of $R^a$ is phenyl.

26. The compound according to claim 7, 9, 10, or 11 or a pharmaceutically acceptable salt, enantiomer or diastereomer thereof, wherein at least one of said 1 to 3 groups of $R^a$ is $C_{5-10}$heterocyclyl optionally substituted with 1 to 3 groups of $R^b$.

27. The compound according to claim 7, 9, 10, or 11 or a pharmaceutically acceptable salt, enantiomer or diastereomer thereof, wherein at least one of said 1 to 3 groups of $R^a$ is 1,3-benzodioxole optionally substituted with 1 to 3 groups of $R^b$.

28. The compound according to claim 7, 9, 10, or 11 or a pharmaceutically acceptable salt, enantiomer or diastereomer thereof, wherein at least one of said 1 to 3 groups of $R^a$ is 1H-pyrrolo[2,3-b]pyridine optionally substituted with 1 to 3 groups of $R^b$.

29. A compound which is 1-biphenyl-3-yl-5-hydroxy-2-(1-hydroxyethyl)pyridin-4(1H)-one or a pharmaceutically acceptable salt, enantiomer or diastereomer thereof.

30. A compound which is 1-biphenyl-3-yl-5-hydroxy-2-(1-hydroxy-2-phenylethyl)pyridin-4(1H)-one or a pharmaceutically acceptable salt, enantiomer or diastereomer thereof.

31. A compound which is 1-(biphenyl-3-yl)-5-hydroxy-2-(methylamino)pyridin-4(1H)-one or a pharmaceutically acceptable salt, enantiomer or diastereomer thereof.

32. A compound which is 2-amino-1-(biphenyl-3-yl)-5-hydroxypyridin-4(1H)-one or a pharmaceutically acceptable salt, enantiomer or diastereomer thereof.

33. A compound which is 1-[3-(5-chloro-1H-pyrrolo[2,3-b]pyridin-4-yl)phenyl]-5-hydroxy-2-(1-hydroxyethyl)-pyridin-4(1H)-one or a pharmaceutically acceptable salt, enantiomer or diastereomer thereof.

34. A compound represented by structural formula I:

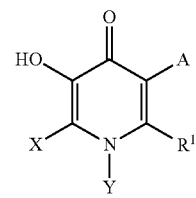

or a pharmaceutically acceptable salt, enantiomer or diastereomer thereof, wherein:

$R^1$ is $C_{1-10}$ alkyl optionally substituted with 1 to 3 groups independently selected from halo, OH, O—$C_{1-6}$ alkyl, $NR^2R^3$, $CF_3$, $C_{6-10}$ aryl, $C_{5-10}$ heterocyclyl, $C_{6-10}$ aryl, and cyano; provided that $R^1$ contains no more than one aryl or heterocyclyl;

$R^2$ and $R^3$ are independently selected from H, OH, $C_{1-6}$ alkyl and $N(CH_3)_2$;

A and X are each hydrogen;

Y is phenyl substituted with 1 to 3 groups of $R^a$;

each $R^a$ is independently selected from $C_{1-6}$ alkyl, halogen, $(CH_2)_nCF_3$, $OR^2$, $(CH_2)_nC_{5-10}$ heterocyclyl, $(CH_2)_n$ $C_{6-10}$aryl, $O(CH_2)_nC_{6-10}$ aryl, and $O(CH_2)_nC_{5-10}$ heterocyclyl, said alkyl, heterocyclyl and aryl are optionally substituted with 1 to 3 groups of $R^b$; provided that at least one of said $R^a$ on Y is aryl or heterocyclyl optionally substituted with 1 to 3 groups of $R^b$ and no more than one of said $R^a$ is $(CH_2)_nC_{5-10}$heterocyclyl, $(CH_2)_n$ $C_{6-10}$aryl, $O(CH_2)_nC_{6-10}$ aryl, or $O(CH_2)nC_{5-10}$ heterocyclyl;

each $R^b$ is independently selected from $C_{1-6}$ alkyl, halogen, $CHF_2$, $N(R^2)_2$, $CH_2OH$, $OR^2$, $(CH_2)_nCF_3$, and CN; and n represents 0 to 5.

35. The compound according to claim 34, wherein $R^1$ is $C_{1-10}$ alkyl optionally substituted with 1 to 3 groups selected from OH and $CF_3$.

36. The compound according to claim 34 or a pharmaceutically acceptable salt, enantiomer or diastereomer thereof, wherein:

$R^a$ is selected from $C_{6-10}$ aryl and $C_{5-10}$heterocyclyl, and said aryl and heterocyclyl are optionally substituted with 1 to 3 groups of $R^b$; and each $R^b$ is independently selected from $C_{1-6}$ alkyl, halogen, $CHF_2$, $N(R^2)_2$, $CH_2OH$, $OR^2$, $(CH_2)_nCF_3$, and CN.

37. The compound according to claim 34 or a pharmaceutically acceptable salt, enantiomer or diastereomer thereof, wherein $R^a$ is selected from naphthyridine, indolyl, benzodioxaolyl, pyridyl, furopyridinyl, isoindolyl, pyridooxazinyl, pyrrolopyridinyl, quinoxalinyl, quinazolinyl, quinolinyl, isoquinolinyl, phenyl, indazolyl, [1,2,4]triazolo[1,5-a]pyridine, 1,2,3,4-tetrahydroisoquinoline, 1,3-benzodioxole, 1-benzothiophene, 1H-indazole, 1H-pyrrolo[2,3-b]pyridine, 1H-pyrrolo[2,3-c]pyridine, 1H-pyrrolo[3,2-b]pyridine, 1H-pyrrolo[3,2-c]pyridine, 2,1,3-benzoxadiazole, 3,4-dihydro-2H-pyrido[3,2-b][1,4]oxazine, 3H-imidazo[4,5-b]pyridine, 4,5,6,7-tetrahydropyrazolo[1,5-a]pyridine, furo[2,3-c]pyridine, furo[3,2-b]pyridine, imidazo[1,2-a]pyridinen, quinazoline, and thieno[3,2-c]pyridin-4(5H)-one, any of which is optionally substituted with 1 to 3 groups of $R^b$.

38. A compound represented by structural formula I:

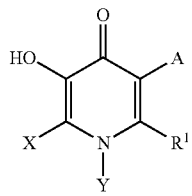

or a pharmaceutically acceptable salt, enantiomer or diastereomer thereof, wherein:
$R^1$ is $C_{1-10}$ alkyl optionally substituted with 1 to 3 groups independently selected from halo, OH, O—$C_{1-6}$ alkyl, $NR^2R^3$, $CF_3$, $C_{6-10}$ aryl, $C_{5-10}$ heterocyclyl, $OC_{6-10}$ aryl, and cyano; provided that $R^1$ contains no more than one aryl or heterocyclyl;
$R^2$ and $R^3$ are independently selected from H, OH, $C_{1-6}$ alkyl and $N(CH_3)_2$;
A and X are each hydrogen;
Y is phenyl substituted with 1 to 3 groups of $R^a$;
$R^a$ is is $C_{6-10}$aryl optionally substituted with 1 to 3 groups of $R^b$;
each $R^b$ is independently selected from $C_{1-6}$ alkyl, halogen, $CHF_2$, —O—, $N(R^2)_2$, $CH_2OH$, $OR^2$, $(CH_2)_nCF_3$, and CN; and
n represents 0 to 5.

39. The compound according to claim 38 or a pharmaceutically acceptable salt, enantiomer or diastereomer thereof, wherein $R^a$ is phenyl optionally substituted with 1 to 3 groups of $R^b$.

40. The compound according to claim 38 or a pharmaceutically acceptable salt, enantiomer or diastereomer thereof, wherein $R^a$ is phenyl.

41. A compound represented by structural formula I:

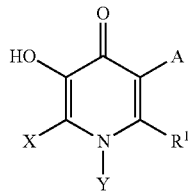

or a pharmaceutically acceptable salt, enantiomer or diastereomer thereof, wherein:
$R^1$ is $C_{1-10}$ alkyl optionally substituted with 1 to 3 groups independently selected from halo, OH, O—$C_{1-6}$ alkyl, $NR^2R^3$, $CF_3$, $C_{6-10}$ aryl, $C_{5-10}$ heterocyclyl, $OC_{6-10}$ aryl, and cyano; provided that $R^1$ contains no more than one aryl or heterocyclyl;
$R^2$ and $R^3$ are independently selected from H, OH, $C_{1-6}$ alkyl and $N(CH_3)_2$;
A and X are each hydrogen;
Y is phenyl substituted with 1 to 3 groups of $R^a$;
$R^a$ is is $C_{5-10}$heterocyclyl optionally substituted with 1 to 3 groups of $R^b$;
each $R^b$ is independently selected from $C_{1-6}$ alkyl, halogen, $CHF_2$, —O—, $N(R^2)_2$, $CH_2OH$, $OR^2$, $(CH_2CF_3$, and CN; and
n represents 0 to 5.

42. The compound according to claim 41 or a pharmaceutically acceptable salt, enantiomer or diastereomer thereof, wherein $R^a$ is 1,3-benzodioxole optionally substituted with 1 to 3 groups of $R^b$.

43. The compound according to claim 41 or a pharmaceutically acceptable salt, enantiomer or diastereomer thereof, wherein $R^a$ is 1H-pyrrolo[2,3-b]pyridine optionally substituted with 1 to 3 groups of $R^b$.

44. A compound represented by structural formula II:

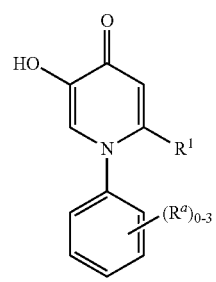

or a pharmaceutically acceptable salt, enantiomer or diastereomer thereof, wherein:
$R^1$ is $NR^2R^3$;
$R^2$ and $R^3$ are independently selected from H and $C_{1-6}$ alkyl;
each $R^a$ is independently selected from $C_{1-6}$ alkyl, halogen, $(CH_2)_nCF_3$, $OR^2$, $(CH_2)_nC_{5-10}$ heterocyclyl, $(CH_2)_n C_{6-10}$aryl, $O(CH_2)_nC_{6-10}$ aryl, or $O(CH_2)_nC_{5-10}$ heterocyclyl, said alkyl, heterocyclyl and aryl are optionally substituted with 1 to 3 groups of $R^b$;
each $R^b$ is independently selected from $C_{1-6}$ alkyl, halogen, $CHF_2$, $N(R^2)_2$, $CH_2OH$, $OR^2$, $(CH_2)_nCF_3$, and CN; and
n represents 0 to 5;
provided that no more than one of said $R^a$ is $(CH_2)_nC_{5-10}$ heterocyclyl, $(CH_2)_nC_{6-10}$aryl, $O(CH_2)_nC_{6-10}$ aryl, or $O(CH_2)_nC_{5-10}$ heterocyclyl.

45. The compound according to claim 44 or a pharmaceutically acceptable salt, enantiomer or diastereomer thereof, wherein each of $R^2$ and $R^3$ is H.

46. The compound according to claim 44 or a pharmaceutically acceptable salt, enantiomer or diastereomer thereof, wherein each of $R^2$ and $R^3$ is $C_{1-6}$ alkyl.

47. The compound according to claim 44 or a pharmaceutically acceptable salt, enantiomer or diastereomer thereof, wherein $R^a$ is $(CH_2)_nC_{6-10}$aryl optionally substituted with 1 to 3 groups of $R^b$.

48. The compound according to claim 44 or a pharmaceutically acceptable salt, enantiomer or diastereomer thereof, wherein $R^a$ is phenyl.

49. A compound of structural formula I:

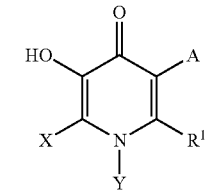

or a pharmaceutically acceptable salt, enantiomer or diastereomer thereof, wherein:

A represents B(OH)$_2$, NO$_2$, halo, OH, C(O)NH(CH$_2$)$_n$C(O)N(R$^3$)$_2$, C$_{3-10}$cycloalkyl, or C$_{1-6}$ alkyl;

X represents hydrogen;

Y represents phenyl or pyridyl, any of which is optionally substituted with 1 to 3 groups of R$^a$;

R$^1$ represents hydrogen;

R$^2$ and R$^3$ are independently selected from H, OH, C$_{1-6}$ alkyl and N(CH$_3$)$_2$;

each R$^a$ independently represents C$_{1-6}$ alkyl, halogen, hydroxyl, (CH$_2$)$_n$CF$_3$, OCHF$_2$, OCF$_3$, C$_{3-6}$cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, (CH$_2$)$_n$C(O)OR$^2$, SO$_2$R$^2$, OR$^2$, (CH$_2$)$_n$C$_{5-10}$ heterocyclyl, NH(CH$_2$)$_n$C$_{5-10}$ heterocyclyl, (CH$_2$)$_n$C$_{6-10}$ aryl, O(CH$_2$)$_n$C$_{6-10}$ aryl, or O(CH$_2$)$_n$C$_{5-10}$ heterocyclyl, said cycloalkyl, heterocyclyl and aryl optionally substituted with 1 to 3 groups of R$^b$;

each R$^b$ independently represents C$_{1-6}$ alkyl, halogen, CHF$_2$, N(R$^2$)$_2$, CH$_2$OH, OR$^2$, (CH$_2$)$_n$CF$_3$, or CN; and n represents 0 to 5; and provided that no more than one of said R$^a$ of Y is cycloalkyl, heterocyclyl or aryl.

50. The compound according to claim 49 or a pharmaceutically acceptable salt, enantiomer or diastereomer thereof, wherein Y is phenyl optionally substituted with 1 to 3 groups of R$^a$.

51. The compound according to claim 49 or a pharmaceutically acceptable salt, enantiomer or diastereomer thereof, wherein Y is phenyl substituted with R$^a$.

52. The compound according to claim 49 or a pharmaceutically acceptable salt, enantiomer or diastereomer thereof, wherein:
Y is phenyl substituted with R$^a$; and
R$^a$ is phenyl.

53. The compound according to claim 49 or a pharmaceutically acceptable salt, enantiomer or diastereomer thereof, wherein X is hydrogen; and A is C$_{1-6}$ alkyl.

54. The compound according to claim 49 or a pharmaceutically acceptable salt, enantiomer or diastereomer thereof, wherein:
X is hydrogen; and
A is B(OH)$_2$.

55. The compound according to claim 49 or a pharmaceutically acceptable salt, enantiomer or diastereomer thereof, wherein:
X is hydrogen;
A is B(OH)$_2$; and
Y is phenyl optionally substituted with 1 to 3 groups of R$^a$.

56. The compound according to claim 49 or a pharmaceutically acceptable salt, enantiomer or diastereomer thereof, wherein:
X is hydrogen; and
A is OH.

57. The compound according to claim 49 or a pharmaceutically acceptable salt, enantiomer or diastereomer thereof, wherein:
X is hydrogen;
A is OH; and
Y is pyridyl optionally substituted with 1 to 3 groups of R$^a$.

58. A compound which is:
5-hydroxy-2-(hydroxymethyl)-1-(4-morpholin-4-ylphenyl)pyridin-4(1H)-one ;
1-(3,5-dimethylphenyl)-5-hydroxy-2-(hydroxymethyl)pyridin-4(1H)-one;
5-hydroxy-2-(hydroxymethyl)-1-(3-methoxyphenyl)pyridin-4(1H)-one ;
1-[3-(dimethylamino)phenyl]-5-hydroxy-2-(hydroxymethyl)pyridin-4(1H)-one
or a pharmaceutically acceptable salts, enantiomers, or diastereomers thereof.

59. A compound which is:
3-hydroxy-1-phenylpyridin-4(1H)-one;
1-biphenyl-4-yl-3-hydroxypyridin-4(1H)-one;
1-(4-butylphenyl)-3-hydroxypyridin-4(1H)-one;
3-hydroxy-1-[4-(trifluoromethyl)phenyl]pyridin-4(1H)-one;
1-[4-chloro-3-(trifluoromethyl)phenyl]-3-hydroxypyridin-4(1H)-one;
1-(2,4-dichlorophenyl)-3-hydroxypyridin-4(1H)-one;
1-(3,5-dichlorophenyl)-3-hydroxypyridin-4(1H)-one;
3-hydroxy-1-(3-phenoxyphenyl)pyridin-4(1H)-one;
1-(3-chlorophenyl)-3-hydroxypyridin-4(1H)-one;
1-(2-fluoro-5-methoxyphenyl)-3-hydroxypyridin-4(1H)-one;
1-{3-chloro-4-[(4-chlorophenyl)carbonyl]phenyl}-3-hydroxypyridin-4(1H)-one;
1-(3-fluoro-5-methoxyphenyl)-3-hydroxypyridin-4(1H)-one;
1-[3-butoxy-5-(trifluoromethyl)phenyl]-3-hydroxypyridin-4(1H)-one;
1-(3-bromo-5-fluoro-4-methylphenyl)-3-hydroxypyridin-4(1H)-one;
2'-fluoro-5'-(3-hydroxy-4-oxopyridin-1(4H)-yl)-4-(trifluoromethyl)biphenyl-2-carbonitrile;
1-[4-(3-chlorophenoxy)-3-(trifluoromethyl)phenyl]-3-hydroxypyridin-4(1H)-one;
N-[2-chloro-4-(3-hydroxy-4-oxopyridin-1(4H)-phenyl]pentanamide;
1-[3-fluoro-5-(pyridin-3-yloxy)phenyl]-3-hydroxypyridin-4(1H)-one;
1-[3-(6-fluoropyridin-3-yl)phenyl]-3-hydroxypyridin-4(1H)-one;
3-hydroxy-1-[3-(1-methyl-1H-pyrazol-4-yl)phenyl]pyridin-4(1H)-one;
3-hydroxy-1-(3-pyridin-4-ylphenyl)pyridin-4(1H)-one;
3-hydroxy-1-{3-1-methyl-3-(trifluoromethyl)-1H-pyrazol-5-yl]phenyl}pyridin-4(1H)-one;
1-[3-bromo-4-(trifluoromethoxy)phenyl]-3-hydroxypyridin-4(1H)-one;
1-(4-ethoxypheny 1)-3-hydroxypyridin-4(1H)-one;
3-hydroxy-1-[4-methoxy-3-(1-methylethyl)phenyl]pyridin-4(1H)-one;
3-hydroxy-1-[4-(3-pyridin-4-ylpropoxy)phenyl]pyridin-4(1H)-one;
3-hydroxy-1-[4-(2-morpholin-4-ylethoxy)phenyl]pyridin-4(1H)-one;
1-[3-chloro-4-(diethylamino)phenyl]-3-hydroxypyridin-4(1H)-one;
3-hydroxy-1-(4-{[4-(hydroxymethyl)cyclohexyl]methoxy}phenyl)pyridin-4(1H)-one;
1-[4-(1,3-benzothiazol-2-ylamino)phenyl]-3-hydroxypyridin-4(1H)-one;
3-hydroxy-1-[4-(4-pyridin-4-ylpiperazin-1-yl)phenyl]pyridin-4(1H)-one ;
1-[4-(dimethylamino)phenyl]-3-hydroxypyridin-4(1H)-one;
3-hydroxy-1-{4-[3-pyridin-3-yl-5-(trifluoromethyl)-1H-pyrazol-1-yl]phenyl}pyridin-4(1H)-one;
1-[4-(cyclopentyloxy)phenyl]-3-hydroxypyridin-4(1I1)-one;
3-hydroxy-1-(4-morpholin-4-ylphenyl)pyridin-4(1H)-one;

3-hydroxy-1-[4-(4-methoxyphenoxy)phenyl]pyridin-4(1H)-one;
3-hydroxy-1-[4-(1H-pyrazol-1-yl)phenyl]pyridin-4(1H)-one;
1-{3-[3,5-bis(trifluoromethyl)-1H-pyrazol-1-yl]phenyl}-3-hydroxypyridin-4(1H)-one;
3-hydroxy-1-[3-(1H-pyrrolo[3,2-b]pyridin-6-yl)phenyl]pyridin-4(1H)-one;
1-(6-chlorobiphenyl-3-yl)-3-hydroxypyridin-4(1H)-one;
3-hydroxy-1-[3-(1H-indazol-4-yl)phenyl]pyridin-4(1H)-one;
3-hydroxy-1-(4'-pyridin-2-ylbiphenyl-3-yl)pyridin-4(1H)-one;
1-[3-(5,6-dihydro-4H-pyrrolo[1,2-b]pyrazol-3-yl)phenyl]-3-hydroxypyridin-4(1H)-one;
3-hydroxy-1-(3-isoquinolin-4-yl)phenyl]pyridin-4(1H)-one;
5-(3-hydroxy-4-oxopyridin-1(4H)-yl)biphenyl-3-carboxylic acid;
3-hydroxy-6'-phenyl-4H-1,2'-bipyridin-4-one;
3-hydroxy-4'-phenyl-4H-1,2'-bipyridin-4-one;
3-hydroxy-6'-quinolin-5-yl-4H-1,2'-bipyridin-4-one;
6'-(8-fluoro-2-methylquinolin-7-yl)-3-hydroxy-4H-1,2'-bipyridin-4-one;
6'-biphenyl-3-yl-3-hydroxy-4H-1,2'-bipyridin-4-one;
3-hydroxy-3'-phenyl-4H-1,2'-bipyridin-4-one;
4'-(4-tert-butylphenyl)-3-hydroxy-4H-1,2'-bipyridin-4-one;
4'-(3,4-dichlorophenyl)-3-hydroxy-4H-1,2'-bipyridin-4-one;
3-hydroxy-4'[4-(2-methylpropyl)phenyl]-4H-1,2'-bippidin-4-one;
4'[2-fluoro-4-(trifluoromethyl)phenyl]-3-hydroxy-4H-1,2'-bipyridin-4-one;
3-hydroxy-4'[1-(2-methylpropyl)-1H-pyrazol-4-yl]-4H-1,2'-bipyridin-4-one;
3-hydroxy-4'-quinolin-5-yl-4H-1,2'-bipyridin-4-one;
4'[4-(difluoromethoxy)phenyl]-3-hydroxy-4H-1,2'-bipyridin-4-one;
4'-(5-chloro-1H-pyrrolo[2,3-b])pyridin-4-yl)-3-hydroxy-4H-1,2'-bipyridin-4-one;
3"-fluoro-3-hydroxy-4H-1,2':4',4"-terpyridin-4-one;
3-hydroxy-6"-(trifluoromethyl)-4H-1,2':4',2"-terpyridin-4-one;
4'-(2-tert-butyl-1,3-thiazol-4-yl)-3-hydroxy-4H-1,2'-bipyridin-4-one;
3-hydroxy-6"-(4-methylpiperazin-1-yl)-4H-1,2':4',2"-terpyridin-4-one;
3-hydroxy-6"-(2-methyl-1H-imidazol-1-yl)-4H-1,2':4',2"-terpyridin-4-one;
4'-(4-cyclopropylphenyl)-3'-fluoro-3-hydroxy-4H-1,2'-bipyridin-4-one;
3'-fluoro-3-hydroxy-4'-(1,2,3,4-tetrahydroisoquinolin-6-yl)-4H-1,2'-bipyridin-4-one;
3'-fluoro-3-hydroxy-4'-quinolin-5-yl-4H-1,2'-bipyridin-4-one;
3'-fluoro-3-hydroxy-4'[1,2,4]triazolo[1,5-a]pyridin-7-yl-4H-1,2'-bipyridin-4-one;
3'-fluoro-3-hydroxy-4'-(1H-pyrrolo[2,3-b]pyridin-5-yl)-4H-1,2'-bipyridin-4-one;
3'-fluoro-3-hydroxy-4'-(1-methyl-1H-indazol-6-yl)-4H-1,2'-bipyridin-4-one ;
3'-fluoro-3-hydroxy-4'-(3-methyl-3H-imidazo[4,5-b]pyridin-6-yl)-4H-1,2'-bipyridin-4-one; 3'-fluoro-3-hydroxy-4'-phenyl-4H-1,2'-bipyridin-4-one;
3'-fluoro-3-hydroxy-4'-imidazo[1,2-a]pyridin-6-yl-4H-1,2'-bipyridin-4-one;
4'-(4-chloro-3-fluorophenyl)-3'-fluoro-3-hydroxy-4H-,2'-bipyridin-4-one;
or a pharmaceutically acceptable salts, and individual enantiomer& or vend diastereomer & thereof.

60. A compound which is:
1-biphenyl-3-yl-2-[2-(2,3-dihydro-1,4-benzodioxin-2-yl)ethyl]-5-hydroxypylidin-4(1H)-one;
1-biphenyl-3-yl-2-(2-biphenyl-2-yl-2-hydroxyethyl)-5-hydroxypyridin-4(1H)-one;
2-[cyclohexyl(hydroxy)methyl]-5-hydroxy-1-(3-isoquinolin-4-ylphenyl)pyridin-4(1H)-one;
1-biphenyl-3-yl-2-(cyclopentylmethyl)-5-hydroxypyridin-4(1H)-one;
1-biphenyl-3-yl-2-(2-cyclopropylethyl)-5-hydroxypyridin-4(1H)-one;
2-[cyclopropyl(hydroxy)methyl]-5-hydroxy-1-(3-isoquinolin-4-ylphenyl)pyridin-4(1H)-one;
1-biphenyl-3-yl-2-[2-(5-cyclopropyl-1,2,4-oxadiazol-3-yl)-1-methylethyl]-5-hydroxypyridin-4(1H)-one;
3-(1-biphenyl-3-yl-5-hydroxy-4-oxo-1,4-dihydropyridin-2-yl)-N,N-diethylpropanamide;
1-biphenyl-3-yl-2-(difluoromethyl)-5-hydroxypyridin-4(1H)-one;
1-biphenyl-3-yl-2-(dimethylamino)-5-hydroxypyridin-4(1H)-one ;
5-hydroxy-2-(2-hydroxy-1,3-dimethylbutyl)-1-phenylpyridin-4(1H)-one;
1-biphenyl-3-yl-2-(fluoromethyl)-5-hydroxypyridin-4(1H)-one;
1-biphenyl-3-yl-N-3-(dimethylamino)-3-oxopropyl]-5-hydroxy-4-oxo-1,4-dihydropyridine-3-carboxamide;
2-[(1-biphenyl-3-yl-5-hydroxy-4-oxo-1,4-dihydropyridin-2-yl)methyl]isoquinolin-3(2H)-one;
1-biphenyl-3-yl-5-hydroxy-2-(methoxymethyl)pyridin-4(1H)-one;
5-hydroxy-2-methyl-1-[3-(1,3,5-trimethyl-1H-pyrazol-4-yl)phenyl]pyridin-4(1H)-one;
5-hydroxy-1-[3-(2-methoxypyridin-3-yl)phenyl]-2-methylpyridin-4(1H)-one;
5-hydroxy-1-[3-(1H-indol-5-yl)phenyl]-2-methylpyridin-4(1H)-one;
N-[4'-(5-hydroxy-2-methyl-4-oxopyridin-1(4H)-yl)biphenyl-2-yl]-4-methylbenzenesulfonamide;
5-hydroxy-1-{4'-[(4-hydroxypiperidin-1-yl)carbonyl]biphenyl-4-yl}-2-methylpyridin-4(1H)-one;
4'-(5-hydroxy-2-methyl-4-oxopyridin-1(4H)-yl)-4-methylbiphenyl-2-carbonitrile;
1-[3'-(1,1-dioxidothiomorpholin-4-yl)biphenyl-4-yl]-5-hydroxy-2-methylpyridin-4(1H)-one;
5-hydroxy-1-[3'-(3-hydroxypropyl)biphenyl-4-yl]-2-methylpyridin-4(1H)-one;
1-[4-(4-fluorobenzyl)phenyl]-5-hydroxy-2-methylpyridin-4(1H)-one;
1-[2'-(difluoromethoxy)biphenyl-4-yl]-5-hydroxy-2-methylpyridin-4(1H)-one;
5-hydroxy-2-methyl-1(3-[1,2,4]triazolo[1,5-a]pyridin-6-ylphenyl)pyridin-4(1H)-one;
4-[3-(5-hydroxy-2-methyl-4-oxopyridin-1(4H)-yl)phenyl]-2,3-dihydro-1H-isoindol-1-one;
5-hydroxy-1-{3-[2-(hydroxymethyl)pyridin-4-yl[phenyl}-2-methylpyridin-4(1H)-one;
1-biphenyl-3-yl-5-hydroxy-2-methylpyridin-4(1H)-one;
5-hydroxy-2-methyl-4'-phenyl-414-1,2'-bipyridin-4-one;
1-biphenyl-3-yl-5-hydroxy-2-(1-methylethyl)pyridin-4(1H)-one;
1-(2'-fluorobiphenyl-3-yl)-5-hydroxy-2-(1-methylethyp-pyridin-4(1H)-one;

5-hydroxy-2-(1-methylethyl)-1-(3-pyridin-3-ylphenyl) pyridin-4(1H)-one;

1-[3-(6-fluoropyridin-3-yl)phenyl]-5-hydroxy-2-(1-methylethyl)pyridin-4(1H)-one;

5-hydroxy-2-(1-methylethyl)-1-[3-(1-methyl-1H-indol-5-yl)phenyl]pyridin-4(1H)-one;

5-hydroxy-2-(1-methylethyl)-1-[3-(1-propyl-1H-pyrazol-4-yl)phenyl]pyridin-4(1H)-one;

5-hydroxy-2-(1-methylethyl)-1-[3-(1H-pyrrolo[3,2-b]pyridin-6-yl)phenyl]pyridin-4(1H)-one;

5-hydroxy-2-(1-methylethyl)-1-{3-[2-(trifluoromethyl)pyridin-4-yl]phenyl}pyridin-4(1H)-one;

5-hydroxy-2-(1-methylethyl)-1-[3-(3-methyl-3H-imidazo[4,5-b]pyridin-6-yl)phenyl]pyridin-4(1H)-one;

5-hydroxy-1-(3-imidazo[1,2-a]pyridin-6-ylphenyl)-2-(1-methylethyl)pyridin-4(1H)-one;

1-[3-(2-fluoropyridin-4-yl)phenyl]-5-hydroxy-2-methylethyl)pyridin-4(1H)-one;

1-biphenyl-3-yl-2-[2-(4-tert-butylphenyl)-1-methylethyl]-5-hydroxypyridin-4(1H)-one;

1-biphenyl-3-yl-5-hydroxy-2-(2-methylpropyl)pyridin-4(1H)-one;

5-hydroxy-1-(3-isoquinolin-4-ylphenyl)-2-[1-(methylsulfInyL)ethyl]pyrudin-4(1H)-one;

1-biphenyl-3-yl-5-hydroxy-2-morpholin-4-ylpyridin-4(1H)-one;

5-hydroxy-2-phenyl-1-(3-quinolin-5-ylphenyl)pyridin-4(1H)-one;

1-biphenyl-3-yl-2-{1,1-dimethyl-2-[3-(trifluoromethyl)phenyl]ethyl}-5-hydroxypyridin-4(1H)-one;

1-biphenyl-3-yl-5-hydroxy-2-[(E)-2-phenylethenyl]pyridin-4(1H)-one;

1-biphenyl-3-yl-2-{2-[3-fluoro-4-(trifluoromethyl)phenyll ethyl}-5-hydroxypyridin-4(1H)-one;

1-biphenyl-3-yl-2-[2-(2-fluorophenyl)-2-hydroxyethyl]-5-hydroxypyridin-4(1H)-one;

3-[2-(1-biphenyl-3-yl-5-hydroxy-4-oxo-1,4-dihydropyridin-2-yl)- -hydroxyethyl]benzonitrile;

1-biphenyl-3-yl-5-hydroxy-2-[2-hydroxy-2-(3-methoxyphenyl)ethyl]pyridin-4(1H)-one;

1-biphenyl-3-yl-2-[2-(4-tert-butylphenyl)-2-hydroxyethyl]-5-hydroxypyridin-4(1H)-one;

1-biphenyl-3-yl-2-{2-[3-fluoro-4-(trifluoromethyl)phenyl]-2-hydroxyethyl}-5-hydroxypyridin-4(1H)-one;

1-biphenyl-3-yl-2-[2(3,4-difluorophenyl)-1-hydroxyethyl]-5-hydroxypyridin-4(1H)-one;

5-hydroxy-2-(1-hydroxy-2-phenylethyl)-1-phenylpyridin-4(1H)-one;

2-[2-(3,4-difluorophenyl)-1-hydroxyethyl]-5-hydroxy-1-phenylpyridin-4(1H)-one;

5-hydroxy-2-[1-hydroxy-2-(2-methylphenyl)ethyl]-1-phenylpyridin-4(1H)-one;

3-[2-hydroxy-2-(5-hydroxy-4-oxo-1-phenyl-1,4-dihydropridin-2-yl)ethyl]benzonitrile;

1-biphenyl-3-yl-2-[(3,4-difluorophenyl)(hydroxy)methyl]-5-hydroxypyridin-4(1H)-one;

1-biphenyl-3-yl-2-[(4-chloro-3-fluorophenyl)(hydroxy)methyl]-5-hydroxypyridin-4(1H)-one;

1-biphenyl-3-yl-2-[(4-fluorophenyl)(hydroxy)methyl]-5-hydroxypyridin-4(1H)-one;

5-hydroxy-2-[hydroxy(3-methylphenyL)methyl]-1-phenylpyridin-4(1H)-one;

5-hydroxy-2-[hydroxy(3-methoxyphenyL)methyl]-1-phenylpyridin-4(1H)-one;

5-hydroxy-2-(2-hydroxy-1-methyl-4-phenylbutyl)-1-phenylpyridin-4(1H)-one;

5-hydroxy-2-(1-methyl-2-phenylethyl)-1-phenylpyridin-4(1H)-one;

1-biphenyl-3-yl-2-{2-[4-chloro-3-(trifluoromethyl)phenyl]-1-methylethyl}-5-hydroxypyridin-4(1H)-one;

2-[2-(2,3-difluorophenyl)-1-methylethyl]-5-hydroxy-1-phenylpyridin-4(1H)-one;

2-[2-(3-fluorophenyl)-1-methylethyl]-5-hydroxy-1-phenylpyridin-4(1H)-one;

2-[2-(3,5-dimethylphenyl)-1-methylethyl]-5-hydroxy-1-phenylpyridin-4(1H)-one;

2-(2-cyclohexyl-1-methylethyl)-5-hydroxy-1-phenylpyridin-4(1H)-one;

5-hydroxy-2-[2-hydroxy-2-(3-methoxyphenyl)-1-methylethyl]-1-phenylpyridin-4(1H)-one;

1-biphenyl-3-yl-5-hydroxy-2-[2-(5-phenyl-1,2,4-oxadiazol-3-yl)ethyl]pyridin-4(1H)-one;

1-biphenyl-3-yl-2-{2-[2-(2-fluorophenyl)-5-methyl-1,3-oxazol-4-yl]-1-methylethyl}-5-hydroxypyridin-4(1H)-one;

1-biphenyl-3-yl-5-hydroxy-2-[2-hydroxy-2-(2-methoxypyrimidin-5-yl)ethyl]pyridin-4(1H)-one;

1-biphenyl-3-yl-5-hydroxy-2-[2-hydroxy-2-(1,3-thiazol-4-yl)ethylfpyridin-4(1H)-one;

1-biphenyl-3-yl-5-hydroxy-2-(trimethylsilyl)pyridine-4(1H)-one;

or a pharmaceutically acceptable salts, and-individual enantiomers, or and diastereomers thereof.

61. A pharmaceutical composition comprising an inert carrier and an effective amount of a compound according to claim 11.

62. The composition according to claim 61 further comprising one or more therapeutically active compounds selected from the group consisting of opiate agonists or antagonists, calcium channel antagonists, 5HT, 5-HT$_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NKI) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical anti-depressants, benzodiazepines, corticotropin releasing factor (CRF) antagonists, neurontin (gabapentin) and pregabalin.

63. A pharmaceutical composition comprising an inert carrier and an effective amount of a compound according to claim 34.

64. The composition according to claim 12 or 63 further comprising one or more therapeutically active compounds selected from the group consisting of opiate agonists or antagonists, calcium channel antagonists, 5HT, 5-HT$_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NKI) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical anti-depressants, benzodiazepines, corticotropin releasing factor (CRF) antagonists, neurontin (gabapentin) and pregabalin.

65. A pharmaceutical composition comprising an inert carrier and an effective amount of a compound according to claim 44.

66. The composition according to claim 65 further comprising one or more therapeutically active compounds selected from the group consisting of opiate agonists or antagonists, calcium channel antagonists, 5HT, 5-HT$_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NKI) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical anti-depressants, benzodiazepines, corticotropin releasing factor (CRF) antagonists, neurontin (gabapentin) and pregabalin.

67. A pharmaceutical composition comprising an inert carrier and an effective amount of a compound according to claim 49.

68. The composition according to claim 67 further comprising one or more therapeutically active compounds selected from the group consisting of opiate agonists or antagonists, calcium channel antagonists, 5HT, 5-HT$_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NKI) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical anti-depressants, benzodiazepines, corticotropin releasing factor (CRF) antagonists, neurontin (gabapentin) and pregabalin.

69. A compound of structural formula I:

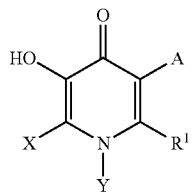

or a pharmaceutically acceptable salt, enantiomer or diastereomer thereof, wherein:
A represents hydrogen, B(OH)$_2$, halo, OH, C$_{3-10}$cycloalkyl, or C$_{1-6}$ alkyl;
X represents hydrogen or C$_{1-6}$ alkyl;
Y represents benzimidazolyl, benzthiazolyl, benzoxazolyl, benzpiperidinyl, quinolyl, indolyl, tetrahydroquinoline, indazolyl, or pyridyl, any of which is optionally substituted with 1 to 3 groups of R$^a$, provided that no more than one of said R$^a$ is cycloalkyl, heterocyclyl or aryl;
R$^1$ represents hydrogen, NR$^2$R$^3$ or C$_{1-10}$alkyl, said alkyl optionally substituted with 1 to 3 groups of C$_{3-6}$ cycloalkyl, halo, OH, CF$_3$, OR$^2$, NR$^2$R$^3$, cyano, C$_{6-10}$ aryl, and C$_{5-10}$ heterocyclyl, wherein said aryl and heterocyclyl optionally substituted with 1 to 3 groups of C$_{1-6}$alkyl, halogen, hydroxyl, CF$_3$, OCF$_3$, OCHF$_2$, CN, OR$^2$, NR$^2$R$^3$;
each of R$^2$ and R$^3$ independently represent H, OH, C$_{1-6}$ alkyl and N(CH$_3$)$_2$;
each R$^a$ independently represents C$_{1-6}$ alkyl, halogen, hydroxyl, CF$_3$, OCHF$_2$, OCF$_3$, C$_{3-6}$cycloalkyl, O(CH$_2$)$_n$C$_{3-6}$ cycloalkyl, NR$^2$C(O)R$^2$ NR$_2$C(O)R$^2$, C(O)N(R$^2$)$_2$, C(R$^2$)$_2$OR$^2$, C(O)R$^2$, NO$_2$, CN, N(R$^2$)$_2$, SO$_2$R$^2$, OR$^2$, (CH$_2$)$_n$C$_{5-10}$heterocyclyl, NH(CH$_2$)$_n$C$_{5-10}$heterocyclyl, (CH$_2$)$_n$C$_{6-10}$ aryl, O(CH$_2$)$_n$C$_{6-10}$ aryl, or O(CH$_2$)$_n$C$_{5-10}$heterocyclyl, said cycloalkyl, heterocyclyl and aryl optionally substituted with 1 to 3 groups of R$^b$;
each R$^b$ independently represents C$_{1-6}$ alkyl, halogen, CHF$_2$, N(R$^2$)$_2$, S(O)$_2$NR$^2$R$^3$, (CH$_2$)$_n$C$_{6-10}$ aryl, (CH$_2$)$_n$heterocyclyl, C(O)(CH$_2$)$_n$heterocyclyl, NH(CH$_2$)$_n$heterocyclyl, C(O)NHC$_{3-6}$cycloalkyl, CH$_2$OH, CF$_3$, —O—, OR$^2$, C$_{3-6}$ cycloalkyl, or CN; and
n represents 0 to 5.

70. The compound of claim 69, wherein
A represents hydrogen;
X represents hydrogen;
Y represents pyridyl or benzimidazolyl, any of which optionally substituted with 1 to 3 groups of R$^a$; and
R$^1$ represents C$_{1-10}$alkyl, said alkyl optionally substituted with 1 to 3 groups of C$_{3-6}$ cycloalkyl, halo, OH, CF$_3$, OR$^2$, NR$^2$R$^3$, cyano, C$_{6-10}$ aryl, and heterocyclyl, wherein said aryl and heterocyclyl optionally substituted with 1 to 3 groups of C$_{1-6}$alkyl, halogen, hydroxyl, CF$_3$, OCF$_3$, OCHF$_2$, CN, OR$^2$, NR$^2$R$^3$.

71. The compound of claim 69, wherein
A represents hydrogen;
X represents hydrogen;
Y represents pyridyl or benzimidazolyl, any of which optionally substituted with 1 to 3 groups of R$^a$;
R$^1$ represents hydrogen or C$_{1-10}$alkyl; and
each R$^a$ independently represents C$_{1-6}$ alkyl, halogen, hydroxyl, (CH$_2$)$_n$CF$_3$, OCHF$_2$, OCF$_3$, C$_{3-6}$cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, (CH$_2$)$_n$C(O)OR$^2$, SO$_2$R$^2$, OR$^2$, (CH$_2$)$_n$C$_{5-10}$heterocyclyl, NH(CH$_2$)$_n$C$_{5-10}$heterocyclyl, (CH$_2$)$_n$C$_{6-10}$ aryl, O(CH$_2$)$_n$C$_{6-10}$ aryl, or O(CH$_2$)$_n$C$_{5-10}$heterocyclyl, said cycloalkyl, heterocyclyl and aryl optionally substituted with 1 to 3 groups of R$^b$; and
each R$^b$ independently represents C$_{1-6}$ alkyl, halogen, CHF$_2$, N(R$^2$)$_2$, CH$_2$OH, OR$^2$, (CH$_2$)$_n$CF$_3$, or CN.

72. The compound of claim 71, wherein
A, X, and R$^1$ each represent hydrogen;
Y represents pyridyl or benzimidazolyl, any of which optionally substituted with 1 to 3 groups of R$^a$, provided that at least one of said R$^a$ is selected from (CH$_2$)$_n$C$_{6-10}$ aryl, or (CH$_2$)$_n$C$_{5-10}$heterocyclyl.

73. A compound of structural formula I:

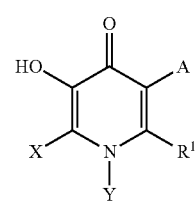

or a pharmaceutically acceptable salt, enantiomer or diastereomer thereof, wherein:

A represents hydrogen, B(OH)$_2$, halo, OH, C$_{3-10}$cycloalkyl, or C$_{1-6}$ alkyl;

X represents hydrogen or C$_{1-6}$ alkyl;

Y represents phenyl optionally substituted with 1 to 3 groups of R$^a$, wherein at least one of said 1 to 3 groups of R$^a$ represents hydroxyl, CF$_3$, OCHF$_2$, OCF$_3$, C$_{3-6}$cycloalkyl, O(CH$_2$)$_n$C$_{3-6}$ cycloalkyl, NR$^2$C(O)R$^2$ NR$_2$C(O)R$^2$, C(O)N(R$^2$)$_2$, C(R$^2$)$_2$OR$^2$, C(O)R$^2$, NO$_2$, CN, N(R$^2$)$_2$, SO$_2$R$^2$, OR$^2$, (CH$_2$)$_n$C$_{5-10}$heterocyclyl, NH(CH$_2$)$_n$C$_{5-10}$heterocyclyl, (CH$_2$)$_n$C$_{6-10}$ aryl, O(CH$_2$)$_n$C$_{6-10}$ aryl, or O(CH$_2$)$_n$C$_{5-10}$heterocyclyl, said cycloalkyl, heterocyclyl and aryl optionally substituted with 1 to 3 groups of R$^b$, provided that no more than one of said R$^a$ is cycloalkyl, heterocyclyl or aryl;

R$^1$ represents NR$^2$R$^3$ or C$_{1-10}$alkyl, said alkyl optionally substituted with 1 to 3 groups of C$_{3-6}$ cycloalkyl, halo, OH, CF$_3$, OR$^2$, NR$^2$R$^3$, cyano, C$_{6-10}$ aryl, and heterocyclyl, wherein said aryl and heterocyclyl optionally substituted with 1 to 3 groups of C$_{1-6}$alkyl, halogen, hydroxyl, CF$_3$, OCF$_3$, OCHF$_2$, CN, OR$^2$, and NR$^2$R$^3$;

each of R$^2$ and R$^3$ independently represent H, OH, or C$_{1-6}$ alkyl;

each R$^a$ independently represents C$_{1-6}$ alkyl, halogen, hydroxyl, (CH$_2$)$_n$CF$_3$, OCHF$_2$, OCF$_3$, C$_{3-6}$cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, (CH$_2$)$_n$C(O)OR$^2$, SO$_2$R$^2$, OR$^2$, (CH$_2$)$_n$C$_{5-10}$heterocyclyl, NH(CH$_2$)$_n$C$_{5-10}$heterocyclyl, (CH$_2$)$_n$C$_{6-10}$ aryl, O(CH$_2$)$_n$C$_{6-10}$ aryl, or O(CH$_2$)$_n$C$_{5-10}$heterocyclyl, said cycloalkyl, heterocyclyl and aryl optionally substituted with 1 to 3 groups of R$^b$;

each R$^b$ independently represents C$_{1-6}$ alkyl, halogen, CHF$_2$, N(R$^2$)$_2$, CH$_2$OH, OR$^2$, (CH$_2$)$_n$CF$_3$, or CN; and n represents 0 to 5.

74. The compound of claim 73, wherein:
A and X each represents hydrogen;
Y represents phenyl optionally substituted with 1 to 3 groups of R$^a$, wherein at least one of said 1 to 3 groups of R$^a$ is selected from (CH$_2$)$_n$C$_{5-10}$heterocyclyl and (CH$_2$)$_n$C$_{6-10}$ aryl, said aryl and heterocyclyl optionally substituted with 1 to 3 groups of R$^b$; and
R$^1$ represents C$_{1-10}$alkyl, said alkyl optionally substituted with 1 to 3 groups of C$_{3-6}$ cycloalkyl, halo, OH, CF$_3$, OR$^2$, NR$^2$R$^3$, cyano, C$_{6-10}$ aryl, and C$_{5-10}$heterocyclyl, wherein said aryl and heterocyclyl optionally substituted with 1 to 3 groups of C$_{1-6}$alkyl, halogen, hydroxyl, CF$_3$, OCF$_3$, OCHF$_2$, CN, OR$^2$, and NR$^2$R$^3$.

75. The compound of claim 73, wherein:
A and X each represents hydrogen;
Y represents phenyl optionally substituted with 1 to 3 groups of Ra, wherein at least one of said 1 to 3 groups of R$^a$ is selected from (CH$_2$)$_n$C$_{5-10}$heterocyclyl and (CH$_2$)$_n$C$_{6-10}$ aryl, said aryl and heterocyclyl optionally substituted with 1 to 3 groups of R$^b$; and
R$^1$ represents C$_{1-10}$alkyl, said alkyl optionally substituted with 1 to 3 groups of OH and C$_{6-10}$ aryl.

76. The compound of claim 73, wherein:
A and X each represents hydrogen;
Y represents phenyl optionally substituted with 1 to 3 groups of R$^a$, wherein at least one of said 1 to 3 groups of R$^a$ is selected from (CH$_2$)$_n$C$_{5-10}$heterocyclyl and (CH$_2$)$_n$C$_{6-10}$ aryl, said aryl and heterocyclyl optionally substituted with 1 to 3 groups of R$^b$; and
R$^1$ represents C$_{1-10}$alkyl, said alkyl optionally substituted with 1 to 3 groups of OH and CF$_3$.

77. The compound of claim 73, wherein:
A and X each represents hydrogen;
Y represents phenyl optionally substituted with 1 to 3 groups of R$^a$, wherein at least one of said 1 to 3 groups of R$^a$ is selected from (CH$_2$)$_n$C$_{5-10}$heterocyclyl and (CH$_2$)$_n$C$_{6-10}$ aryl, said aryl and heterocyclyl optionally substituted with 1 to 3 groups of R$^b$; and
R$^1$ represents hydrogen or CH(OH)CH$_3$.

78. A compound of structural forumla I:

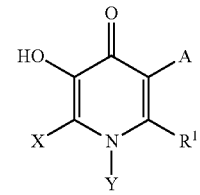

I or a pharmaceutically acceptable salt, enantiomer or diatereomer thereof, wherein:

A and X each represents hydrogen;

Y represents phenyl optionally substituted with 1 to 3 groups of R$^a$, wherein at least one of said 1 to 3 groups of R$^a$ is selected from (CH$_2$)$_n$C$_{5-10}$heterocyclyl and (CH$_2$)$_n$C$_{6-10}$ aryl, said aryl and heterocyclyl optionally substituted with 1 to 3 groups of R$^b$; provided that no more than one of said R$^a$ on Y is cycloalkyl, heterocyclyl or aryl;

each R$^a$ independently represents C$_{1-6}$ alkyl, halogen, hydroxyl, (CH$_2$)$_n$CF$_3$, OCHF$_2$, OCF$_3$, c$_{3-6}$cycloalkyl, O(CH$_2$)$_n$C$_{3-6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, (CH$_2$)$_n$C(O)OR$^2$, SO$_2$R$^2$, OR$^2$, (CH$_2$)$_n$C$_{5-10}$heterocyclyl, NH(CH$_2$)$_n$C$_{5-10}$heterocyclyl, (CH$_2$)$_n$C$_{6-10}$aryl, O(CH$_2$)$_n$C$_{6-10}$aryl, or O(CH$_2$)$_n$C$_{5-10}$heterocyclyl, said cycloalkyl, heterocyclyl and aryl optionally substituted with 1 to 3 groups of R$^b$;

each R$^b$ independently represents C$_{1-6}$alkyl, halogen, CHF$_2$, N(R$^2$)$_2$, CH$_2$OH, OR$^2$, (CH$_2$)$_n$CF$_3$, or CN;

R$^1$ represents NR$^2$R$^3$;

each of R$^2$ and R$^3$ independently represent H or C$_{1-6}$alkyl; and n represents 0 to 5.

79. The compound according to claim 1 which is:
1-biphenyl-3-yl-2-(2-biphenyl-2-yl-2-hydroxyethyl)-5-hydroxypyridin-4(1H)-one;
2-[cyclohexyl(hydroxy)methyl]-5-hydroxy-1-(3-isoquinolin-4-ylphenyl)pyridin-4(1H)-one;
1-biphenyl-3-yl-2-(cyclopentylmethyl)-5-hydroxypyridin-4(1H)-one;
1-biphenyl-3-yl-2-(2-cyclopropylethyl)-5-hydroxypyridin-4(1H)-one;
2-[cyclopropyl(hydroxy)methyl]-5-hydroxy-1-(3-isoquinolin-4-ylphenyl)pyridin-4(1H)-one;
1-biphenyl-3-yl-2-[2-(5-cyclopropyl-1,2,4-oxadiazol-3-yl)-1-methylethyl]-5-hydroxypyridin-4(1H)-one;
1-biphenyl-3-yl-2-(difluoromethyl)-5-hydroxypyridin-4(1H)-one;
1-biphenyl-3-yl-2-(dimethylamino)-5-hydroxypyridin-4(1H)-one;
5-hydroxy-2-(2-hydroxy-1,3-dimethylbutyl)-1-phenylpyridin-4(1H)-one;
1-biphenyl-3-yl-2-(fluoromethyl)-5-hydroxypyridin-4(1H)-one;

1-biphenyl-3-yl-5-hydroxy-2-(methoxymethyl)pyridin-4(1H)-one;
1-biphenyl-3-yl-5-hydroxy-2-methylethyl)pyridin-4(1H)-one;
1-(2'-fluorobiphenyl-3-yl)-5-hydroxy-2-methylethyl)pyridin-4(1H)-one;
5-hydroxy-2-(1-methylethyl)-1-(3-pyridin-3-ylphenyl)pyridin-4(1H)-one;
1-[3-(6-fluoropyridin-3-yl)phenyl]-5-hydroxy-2-methylethyl)pyridin-4(1H)-one;
5-hydroxy-2-(1-methylethyl)-1-[3-(1-methyl-1H-indol-5-yl)phenyl]pyridin-4(1H)-one;
5-hydroxy-2-(1-methylethyl)-1-[3-(1-propyl-1H-pyrazol-4-yl)phenyl]pyridin-4(1H)-one;
5-hydroxy-2-(1-methylethyl)-1-[3-(1H-pyrrolo[3,2-b]pyridin-6-yl)phenyl]pyridin-4(1H)-one;
5-hydroxy-2-(1-methylethyl)-1-{3-[2-(trifluoromethyl)pyridin-4-yl]phenyl}pyridin-4(1H)-one;
5-hydroxy-2-(1-methylethyl)-1-[3-(3-methyl-3H-imidazo[4,5-b]pyridin-6-yl)phenyl]pyridin-4(1H)-one;
5-hydroxy-1-(3-imidazo[1,2-a]pyridin-6-ylphenyl)-2-(1-methylethyl)pyridin-4(1H)-one;
1-[3-(2-fluoropyridin-4-yl)phenyl]-5-hydroxy-2-methylethyl)pyridin-4(1H)-one;
1-biphenyl-3-yl-2-[2-(4-tert-butylphenyl)-1-methylethyl]-5-hydroxypyridin-4(1H)-one;
1-biphenyl-3-yl-5-hydroxy-2-(2-methylpropyl)pyridin-4(1H)-one;
1-biphenyl-3-yl-2-{2-[3-fluoro-4-(trifluoromethyl)phenyl]ethyl}-5-hydroxypyridin-4(1H)-one;
1-biphenyl-3-yl-2-[2-(2-fluorophenyl)-2-hydroxyethyl]-5-hydroxypyridin-4(1H)-one;
1-biphenyl-3-yl-5-hydroxy-2-[2-hydroxy-2-(3-methoxyphenyl)ethyl]pyridin-4(1H)-one;
1-biphenyl-3-yl-2-[2-(4-tert-butylphenyl)-2-hydroxyethyl]-5-hydroxypyridin-4(1H)-one;
1-biphenyl-3-yl-2-{2-[3-fluoro-4-(trifluoromethyl)phenyl]-2-hydroxyethyl}-5-hydroxypyridin-4(1H)-one;
1-biphenyl-3-yl-2-[2-(3,4-difluorophenyl)-1-hydroxyethyl]-5-hydroxypyridin-4(1H)-one;
5-hydroxy-2-(1-hydroxy-2-phenylethyl)-1-phenylpyridin-4(1H)-one;
2-[2-(3,4-difluorophenyl)-1-hydroxyethyl]-5-hydroxy-1-phenylpyridin-4(1H)-one;
5-hydroxy-2-[1-hydroxy-2-(2-methylphenyl)ethyl]-1-phenylpyridin-4(1H)-one;
1-biphenyl-3-yl-2-[(3,4-difluorophenyl)(hydroxy)methyl]-5-hydroxypyridin-4(1H)-one;
1-biphenyl-3-yl-2-[(4-chloro-3-fluorophenyl)(hydroxy)methyl]-5-hydroxypyridin-4(1H)-one;
1-biphenyl-3-yl-2-[(4-fluorophenyl)(hydroxy)methyl]-5-hydroxypyridin-4(1H)-one;
5-hydroxy-2-[hydroxy(3-methylphenyl)methyl]-1-phenylpyridin-4(1H)-one;
5-hydroxy-2-[hydroxy(3-methoxyphenyl)methyl]-1-phenylpyridin-4(1H)-one;
5-hydroxy-2-(2-hydroxy-1-methyl-4-phenylbutyl)-1-phenylpyridin-4(1H)-one;
5-hydroxy-2-(1-methyl-2-phenylethyl)-1-phenylpyridin-4(1H)-one;
1-biphenyl-3-yl-2-{2-[4-chloro-3-(trifluoromethyl)phenyl]-1-methylethyl}-5-hydroxypyridin-4(1H)-one;
2-[2-(2,3-difluorophenyl)-1-methylethyl]-5-hydroxy-1-phenylpyridin-4(1H)-one;
2-[2-(3-fluorophenyl)-1-methylethyl]-5-hydroxy-1-phenylpyridin-4(1H)-one;
2-[2-(3,5-dimethylphenyl)-1-methylethyl]-5-hydroxy-1-phenylpyridin-4(1H)-one;
2-(2-cyclohexyl-1-methylethyl)-5-hydroxy-1-phenylpyridin-4(1H)-one;
5-hydroxy-2-[2-hydroxy-2-(3-methoxyphenyl)-1-methylethyl]-1-phenylpyridin-4(1H)-one;
1-biphenyl-3-yl-5-hydroxy-2-[2-hydroxy-2-(2-methoxypyrimidin-5-yl)ethyl]pyridin-4(1H)-one;
1-biphenyl-3-yl-5-hydroxy-2-[2-hydroxy-2-(1,3-thiazol-4-yl)ethyl]pyridin-4(1H)-one;
or a pharmaceutically acceptable salt, enantiomer, or diastereomer thereof.

80. The compound according to claim 73 which is:
5-hydroxy-2-(hydroxymethyl)-1-(4-morpholin-4-ylphenyl)pyridin-4(1H)-one;
1-(3,5-dimethylphenyl)-5-hydroxy-2-(hydroxymethyl)pyridin-4(1H)-one;
5-hydroxy-2-(hydroxymethyl)-1-(3-methoxyphenyl)pyridin-4(1H)-one;
1-[3-(dimethylamino)phenyl]-5-hydroxy-2-(hydroxymethyl)pyridin-4(1H)-one;
1-[3'-(1,1-dioxidothiomorpholin-4-yl)biphenyl-4-yl]-5-hydroxy-2-methylpyridin-4(1H)-one;
5-hydroxy-1-[3'-(3-hydroxypropyl)biphenyl-4-yl]-2-methylpyridin-4(1H)-one;
1-[4-(4-fluorobenzyl)phenyl]-5-hydroxy-2-methylpyridin-4(1H)-one;
1-[2'-(difluoromethoxy)biphenyl-4-yl]-5-hydroxy-2-methylpyridin-4(1H)-one;
5-hydroxy-2-methyl-1-(3-[1,2,4]triazolo[1,5-a]pyridin-6-ylphenyl)pyridin-4(1H)-one;
1-biphenyl-3-yl-3-chloro-5-hydroxy-2-(hydroxymethyl)pyridin-4(1H)-one;
5-hydroxy-2-(hydroxymethyl)-5'-phenyl-4H-1,3'-bipyridin-4-one;
or a pharmaceutically acceptable salt, enantiomer, or diastereomer thereof.

81. The compound according to claim 69 which is:
3-hydroxy-1-(6-methoxy-4-methylquinolin-8-yl)pyridin-4(1H)-one;
1-(2-tert-butyl-1H-indol-5-yl)-3-hydroxypyridin-4(1H)-one;
1-[2-(3,4-difluorophenyl)-1,3-benzoxazol-5-yl]-3-hydroxypyridin-4(1H)-one;
3-hydroxy-1-[2-(4-methylphenyl)-1H-benzimidazol-5-yl]pyridin-4(1H)-one;
1-(1,3-benzothiazol-5-yl)-3-hydroxypyridin-4(1H)-one;
3-hydroxy-1-(1-phenyl-1H-indazol-6-yl)pyridin-4(1H)-one;
3-hydroxy-1-(1H-indazol-6-yl)pyridin-4(1H)-one;
3-hydroxy-1-[2-(1,3-thiazol-4-yl)-1H-benzimidazol-4-yl]pyridin-4(1H)-one;
3-hydroxy-1-[2-(1,3-oxazol-2-yl)-1H-benzimidazol-5-yl]pyridin-4(1H)-one;
1-(1-acetyl-1,2,3,4-tetrahydroquinolin-7-yl)-3-hydroxypyridin-4(1H)-one;
1-(2-biphenyl-4-yl-1H-benzimidazol-5-yl)-3-hydroxypyridin-4(1H)-one;
3-hydroxy-1-(2-phenylpyrimidin-4-yl)pyridin-4(1H)-one;
3-hydroxy-6'-phenyl-4H-1,2'-bipyridin-4-one;
3-hydroxy-4'-phenyl-4H-1,2'-bipyridin-4-one;
3-hydroxy-6'-quinolin-5-yl-4H-1,2'-bipyridin-4-one;
1-{1-[2,4-bis(trifluoromethyl)benzyl]-1H-benzimidazol-4-yl}-3-hydroxypyridin-4(1H)-one;
1-[1-(2-chlorobenzyl)-1H-benzimidazol-4-yl]-3-hydroxypyridin-4(1H)-one;

1-[1-(2-Chloro-6-fluorobenzyl)-1H-benzimidazol-4-yl]-5-hydroxy-2-methylpyridin-4(1H)-one;
or a pharmaceutically acceptable salt, enantiomer, or diastereomer thereof.

82. The compound of claim 1, which is 5-hydroxy-1-(3-imidazo[1,2-a]pyridin-6-ylphenyl)-2-(1-methylethyl)pyridin-4(1H)-one or a pharmaceutically acceptable salt, enantiomer or diastereomer thereof.

83. The compound of claim 1, which is 2-(2-cyclohexyl-1-methylethyl)-5-hydroxy-1-phenylpyridin-4(1H)-one or a pharmaceutically acceptable salt, enantiomer or diastereomer thereof.

84. The compound of claim 49, which is [1-(biphenyl-3-yl)-5-hydroxy-4-oxo-1,4-dihydropyridin-3-yl]boronic acid or a pharmaceutically acceptable salt, enantiomer or diastereomer thereof.

85. The compound of claim 69, which is 3-hydroxy-1-(1-phenyl-1H-indazol-6-yl)pyridin-4(1H)-one or a pharmaceutically acceptable salt, enantiomer or diastereomer thereof.

86. The compound of claim 71, which is 5-hydroxy-2-(hydroxymethyl)-1-(3-methoxyphenyl)pyridin-4(1H)-one or a pharmaceutically acceptable salt, enantiomer or diastereomer thereof.

* * * * *